US006096753A

United States Patent [19]
Spohr et al.

[11] Patent Number: 6,096,753
[45] Date of Patent: Aug. 1, 2000

[54] SUBSTITUTED PYRIMIDINONE AND PYRIDONE COMPOUNDS AND METHODS OF USE

[75] Inventors: Ulrike D. Spohr; Michael J. Malone, both of Boulder; Nathan B. Mantlo, Lafayette, all of Colo.

[73] Assignee: Amgen Inc., Thousand Oaks, Calif.

[21] Appl. No.: 08/985,346

[22] Filed: Dec. 4, 1997

Related U.S. Application Data

[63] Continuation-in-part of application No. 08/976,053, Nov. 21, 1997, abandoned.
[60] Provisional application No. 60/032,128, Dec. 5, 1996, and provisional application No. 60/050,950, Jun. 13, 1997.
[51] Int. Cl.$^7$ .................... A61K 31/506; A61K 31/513; A61P 19/00; C07D 239/24
[52] U.S. Cl. .................. 514/269; 514/227.8; 514/235.8; 514/249; 514/255; 514/275; 544/60; 544/123; 544/238; 544/295; 544/296; 544/297; 544/319; 544/320; 544/321; 544/326; 544/328
[58] Field of Search .............................. 514/227.8, 235.8, 514/249, 255, 269, 275; 544/60, 123, 238, 295, 296, 297, 319, 320, 321, 326, 328

[56] References Cited

U.S. PATENT DOCUMENTS

| | | | |
|---|---|---|---|
| 3,929,807 | 12/1975 | Fitzi | 260/294.8 |
| 4,578,459 | 3/1986 | Durant et al. | 544/8 |
| 4,990,512 | 2/1991 | Perrior et al. | 514/269 |
| 5,100,897 | 3/1992 | Allen et al. | 514/269 |
| 5,162,325 | 11/1992 | Chakravarty et al. | 514/259 |
| 5,298,481 | 3/1994 | Tice | 504/242 |
| 5,300,477 | 4/1994 | Tice | 504/242 |
| 5,434,157 | 7/1995 | Wierenga et al. | 514/272 |
| 5,518,994 | 5/1996 | Kawamura et al. | 504/242 |

FOREIGN PATENT DOCUMENTS

| | | |
|---|---|---|
| 2020370 | 7/1991 | Canada . |
| 039051 | 11/1981 | European Pat. Off. . |
| 0481448 | 4/1992 | European Pat. Off. . |
| 1271116 | 6/1968 | Germany . |
| 6-135934 | 5/1994 | Japan . |
| 1 238 959 | 7/1971 | United Kingdom . |
| WO 92/02513 | 2/1992 | WIPO . |
| WO 92/10190 | 6/1992 | WIPO . |
| WO 92/10498 | 6/1992 | WIPO . |
| WO 92/12154 | 7/1992 | WIPO . |
| WO 93/14081 | 7/1993 | WIPO . |
| WO 95/35304 | 12/1995 | WIPO . |
| WO 96/03387 | 2/1996 | WIPO . |
| WO 96/21452 | 7/1996 | WIPO . |
| WO 96/21654 | 7/1996 | WIPO . |
| WO 96/24584 | 8/1996 | WIPO . |
| WO 97/12876 | 4/1997 | WIPO . |
| WO 97/16442 | 5/1997 | WIPO . |
| WO 97/38992 | 10/1997 | WIPO . |
| WO 98/03484 | 1/1998 | WIPO . |

OTHER PUBLICATIONS

Mirkin et al., J. of the American Chemical Society, vol. 112(7), 2809–10 (1990).
Komatsu et al., Tetrahedron Letters, vol. 22(38), 3769–72 (1981).
Ohshiro et al., Heterocycles, vol. 22(3), 549–59 (1984).
Mortimer, Australian Journal of Chemistry, vol. 21(2), 467–76 (1968).
Takahashi et al., Chemistry Letters, No. 6, 1229–32 (1987).
Magdesieva et al., Chemistry of Heterocyclic Compounds, vol. 13(9), 1177–80 (1978).
Youssefyeh et al., Journal of the Chemical Society, No. 23, 2649–54 (1974).
Barr et al., Journal of the Chemical Society, No. 5, 1147–9 (1980).
Capuano et al., Liebigs Annalen Der Chemie, No. 4, 331–4 (1991).
Gilchrist et al., Journal of the Chemical Society, No. 19, 1969–72 (1975).
Gilchrist et al., Journal of the Chemical Society, No. 12, 487–8 (1974).
Giammanco et al., Atti Della Accademia di Scienze Lettere E Arti Di Palermo, vol. 30, 93–107 (1971).
Giammanco et al., Annali di Chimica, vol. 60(3), 188–97 (1970).
Giammanco, Atti Della Accademia di Scienze Lettere E Arti Di Palermo, vol. 27, 469–83 (1968).
Patent Abstracts of Japan, vol. 10(230), Publication No. 61 063680 (1996).
Yerxa et al., Tetrahedron, vol. 50(21), 6173–80 (1994).
Kotani et al., Tetrahedron, vol. 30(17), 3027–30 (1974).
STN printout for Eicher et al., Reaction of Diphenylcyclopropenone with Guanidines, Liebigs Ann. Chem., vol. 8, pp. 1337–1353, 1981.
STN printout for Jones et al., N–Oxides, N–imides, and N–ylides of Five–Membered Heterocycles, J. Chem. Sci., Perkin Trans. 1, vol. 21, pp. 2259–2264, 1976.
STN printout for Yoshida et al., The Cycloaddition Reaction of N–imidoyl Sulfoximides with Diphenylcyclopropenone to Yield Pyrimidinone or Pyrrolinone Derivatives, Bull. Chem. Soc. Japan, vol. 56, No. 8, pp. 2438–2441, 1983.

(List continued on next page.)

*Primary Examiner*—Mukund J. Shah
*Assistant Examiner*—Brenda Coleman
*Attorney, Agent, or Firm*—Steven Odre; Ron Levy; Frank Ungemach

[57] ABSTRACT

Selected novel substituted pyrimidinone and pyridone compounds are effective for prophylaxis and treatment of diseases, such as TNF-α, IL-1β, IL-6 and/or IL-8 mediated diseases, and other maladies, such as pain and diabetes. The invention encompasses novel compounds, analogs, prodrugs and pharmaceutically acceptable salts thereof, pharmaceutical compositions and methods for prophylaxis and treatment of diseases and other maladies or conditions involving inflammation, pain, diabetes and the like. The subject invention also relates to processes for making such compounds as well as to intermediates useful in such processes.

30 Claims, No Drawings

OTHER PUBLICATIONS

STN printout for Takahashi et al., Synthesis of 3–Substituted 5,6–Diphenylpyrimidin–4–ones from Diphenylcyclopropenone and N–substituted Amide Oximes, Heterocycles, vol. 22, No. 3, pp. 581–584, 1984.
Agathocleous and Shaw, J. Chem. Soc. Perkin Trans. I, 2555 (1993).
Baracos et al., New Eng. J. Med., 308, 553 (1983).
Bayer and Hartmann, Arch. Pharm. (Wwinheim) 324, 815 (1991).
Benneche et al., Acta Chem Scand. B 42, 384–389 (1988).
Bennett et al., J. Med. Chem. 21, 623 (1978).
Berge et al., J. Pharm. Sci. 66, 1 (1977).
Beutler et. al., J. Immunol. 135, 3969 (1985).
Beyaert et al., EMBO Journal 1996, vol. 15, p 1914–23.
Brahn et al., Lymphokine Cytokine Res. 11, 253 (1992).
Bredereck et. al., Chem. Ber. 97, 3407–3417 (1964).
Brown, D. J., Heterocyclic Compounds: the Pyrimidines, Chapter 3, 1994, John Wiley & Sons.
Chandrasekhar et al., Clinical Immunol. Immunopathol. 55, 382 (1990).
Clouse et al., J. Immunol. 142, 431 (1989).
Cooper, Clin. Exp. Immunol. 89, 244 (1992).
Courtenay, J. S., Nature (1980), vol. 283, p 666.
Davies et al., J.Chem.Soc., Chem.Commun., 1153 (1993).
Dinarello, Eur. Cytokine Netw. 5, 517–531 (1994).
Efimovsky and Rumpf, Bull. Soc. Chim. FR. 648–649 (1954).
El–Rayyes and Al–Hajjar, J. Heterocycl. Chem. 21, 1473 (1984).
Firestein, Am. J. Pathol. 140, 1309 (1992).
Folks et al., J. Immunol. 136, 40 (1986).
Gallagher et al, Biorg. Med. Chem. Lett. 1995, 1171–1176.
Hronowski and Szarek, Can. J. Chem. 63, 2787 (1985).
Joosten et al, Arthritis & Rheumatism 39:797–809 (1996).
Kabbe, Lieb. Ann. Chem. 704, 144 (1967).
Katritzky and Rachwal, J. Heterocyclic Chem. 32, 1007 (1995).
Lahdevirta et al., Am. J. Med. 85, 289 (1988).
Lee et al, Circulatory Shock 44:97–103 (1995).
Lee et al., Nature 372:739 (1994).
Legrand and Lozac'h, Bull. Soc. Chim. Fr., 79–81 (1955).
Liu et al., Neurosci. Lett. 164, 125 (1993).
Liu et al., Stroke 25, 1481 (1994).
Maini et al., Immunological Reviews, pp. 195–223 (1995).
Mathes and Sauermilch, Chem. Ber. 88, 1276–1283 (1955).
Peters et al., J. Heterocyclic Chem. 27, 2165–2173 (1990).
Sakasi et al., Heterocycles 13, 235 (1978).
Sandosham and Undheim, Acta Chem. Scand. 43, 684–689 (1989).
Shaw and Warrener, J. Chem. Soc. 153–156 (1958).
Shohami et al., J. Cereb. Blood Flow Metab. 14. 615 (1994).
Simchen, G., Chem. Ber. 103, 389–397 (1970).
Stanonis, J. Org. Chem. 22, 475 1957).
Swingle, K. F., in R. A. Scherrer and M. W. Whitehouse, Eds., Antiinflammatory Agents, Chemistry and Pharmacology, vol. 13–II, Academic, New York, 1974, p. 33–122, Chapter 2.
Trentham et al J. Exp. Med. (1977) vol. 146, p 857.
Wheeler, Journal of Labelled Compounds and Radiopharmaceuticals, vol. XXXI, No. 4, pp. 305–312 (1992).
Winter et al Proc. Soc. Exp. Biol. Med. (1962) vol. 111, p 544.
Baldwin et al (Synlett. 51–53, 1993).
Basha and Debernardis Tetrahedron Lett, vol. 25, 5271, 1984.
Brunner et al., Eur. J. Med. Chem. 25, 35–44, 1990.
Bundgaard J. Med. Chem., vol. 32, 2503 (1989).
Cohen and S. Y. Weinstein, J. Am. Chem. Soc. 86, 725–728, 1964.
Davies and I.A.S. Walters, J. Chem. Soc. Perkin Trans.I, 1129–1139 (1994).
Dornow and Fust, Chem. Ber. 87, 985, 1954.
Freifelder and R. B. Hasbrouck, J. Am. Chem. Soc. 82, 696–698, 1960.
Hendry et al Tetrahedron Lett, vol. 28, 4597 (1987).
Kojima and J. Fujita, Bull. Chem. Soc. Jpn. 55, 1454–1459, 1982.
Konieczny and Cushman Tetrahedron Lett, vol. 33, 6939, 1992.
Lang, et al., Endocrinol. 130, 43–52, 1992.
Leanna et al., Tetrahedron Lett., vol. 34, No. 28, 4485 (1993).
Mitchell and T.M. Koenig, Synth. Comm. 25 (8), 1231–1238, 1995.
Svensson and Tunek, Drug Metabolism Reviews, vol. 19(2), 165 (1988).
Szalkowski et al., Endocrinol. 136, 1474–1481, 1995.
Ten Hoeve and H. Wynberg, Synth. Commun. 24 (15), 2215–2221, 1994.
Dey et al., Tetrahedron, vol. 51, No. 27, pp. 7459–7468 (1995).
Takahashi et al., Heterocycles, vol. 22, No. 3, pp. 581–584 (1984).
Yoshida et al., Bulletin of the Chemical Society of Japan, vol. 56, No. 8, pp. 2438–2441 (1983).

SUBSTITUTED PYRIMIDINONE AND PYRIDONE COMPOUNDS AND METHODS OF USE

BACKGROUND OF THE INVENTION

This application is a continuation-in-part of U.S. application Ser. No. 08/976,053 filed Nov. 21, 1997, now abandoned, which claims the benefit of U.S. provisional application Ser. No. 60/032,128 filed Dec. 5, 1996, and U.S. provisional application Ser. No. 60/050,950 filed Jun. 13, 1997 each of which are incorporated herein by reference in their entirety. The present invention comprises a new class of compounds useful in treating diseases, such as TNF-α, IL-1β, IL-6 and/or IL-8 mediated diseases and other maladies, such as pain and diabetes. In particular, the compounds of the invention are useful for the prophylaxis and treatment of diseases or conditions involving inflammation. This invention also relates to intermediates and processes useful in the preparation of such compounds.

Interleukin-1 (IL-1) and Tumor Necrosis Factor α (TNF-α) are pro-inflammatory cytokines secreted by a variety of cells, including monocytes and macrophages, in response to many inflammatory stimuli (e.g., lipopolysaccharide—LPS) or external cellular stress (e.g., osmotic shock and peroxide).

Elevated levels of TNF-α and/or IL-1 over basal levels have been implicated in mediating or exacerbating a number of disease states including rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

It has been reported that TNF-α plays a role in head trauma, stroke, and ischemia. For instance, in animal models of head trauma (rat), TNF-α levels increased in the contused hemisphere (Shohami et al., *J. Cereb. Blood Flow Metab.* 14, 615 (1994)). In a rat model of ischemia wherein the middle cerebral artery was occluded, the levels of TNF-α mRNA of TNF-α increased (Feurstein et al., *Neurosci. Lett.* 164, 125 (1993)). Administration of TNF-α into the rat cortex has been reported to result in significant neutrophil accumulation in capillaries and adherence in small blood vessels. TNF-α promotes the infiltration of other cytokines (IL-1β, IL-6) and also chemokines, which promote neutrophil infiltration into the infarct area (Feurstein, *Stroke* 25, 1481 (1994)). TNF-α has also been implicated to play a role in type II diabetes (Endocrinol. 130, 43–52, 1994; and Endocrinol. 136, 1474–1481, 1995).

TNF-α appears to play a role in promoting certain viral life cycles and disease states associated with them. For instance, TNF-α secreted by monocytes induced elevated levels of HIV expression in a chronically infected T cell clone (Clouse et al., *J. Immunol.* 142, 431 (1989)). Lahdevirta et al., (*Am. J. Med.* 85, 289 (1988)) discussed the role of TNF-α in the HIV associated states of cachexia and muscle degradation.

TNF-α is upstream in the cytokine cascade of inflammation. As a result, elevated levels of TNF-α may lead to elevated levels of other inflammatory and proinflammatory cytokines, such as IL-1, IL-6, and IL-8.

Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type I and type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1.

TNF-α and IL-1 appear to play a role in pancreatic β cell destruction and diabetes. Pancreatic β cells produce insulin which helps mediate blood glucose homeostasis. Deterioration of pancreatic β cells often accompanies type I diabetes. Pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production.

In rheumatoid arthritis models in animals, multiple intraarticular injections of IL-1 have led to an acute and destructive form of arthritis (Chandrasekhar et al., *Clinical Immunol Immunopathol.* 55, 382 (1990)). In studies using cultured rheumatoid synovial cells, IL-1 is a more potent inducer of stromelysin than is TNF-α (Firestein, *Am. J. Pathol.* 140, 1309 (1992)). At sites of local injection, neutrophil, lymphocyte, and monocyte emigration has been observed. The emigration is attributed to the induction of chemokines (e.g., IL-8), and the up-regulation of adhesion molecules (Dinarello, *Eur. Cytokine Netw.* 5, 517–531 (1994)).

IL-1 also appears to play a role in promoting certain viral life cycles. For example, cytokine-induced increase of HIV expression in a chronically infected macrophage line has been associated with a concomitant and selective increase in IL-1 production (Folks et al., *J. Immunol.* 136, 40 (1986)). Beutler et al. (*J. Immunol.* 135, 3969 (1985)) discussed the role of IL-1 in cachexia. Baracos et al. (*New Eng. J. Med.* 308, 553 (1983)) discussed the role of IL-1 in muscle degeneration.

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis (CIA) in rats and mice), intra-articular administration of TNF-α either prior to or after the induction of CIA led to an accelerated onset of arthritis and a more severe course of the disease (Brahn et al., *Lymphokine Cytokine Res.* 11, 253 (1992); and Cooper, *Clin. Exp. Immunol.* 898, 244 (1992)).

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminished neutrophil infiltration.

Several approaches have been taken to block the effect of TNF-α. One approach involves using soluble receptors for TNF-α (e.g., TNFR-55 or TNFR-75), which have demonstrated efficacy in animal models of TNF-α-mediated disease states. A second approach to neutralizing TNF-α using a monoclonal antibody specific to TNF-α, cA2, has demonstrated improvement in swollen joint count in a Phase II human trial of rheumatoid arthritis (Feldmann et al., *Immunological Reviews*, pp. 195–223 (1995)). These approaches block the effects of TNF-α and IL-1 by either protein sequestration or receptor antagonism.

U.S. Pat. No. 5,100,897, incorporated herein by reference in its entirety, describes pyrimidinone compounds useful as angiotensin II antagonists wherein one of the pyrimidinone ring nitrogen atoms is substituted with a substituted phenylmethyl or phenethyl radical.

U.S. Pat. No. 5,162,325, incorporated herein by reference in its entirety, describes pyrimidinone compounds useful as angiotensin II antagonists wherein one of the pyrimidinone ring nitrogen atoms is substituted with a substituted phenylmethyl radical.

EP 481448, incorporated herein by reference in its entirety, describes pyrimidinone compounds useful as angiotensin II antagonists wherein one of the pyrimidinone ring nitrogen atoms is substituted with a substituted phenyl, phenylmethyl or phenethyl radical.

CA 2,020,370, incorporated herein by reference in its entirety, describes pyrimidinone compounds useful as angiotensin II antagonists wherein one of the pyrimidinone ring nitrogen atoms is substituted with a substituted biphenylaliphatic hydrocarbon radical.

BRIEF DESCRIPTION OF THE INVENTION

The present invention comprises a new class of compounds useful in the prophylaxis and treatment of diseases, such as TNF-α, IL-1β, IL-6 and/or IL-8 mediated diseases and other maladies, such as pain and diabetes. In particular, the compounds of the invention are useful for the prophylaxis and treatment of diseases or conditions involving inflammation. Accordingly, the invention also comprises pharmaceutical compositions comprising the compounds, methods for the prophylaxis and treatment of TNF-α, IL-1β, IL-6 and/or IL-8 mediated diseases, such as inflammatory, pain and diabetes diseases, using the compounds and compositions of the invention, and intermediates and processes useful for the preparation of the compounds of the invention.

The compounds of the invention are represented by the following general structure:

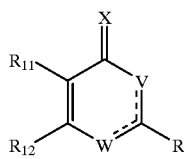

wherein the dashed lines represent a double bond between C(R) and V or W (i.e., —V=C(R)— or —W=C(R)—) and V, W, X, R, $R^{11}$ and $R^{12}$ are defined below.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In accordance with the present invention, there is provided compounds of the formula:

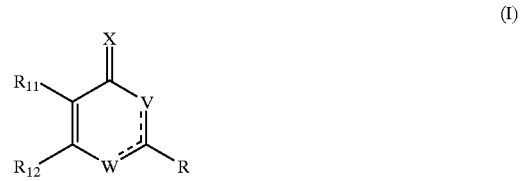

(I)

or a pharmaceutically acceptable salt thereof, wherein

X is O, S or $NR_5$; preferably, X is O or S; and most preferably, X is O;

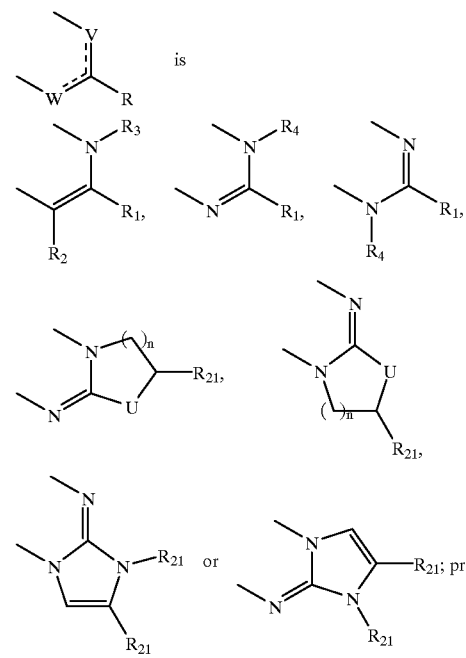

that the combined total number of aryl, heteroaryl, cycloalkyl and heterocyclyl radicals in —VC(R)W— is 0–3, preferably, 0–2, most preferably, 0–1;

a first preferred subgroup of

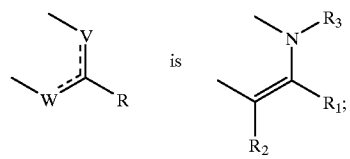

a second preferred subgroup of

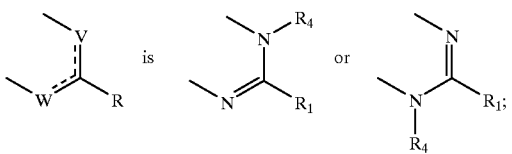

a third preferred subgroup of

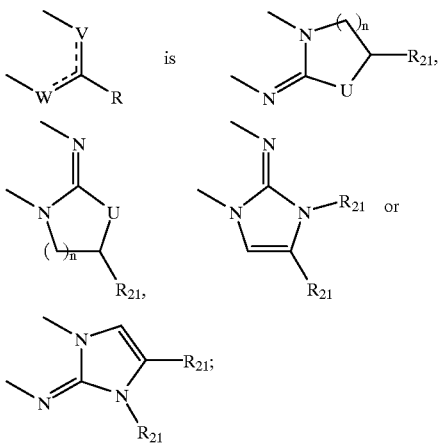

more preferably,

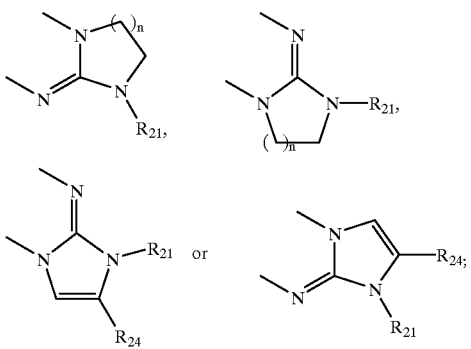

most preferably,

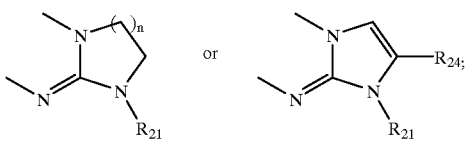

U is $NR_{21}$ or $CHR_{21}$; preferably, U is $NR_{21}$;

n is an integer of 1–3;

$R_1$ and $R_2$ are each independently —Y or —Z—Y, and $R_3$ and $R_4$ are each independently —Z—Y; provided that $R_4$ is other than a substituted-aryl, (substituted-aryl)methyl or (substituted-aryl)ethyl radical, and the total number of aryl, heteroaryl, cycloalkyl and heterocyclyl radicals in each —Y and —Z—Y is 0–3; preferably, 0–2; more preferably, 0–1;

preferably, $R_2$ is a radical of hydrogen, $C_1$–$C_4$ alkyl, halo, cyano, hydroxy, $C_1$–$C_4$ alkoxy, $C_1$–$C_2$ haloalkoxy of 1–3 halo radicals, $C_1$–$C_4$ alkylthio, amino, $C_1$–$C_4$ alkylamino, di-($C_1$–$C_4$ alkyl)amino or $C_1$–$C_2$ haloalkyl of 1–3 halo radicals; more preferably, $R_2$ is a radical of hydrogen, $C_1$–$C_4$ alkyl, halo, cyano, hydroxy, $C_1$–$C_4$ alkoxy, trifluoromethoxy or trifluoromethyl; most preferably, $R_2$ is a hydrogen radical;

preferably, $R_3$ is a hydrogen radical or (1) $C_1$–$C_8$ alkyl or $C_2$–$C_8$ alkenyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio or halo, and (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl, trifluoromethoxy or trifluoromethyl radicals; or (2) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, trifluoromethoxy or trifluoromethyl radicals;

more preferably, $R_3$ is a hydrogen radical or (1) $C_1$–$C_8$ alkyl radical optionally substituted by 1–2 radicals of amino, $C_1$–$C_4$ alkylamino, di-($C_1$–$C_4$ alkyl) amino, hydroxy, $C_1$–$C_4$ alkoxy or aryl or heteroaryl optionally substituted by 1–3 radicals of amino, $C_1$–$C_4$ alkylamino, di-($C_1$–$C_4$ alkyl)amino, $C_1$–$C_4$ alkoxy, $C_1$–$C_4$ alkylthio, halo, $C_1$–$C_4$ alkyl, trifluoromethoxy or trifluoromethyl radicals; or (2) aryl or heteroaryl radical optionally substituted by 1–3 radicals of amino, $C_1$–$C_4$ alkylamino, di-($C_1$–$C_4$ alkyl) amino, $C_1$–$C_4$ alkoxy, $C_1$–$C_4$ alkylthio, cyano, halo, $C_1$–$C_4$ alkyl, trifluoromethoxy or trifluoromethyl radicals;

more preferably, $R_3$ is a hydrogen radical or $C_1$–$C_8$ alkyl radical optionally substituted by 1–2 radicals of amino, $C_1$–$C_4$ alkylamino, di-($C_1$–$C_4$ alkyl)amino, hydroxy, $C_1$–$C_4$ alkoxy or aryl or heteroaryl optionally substituted by 1–3 radicals of amino, $C_1$–$C_4$ alkylamino, di-($C_1$–$C_4$ alkyl)amino, $C_1$–$C_4$ alkoxy, $C_1$–$C_4$ alkylthio, halo, $C_1$–$C_4$ alkyl, trifluoromethoxy or trifluoromethyl radicals;

more preferably, $R_3$ is a radical of hydrogen or $C_1$–$C_4$ alkyl; more preferably, $R_3$ is a hydrogen, methyl or ethyl radical; preferably, $R_4$ is (1) $C_1$–$C_8$ alkyl or $C_2$–$C_8$ alkenyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio or halo, and (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl, trifluoromethoxy or trifluoromethyl radicals; or (2) heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, trifluoromethoxy or trifluoromethyl radicals;

more preferably, $R_4$ is (1) $C_1$–$C_8$ alkyl radical optionally substituted by 1–2 radicals of amino, $C_1$–$C_4$ alkylamino, di-($C_1$–$C_4$ alkyl)amino, hydroxy, $C_1$–$C_4$ alkoxy or aryl or heteroaryl optionally substituted by 1–3 radicals of amino, $C_1$–$C_4$ alkylamino, di-($C_1$–$C_4$ alkyl)amino, $C_1$–$C_4$ alkoxy, $C_1$–$C_4$ alkylthio, halo, $C_1$–$C_4$ alkyl, trifluoromethoxy or trifluoromethyl radicals; or (2) heteroaryl radical optionally substituted by 1–3 radicals of amino, $C_1$–$C_4$ alkylamino, di-($C_1$–$C_4$ alkyl)amino, $C_1$–$C_4$ alkoxy, $C_1$–$C_4$ alkylthio, cyano, halo, $C_1$–$C_4$ alkyl, trifluoromethoxy or trifluoromethyl radicals;

more preferably, $R_4$ is a $C_1$–$C_8$ alkyl radical optionally substituted by 1–2 radicals of amino, $C_1$–$C_4$ alkylamino, di-($C_1$–$C_4$ alkyl)amino, hydroxy, $C_1$–$C_4$ alkoxy or aryl or heteroaryl optionally substituted by 1–3 radicals of amino, $C_1$–$C_4$ alkylamino, di-($C_1$–$C_4$ alkyl)amino, $C_1$–$C_4$ alkoxy, $C_1$–$C_4$ alkylthio, halo, $C_1$–$C_4$ alkyl, trifluoromethoxy or trifluoromethyl radicals;

more preferably, $R_4$ is a $C_1$–$C_4$ alkyl radical; most preferably, $R_4$ is a methyl or ethyl radical;

wherein each Z is independently a (1) alkyl, alkenyl or alkynyl radical optionally substituted by (a) 1–3 radicals of amino, alkylamino, dialkylamino, alkanoylamino, alkoxycarbonylamino, alkylsulfonylamino, hydroxy, alkoxy, alkylthio or halo, and (b) 1–2 radicals of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, halo, alkyl or haloalkyl;

(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, alkyl or haloalkyl; or (3) aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;

preferably, each Z is independently a (1) $C_1$–$C_8$ alkyl, $C_2$–$C_8$ alkenyl or $C_2$–$C_8$ alkynyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio or halo, and (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl or $C_1$–$C_4$ haloalkyl of 1–3 halo radicals;

(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

more preferably, each Z is independently a (1) $C_1$–$C_8$ alkyl, $C_2$–$C_8$ alkenyl or $C_2$–$C_8$ alkynyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio or halo, and (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl or $C_1$–$C_4$ haloalkyl of 1–3 halo radicals;

(2) heterocyclyl radical optionally substituted by 1–2 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

more preferably, each Z is independently a (1) $C_1$–$C_8$ alkyl or $C_2$–$C_8$ alkenyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio or halo, and (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, halo, $C_1$–$C_4$ alkyl or $C_1$–$C_2$ haloalkyl of 1–3 halo radicals;

(2) heterocyclyl radical optionally substituted by 1–2 radicals of amino, di-($C_1$–$C_4$ alkyl)amino, ($C_1$–$C_4$ alkoxy)carbonylamino, hydroxy, $C_1$–$C_4$ alkoxy, $C_1$–$C_4$ alkylthio or $C_1$–$C_4$ alkyl radicals; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

more preferably, each Z is independently a (1) $C_1$–$C_4$ alkyl or $C_2$–$C_5$ alkenyl radical optionally substituted by (a) 1–3 radicals of amino, di-($C_1$–$C_2$ alkyl)amino, $C_1$–$C_5$ alkanoylamino, ($C_1$–$C_4$ alkoxy) carbonylamino, hydroxy, $C_1$–$C_2$ alkoxy, $C_1$–$C_2$ alkylthio or halo, and (b) 1–2 radicals of heterocyclyl, aryl or heteroaryl optionally substituted by 1–3 radicals of amino, $C_1$–$C_4$ alkylamino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, halo, $C_1$–$C_4$ alkyl or trifluoromethyl radicals;

(2) heterocyclyl radical optionally substituted by 1–2 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio or $C_1$–$C_4$ alkyl radicals; or (3) aryl or heteroaryl radical optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl radicals;

more preferably, each Z is independently a (1) $C_1$–$C_4$ alkyl or $C_2$–$C_5$ alkenyl radical optionally substituted by (a) 1–3 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio or halo, and (b) 1–2 radicals of aryl or heteroaryl optionally substituted by 1–2 radicals of amino, di-($C_1$–$C_2$ alkyl)amino, acetamido, ($C_1$–$C_4$ alkoxy)carbonylamino, hydroxy, $C_1$–$C_2$ alkoxy, $C_1$–$C_2$ alkylthio, halo, $C_1$–$C_4$ alkyl or trifluoromethyl radicals; or (2) aryl or heteroaryl radical optionally substituted by 1–3 radicals of amino, di-($C_1$–$C_2$ alkyl)amino, acetamido, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl radicals;

more preferably, each Z is independently a $C_1$–$C_4$ alkyl radical optionally substituted by 1–2 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio, halo or aryl or heteroaryl optionally substituted by 1–2 radicals of hydroxy, $C_1$–$C_2$ alkoxy, $C_1$–$C_2$ alkylthio, halo, $C_1$–$C_4$ alkyl or trifluoromethyl radicals; and most preferably, each Z is independently a $C_1$–$C_4$ alkyl radical optionally substituted by 1–2 radicals of amino, t-butoxycarbonylamino, dimethylamino, hydroxy, methoxy, methylthio or halo radicals;

each Y is independently a (1) hydrogen radical;

(2) halo or nitro radical;

(3) —C(O)—$R_{20}$ or —C($NR_5$)—$NR_5R_{21}$ radical;

(4) —$OR_{21}$, —O—C(O)—$R_{21}$, —O—C(O)—$NR_5R_{21}$ or —O—C(O)—$NR_{22}$—S(O)$_2$—$R_{20}$ radical;

(5) —$SR_{21}$, —S(O)—$R_{20}$, —S(O)$_2$—$R_{20}$, —S(O)$_2$—$NR_5R_{21}$, —S(O)$_2$—$NR_{22}$—C(O)—$R_{21}$, —S(O)$_2$—$NR_{22}$—C(O)—$OR_{20}$ or —S(O)$_2$—$NR_{22}$—C(O)—$NR_5R_{21}$ radical; or (6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;

preferably, each Y is independently a (1) hydrogen radical;

(2) halo radical;

(3) —C(O)—$R_{20}$ or —C($NR_5$)—$NR_5R_{21}$ radical;

(4) —$OR_{21}$, —O—C(O)—$R_{21}$ or —O—C(O)—$NR_5R_{21}$ radical;

(5) —$SR_{21}$, —S(O)—$R_{20}$, —S(O)$_2$—$R_{20}$ or —S(O)$_2$—$NR_5R_{21}$ radical; or (6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;

more preferably, each Y is independently a (1) hydrogen radical;

(2) —C(O)—$R_{20}$ radical;

(3) —$OR_{21}$, —$SR_{21}$, —S(O)—$R_{20}$, —S(O)$_2$—$R_{20}$ or —S(O)$_2$—$NR_5R_{21}$ radical; or (4) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—S(O)$_2$—$R_{20}$ or —$NR_{22}$—S(O)$_2$—$NR_5R_{21}$ radical;

more preferably, each Y is independently a (1) hydrogen radical;

(2) —C(O)—$R_{20}$ radical;

(3) —$OR_{21}$, —$SR_{21}$, —S(O)—$R_{20}$, —S(O)$_2$—$R_{20}$ or —S(O)$_2$—$NR_{5}R_{21}$ radical; or (4) —$NR_5R_{21}$, —$NR_{22}$—C(O)—$R_{21}$ or —$NR_{22}$—S(O)$_2$—$R_{20}$ radical;

more preferably, each Y is independently a (1) —C(O)—$R_{20}$ radical;

(2) —$OR_{21}$, —$SR_{21}$, —S(O)—$R_{20}$, —S(O)$_2$—$R_{20}$ or —S(O)$_2$—$NR_5R$ radical; or (3) —$NR_5R_{21}$, —$NR_{22}$—C(O)—$R_{21}$ or —$NR_{22}$—S(O)$_2$—$R_{20}$ radical.

most preferably, each Y is independently a —$OR_{21}$, —$SR_{21}$ or —$NR_5R_{21}$ radical;

wherein each $R_5$ is independently (1) hydrogen radicals;

(2) alkyl, alkenyl or alkynyl radicals optionally substituted by 1–3 radicals of amino, alkylamino, dialkylamino, hydroxy, alkoxy, alkylthio, —$SO_3H$ or halo; or (3) aryl, heteroaryl, aralkyl, heteroaralkyl, heterocyclyl, heterocyclylalkyl, cycloalkyl or cycloalkylalkyl radicals optionally substituted by 1–3 radicals of amino, alkylamino, dialkylamino, hydroxy, alkoxy, alkylthio, alkyl or haloalkyl;

preferably, each $R_5$ is independently (1) hydrogen radicals;

(2) $C_1$–$C_8$ alkyl, $C_2$–$C_8$ alkenyl or $C_2$–$C_8$ alkynyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, —$SO_3H$ or halo; or (3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals;

more preferably, each $R_5$ is independently (1) hydrogen radicals;

(2) $C_1$–$C_4$ alkyl, $C_2$–$C_5$ alkenyl or $C_2$–$C_5$ alkynyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, —$SO_3H$ or halo; or (3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals;

more preferably, each $R_5$ is independently (1) hydrogen radicals;

(2) $C_1$–$C_4$ alkyl or $C_2$–$C_5$ alkenyl radicals optionally substituted by 1–3 radicals of amino, di-($C_1$–$C_4$-alkyl)amino, hydroxy, $C_1$–$C_4$ alkoxy, $C_1$–$C_4$ alkylthio, —$SO_3H$ or halo; or (3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radicals optionally substituted by 1–3 radicals of amino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_2$ haloalkyl of 1–3 halo radicals;

more preferably, each $R_5$ is independently (1) hydrogen radical;

(2) $C_1$–$C_4$ alkyl radical optionally substituted by 1–3 radicals of amino, di-($C_1$–$C_2$-alkyl)amino, hydroxy, $C_1$–$C_2$ alkoxy, $C_1$–$C_2$ alkylthio or halo; or (3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radicals optionally substituted by 1–3 radicals of amino, di-($C_1$–$C_2$-alkyl)amino, hydroxy, $C_1$–$C_2$ alkoxy, $C_1$–$C_2$ alkylthio, methoxy, methylthio, $C_1$–$C_4$ alkyl or trifluoromethyl radicals;

more preferably, each $R_5$ is independently (1) hydrogen radical;

(2) $C_1$–$C_4$ alkyl radical optionally substituted by 1–3 halo radicals; or (3) phenyl-$C_1$–$C_2$-alkyl or heteroaryl-$C_1$–$C_2$-alkyl, radicals optionally substituted by 1–3 radicals of amino, dimethylamino, hydroxy, methoxy, methylthio, methyl or trifluoromethyl radicals;

more preferably, each $R_5$ is independently hydrogen or $C_1$–$C_4$ alkyl radical; and most preferably, each $R_5$ is a hydrogen radical;

wherein each $R_{20}$ is independently (1) alkyl, alkenyl or alkynyl radicals optionally substituted by 1–3 radicals of amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfinyl, alkylsulfonyl, halo or aralkoxy, aralkylthio, aralkylsulfonyl, cycloalkyl, heterocyclyl, aryl or heteroaryl radicals optionally substituted by 1–3 radicals of amino, alkylamino, dialkylamino, alkanoylamino, alkoxycarbonylamino, alkylsulfonylamino, alkanoyl, hydroxy, alkoxy, alkylthio, alkylsulfinyl, alkylsulfonyl, halo, alkyl or haloalkyl;

(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, alkyl or haloalkyl; or (3) aryl or heteroaryl radicals optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl or haloalkyl;

preferably, each $R_{20}$ is independently (1) $C_1$–$C_8$ alkyl, $C_2$–$C_8$ alkenyl or $C_2$–$C_8$ alkynyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, $C_1$–$C_4$ alkyl or $C_1$–$C_4$ haloalkyl of 1–3 halo radicals;

(2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

more preferably, each $R_{20}$ is independently (1) $C_1$–$C_8$ alkyl, $C_2$–$C_5$ alkenyl or $C_2$–$C_5$ alkynyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, $C_1$–$C_4$ alkyl or $C_1$–$C_4$ haloalkyl of 1–3 halo radicals;

(2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

more preferably, each $R_{20}$ is independently (1) $C_1$–$C_8$ alkyl or $C_2$–$C_5$ alkenyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)—N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, halo, $C_1$–$C_4$ alkyl or $C_1$–$C_2$ haloalkyl of 1–3 halo radicals;

(2) heterocyclyl radical optionally substituted by 1–2 radicals of amino, $C_1$–$C_4$ alkylamino, di-($C_1$–$C_4$ alkyl) amino, $C_1$–$C_5$ alkanoylamino, ($C_1$–$C_4$ alkoxy)

carbonylamino, hydroxy, $C_1-C_4$ alkoxy, $C_1-C_4$ alkylthio or $C_1-C_4$ alkyl; or (3) aryl or heteroaryl radicals optionally substituted by 1–3 radicals of amino, $C_1-C_4$ alkylamino, di-($C_1-C_4$ alkyl)amino, $C_1-C_5$ alkanoylamino, ($C_1-C_4$ alkoxy) carbonylamino, $C_1-C_4$ alkylsulfonylamino, ($C_1-C_4$ alkoxy)carbonyl, hydroxy, $C_1-C_4$ alkoxy, $C_1-C_4$ alkylthio, cyano, halo, azido, $C_1-C_4$ alkyl or $C_1-C_2$ haloalkyl of 1–3 halo radicals;

more preferably, each $R_{20}$ is independently (1) $C_1-C_8$ alkyl or $C_2-C_5$ alkenyl radicals optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, N-(($C_1-C_4$ alkoxy)carbonyl)—N-($C_1-C_4$ alkyl)amino, aminocarbonylamino, hydroxy, $C_1-C_4$ alkoxy, $C_1-C_4$ alkylthio, $C_1-C_4$ alkylsulfinyl, $C_1-C_4$ alkylsulfonyl, halo or aryl-$C_1-C_4$-alkoxy, aryl-$C_1-C_4$-alkylthio, aryl-$C_1-C_4$-alkylsulfonyl, $C_3-C_6$ cycloalkyl, heterocyclyl, aryl or heteroaryl radicals optionally substituted by 1–3 radicals of amino, $C_1-C_4$ alkylamino, di-($C_1-C_4$ alkyl)amino, $C_1-C_5$ alkanoylamino, ($C_1-C_4$ alkoxy) carbonylamino, $C_1-C_4$ alkylsulfonylamino, $C_1-C_5$ alkanoyl, hydroxy, $C_1-C_4$ alkoxy, $C_1-C_4$ alkylthio, halo, $C_1-C_4$ alkyl or $C_1-C_2$ haloalkyl of 1–3 halo radicals;

(2) heterocyclyl radical optionally substituted by 1–2 radicals of amino, di-($C_1-C_4$ alkyl)amino, ($C_1-C_4$ alkoxy)carbonylamino, hydroxy, $C_1-C_4$ alkoxy, $C_1-C_4$ alkylthio or $C_1-C_4$ alkyl; or (3) aryl or heteroaryl radicals optionally substituted by 1–2 radicals of amino, $C_1-C_4$ alkylamino, di-($C_1-C_4$ alkyl)amino, acetamido, ($C_1-C_4$ alkoxy)carbonylamino, $C_1-C_4$ alkylsulfonylamino, ($C_1-C_4$ alkoxy)carbonyl, hydroxy, $C_1-C_4$ alkoxy, $C_1-C_4$ alkylthio, cyano, halo, azido, $C_1-C_4$ alkyl or trifluoromethyl radicals;

more preferably, each $R_{20}$ is independently (1) $C_1-C_8$ alkyl radicals optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, N-(($C_1-C_4$ alkoxy)carbonyl)—N-($C_1-C_4$ alkyl)amino, aminocarbonylamino, hydroxy, $C_1-C_4$ alkoxy, $C_1-C_4$ alkylthio, $C_1-C_4$ alkylsulfinyl, $C_1-C_4$ alkylsulfonyl, halo or $C_3-C_6$ cycloalkyl, heterocyclyl, aryl or heteroaryl radicals optionally substituted by 1–2 radicals of amino, di-($C_1-C_4$ alkyl)amino, $C_1-C_5$ alkanoylamino, ($C_1-C_4$ alkoxy)carbonylamino, $C_1-C_4$ alkylsulfonylamino, hydroxy, $C_1-C_4$ alkoxy, $C_1-C_4$ alkylthio, halo, $C_1-C_4$ alkyl or trifluoromethyl radicals;

(2) heterocyclyl radical optionally substituted by 1–2 radicals of hydroxy, $C_1-C_4$ alkoxy, $C_1-C_4$ alkylthio or $C_1-C_4$ alkyl; or (3) aryl or heteroaryl radicals optionally substituted by 1–2 radicals of ($C_1-C_4$ alkoxy)carbonyl, amino, $C_1-C_4$ alkylamino, di-($C_1-C_4$ alkyl)amino, hydroxy, $C_1-C_4$ alkoxy, $C_1-C_4$ alkylthio, cyano, halo, azido, $C_1-C_4$ alkyl or trifluoromethyl radicals;

more preferably, each $R_{20}$ is independently (1) $C_1-C_6$ alkyl radicals optionally substituted by 1–3 radicals of amino, methylamino, dimethylamino, t-butoxycarbonylamino, N-((t-butoxy)carbonyl)—N-(methyl)amino, aminocarbonylamino, hydroxy, butoxy, methoxy, butylthio, methylthio, methylsulfinyl, methylsulfonyl, halo or $C_5-C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals;

(2) heterocyclyl radical optionally substituted by 1–2 radicals of hydroxy or $C_1-C_4$ alkyl; or (3) aryl or heteroaryl radicals optionally substituted by 1–2 radicals of amino, dimethylamino, hydroxy, methoxy, methylthio, halo, methyl or trifluoromethyl radicals;

more preferably, each $R_{20}$ is independently (1) $C_1-C_6$ alkyl radicals optionally substituted by 1–3 radicals of amino, methylamino, dimethylamino, t-butoxycarbonylamino, N-((t-butoxy)carbonyl)—N-(methyl)amino, aminocarbonylamino, hydroxy, butoxy, methoxy, butylthio, methylthio, methylsulfinyl, methylsulfonyl, halo or $C_5-C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals;

(2) heterocyclyl radical; or (3) aryl or heteroaryl radicals optionally substituted by 1–2 radicals of amino, dimethylamino, hydroxy, methoxy, methylthio, halo, methyl or trifluoromethyl radicals;

most preferably, each $R_{20}$ is independently (1) $C_1-C_6$ alkyl radicals optionally substituted by 1–3 radicals of amino, methylamino, dimethylamino, hydroxy or phenyl or heteroaryl radicals optionally substituted by 1–2 radicals of amino, dimethylamino, hydroxy, methoxy, methylthio, halo, methyl or trifluoromethyl radicals;

(2) heterocyclyl radical; or (3) aryl or heteroaryl radicals optionally substituted by 1–2 radicals of amino, dimethylamino, hydroxy, methoxy, methylthio, halo, methyl or trifluoromethyl radicals;

each $R_{21}$ is independently hydrogen radical or $R_{20}$;

each $R_{22}$ is independently (1) hydrogen radical;

(2) alkyl radical optionally substituted by a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; or (3) heterocyclyl, aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; provided when Z is a bond and Y is —$NR_{22}$—C(O)—$NH_2$, then $R_{22}$ is other then an optionally substituted aryl radical;

preferably, each $R_{22}$ is independently (1) hydrogen radical;

(2) $C_1-C_4$ alkyl radical optionally substituted by a radical of heterocyclyl, aryl or heteroaryl optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; or (3) heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; provided when Z is a bond and Y is —$NR_{22}$—C(O)—$NH_2$, then $R_{22}$ is other then an optionally substituted aryl radical;

more preferably, each $R_{22}$ is independently (1) hydrogen radical; or (2) $C_1$–$C_4$ alkyl radical optionally substituted by a radical of phenyl or heteroaryl optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

more preferably, each $R_{22}$ is independently hydrogen or $C_1$–$C_4$ alkyl radical; and most preferably, each $R_{22}$ is independently hydrogen or methyl radical;

$R_{11}$ and $R_{12}$ are each independently an aryl or heteroaryl radical optionally substituted by 1–3 radicals of (1) $R_{30}$;

(2) halo or cyano radicals;

(3) —C(O)—$R_{30}$, —C(O)—$OR_{29}$, —C(O)—$NR_{31}R_{32}$ or —C($NR_{31}$)—$NR_{31}R_{32}$ radicals;

(4) —$OR_{29}$, —O—C(O)—$R_{29}$, —O—C(O)—$NR_{31}R_{32}$ or —O—C(O)—$NR_{33}$—S(O)$_2$—$R_{30}$ radicals;

(5) —$SR_{29}$, —S(O)—$R_{30}$, —S(O)$_2$—$R_{30}$, —S(O)$_2$—$NR_{31}R_{32}$, —S(O)$_2$—$NR_{33}$—C(O)—$R_{30}$, —S(O)$_2$—$NR_{33}$—C(O)—$OR_{30}$ or —S(O)$_2$—$NR_{33}$—C(O)—$NR_{31}R_{32}$ radicals; or (6) —$NR_{31}R_{32}$, —$NR_{33}$—C(O)—$R_{29}$, —$NR_{33}$—C(O)—$OR_{30}$, —$NR_{33}$—C(O)—$NR_{31}R_{32}$, —$NR_{33}$—C($NR_{31}$)—$NR_{31}R_{32}$, —$NR_{33}$—S(O)$_2$—$R_{30}$ or —$NR_{33}$—S(O)$_2$—$NR_{31}R_{32}$ radicals;

provided that (1) $R_{11}$ is other than a 4-pyridyl, 4-pyrimidinyl, 4-quinolyl or 6-isoquinolinyl radical optionally substituted by 1–2 substituents; and (2) the total number of aryl, heteroaryl, cycloalkyl and heterocyclyl radicals substituted on each of $R_{11}$ and $R_{12}$ is 0–1;

preferably, $R_{11}$ and $R_{12}$ are each independently an aryl or heteroaryl radical optionally substituted by 1–2 radicals of (1) $R_{30}$;

(2) halo or cyano radicals;

(3) —C(O)—$R_{30}$, —C(O)—$OR_{29}$, —C(O)—$NR_{31}R_{32}$ or —C($NR_{31}$)—$NR_{31}R_{32}$ radicals;

(4) —$OR_{29}$, —O—C(O)—$R_{29}$, —O—C(O)—$NR_{31}R_{32}$ or —O—C(O)—$NR_{33}$—S(O)$_2$—$R_{30}$ radicals;

(5) —$SR_{29}$, —S(O)—$R_{30}$, —S(O)$_2$—$R_{30}$, —S(O)$_2$—$NR_{31}R_{32}$, —S(O)$_2$—$NR_{33}$—C(O)—$R_{30}$, —S(O)$_2$—$NR_{33}$—C(O)—$OR_{30}$ or —S(O)$_2$—$NR_{33}$—C(O)—$NR_{31}R_{32}$ radicals; or (6) —$NR_{31}R_{32}$, —$NR_{33}$—C(O)—$R_{29}$, —$NR_{33}$—C(O)—$OR_{30}$, —$NR_{33}$—C(O)—$NR_{31}R_{32}$, —$NR_{33}$—C($NR_{31}$)—$NR_{31}R_{32}$, —$NR_{33}$—S(O)$_2$—$R_{30}$ or —$NR_{33}$—S(O)$_2$—$NR_{31}R_{32}$ radicals;

provided that (1) $R_{11}$ is other than a 4-pyridyl, 4-pyrimidinyl, 4-quinolyl or 6-isoquinolinyl radical optionally substituted by 1–2 substituents; and (2) the total number of aryl, heteroaryl, cycloalkyl and heterocyclyl radicals substituted on each of $R_{11}$ and $R_{12}$ is 0–1;

more preferably, $R_{11}$ and $R_{12}$ are each independently an aryl or heteroaryl radical optionally substituted by 1–2 radicals of (1) $R_{30}$;

(2) halo or cyano radicals;

(3) —C(O)—$R_{30}$, —C(O)—$OR_{29}$, —C(O)—$NR_{31}R_{32}$ or —C($NR_{31}$)—$NR_{31}R_{32}$ radicals; or (4) —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$, —$NR_{33}$—C(O)—$R_{29}$ or —$NR_{33}$—C(O)—$OR_{30}$ radicals;

more preferably, $R_{11}$ is an aryl radical and $R_{12}$ is a heteroaryl radical, wherein the aryl and heteroaryl radicals are optionally substituted by 1–2 radicals of (1) $R_{30}$;

(2) halo or cyano radicals;

(3) —C(O)—$R_{30}$, —C(O)—$OR_{29}$, —C(O)—$NR_{31}R_{32}$ or —C($NR_{31}$)—$NR_{31}R_{32}$ radicals; or (4) —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals;

more preferably, $R_{11}$ is an aryl radical and $R_{12}$ is a heteroaryl radical, wherein the aryl and heteroaryl radicals are optionally substituted by 1–2 radicals of (1) $R_{30}$;

(2) halo or cyano radicals; or (3) —C(O)—$NR_{31}R_{32}$, —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals;

more preferably, $R_{11}$ is an aryl radical optionally substituted by 1–2 radicals of (1) $R_{30}$; (2) halo or cyano radicals; or (3) —C(O)—$NR_{31}R_{32}$, —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals; more preferably, $R_{11}$ is an aryl radical optionally substituted by 1–2 radicals of amino, dimethylamino, acetamido, hydroxy, halo, cyano, methoxy, methylthio, methylsulfinyl, methylsulfonyl, aminocarbonyl, methyl or trifluoromethyl radicals; more preferably, $R_{11}$ is an unsubstituted phenyl or naphthyl radical or a phenyl radical substituted by 1–2 radicals of amino, dimethylamino, acetamido, hydroxy, halo, cyano, methoxy, methylthio, methylsulfinyl, methylsulfonyl, aminocarbonyl, methyl or trifluoromethyl radicals; and most preferably, $R_{11}$ is an unsubstituted phenyl radical or a phenyl radical substituted by 1–2 radicals of amino, dimethylamino, acetamido, hydroxy, halo, cyano, methoxy, methylthio, methylsulfonyl, methyl or trifluoromethyl radicals;

more preferably, $R_{12}$ is a heteroaryl radical optionally substituted by 1–2 radicals of (1) $R_{30}$; (2) halo or cyano radicals; or (3) —C(O)—$NR_{31}R_{32}$, —$OR_{29}$, —$SR_{29}$, —$NR_{31}R_{32}$ or —$NR_{33}$—C(O)—$R_{29}$ radicals; more preferably, $R_{12}$ is a heteroaryl radical optionally substituted by 1–2 radicals of amino, dimethylamino, acetamido, hydroxy, halo, cyano, methoxy, methyl or trifluoromethyl radicals; more preferably, $R_{12}$ is a 4-pyridyl, 4-quinolinyl, 4-imidazolyl or 4-pyrimidinyl radical optionally substituted by a radical of amino, dimethylamino, acetamido, hydroxy, halo, cyano, methoxy, methyl or trifluoromethyl radicals; and most preferably, $R_{12}$ is a 4-pyridyl radical optionally substituted by a radical of amino, dimethylamino, acetamido, hydroxy, halo, cyano, methoxy, methyl or trifluoromethyl radicals;

wherein each $R_{30}$ is independently (1) alkyl, alkenyl or alkynyl radicals optionally substituted by 1–3 radicals of —$NR_{31}R_{31}$, —$CO_2R_{23}$, hydroxy, alkoxy, alkylthio, alkylsulfinyl, alkylsulfonyl, cyano, halo or aralkoxy, aralkylthio, aralkylsulfonyl, heterocyclyl, aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl;

(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;

preferably, each $R_{30}$ is independently (1) $C_1$–$C_4$ alkyl, $C_2$–$C_4$ alkenyl or $C_2$–$C_4$ alkynyl radicals optionally substituted by 1–3 radicals of —$NR_{31}R_{31}$, —$CO_2R_{23}$, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo or aryl-$C_1$–$C_4$-alkoxy, aryl-$C_1$–$C_4$-alkylthio, aryl-$C_1$–$C_4$-alkylsulfonyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

more preferably, each $R_{30}$ is independently (1) $C_1$–$C_4$ alkyl radical optionally substituted by 1–3 radicals of (a) —$NR_{31}R_{31}$;

(b) $C_1$–$C_4$ alkoxy-carbonyl or phenoxycarbonyl or phenylmethoxycarbonyl optionally substituted by 1–3 radicals of amino, alkylamino, di-($C_1$–$C_4$-alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or trifluoromethyl; or (c) hydroxy, $C_1$–$C_4$ alkoxy, $C_1$–$C_4$ alkylthio, or phenyl-$C_1$–$C_4$-alkoxy, phenyl-$C_1$–$C_4$-alkylthio, heterocyclyl, phenyl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

(2) $C_1$–$C_4$ haloalkyl of 1–3 halo radical; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl radicals;

more preferably, each $R_{30}$ is independently (1) $C_1$–$C_4$ alkyl radical optionally substituted by (a) amino, $C_1$–$C_4$ alkylamino or di-($C_1$–$C_4$-alkyl) amino radicals; or (b) hydroxy, $C_1$–$C_4$ alkoxy, heterocyclyl, phenyl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl radicals;

(2) $C_1$–$C_2$ haloalkyl of 1–3 halo radical; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl radicals;

more preferably, each $R_{30}$ is independently (1) $C_1$–$C_4$ alkyl radical optionally substituted by a phenyl or heteroaryl radical optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals;

(2) trifluoromethyl radical; or (3) aryl or heteroaryl radicals optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals;

more preferably, each $R_{30}$ is independently (1) $C_1$–$C_4$ alkyl radical optionally substituted by a phenyl or heteroaryl radical optionally substituted by 1–3 radicals of amino, dimethylamino, acetamido, hydroxy, halo, methoxy, methyl or trifluoromethyl radicals;

(2) trifluoromethyl radical; or (3) aryl or heteroaryl radicals optionally substituted by 1–3 radicals of amino, dimethylamino, acetamido, hydroxy, halo, methoxy, methyl or trifluoromethyl radicals;

most preferably, $R_{30}$ is independently (1) $C_1$–$C_4$ alkyl radical optionally substituted by a phenyl or heteroaryl radical optionally substituted by 1–2 radicals of amino, dimethylamino, acetamido, hydroxy, halo, methoxy, methyl or trifluoromethyl radicals;

(2) trifluoromethyl radical; or (3) aryl or heteroaryl radicals optionally substituted by 1–3 radicals of amino, dimethylamino, acetamido, hydroxy, halo, methoxy, methyl or trifluoromethyl radicals;

each $R_{29}$ is independently hydrogen radical or $R_{30}$; and most preferably, $R_{29}$ is an aryl or heteroaryl radicals optionally substituted by 1–2 radicals of amino, dimethylamino, acetamido, hydroxy, halo, methoxy, methyl or trifluoromethyl radicals;

each $R_{31}$ is independently (1) hydrogen radicals;

(2) alkyl radical optionally substituted by an cycloalkyl, aryl, heterocyclyl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{31}$ is independently (1) hydrogen radicals;

(2) $C_1$–$C_4$ alkyl radical optionally substituted by an $C_3$–$C_8$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{31}$ is independently (1) hydrogen radicals; or (2) $C_1$–$C_4$ alkyl radical optionally substituted by an phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, $C_1$–$C_4$ alkyl or trifluoromethyl radicals;

more preferably, each $R_{31}$ is independently hydrogen or $C_1$–$C_4$ alkyl radicals; and most preferably, each $R_{31}$ is independently hydrogen, methyl or ethyl radicals;

each $R_{32}$ is independently (1) hydrogen radicals;

(2) alkyl radical optionally substituted by an cycloalkyl, aryl, heterocyclyl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{32}$ is independently (1) hydrogen radicals;

(2) $C_1$–$C_4$ alkyl radical optionally substituted by an $C_3$–$C_8$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{32}$ is independently (1) hydrogen radicals;

(2) $C_1$–$C_4$ alkyl radical optionally substituted by an $C_3$–$C_6$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_6$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{32}$ is independently (1) hydrogen radicals;

(2) $C_1$–$C_4$ alkyl radical optionally substituted by phenyl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, hydroxy, $C_1$–$C_4$ alkoxy, $C_1$–$C_4$ alkyl or trifluoromethyl radicals; or (3) phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkyl or trifluoromethyl radicals;

more preferably, each $R_32$ is independently (1) hydrogen radicals;

(2) $C_1$–$C_4$ alkyl radical or $C_1$–$C_2$ alkyl radical substituted by phenyl or heteroaryl radical optionally substituted by 1–3 radicals of amino, dimethylamino, acetamido, hydroxy, methoxy, methyl or trifluoromethyl radicals; or (3) phenyl or heteroaryl radical optionally substituted by 1–3 radicals of amino, dimethylamino, acetamido, hydroxy, methoxy, methyl or trifluoromethyl radicals;

most preferably, $R_{32}$ is independently (1) hydrogen or $C_1$–$C_4$ alkyl radical; or (2) phenyl or heteroaryl radical optionally substituted by 1–2 radicals of amino, dimethylamino, acetamido, hydroxy, methoxy, methyl or trifluoromethyl radicals; and wherein each $R_{33}$ is independently (1) hydrogen radical; or (2) alkyl radical optionally substituted by a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{33}$ is independently
(1) hydrogen radical; or
(2) $C_1$–$C_4$ alkyl radical optionally substituted by a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{33}$ is independently hydrogen or $C_1$–$C_4$ alkyl radical; and most preferably, each $R_{33}$ is independently hydrogen or methyl radical.

The compounds of this invention may have in general several asymmetric centers and are typically depicted in the form of racemic mixtures. This invention is intended to encompass racemic mixtures, partially racemic mixtures and separate enantiomers and diasteromers.

Compounds of interest include the following:

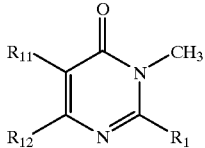

wherein $R^{11}$, $R^{12}$, and $R^1$ are one of the combinations given in the following table:

| $R^{11}$ | $R^{12}$ | $R^1$ |
|---|---|---|
| Phenyl | 4-pyridyl | 1-piperazinyl |
| 4-fluorophenyl | 4-pyridyl | 1-piperazinyl |
| 3-fluorophenyl | 4-pyridyl | 1-piperazinyl |
| 2-fluorophenyl | 4-pyridyl | 1-piperazinyl |
| 4-chlorophenyl | 4-pyridyl | 1-piperazinyl |
| 3-chlorophenyl | 4-pyridyl | 1-piperazinyl |
| 2-chlorophenyl | 4-pyridyl | 1-piperazinyl |
| 4-tolyl | 4-pyridyl | 1-piperazinyl |
| 3-tolyl | 4-pyridyl | 1-piperazinyl |
| 2-tolyl | 4-pyridyl | 1-piperazinyl |
| 4-trifluoromethylphenyl | 4-pyridyl | 1-piperazinyl |
| 3-trifluoromethylphenyl | 4-pyridyl | 1-piperazinyl |
| 2,6-dichlorophenyl | 4-pyridyl | 1-piperazinyl |
| 2,6-dimethylphenyl | 4-pyridyl | 1-piperazinyl |
| 3,4-dichlorophenyl | 4-pyridyl | 1-piperazinyl |
| 3,4-dimethylphenyl | 4-pyridyl | 1-piperazinyl |
| 2,4-dichlorophenyl | 4-pyridyl | 1-piperazinyl |
| 2,4-dimethylphenyl | 4-pyridyl | 1-piperazinyl |
| Phenyl | 2-amino-4-pyridyl | 1-piperazinyl |
| 4-fluorophenyl | 2-amino-4-pyridyl | 1-piperazinyl |
| 3-fluorophenyl | 2-amino-4-pyridyl | 1-piperazinyl |
| 2-fluorophenyl | 2-amino-4-pyridyl | 1-piperazinyl |
| 4-chlorophenyl | 2-amino-4-pyridyl | 1-piperazinyl |
| 3-chlorophenyl | 2-amino-4-pyridyl | 1-piperazinyl |
| 2-chlorophenyl | 2-amino-4-pyridyl | 1-piperazinyl |
| 4-tolyl | 2-amino-4-pyridyl | 1-piperazinyl |
| 3-tolyl | 2-amino-4-pyridyl | 1-piperazinyl |
| 2-tolyl | 2-amino-4-pyridyl | 1-piperazinyl |
| 4-trifluoromethylphenyl | 2-amino-4-pyridyl | 1-piperazinyl |
| 3-trifluoromethylphenyl | 2-amino-4-pyridyl | 1-piperazinyl |
| 2,6-dichlorophenyl | 2-amino-4-pyridyl | 1-piperazinyl |
| 2,6-dimethylphenyl | 2-amino-4-pyridyl | 1-piperazinyl |
| 3,4-dichlorophenyl | 2-amino-4-pyridyl | 1-piperazinyl |
| 3,4-dimethylphenyl | 2-amino-4-pyridyl | 1-piperazinyl |
| 2,4-dichlorophenyl | 2-amino-4-pyridyl | 1-piperazinyl |
| 2,4-dimethylphenyl | 2-amino-4-pyridyl | 1-piperazinyl |
| Phenyl | 2-acetamido-4-pyridyl | 1-piperazinyl |
| 4-fluorophenyl | 2-acetamido-4-pyridyl | 1-piperazinyl |
| 3-fluorophenyl | 2-acetamido-4-pyridyl | 1-piperazinyl |
| 2-fluorophenyl | 2-acetamido-4-pyridyl | 1-piperazinyl |
| 4-chlorophenyl | 2-acetamido-4-pyridyl | 1-piperazinyl |
| 3-chlorophenyl | 2-acetamido-4-pyridyl | 1-piperazinyl |
| 2-chlorophenyl | 2-acetamido-4-pyridyl | 1-piperazinyl |
| 4-tolyl | 2-acetamido-4-pyridyl | 1-piperazinyl |
| 3-tolyl | 2-acetamido-4-pyridyl | 1-piperazinyl |
| 2-tolyl | 2-acetamido-4-pyridyl | 1-piperazinyl |
| 4-trifluoromethylphenyl | 2-acetamido-4-pyridyl | 1-piperazinyl |
| 3-trifluoromethylphenyl | 2-acetamido-4-pyridyl | 1-piperazinyl |
| 2,6-dichlorophenyl | 2-acetamido-4-pyridyl | 1-piperazinyl |
| 2,6-dimethylphenyl | 2-acetamido-4-pyridyl | 1-piperazinyl |
| 3,4-dichlorophenyl | 2-acetamido-4-pyridyl | 1-piperazinyl |
| 3,4-dimethylphenyl | 2-acetamido-4-pyridyl | 1-piperazinyl |
| 2,4-dichlorophenyl | 2-acetamido-4-pyridyl | 1-piperazinyl |
| 2,4-dimethylphenyl | 2-acetamido-4-pyridyl | 1-piperazinyl |
| Phenyl | 2-amino-4-pyrimidinyl | 1-piperazinyl |
| 4-fluorophenyl | 2-amino-4-pyrimidinyl | 1-piperazinyl |
| 3-fluorophenyl | 2-amino-4-pyrimidinyl | 1-piperazinyl |
| 2-fluorophenyl | 2-amino-4-pyrimidinyl | 1-piperazinyl |
| 4-chlorophenyl | 2-amino-4-pyrimidinyl | 1-piperazinyl |
| 3-chlorophenyl | 2-amino-4-pyrimidinyl | 1-piperazinyl |
| 2-chlorophenyl | 2-amino-4-pyrimidinyl | 1-piperazinyl |
| 4-tolyl | 2-amino-4-pyrimidinyl | 1-piperazinyl |
| 3-tolyl | 2-amino-4-pyrimidinyl | 1-piperazinyl |
| 2-tolyl | 2-amino-4-pyrimidinyl | 1-piperazinyl |

-continued

| R¹¹ | R¹² | R¹ |
|---|---|---|
| 4-trifluoro-methylphenyl | 2-amino-4-pyrimidinyl | 1-piperazinyl |
| 3-trifluoro-methylphenyl | 2-amino-4-pyrimidinyl | 1-piperazinyl |
| 2,6-dichlorophenyl | 2-amino-4-pyrimidinyl | 1-piperazinyl |
| 2,6-dimethyl phenyl | 2-amino-4-pyrimidinyl | 1-piperazinyl |
| 3,4-dichlorophenyl | 2-amino-4-pyrimidinyl | 1-piperazinyl |
| 3,4-dimethyl phenyl | 2-amino-4-pyrimidinyl | 1-piperazinyl |
| 2,4-dichlorophenyl | 2-amino-4-pyrimidinyl | 1-piperazinyl |
| 2,4-dimethyl phenyl | 2-amino-4-pyrimidinyl | 1-piperazinyl |
| Phenyl | 4-pyridyl | 2-(2-chlorophenyl)ethylamino |
| 4-fluorophenyl | 4-pyridyl | 2-(2-chlorophenyl)ethylamino |
| 3-fluorophenyl | 4-pyridyl | 2-(2-chlorophenyl)ethylamino |
| 2-fluorophenyl | 4-pyridyl | 2-(2-chlorophenyl)ethylamino |
| 4-chlorophenyl | 4-pyridyl | 2-(2-chlorophenyl)ethylamino |
| 3-chlorophenyl | 4-pyridyl | 2-(2-chlorophenyl)ethylamino |
| 2-chlorophenyl | 4-pyridyl | 2-(2-chlorophenyl)ethylamino |
| 4-tolyl | 4-pyridyl | 2-(2-chlorophenyl)ethylamino |
| 3-tolyl | 4-pyridyl | 2-(2-chlorophenyl)ethylamino |
| 2-tolyl | 4-pyridyl | 2-(2-chlorophenyl)ethylamino |
| 4-trifluoro-methylphenyl | 4-pyridyl | 2-(2-chlorophenyl)ethylamino |
| 3-trifluoro-methylphenyl | 4-pyridyl | 2-(2-chlorophenyl)ethylamino |
| 2,6-dichlorophenyl | 4-pyridyl | 2-(2-chlorophenyl)ethylamino |
| 2,6-dimethyl phenyl | 4-pyridyl | 2-(2-chlorophenyl)ethylamino |
| 3,4-dichlorophenyl | 4-pyridyl | 2-(2-chlorophenyl)ethylamino |
| 3,4-dimethyl phenyl | 4-pyridyl | 2-(2-chlorophenyl)ethylamino |
| 2,4-dichlorophenyl | 4-pyridyl | 2-(2-chlorophenyl)ethylamino |
| 2,4-dimethyl phenyl | 4-pyridyl | 2-(2-chlorophenyl)ethylamino |
| 4-fluorophenyl | 4-pyridyl | 3-(3-fluorophenyl)propylamino |
| 4-fluorophenyl | 2-amino-4-pyrimidinyl | 3-(3-fluorophenyl)propylamino |
| benzyl | 4-pyridyl | 3-phenylpropylamino |
| benzyl | 4-pyridyl | 2-(4-fluorophenyl)ethylamino |
| 2-thienyl | 4-pyridyl | 3-phenylpropylamino |
| 2-thienyl | 4-pyridyl | 2-(4-fluorophenyl)ethylamino |
| cyclohexyl | 4-pyridyl | 3-phenylpropylamino |
| cyclohexyl | 4-pyridyl | 2-(4-fluorophenyl)ethylamino |
| tert-butyl | 4-pyridyl | 3-phenylpropylamino |
| tert-butyl | 4-pyridyl | 2-(4-fluorophenyl)ethylamino |
| 4-fluorophenyl | 4-piperidinyl | 3-phenylpropylamino |
| 4-fluorophenyl | 4-piperidinyl | 2-(4-fluorophenyl)ethylamino |
| 4-fluorophenyl | 4-pyranyl | 3-phenylpropylamino |
| 4-fluorophenyl | 4-pyranyl | 2-(4-fluorophenyl)ethylamino |
| Phenyl | 2-amino-4-pyridyl | 2-(2-chlorophenyl)ethylamino |
| 4-fluorophenyl | 2-amino-4-pyridyl | 2-(2-chlorophenyl)ethylamino |
| 3-fluorophenyl | 2-amino-4-pyridyl | 2-(2-chlorophenyl)ethylamino |
| 2-fluorophenyl | 2-amino-4-pyridyl | 2-(2-chlorophenyl)ethylamino |
| 4-chlorophenyl | 2-amino-4-pyridyl | 2-(2-chlorophenyl)ethylamino |
| 3-chlorophenyl | 2-amino-4-pyridyl | 2-(2-chlorophenyl)ethylamino |
| 2-chlorophenyl | 2-amino-4-pyridyl | 2-(2-chlorophenyl)ethylamino |
| 4-tolyl | 2-amino-4-pyridyl | 2-(2-chlorophenyl)ethylamino |
| 3-tolyl | 2-amino-4-pyridyl | 2-(2-chlorophenyl)ethylamino |
| 2-tolyl | 2-amino-4-pyridyl | 2-(2-chlorophenyl)ethylamino |
| 4-trifluoro-methylphenyl | 2-amino-4-pyridyl | 2-(2-chlorophenyl)ethylamino |
| 3-trifluoro-methylphenyl | 2-amino-4-pyridyl | 2-(2-chlorophenyl)ethylamino |
| 2,6-dichlorophenyl | 2-amino-4-pyridyl | 2-(2-chlorophenyl)ethylamino |
| 2,6-dimethyl phenyl | 2-amino-4-pyridyl | 2-(2-chlorophenyl)ethylamino |
| 3,4-dichlorophenyl | 2-amino-4-pyridyl | 2-(2-chlorophenyl)ethylamino |
| 3,4-dimethyl phenyl | 2-amino-4-pyridyl | 2-(2-chlorophenyl)ethylamino |
| 2,4-dichlorophenyl | 2-amino-4-pyridyl | 2-(2-chlorophenyl)ethylamino |
| 2,4-dimethyl phenyl | 2-amino-4-pyridyl | 2-(2-chlorophenyl)ethylamino |
| Phenyl | 2-acetamido-4-pyridyl | 2-(2-chlorophenyl)ethylamino |
| 4-fluorophenyl | 2-acetamido-4-pyridyl | 2-(2-chlorophenyl)ethylamino |
| 3-fluorophenyl | 2-acetamido-4-pyridyl | 2-(2-chlorophenyl)ethylamino |
| 2-fluorophenyl | 2-acetamido-4-pyridyl | 2-(2-chlorophenyl)ethylamino |
| 4-chlorophenyl | 2-acetamido-4-pyridyl | 2-(2-chlorophenyl)ethylamino |
| 3-chlorophenyl | 2-acetamido-4-pyridyl | 2-(2-chlorophenyl)ethylamino |
| 2-chlorophenyl | 2-acetamido-4-pyridyl | 2-(2-chlorophenyl)ethylamino |
| 4-tolyl | 2-acetamido-4-pyridyl | 2-(2-chlorophenyl)ethylamino |
| 3-tolyl | 2-acetamido-4-pyridyl | 2-(2-chlorophenyl)ethylamino |
| 2-tolyl | 2-acetamido-4-pyridyl | 2-(2-chlorophenyl)ethylamino |
| 4-trifluoro-methylphenyl | 2-acetamido-4-pyridyl | 2-(2-chlorophenyl)ethylamino |
| 3-trifluoro-methylphenyl | 2-acetamido-4-pyridyl | 2-(2-chlorophenyl)ethylamino |
| 2,6-dichlorophenyl | 2-acetamido-4-pyridyl | 2-(2-chlorophenyl)ethylamino |
| 2,6-dimethyl phenyl | 2-acetamido-4-pyridyl | 2-(2-chlorophenyl)ethylamino |
| 3,4-dichlorophenyl | 2-acetamido-4-pyridyl | 2-(2-chlorophenyl)ethylamino |
| 3,4-dimethyl phenyl | 2-acetamido-4-pyridyl | 2-(2-chlorophenyl)ethylamino |
| 2,4-dichlorophenyl | 2-acetamido-4-pyridyl | 2-(2-chlorophenyl)ethylamino |
| 2,4-dimethyl phenyl | 2-acetamido-4-pyridyl | 2-(2-chlorophenyl)ethylamino |
| Phenyl | 2-amino-4-pyrimidinyl | 2-(2-chlorophenyl)ethylamino |
| 4-fluorophenyl | 2-amino-4-pyrimidinyl | 2-(2-chlorophenyl)ethylamino |
| 3-fluorophenyl | 2-amino-4-pyrimidinyl | 2-(2-chlorophenyl)ethylamino |

-continued

| R[11] | R[12] | R[1] |
|---|---|---|
| 2-fluorophenyl | 2-amino-4-pyrimidinyl | 2-(2-chlorophenyl)ethylamino |
| 4-chlorophenyl | 2-amino-4-pyrimidinyl | 2-(2-chlorophenyl)ethylamino |
| 3-chlorophenyl | 2-amino-4-pyrimidinyl | 2-(2-chlorophenyl)ethylamino |
| 2-chlorophenyl | 2-amino-4-pyrimidinyl | 2-(2-chlorophenyl)ethylamino |
| 4-tolyl | 2-amino-4-pyrimidinyl | 2-(2-chlorophenyl)ethylamino |
| 3-tolyl | 2-amino-4-pyrimidinyl | 2-(2-chlorophenyl)ethylamino |
| 2-tolyl | 2-amino-4-pyrimidinyl | 2-(2-chlorophenyl)ethylamino |
| 4-trifluoromethylphenyl | 2-amino-4-pyrimidinyl | 2-(2-chlorophenyl)ethylamino |
| 3-trifluoromethylphenyl | 2-amino-4-pyrimidinyl | 2-(2-chlorophenyl)ethylamino |
| 2,6-dichlorophenyl | 2-amino-4-pyrimidinyl | 2-(2-chlorophenyl)ethylamino |
| 2,6-dimethylphenyl | 2-amino-4-pyrimidinyl | 2-(2-chlorophenyl)ethylamino |
| 3,4-dichlorophenyl | 2-amino-4-pyrimidinyl | 2-(2-chlorophenyl)ethylamino |
| 3,4-dimethylphenyl | 2-amino-4-pyrimidinyl | 2-(2-chlorophenyl)ethylamino |
| 2,4-dichlorophenyl | 2-amino-4-pyrimidinyl | 2-(2-chlorophenyl)ethylamino |
| 2,4-dimethylphenyl | 2-amino-4-pyrimidinyl | 2-(2-chlorophenyl)ethylamino |
| Phenyl | 4-pyridyl | 3-imidazolylpropylamino |
| 4-fluorophenyl | 4-pyridyl | 3-imidazolylpropylamino |
| 3-fluorophenyl | 4-pyridyl | 3-imidazolylpropylamino |
| 2-fluorophenyl | 4-pyridyl | 3-imidazolylpropylamino |
| 4-chlorophenyl | 4-pyridyl | 3-imidazolylpropylamino |
| 3-chlorophenyl | 4-pyridyl | 3-imidazolylpropylamino |
| 2-chlorophenyl | 4-pyridyl | 3-imidazolylpropylamino |
| 4-tolyl | 4-pyridyl | 3-imidazolylpropylamino |
| 3-tolyl | 4-pyridyl | 3-imidazolylpropylamino |
| 2-tolyl | 4-pyridyl | 3-imidazolylpropylamino |
| 4-trifluoromethylphenyl | 4-pyridyl | 3-imidazolylpropylamino |
| 3-trifluoromethylphenyl | 4-pyridyl | 3-imidazolylpropylamino |
| 2,6-dichlorophenyl | 4-pyridyl | 3-imidazolylpropylamino |
| 2,6-dimethylphenyl | 4-pyridyl | 3-imidazolylpropylamino |
| 3,4-dichlorophenyl | 4-pyridyl | 3-imidazolylpropylamino |
| 3,4-dimethylphenyl | 4-pyridyl | 3-imidazolylpropylamino |
| 2,4-dichlorophenyl | 4-pyridyl | 3-imidazolylpropylamino |
| 2,4-dimethylphenyl | 4-pyridyl | 3-imidazolylpropylamino |
| Phenyl | 2-amino-4-pyridyl | 3-imidazolylpropylamino |
| 4-fluorophenyl | 2-amino-4-pyridyl | 3-imidazolylpropylamino |
| 3-fluorophenyl | 2-amino-4-pyridyl | 3-imidazolylpropylamino |
| 2-fluorophenyl | 2-amino-4-pyridyl | 3-imidazolylpropylamino |
| 4-chlorophenyl | 2-amino-4-pyridyl | 3-imidazolylpropylamino |
| 3-chlorophenyl | 2-amino-4-pyridyl | 3-imidazolylpropylamino |
| 2-chlorophenyl | 2-amino-4-pyridyl | 3-imidazolylpropylamino |
| 4-tolyl | 2-amino-4-pyridyl | 3-imidazolylpropylamino |
| 3-tolyl | 2-amino-4-pyridyl | 3-imidazolylpropylamino |
| 2-tolyl | 2-amino-4-pyridyl | 3-imidazolylpropylamino |
| 4-trifluoromethylphenyl | 2-amino-4-pyridyl | 3-imidazolylpropylamino |
| 3-trifluoromethylphenyl | 2-amino-4-pyridyl | 3-imidazolylpropylamino |
| 2,6-dichlorophenyl | 2-amino-4-pyridyl | 3-imidazolylpropylamino |
| 2,6-dimethylphenyl | 2-amino-4-pyridyl | 3-imidazolylpropylamino |
| 3,4-dichlorophenyl | 2-amino-4-pyridyl | 3-imidazolylpropylamino |
| 3,4-dimethylphenyl | 2-amino-4-pyridyl | 3-imidazolylpropylamino |
| 2,4-dichlorophenyl | 2-amino-4-pyridyl | 3-imidazolylpropylamino |
| 2,4-dimethylphenyl | 2-amino-4-pyridyl | 3-imidazolylpropylamino |
| Phenyl | 2-acetamido-4-pyridyl | 3-imidazolylpropylamino |
| 4-fluorophenyl | 2-acetamido-4-pyridyl | 3-imidazolylpropylamino |
| 3-fluorophenyl | 2-acetamido-4-pyridyl | 3-imidazolylpropylamino |
| 2-fluorophenyl | 2-acetamido-4-pyridyl | 3-imidazolylpropylamino |
| 4-chlorophenyl | 2-acetamido-4-pyridyl | 3-imidazolylpropylamino |
| 3-chlorophenyl | 2-acetamido-4-pyridyl | 3-imidazolylpropylamino |
| 2-chlorophenyl | 2-acetamido-4-pyridyl | 3-imidazolylpropylamino |
| 4-tolyl | 2-acetamido-4-pyridyl | 3-imidazolylpropylamino |
| 3-tolyl | 2-acetamido-4-pyridyl | 3-imidazolylpropylamino |
| 2-tolyl | 2-acetamido-4-pyridyl | 3-imidazolylpropylamino |
| 4-trifluoromethylphenyl | 2-acetamido-4-pyridyl | 3-imidazolylpropylamino |
| 3-trifluoromethylphenyl | 2-acetamido-4-pyridyl | 3-imidazolylpropylamino |
| 2,6-dichlorophenyl | 2-acetamido-4-pyridyl | 3-imidazolylpropylamino |
| 2,6-dimethylphenyl | 2-acetamido-4-pyridyl | 3-imidazolylpropylamino |
| 3,4-dichlorophenyl | 2-acetamido-4-pyridyl | 3-imidazolylpropylamino |
| 3,4-dimethylphenyl | 2-acetamido-4-pyridyl | 3-imidazolylpropylamino |
| 2,4-dichlorophenyl | 2-acetamido-4-pyridyl | 3-imidazolylpropylamino |
| 2,4-dimethylphenyl | 2-acetamido-4-pyridyl | 3-imidazolylpropylamino |
| Phenyl | 2-amino-4-pyrimidinyl | 3-imidazolylpropylamino |
| 4-fluorophenyl | 2-amino-4-pyrimidinyl | 3-imidazolylpropylamino |
| 3-fluorophenyl | 2-amino-4-pyrimidinyl | 3-imidazolylpropylamino |
| 2-fluorophenyl | 2-amino-4-pyrimidinyl | 3-imidazolylpropylamino |
| 4-chlorophenyl | 2-amino-4-pyrimidinyl | 3-imidazolylpropylamino |
| 3-chlorophenyl | 2-amino-4-pyrimidinyl | 3-imidazolylpropylamino |
| 2-chlorophenyl | 2-amino-4-pyrimidinyl | 3-imidazolylpropylamino |
| 4-tolyl | 2-amino-4-pyrimidinyl | 3-imidazolylpropylamino |
| 3-tolyl | 2-amino-4-pyrimidinyl | 3-imidazolylpropylamino |
| 2-tolyl | 2-amino-4-pyrimidinyl | 3-imidazolylpropylamino |
| 4-trifluoromethylphenyl | 2-amino-4-pyrimidinyl | 3-imidazolylpropylamino |
| 3-trifluoromethylphenyl | 2-amino-4-pyrimidinyl | 3-imidazolylpropylamino |
| 2,6-dichlorophenyl | 2-amino-4-pyrimidinyl | 3-imidazolylpropylamino |

-continued

| R11 | R12 | R1 |
|---|---|---|
| 2,6-dimethyl phenyl | 2-amino-4-pyrimidinyl | 3-imidazolylpropylamino |
| 3,4-dichlorophenyl | 2-amino-4-pyrimidinyl | 3-imidazolylpropylamino |
| 3,4-dimethyl phenyl | 2-amino-4-pyrimidinyl | 3-imidazolylpropylamino |
| 2,4-dichlorophenyl | 2-amino-4-pyrimidinyl | 3-imidazolylpropylamino |
| 2,4-dimethyl phenyl | 2-amino-4-pyrimidinyl | 3-imidazolylpropylamino |
| 4-fluorophenyl | 4-pyridyl | 2-(2-chlorophenyl-1-methyl)ethyl)amino |
| 4-fluorophenyl | 2-acetamido-4-pyridyl | 2-(2-chlorophenyl-1-methyl)ethyl)amino |
| 4-fluorophenyl | 2-amino-4-pyrimidinyl | 2-(2-chlorophenyl-1-methyl)ethyl)amino |
| 3-fluorophenyl | 4-pyridyl | (S)-tetrahydroisoquinol-3-ylmethylenamino |
| 2-fluorophenyl | 2-amino-4-pyridyl | (S)-3-benzylpiperazinyl |
| 3-chlorophenyl | 2-acetamido-4-pyridyl | (S)-2-N-isopropylamino-3-phenylpropylamino |
| 2-chlorophenyl | 2-amino-4-pyrimidinyl | (S)-2-N-glycylamino-3-phenylpropylamino |
| 4-tolyl | 4-pyridyl | (S)-2-amino-3-phenylpropylamino |
| 3-tolyl | 2-amino-4-pyridyl | (R)-2-amino-3-phenylpropylamino |
| 2-tolyl | 2-acetamido-4-pyridyl | 3-amino-3-phenylpropylamino |
| 4-trifluoromethylphenyl | 2-amino-4-pyrimidinyl | (S)-2-amino-3-(2-fluorophenyl)propylamino |
| 3-trifluoromethylphenyl | 4-pyridyl | (S)-2-amino-3-(2-methylphenyl)propylamino |
| 2,6-dichlorophenyl | 2-amino-4-pyridyl | 3-amino-3-(2-fluorophenyl)propylamino |
| 2,6-dimethyl phenyl | 2-acetamido-4-pyridyl | 3-amino-3-(2-methylphenyl)propylamino |
| 3,4-dichlorophenyl | 2-amino-4-pyrimidinyl | 2-amino-2-methyl-3-phenylpropylamino |
| 3,4-dimethyl phenyl | 4-pyridyl | 3-amino-2-methyl-3-phenylpropylamino |
| 3-fluorophenyl | 2-amino-4-pyridyl | (S)-2-amino-3-phenylpropylamino |
| 2-fluorophenyl | 2-acetamido-4-pyridyl | (S)-2-amino-3-(2-fluorophenyl)propylamino |
| 3-chlorophenyl | 2-amino-4-pyrimidinyl | (S)-2-amino-3-(2-methylphenyl)propylamino |
| 2-chlorophenyl | 4-pyridyl | (S)-2-N-isopropylamino-3-phenylpropylamino |
| 4-tolyl | 2-amino-4-pyridyl | (S)-2-N-glycylamino-3-phenylpropylamino |
| 3-tolyl | 2-acetamido-4-pyridyl | 2-amino-2-methyl-3-phenylpropylamino |
| 2-tolyl | 2-amino-4-pyrimidinyl | (R)-2-amino-3-phenylpropylamino |
| 4-trifluoromethylphenyl | 4-pyridyl | 3-amino-3-phenylpropylamino |
| 3-trifluoromethylphenyl | 2-amino-4-pyridyl | 3-amino-3-(2-fluorophenyl)propylamino |
| 2,6-dichlorophenyl | 2-acetamido-4-pyridyl | 3-amino-3-(2-methylphenyl)propylamino |
| 2,6-dimethyl phenyl | 2-amino-4-pyrimidinyl | 3-amino-2-methyl-3-phenylpropylamino |
| 3,4-dichlorophenyl | 4-pyridyl | (S)-tetrahydroisoquinol-3-ylmethylenamino |
| 3,4-dimethyl phenyl and | 4-pyridyl | (S)-3-benzylpiperazinyl |

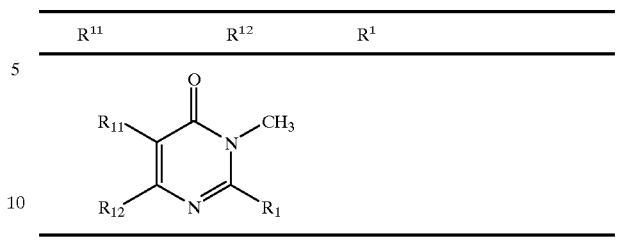

wherein $R^{11}$, $R^{12}$, and $R^1$ are one of the combinations given in the following table:

| R11 | R12 | R1 |
|---|---|---|
| Phenyl | 4-pyridyl | 4-pyridyl |
| 4-fluorophenyl | 4-pyridyl | 4-pyridyl |
| 3-fluorophenyl | 4-pyridyl | 4-pyridyl |
| 2-fluorophenyl | 4-pyridyl | 4-pyridyl |
| 4-chlorophenyl | 4-pyridyl | 4-pyridyl |
| 3-chlorophenyl | 4-pyridyl | 4-pyridyl |
| 2-chlorophenyl | 4-pyridyl | 4-pyridyl |
| 4-tolyl | 4-pyridyl | 4-pyridyl |
| 3-tolyl | 4-pyridyl | 4-pyridyl |
| 2-tolyl | 4-pyridyl | 4-pyridyl |
| 4-trifluoromethylphenyl | 4-pyridyl | 4-pyridyl |
| 3-trifluoromethylphenyl | 4-pyridyl | 4-pyridyl |
| 2,6-dichlorophenyl | 4-pyridyl | 4-pyridyl |
| 2,6-dimethyl phenyl | 4-pyridyl | 4-pyridyl |
| 3,4-dichlorophenyl | 4-pyridyl | 4-pyridyl |
| 3,4-dimethyl phenyl | 4-pyridyl | 4-pyridyl |
| 2,4-dichlorophenyl | 4-pyridyl | 4-pyridyl |
| 2,4-dimethyl phenyl | 4-pyridyl | 4-pyridyl |
| Phenyl | 2-amino-4-pyridyl | 4-pyridyl |
| 4-fluorophenyl | 2-amino-4-pyridyl | 4-pyridyl |
| 3-fluorophenyl | 2-amino-4-pyridyl | 4-pyridyl |
| 2-fluorophenyl | 2-amino-4-pyridyl | 4-pyridyl |
| 4-chlorophenyl | 2-amino-4-pyridyl | 4-pyridyl |
| 3-chlorophenyl | 2-amino-4-pyridyl | 4-pyridyl |
| 2-chlorophenyl | 2-amino-4-pyridyl | 4-pyridyl |
| 4-tolyl | 2-amino-4-pyridyl | 4-pyridyl |
| 3-tolyl | 2-amino-4-pyridyl | 4-pyridyl |
| 2-tolyl | 2-amino-4-pyridyl | 4-pyridyl |
| 4-trifluoromethylphenyl | 2-amino-4-pyridyl | 4-pyridyl |
| 3-trifluoromethylphenyl | 2-amino-4-pyridyl | 4-pyridyl |
| 2,6-dichlorophenyl | 2-amino-4-pyridyl | 4-pyridyl |
| 2,6-dimethyl phenyl | 2-amino-4-pyridyl | 4-pyridyl |
| 3,4-dichlorophenyl | 2-amino-4-pyridyl | 4-pyridyl |
| 3,4-dimethyl phenyl | 2-amino-4-pyridyl | 4-pyridyl |
| 2,4- | 2-amino-4- | 4-pyridyl |

| R¹¹ | R¹² | R¹ |
|---|---|---|
| dichlorophenyl | pyridyl | |
| 2,4-dimethyl phenyl | 2-amino-4-pyridyl | 4-pyridyl |
| Phenyl | 2-acetamido-4-pyridyl | 4-pyridyl |
| 4-fluorophenyl | 2-acetamido-4-pyridyl | 4-pyridyl |
| 3-fluorophenyl | 2-acetamido-4-pyridyl | 4-pyridyl |
| 2-fluorophenyl | 2-acetamido-4-pyridyl | 4-pyridyl |
| 4-chlorophenyl | 2-acetamido-4-pyridyl | 4-pyridyl |
| 3-chlorophenyl | 2-acetamido-4-pyridyl | 4-pyridyl |
| 2-chlorophenyl | 2-acetamido-4-pyridyl | 4-pyridyl |
| 4-tolyl | 2-acetamido-4-pyridyl | 4-pyridyl |
| 3-tolyl | 2-acetamido-4-pyridyl | 4-pyridyl |
| 2-tolyl | 2-acetamido-4-pyridyl | 4-pyridyl |
| 4-trifluoromethylphenyl | 2-acetamido-4-pyridyl | 4-pyridyl |
| 3-trifluoromethylphenyl | 2-acetamido-4-pyridyl | 4-pyridyl |
| 2,6-dichlorophenyl | 2-acetamido-4-pyridyl | 4-pyridyl |
| 2,6-dimethyl phenyl | 2-acetamido-4-pyridyl | 4-pyridyl |
| 3,4-dichlorophenyl | 2-acetamido-4-pyridyl | 4-pyridyl |
| 3,4-dimethyl phenyl | 2-acetamido-4-pyridyl | 4-pyridyl |
| 2,4-dichlorophenyl | 2-acetamido-4-pyridyl | 4-pyridyl |
| 2,4-dimethyl phenyl | 2-acetamido-4-pyridyl | 4-pyridyl |
| Phenyl | 2-amino-4-pyrimidinyl | 4-pyridyl |
| 4-fluorophenyl | 2-amino-4-pyrimidinyl | 4-pyridyl |
| 3-fluorophenyl | 2-amino-4-pyrimidinyl | 4-pyridyl |
| 2-fluorophenyl | 2-amino-4-pyrimidinyl | 4-pyridyl |
| 4-chlorophenyl | 2-amino-4-pyrimidinyl | 4-pyridyl |
| 3-chlorophenyl | 2-amino-4-pyrimidinyl | 4-pyridyl |
| 2-chlorophenyl | 2-amino-4-pyrimidinyl | 4-pyridyl |
| 4-tolyl | 2-amino-4-pyrimidinyl | 4-pyridyl |
| 3-tolyl | 2-amino-4-pyrimidinyl | 4-pyridyl |
| 2-tolyl | 2-amino-4-pyrimidinyl | 4-pyridyl |
| 4-trifluoromethylphenyl | 2-amino-4-pyrimidinyl | 4-pyridyl |
| 3-trifluoromethylphenyl | 2-amino-4-pyrimidinyl | 4-pyridyl |
| 2,6-dichlorophenyl | 2-amino-4-pyrimidinyl | 4-pyridyl |
| 2,6-dimethyl phenyl | 2-amino-4-pyrimidinyl | 4-pyridyl |
| 3,4-dichlorophenyl | 2-amino-4-pyrimidinyl | 4-pyridyl |
| 3,4-dimethyl phenyl | 2-amino-4-pyrimidinyl | 4-pyridyl |
| 2,4-dichlorophenyl | 2-amino-4-pyrimidinyl | 4-pyridyl |
| 2,4-dimethyl phenyl | 2-amino-4-pyrimidinyl | 4-pyridyl |
| Phenyl | 4-pyridyl | 4-methyl sulfinylphenyl |
| 4-fluorophenyl | 4-pyridyl | 4-methyl sulfinylphenyl |
| 3-fluorophenyl | 4-pyridyl | 4-methyl sulfinylphenyl |
| 2-fluorophenyl | 4-pyridyl | 4-methyl sulfinylphenyl |
| 4-chlorophenyl | 4-pyridyl | 4-methyl sulfinylphenyl |
| 3-chlorophenyl | 4-pyridyl | 4-methyl sulfinylphenyl |
| 2-chlorophenyl | 4-pyridyl | 4-methyl sulfinylphenyl |
| 4-tolyl | 4-pyridyl | 4-methyl sulfinylphenyl |
| 3-tolyl | 4-pyridyl | 4-methyl sulfinylphenyl |
| 2-tolyl | 4-pyridyl | 4-methyl sulfinylphenyl |
| 4-trifluoromethylphenyl | 4-pyridyl | 4-methyl sulfinylphenyl |
| 3-trifluoromethylphenyl | 4-pyridyl | 4-methyl sulfinylphenyl |
| 2,6-dichlorophenyl | 4-pyridyl | 4-methyl sulfinylphenyl |
| 2,6-dimethyl phenyl | 4-pyridyl | 4-methyl sulfinylphenyl |
| 3,4-dichlorophenyl | 4-pyridyl | 4-methyl sulfinylphenyl |
| 3,4-dimethyl phenyl | 4-pyridyl | 4-methyl sulfinylphenyl |
| 2,4-dichlorophenyl | 4-pyridyl | 4-methyl sulfinylphenyl |
| 2,4-dimethyl phenyl | 4-pyridyl | 4-methyl sulfinylphenyl |
| Phenyl | 2-amino-4-pyridyl | 4-methyl sulfinylphenyl |
| 4-fluorophenyl | 2-amino-4-pyridyl | 4-methyl sulfinylphenyl |
| 3-fluorophenyl | 2-amino-4-pyridyl | 4-methyl sulfinylphenyl |
| 2-fluorophenyl | 2-amino-4-pyridyl | 4-methyl sulfinylphenyl |
| 4-chlorophenyl | 2-amino-4-pyridyl | 4-methyl sulfinylphenyl |
| 3-chlorophenyl | 2-amino-4-pyridyl | 4-methyl sulfinylphenyl |
| 2-chlorophenyl | 2-amino-4-pyridyl | 4-methyl sulfinylphenyl |
| 4-tolyl | 2-amino-4-pyridyl | 4-methyl sulfinylphenyl |
| 3-tolyl | 2-amino-4-pyridyl | 4-methyl sulfinylphenyl |
| 2-tolyl | 2-amino-4-pyridyl | 4-methyl sulfinylphenyl |
| 4-trifluoromethylphenyl | 2-amino-4-pyridyl | 4-methyl sulfinylphenyl |
| 3-trifluoromethylphenyl | 2-amino-4-pyridyl | 4-methyl sulfinylphenyl |
| 2,6-dichlorophenyl | 2-amino-4-pyridyl | 4-methyl sulfinylphenyl |
| 2,6-dimethyl phenyl | 2-amino-4-pyridyl | 4-methyl sulfinylphenyl |
| 3,4-dichlorophenyl | 2-amino-4-pyridyl | 4-methyl sulfinylphenyl |
| 3,4-dimethyl phenyl | 2-amino-4-pyridyl | 4-methyl sulfinylphenyl |
| 2,4-dichlorophenyl | 2-amino-4-pyridyl | 4-methyl sulfinylphenyl |
| 2,4-dimethyl phenyl | 2-amino-4-pyridyl | 4-methyl sulfinylphenyl |
| Phenyl | 2-acetamido-4-pyridyl | 4-methyl sulfinylphenyl |
| 4-fluorophenyl | 2-acetamido-4-pyridyl | 4-methyl sulfinylphenyl |
| 3-fluorophenyl | 2-acetamido-4-pyridyl | 4-methyl sulfinylphenyl |
| 2-fluorophenyl | 2-acetamido-4-pyridyl | 4-methyl sulfinylphenyl |
| 4-chlorophenyl | 2-acetamido-4-pyridyl | 4-methyl sulfinylphenyl |
| 3-chlorophenyl | 2-acetamido-4-pyridyl | 4-methyl sulfinylphenyl |
| 2-chlorophenyl | 2-acetamido-4-pyridyl | 4-methyl sulfinylphenyl |
| 4-tolyl | 2-acetamido-4-pyridyl | 4-methyl sulfinylphenyl |
| 3-tolyl | 2-acetamido- | 4-methyl sulfinylphenyl |

-continued

| $R^{11}$ | $R^{12}$ | $R^1$ |
|---|---|---|
| 2-tolyl | 4-pyridyl | 4-methyl sulfinylphenyl |
|  | 2-acetamido-4-pyridyl |  |
| 4-trifluoro-methylphenyl | 2-acetamido-4-pyridyl | 4-methyl sulfinylphenyl |
| 3-trifluoro-methylphenyl | 2-acetamido-4-pyridyl | 4-methyl sulfinylphenyl |
| 2,6-dichlorophenyl | 2-acetamido-4-pyridyl | 4-methyl sulfinylphenyl |
| 2,6-dimethyl phenyl | 2-acetamido-4-pyridyl | 4-methyl sulfinylphenyl |
| 3,4-dichlorophenyl | 2-acetamido-4-pyridyl | 4-methyl sulfinylphenyl |
| 3,4-dimethyl phenyl | 2-acetamido-4-pyridyl | 4-methyl sulfinylphenyl |
| 2,4-dichlorophenyl | 2-acetamido-4-pyridyl | 4-methyl sulfinylphenyl |
| 2,4-dimethyl phenyl | 2-acetamido-4-pyridyl | 4-methyl sulfinylphenyl |
| Phenyl | 2-amino-4-pyrimidinyl | 4-methyl sulfinylphenyl |
| 4-fluorophenyl | 2-amino-4-pyrimidinyl | 4-methyl sulfinylphenyl |
| 3-fluorophenyl | 2-amino-4-pyrimidinyl | 4-methyl sulfinylphenyl |
| 2-fluorophenyl | 2-amino-4-pyrimidinyl | 4-methyl sulfinylphenyl |
| 4-chlorophenyl | 2-amino-4-pyrimidinyl | 4-methyl sulfinylphenyl |
| 3-chlorophenyl | 2-amino-4-pyrimidinyl | 4-methyl sulfinylphenyl |
| 2-chlorophenyl | 2-amino-4-pyrimidinyl | 4-methyl sulfinylphenyl |
| 4-tolyl | 2-amino-4-pyrimidinyl | 4-methyl sulfinylphenyl |
| 3-tolyl | 2-amino-4-pyrimidinyl | 4-methyl sulfinylphenyl |
| 2-tolyl | 2-amino-4-pyrimidinyl | 4-methyl sulfinylphenyl |
| 4-trifluoro-methylphenyl | 2-amino-4-pyrimidinyl | 4-methyl sulfinylphenyl |
| 3-trifluoro-methylphenyl | 2-amino-4-pyrimidinyl | 4-methyl sulfinylphenyl |
| 2,6-dichlorophenyl | 2-amino-4-pyrimidinyl | 4-methyl sulfinylphenyl |
| 2,6-dimethyl phenyl | 2-amino-4-pyrimidinyl | 4-methyl sulfinylphenyl |
| 3,4-dichlorophenyl | 2-amino-4-pyrimidinyl | 4-methyl sulfinylphenyl |
| 3,4-dimethyl phenyl | 2-amino-4-pyrimidinyl | 4-methyl sulfinylphenyl |
| 2,4-dichlorophenyl | 2-amino-4-pyrimidinyl | 4-methyl sulfinylphenyl |
| 2,4-dimethyl phenyl | 2-amino-4-pyrimidinyl | 4-methyl sulfinylphenyl |
| Phenyl | 4-pyridyl | 2,6-dichlorobenzyl |
| 4-fluorophenyl | 4-pyridyl | 2,6-dichlorobenzyl |
| 3-fluorophenyl | 4-pyridyl | 2,6-dichlorobenzyl |
| 2-fluorophenyl | 4-pyridyl | 2,6-dichlorobenzyl |
| 4-chlorophenyl | 4-pyridyl | 2,6-dichlorobenzyl |
| 3-chlorophenyl | 4-pyridyl | 2,6-dichlorobenzyl |
| 2-chlorophenyl | 4-pyridyl | 2,6-dichlorobenzyl |
| 4-tolyl | 4-pyridyl | 2,6-dichlorobenzyl |
| 3-tolyl | 4-pyridyl | 2,6-dichlorobenzyl |
| 2-tolyl | 4-pyridyl | 2,6-dichlorobenzyl |
| 4-trifluoro-methylphenyl | 4-pyridyl | 2,6-dichlorobenzyl |
| 3-trifluoro-methylphenyl | 4-pyridyl | 2,6-dichlorobenzyl |
| 2,6-dichlorophenyl | 4-pyridyl | 2,6-dichlorobenzyl |
| 2,6-dimethyl phenyl | 4-pyridyl | 2,6-dichlorobenzyl |
| 3,4-dichlorophenyl | 4-pyridyl | 2,6-dichlorobenzyl |
| 3,4-dimethyl phenyl | 4-pyridyl | 2,6-dichlorobenzyl |
| 2,4-dichlorophenyl | 4-pyridyl | 2,6-dichlorobenzyl |
| 2,4-dimethyl phenyl | 4-pyridyl | 2,6-dichlorobenzyl |
| Phenyl | 2-amino-4-pyridyl | 2,6-dichlorobenzyl |
| 4-fluorophenyl | 2-amino-4-pyridyl | 2,6-dichlorobenzyl |
| 3-fluorophenyl | 2-amino-4-pyridyl | 2,6-dichlorobenzyl |
| 2-fluorophenyl | 2-amino-4-pyridyl | 2,6-dichlorobenzyl |
| 4-chlorophenyl | 2-amino-4-pyridyl | 2,6-dichlorobenzyl |
| 3-chlorophenyl | 2-amino-4-pyridyl | 2,6-dichlorobenzyl |
| 2-chlorophenyl | 2-amino-4-pyridyl | 2,6-dichlorobenzyl |
| 4-tolyl | 2-amino-4-pyridyl | 2,6-dichlorobenzyl |
| 3-tolyl | 2-amino-4-pyridyl | 2,6-dichlorobenzyl |
| 2-tolyl | 2-amino-4-pyridyl | 2,6-dichlorobenzyl |
| 4-trifluoro-methylphenyl | 2-amino-4-pyridyl | 2,6-dichlorobenzyl |
| 3-trifluoro-methylphenyl | 2-amino-4-pyridyl | 2,6-dichlorobenzyl |
| 2,6-dichlorophenyl | 2-amino-4-pyridyl | 2,6-dichlorobenzyl |
| 2,6-dimethyl phenyl | 2-amino-4-pyridyl | 2,6-dichlorobenzyl |
| 3,4-dichlorophenyl | 2-amino-4-pyridyl | 2,6-dichlorobenzyl |
| 3,4-dimethyl phenyl | 2-amino-4-pyridyl | 2,6-dichlorobenzyl |
| 2,4-dichlorophenyl | 2-amino-4-pyridyl | 2,6-dichlorobenzyl |
| 2,4-dimethyl phenyl | 2-amino-4-pyridyl | 2,6-dichlorobenzyl |
| Phenyl | 2-acetamido-4-pyridyl | 2,6-dichlorobenzyl |
| 4-fluorophenyl | 2-acetamido-4-pyridyl | 2,6-dichlorobenzyl |
| 3-fluorophenyl | 2-acetamido-4-pyridyl | 2,6-dichlorobenzyl |
| 2-fluorophenyl | 2-acetamido-4-pyridyl | 2,6-dichlorobenzyl |
| 4-chlorophenyl | 2-acetamido-4-pyridyl | 2,6-dichlorobenzyl |
| 3-chlorophenyl | 2-acetamido-4-pyridyl | 2,6-dichlorobenzyl |
| 2-chlorophenyl | 2-acetamido-4-pyridyl | 2,6-dichlorobenzyl |
| 4-tolyl | 2-acetamido-4-pyridyl | 2,6-dichlorobenzyl |
| 3-tolyl | 2-acetamido-4-pyridyl | 2,6-dichlorobenzyl |
| 2-tolyl | 2-acetamido-4-pyridyl | 2,6-dichlorobenzyl |
| 4-trifluoro-methylphenyl | 2-acetamido-4-pyridyl | 2,6-dichlorobenzyl |
| 3-trifluoro-methylphenyl | 2-acetamido-4-pyridyl | 2,6-dichlorobenzyl |
| 2,6-dichlorophenyl | 2-acetamido-4-pyridyl | 2,6-dichlorobenzyl |
| 2,6-dimethyl phenyl | 2-acetamido-4-pyridyl | 2,6-dichlorobenzyl |
| 3,4-dichlorophenyl | 2-acetamido-4-pyridyl | 2,6-dichlorobenzyl |
| 3,4-dimethyl phenyl | 2-acetamido-4-pyridyl | 2,6-dichlorobenzyl |
| 2,4-dichlorophenyl | 2-acetamido-4-pyridyl | 2,6-dichlorobenzyl |
| 2,4-dimethyl phenyl | 2-acetamido-4-pyridyl | 2,6-dichlorobenzyl |
| Phenyl | 2-amino-4- | 2,6-dichlorobenzyl |

-continued

| R¹¹ | R¹² | R¹ |
|---|---|---|
| 4-fluorophenyl | 2-amino-4-pyrimidinyl | 2,6-dichlorobenzyl |
| 3-fluorophenyl | 2-amino-4-pyrimidinyl | 2,6-dichlorobenzyl |
| 2-fluorophenyl | 2-amino-4-pyrimidinyl | 2,6-dichlorobenzyl |
| 4-chlorophenyl | 2-amino-4-pyrimidinyl | 2,6-dichlorobenzyl |
| 3-chlorophenyl | 2-amino-4-pyrimidinyl | 2,6-dichlorobenzyl |
| 2-chlorophenyl | 2-amino-4-pyrimidinyl | 2,6-dichlorobenzyl |
| 4-tolyl | 2-amino-4-pyrimidinyl | 2,6-dichlorobenzyl |
| 3-tolyl | 2-amino-4-pyrimidinyl | 2,6-dichlorobenzyl |
| 2-tolyl | 2-amino-4-pyrimidinyl | 2,6-dichlorobenzyl |
| 4-trifluoromethylphenyl | 2-amino-4-pyrimidinyl | 2,6-dichlorobenzyl |
| 3-trifluoromethylphenyl | 2-amino-4-pyrimidinyl | 2,6-dichlorobenzyl |
| 2,6-dichlorophenyl | 2-amino-4-pyrimidinyl | 2,6-dichlorobenzyl |
| 2,6-dimethylphenyl | 2-amino-4-pyrimidinyl | 2,6-dichlorobenzyl |
| 3,4-dichlorophenyl | 2-amino-4-pyrimidinyl | 2,6-dichlorobenzyl |
| 3,4-dimethylphenyl | 2-amino-4-pyrimidinyl | 2,6-dichlorobenzyl |
| 2,4-dichlorophenyl | 2-amino-4-pyrimidinyl | 2,6-dichlorobenzyl |
| 2,4-dimethylphenyl | 2-amino-4-pyrimidinyl | 2,6-dichlorobenzyl |
| Phenyl | 4-pyridyl | 2-(4-fluorophenyl)ethylamino |
| 4-fluorophenyl | 4-pyridyl | 2-(4-fluorophenyl)ethylamino |
| 3-fluorophenyl | 4-pyridyl | 2-(4-fluorophenyl)ethylamino |
| 2-fluorophenyl | 4-pyridyl | 2-(4-fluorophenyl)ethylamino |
| 4-chlorophenyl | 4-pyridyl | 2-(4-fluorophenyl)ethylamino |
| 3-chlorophenyl | 4-pyridyl | 2-(4-fluorophenyl)ethylamino |
| 2-chlorophenyl | 4-pyridyl | 2-(4-fluorophenyl)ethylamino |
| 4-tolyl | 4-pyridyl | 2-(4-fluorophenyl)ethylamino |
| 3-tolyl | 4-pyridyl | 2-(4-fluorophenyl)ethylamino |
| 2-tolyl | 4-pyridyl | 2-(4-fluorophenyl)ethylamino |
| 4-trifluoromethylphenyl | 4-pyridyl | 2-(4-fluorophenyl)ethylamino |
| 3-trifluoromethylphenyl | 4-pyridyl | 2-(4-fluorophenyl)ethylamino |
| 2,6-dichlorophenyl | 4-pyridyl | 2-(4-fluorophenyl)ethylamino |
| 2,6-dimethylphenyl | 4-pyridyl | 2-(4-fluorophenyl)ethylamino |
| 3,4-dichlorophenyl | 4-pyridyl | 2-(4-fluorophenyl)ethylamino |
| 3,4-dimethylphenyl | 4-pyridyl | 2-(4-fluorophenyl)ethylamino |
| 2,4-dichlorophenyl | 4-pyridyl | 2-(4-fluorophenyl)ethylamino |
| 2,4-dimethylphenyl | 4-pyridyl | 2-(4-fluorophenyl)ethylamino |
| Phenyl | 2-amino-4-pyridyl | 2-(4-fluorophenyl)ethylamino |
| 4-fluorophenyl | 2-amino-4-pyridyl | 2-(4-fluorophenyl)ethylamino |
| 3-fluorophenyl | 2-amino-4-pyridyl | 2-(4-fluorophenyl)ethylamino |
| 2-fluorophenyl | 2-amino-4-pyridyl | 2-(4-fluorophenyl)ethylamino |
| 4-chlorophenyl | 2-amino-4-pyridyl | 2-(4-fluorophenyl)ethylamino |
| 3-chlorophenyl | 2-amino-4-pyridyl | 2-(4-fluorophenyl)ethylamino |
| 2-chlorophenyl | 2-amino-4-pyridyl | 2-(4-fluorophenyl)ethylamino |
| 4-tolyl | 2-amino-4-pyridyl | 2-(4-fluorophenyl)ethylamino |
| 3-tolyl | 2-amino-4-pyridyl | 2-(4-fluorophenyl)ethylamino |
| 2-tolyl | 2-amino-4-pyridyl | 2-(4-fluorophenyl)ethylamino |
| 4-trifluoromethylphenyl | 2-amino-4-pyridyl | 2-(4-fluorophenyl)ethylamino |
| 3-trifluoromethylphenyl | 2-amino-4-pyridyl | 2-(4-fluorophenyl)ethylamino |
| 2,6-dichlorophenyl | 2-amino-4-pyridyl | 2-(4-fluorophenyl)ethylamino |
| 2,6-dimethylphenyl | 2-amino-4-pyridyl | 2-(4-fluorophenyl)ethylamino |
| 3,4-dichlorophenyl | 2-amino-4-pyridyl | 2-(4-fluorophenyl)ethylamino |
| 3,4-dimethylphenyl | 2-amino-4-pyridyl | 2-(4-fluorophenyl)ethylamino |
| 2,4-dichlorophenyl | 2-amino-4-pyridyl | 2-(4-fluorophenyl)ethylamino |
| 2,4-dimethylphenyl | 2-amino-4-pyridyl | 2-(4-fluorophenyl)ethylamino |
| Phenyl | 2-acetamido-4-pyridyl | 2-(4-fluorophenyl)ethylamino |
| 4-fluorophenyl | 2-acetamido-4-pyridyl | 2-(4-fluorophenyl)ethylamino |
| 3-fluorophenyl | 2-acetamido-4-pyridyl | 2-(4-fluorophenyl)ethylamino |
| 2-fluorophenyl | 2-acetamido-4-pyridyl | 2-(4-fluorophenyl)ethylamino |
| 4-chlorophenyl | 2-acetamido-4-pyridyl | 2-(4-fluorophenyl)ethylamino |
| 3-chlorophenyl | 2-acetamido-4-pyridyl | 2-(4-fluorophenyl)ethylamino |
| 2-chlorophenyl | 2-acetamido-4-pyridyl | 2-(4-fluorophenyl)ethylamino |
| 4-tolyl | 2-acetamido-4-pyridyl | 2-(4-fluorophenyl)ethylamino |
| 3-tolyl | 2-acetamido-4-pyridyl | 2-(4-fluorophenyl)ethylamino |
| 2-tolyl | 2-acetamido-4-pyridyl | 2-(4-fluorophenyl)ethylamino |
| 4-trifluoromethylphenyl | 2-acetamido-4-pyridyl | 2-(4-fluorophenyl)ethylamino |
| 3-trifluoromethylphenyl | 2-acetamido-4-pyridyl | 2-(4-fluorophenyl)ethylamino |
| 2,6-dichlorophenyl | 2-acetamido-4-pyridyl | 2-(4-fluorophenyl)ethylamino |
| 2,6-dimethylphenyl | 2-acetamido-4-pyridyl | 2-(4-fluorophenyl)ethylamino |
| 3,4-dichlorophenyl | 2-acetamido-4-pyridyl | 2-(4-fluorophenyl)ethylamino |
| 3,4-dimethylphenyl | 2-acetamido-4-pyridyl | 2-(4-fluorophenyl)ethylamino |
| 2,4-dichlorophenyl | 2-acetamido-4-pyridyl | 2-(4-fluorophenyl)ethylamino |
| 2,4-dimethylphenyl | 2-acetamido-4-pyridyl | 2-(4-fluorophenyl)ethylamino |
| Phenyl | 2-amino-4-pyrimidinyl | 2-(4-fluorophenyl)ethylamino |
| 4-fluorophenyl | 2-amino-4-pyrimidinyl | 2-(4-fluorophenyl)ethylamino |
| 3-fluorophenyl | 2-amino-4-pyrimidinyl | 2-(4-fluorophenyl)ethylamino |
| 2-fluorophenyl | 2-amino-4-pyrimidinyl | 2-(4-fluorophenyl)ethylamino |
| 4-chlorophenyl | 2-amino-4-pyrimidinyl | 2-(4-fluorophenyl)ethylamino |
| 3-chlorophenyl | 2-amino-4-pyrimidinyl | 2-(4-fluorophenyl)ethylamino |

-continued

| R¹¹ | R¹² | R¹ |
|---|---|---|
| 2-chlorophenyl | pyrimidinyl 2-amino-4-pyrimidinyl | ethylamino 2-(4-fluorophenyl)ethylamino |
| 4-tolyl | 2-amino-4-pyrimidinyl | 2-(4-fluorophenyl)ethylamino |
| 3-tolyl | 2-amino-4-pyrimidinyl | 2-(4-fluorophenyl)ethylamino |
| 2-tolyl | 2-amino-4-pyrimidinyl | 2-(4-fluorophenyl)ethylamino |
| 4-trifluoromethylphenyl | 2-amino-4-pyrimidinyl | 2-(4-fluorophenyl)ethylamino |
| 3-trifluoromethylphenyl | 2-amino-4-pyrimidinyl | 2-(4-fluorophenyl)ethylamino |
| 2,6-dichlorophenyl | 2-amino-4-pyrimidinyl | 2-(4-fluorophenyl)ethylamino |
| 2,6-dimethylphenyl | 2-amino-4-pyrimidinyl | 2-(4-fluorophenyl)ethylamino |
| 3,4-dichlorophenyl | 2-amino-4-pyrimidinyl | 2-(4-fluorophenyl)ethylamino |
| 3,4-dimethylphenyl | 2-amino-4-pyrimidinyl | 2-(4-fluorophenyl)ethylamino |
| 2,4-dichlorophenyl | 2-amino-4-pyrimidinyl | 2-(4-fluorophenyl)ethylamino |
| 2,4-dimethylphenyl | 2-amino-4-pyrimidinyl | 2-(4-fluorophenyl)ethylamino |
| Phenyl | 4-pyridyl | 3-phenyl-propylamino |
| 4-fluorophenyl | 4-pyridyl | 3-phenyl-propylamino |
| 3-fluorophenyl | 4-pyridyl | 3-phenyl-propylamino |
| 2-fluorophenyl | 4-pyridyl | 3-phenyl-propylamino |
| 4-chlorophenyl | 4-pyridyl | 3-phenyl-propylamino |
| 3-chlorophenyl | 4-pyridyl | 3-phenyl-propylamino |
| 2-chlorophenyl | 4-pyridyl | 3-phenyl-propylamino |
| 4-tolyl | 4-pyridyl | 3-phenyl-propylamino |
| 3-tolyl | 4-pyridyl | 3-phenyl-propylamino |
| 2-tolyl | 4-pyridyl | 3-phenyl-propylamino |
| 4-trifluoromethylphenyl | 4-pyridyl | 3-phenyl-propylamino |
| 3-trifluoromethylphenyl | 4-pyridyl | 3-phenyl-propylamino |
| 2,6-dichlorophenyl | 4-pyridyl | 3-phenyl-propylamino |
| 2,6-dimethylphenyl | 4-pyridyl | 3-phenyl-propylamino |
| 3,4-dichlorophenyl | 4-pyridyl | 3-phenyl-propylamino |
| 3,4-dimethylphenyl | 4-pyridyl | 3-phenyl-propylamino |
| 2,4-dichlorophenyl | 4-pyridyl | 3-phenyl-propylamino |
| 2,4-dimethylphenyl | 4-pyridyl | 3-phenyl-propylamino |
| Phenyl | 2-amino-4-pyridyl | 3-phenyl-propylamino |
| 4-fluorophenyl | 2-amino-4-pyridyl | 3-phenyl-propylamino |
| 3-fluorophenyl | 2-amino-4-pyridyl | 3-phenyl-propylamino |
| 2-fluorophenyl | 2-amino-4-pyridyl | 3-phenyl-propylamino |
| 4-chlorophenyl | 2-amino-4-pyridyl | 3-phenyl-propylamino |
| 3-chlorophenyl | 2-amino-4-pyridyl | 3-phenyl-propylamino |
| 2-chlorophenyl | 2-amino-4-pyridyl | 3-phenyl-propylamino |
| 4-tolyl | 2-amino-4-pyridyl | 3-phenyl-propylamino |
| 3-tolyl | 2-amino-4-pyridyl | 3-phenyl-propylamino |
| 2-tolyl | 2-amino-4-pyridyl | 3-phenyl-propylamino |
| 4-trifluoromethylphenyl | 2-amino-4-pyridyl | 3-phenyl-propylamino |
| 3-trifluoromethylphenyl | 2-amino-4-pyridyl | 3-phenyl-propylamino |
| 2,6-dichlorophenyl | 2-amino-4-pyridyl | 3-phenyl-propylamino |
| 2,6-dimethylphenyl | 2-amino-4-pyridyl | 3-phenyl-propylamino |
| 3,4-dichlorophenyl | 2-amino-4-pyridyl | 3-phenyl-propylamino |
| 3,4-dimethylphenyl | 2-amino-4-pyridyl | 3-phenyl-propylamino |
| 2,4-dichlorophenyl | 2-amino-4-pyridyl | 3-phenyl-propylamino |
| 2,4-dimethylphenyl | 2-amino-4-pyridyl | 3-phenyl-propylamino |
| Phenyl | 2-acetamido-4-pyridyl | 3-phenyl-propylamino |
| 4-fluorophenyl | 2-acetamido-4-pyridyl | 3-phenyl-propylamino |
| 3-fluorophenyl | 2-acetamido-4-pyridyl | 3-phenyl-propylamino |
| 2-fluorophenyl | 2-acetamido-4-pyridyl | 3-phenyl-propylamino |
| 4-chlorophenyl | 2-acetamido-4-pyridyl | 3-phenyl-propylamino |
| 3-chlorophenyl | 2-acetamido-4-pyridyl | 3-phenyl-propylamino |
| 2-chlorophenyl | 2-acetamido-4-pyridyl | 3-phenyl-propylamino |
| 4-tolyl | 2-acetamido-4-pyridyl | 3-phenyl-propylamino |
| 3-tolyl | 2-acetamido-4-pyridyl | 3-phenyl-propylamino |
| 2-tolyl | 2-acetamido-4-pyridyl | 3-phenyl-propylamino |
| 4-trifluoromethylphenyl | 2-acetamido-4-pyridyl | 3-phenyl-propylamino |
| 3-trifluoromethylphenyl | 2-acetamido-4-pyridyl | 3-phenyl-propylamino |
| 2,6-dichlorophenyl | 2-acetamido-4-pyridyl | 3-phenyl-propylamino |
| 2,6-dimethylphenyl | 2-acetamido-4-pyridyl | 3-phenyl-propylamino |
| 3,4-dichlorophenyl | 2-acetamido-4-pyridyl | 3-phenyl-propylamino |
| 3,4-dimethylphenyl | 2-acetamido-4-pyridyl | 3-phenyl-propylamino |
| 2,4-dichlorophenyl | 2-acetamido-4-pyridyl | 3-phenyl-propylamino |
| 2,4-dimethylphenyl | 2-acetamido-4-pyridyl | 3-phenyl-propylamino |
| Phenyl | 2-amino-4-pyrimidinyl | 3-phenyl-propylamino |
| 4-fluorophenyl | 2-amino-4-pyrimidinyl | 3-phenyl-propylamino |
| 3-fluorophenyl | 2-amino-4-pyrimidinyl | 3-phenyl-propylamino |
| 2-fluorophenyl | 2-amino-4-pyrimidinyl | 3-phenyl-propylamino |
| 4-chlorophenyl | 2-amino-4-pyrimidinyl | 3-phenyl-propylamino |
| 3-chlorophenyl | 2-amino-4-pyrimidinyl | 3-phenyl-propylamino |
| 2-chlorophenyl | 2-amino-4-pyrimidinyl | 3-phenyl-propylamino |
| 4-tolyl | 2-amino-4-pyrimidinyl | 3-phenyl-propylamino |
| 3-tolyl | 2-amino-4-pyrimidinyl | 3-phenyl-propylamino |
| 2-tolyl | 2-amino-4-pyrimidinyl | 3-phenyl-propylamino |
| 4-trifluoromethylphenyl | 2-amino-4-pyrimidinyl | 3-phenyl-propylamino |
| 3-trifluoromethylphenyl | 2-amino-4-pyrimidinyl | 3-phenyl-propylamino |
| 2,6-dichlorophenyl | 2-amino-4-pyrimidinyl | 3-phenyl-propylamino |
| 2,6-dimethylphenyl | 2-amino-4-pyrimidinyl | 3-phenyl-propylamino |
| 3,4-dichlorophenyl | 2-amino-4-pyrimidinyl | 3-phenyl-propylamino |
| 3,4-dimethyl | 2-amino-4- | 3-phenyl-propylamino |

| R¹¹ | R¹² | R¹ |
|---|---|---|
| phenyl | pyrimidinyl | |
| 2,4-dichlorophenyl | 2-amino-4-pyrimidinyl | 3-phenyl-propylamino |
| 2,4-dimethyl phenyl | 2-amino-4-pyrimidinyl | 3-phenyl-propylamino |
| Phenyl | 4-pyridyl | (1-methyl-3-phenyl)propylamino |
| 4-fluorophenyl | 4-pyridyl | (1-methyl-3-phenyl)propylamino |
| 3-fluorophenyl | 4-pyridyl | (1-methyl-3-phenyl)propylamino |
| 2-fluorophenyl | 4-pyridyl | (1-methyl-3-phenyl)propylamino |
| 4-chlorophenyl | 4-pyridyl | (1-methyl-3-phenyl)propylamino |
| 3-chlorophenyl | 4-pyridyl | (1-methyl-3-phenyl)propylamino |
| 2-chlorophenyl | 4-pyridyl | (1-methyl-3-phenyl)propylamino |
| 4-tolyl | 4-pyridyl | (1-methyl-3-phenyl)propylamino |
| 3-tolyl | 4-pyridyl | (1-methyl-3-phenyl)propylamino |
| 2-tolyl | 4-pyridyl | (1-methyl-3-phenyl)propylamino. |
| 4-trifluoro-methylphenyl | 4-pyridyl | (1-methyl-3-phenyl)propylamino |
| 3-trifluoro-methylphenyl | 4-pyridyl | (1-methyl-3-phenyl)propylamino |
| 2,6-dichlorophenyl | 4-pyridyl | (1-methyl-3-phenyl)propylamino |
| 2,6-dimethyl phenyl | 4-pyridyl | (1-methyl-3-phenyl)propylamino |
| 3,4-dichlorophenyl | 4-pyridyl | (1-methyl-3-phenyl)propylamino |
| 3,4-dimethyl phenyl | 4-pyridyl | (1-methyl-3-phenyl)propylamino |
| 2,4-dichlorophenyl | 4-pyridyl | (1-methyl-3-phenyl)propylamino |
| 2,4-dimethyl phenyl | 4-pyridyl | (1-methyl-3-phenyl)propylamino |
| Phenyl | 2-amino-4-pyridyl | (1-methyl-3-phenyl)propylamino |
| 4-fluorophenyl | 2-amino-4-pyridyl | (1-methyl-3-phenyl)propylamino |
| 3-fluorophenyl | 2-amino-4-pyridyl | (1-methyl-3-phenyl)propylamino |
| 2-fluorophenyl | 2-amino-4-pyridyl | (1-methyl-3-phenyl)propylamino |
| 4-chlorophenyl | 2-amino-4-pyridyl | (1-methyl-3-phenyl)propylamino |
| 3-chlorophenyl | 2-amino-4-pyridyl | (1-methyl-3-phenyl)propylamino |
| 2-chlorophenyl | 2-amino-4-pyridyl | (1-methyl-3-phenyl)propylamino |
| 4-tolyl | 2-amino-4-pyridyl | (1-methyl-3-phenyl)propylamino |
| 3-tolyl | 2-amino-4-pyridyl | (1-methyl-3-phenyl)propylamino |
| 2-tolyl | 2-amino-4-pyridyl | (1-methyl-3-phenyl)propylamino |
| 4-trifluoro-methylphenyl | 2-amino-4-pyridyl | (1-methyl-3-phenyl)propylamino |
| 3-trifluoro-methylphenyl | 2-amino-4-pyridyl | (1-methyl-3-phenyl)propylamino |
| 2,6-dichlorophenyl | 2-amino-4-pyridyl | (1-methyl-3-phenyl)propylamino |
| 2,6-dimethyl phenyl | 2-amino-4-pyridyl | (1-methyl-3-phenyl)propylamino |
| 3,4-dichlorophenyl | 2-amino-4-pyridyl | (1-methyl-3-phenyl)propylamino |
| 3,4-dimethyl phenyl | 2-amino-4-pyridyl | (1-methyl-3-phenyl)propylamino |
| 2,4-dichlorophenyl | 2-amino-4-pyridyl | (1-methyl-3-phenyl)propylamino |
| 2,4-dimethyl phenyl | 2-amino-4-pyridyl | (1-methyl-3-phenyl)propylamino |
| Phenyl | 2-acetamido-4-pyridyl | (1-methyl-3-phenyl)propylamino |
| 4-fluorophenyl | 2-acetamido-4-pyridyl | (1-methyl-3-phenyl)propylamino |
| 3-fluorophenyl | 2-acetamido-4-pyridyl | (1-methyl-3-phenyl)propylamino |
| 2-fluorophenyl | 2-acetamido-4-pyridyl | (1-methyl-3-phenyl)propylamino |
| 4-chlorophenyl | 2-acetamido-4-pyridyl | (1-methyl-3-phenyl)propylamino |
| 3-chlorophenyl | 2-acetamido-4-pyridyl | (1-methyl-3-phenyl)propylamino |
| 2-chlorophenyl | 2-acetamido-4-pyridyl | (1-methyl-3-phenyl)propylamino |
| 4-tolyl | 2-acetamido-4-pyridyl | (1-methyl-3-phenyl)propylamino |
| 3-tolyl | 2-acetamido-4-pyridyl | (1-methyl-3-phenyl)propylamino |
| 2-tolyl | 2-acetamido-4-pyridyl | (1-methyl-3-phenyl)propylamino |
| 4-trifluoro-methylphenyl | 2-acetamido-4-pyridyl | (1-methyl-3-phenyl)propylamino |
| 3-trifluoro-methylphenyl | 2-acetamido-4-pyridyl | (1-methyl-3-phenyl)propylamino |
| 2,6-dichlorophenyl | 2-acetamido-4-pyridyl | (1-methyl-3-phenyl)propylamino |
| 2,6-dimethyl phenyl | 2-acetamido-4-pyridyl | (1-methyl-3-phenyl)propylamino |
| 3,4-dichlorophenyl | 2-acetamido-4-pyridyl | (1-methyl-3-phenyl)propylamino |
| 3,4-dimethyl phenyl | 2-acetamido-4-pyridyl | (1-methyl-3-phenyl)propylamino |
| 2,4-dichlorophenyl | 2-acetamido-4-pyridyl | (1-methyl-3-phenyl)propylamino |
| 2,4-dimethyl phenyl | 2-acetamido-4-pyridyl | (1-methyl-3-phenyl)propylamino |
| Phenyl | 2-amino-4-pyrimidinyl | (1-methyl-3-phenyl)propylamino |
| 4-fluorophenyl | 2-amino-4-pyrimidinyl | (1-methyl-3-phenyl)propylamino |
| 3-fluorophenyl | 2-amino-4-pyrimidinyl | (1-methyl-3-phenyl)propylamino |
| 2-fluorophenyl | 2-amino-4-pyrimidinyl | (1-methyl-3-phenyl)propylamino |
| 4-chlorophenyl | 2-amino-4-pyrimidinyl | (1-methyl-3-phenyl)propylamino |
| 3-chlorophenyl | 2-amino-4-pyrimidinyl | (1-methyl-3-phenyl)propylamino |
| 2-chlorophenyl | 2-amino-4-pyrimidinyl | (1-methyl-3-phenyl)propylamino |
| 4-tolyl | 2-amino-4-pyrimidinyl | (1-methyl-3-phenyl)propylamino |
| 3-tolyl | 2-amino-4-pyrimidinyl | (1-methyl-3-phenyl)propylamino |
| 2-tolyl | 2-amino-4-pyrimidinyl | (1-methyl-3-phenyl)propylamino |
| 4-trifluoro-methylphenyl | 2-amino-4-pyrimidinyl | (1-methyl-3-phenyl)propylamino |
| 3-trifluoro-methylphenyl | 2-amino-4-pyrimidinyl | (1-methyl-3-phenyl)propylamino |
| 2,6-dichlorophenyl | 2-amino-4-pyrimidinyl | (1-methyl-3-phenyl)propylamino |
| 2,6-dimethyl phenyl | 2-amino-4-pyrimidinyl | (1-methyl-3-phenyl)propylamino |
| 3,4-dichlorophenyl | 2-amino-4-pyrimidinyl | (1-methyl-3-phenyl)propylamino |
| 3,4-dimethyl phenyl | 2-amino-4-pyrimidinyl | (1-methyl-3-phenyl)propylamino |
| 2,4-dichlorophenyl | 2-amino-4-pyrimidinyl | (1-methyl-3-phenyl)propylamino |
| 2,4-dimethyl phenyl | 2-amino-4-pyrimidinyl | (1-methyl-3-phenyl)propylamino |
| 4-fluorophenyl | 4-pyridyl | 4-fluorobenzylamino |
| 4-fluorophenyl | 2-acetamido-4-pyridyl | 4-fluorobenzylamino |
| 4-fluorophenyl | 2-amino-4-pyrimidinyl | 4-fluorobenzylamino |

-continued

| $R^{11}$ | $R^{12}$ | $R^1$ |
|---|---|---|
| 4-fluorophenyl | 4-pyridylnyl | (2-(4-fluorophenyl)-1-methyl-ethyl)amino |
| 4-fluorophenyl | 2-acetamido-4-pyridyl | (2-(4-fluorophenyl)-1-methyl-ethyl)amino |
| 4-fluorophenyl | 2-amino-4-pyrimidinyl | (2-(4-fluorophenyl)-1-methyl-ethyl)amino |
| 4-fluorophenyl | 4-pyridyl | (1,1-dimethyl-2-(4-fluorophenyl)-ethyl)amino |
| 4-fluorophenyl | 2-acetamido-4-pyridyl | (1,1-dimethyl-2-(4-fluorophenyl)-ethyl)amino |
| 4-fluorophenyl | 2-amino-4-pyrimidinyl | (1,1-dimethyl-2-(4-fluorophenyl)-ethyl)amino |
| 4-fluorophenyl | 4-pyridyl | 2-(4-fluorophenyl)-2-methyl-ethylamino |
| 4-fluorophenyl | 2-acetamido-4-pyridyl | (2-(4-fluorophenyl)-2-methyl-ethyl)amino |
| 4-fluorophenyl | 2-amino-4-pyrimidinyl | (2-(4-fluorophenyl)-2-methyl-ethyl)amino |
| 4-fluorophenyl | 4-pyridyl | (2-methyl-2-phenylethyl)amino |
| 4-fluorophenyl | 2-acetamido-4-pyridyl | (2-methyl-2-phenylethyl)amino |
| 4-fluorophenyl | 2-amino-4-pyrimidinyl | (2-methyl-2-phenylethyl)amino |
| 4-fluorophenyl | 4-pyridyl | methyl-(2-phenylethyl)amino |
| 4-fluorophenyl | 2-acetamido-4-pyridyl | methyl-(2-phenylethyl)amino |
| 4-fluorophenyl | 2-amino-4-pyrimidinyl | methyl-(2-phenylethyl)amino |
| 4-fluorophenyl | 4-pyridyl | (2-(4-trifluoromethylphenyl)ethyl)amino |
| 4-fluorophenyl | 2-acetamido-4-pyridyl | (2-(4-trifluoromethylphenyl)ethyl)amino |
| 4-fluorophenyl | 2-amino-4-pyrimidinyl | (2-(4-trifluoromethylphenyl)ethyl)amino |
| 4-fluorophenyl | 4-pyridyl | 2-(4-tolyl)ethylamino |
| 4-fluorophenyl | 2-acetamido-4-pyridyl | 2-(4-tolyl)ethylamino |
| 4-fluorophenyl | 2-amino-4-pyrimidinyl | 2-(4-tolyl)ethylamino |
| 4-fluorophenyl | 4-pyridyl | (2-(3-fluorophenyl)ethyl)amino |
| 4-fluorophenyl | 2-acetamido-4-pyridyl | (2-(3-fluorophenyl)ethyl)amino |
| 4-fluorophenyl | 2-amino-4-pyrimidinyl | (2-(3-fluorophenyl)ethyl)amino |
| 4-fluorophenyl | 4-pyridyl | (2-(2-fluorophenyl)ethyl)amino |
| 4-fluorophenyl | 2-acetamido-4-pyridyl | (2-(2-fluorophenyl)ethyl)amino |
| 4-fluorophenyl | 2-amino-4-pyrimidinyl | (2-(2-fluorophenyl)ethyl)amino |
| 4-fluorophenyl | 4-pyridyl | methyl-(2-(2-pyridyl)ethyl)amino |
| 4-fluorophenyl | 2-acetamido-4-pyridyl | methyl-(2-(2-pyridyl)ethyl)amino |
| 4-fluorophenyl | 2-amino-4-pyrimidinyl | methyl-(2-(2-pyridyl)ethyl)amino |
| 4-fluorophenyl | 4-pyridyl | (1,1-dimethyl-3-phenyl-propyl)amino |
| 4-fluorophenyl | 2-acetamido-4-pyridyl | (1,1-dimethyl-3-phenyl-propyl)amino |
| 4-fluorophenyl | 2-amino-4-pyrimidinyl | (1,1-dimethyl-3-phenyl-propyl)amino |
| 4-fluorophenyl | 4-pyridyl | (3-(4-fluorophenyl)-propyl)amino |
| 4-fluorophenyl | 2-acetamido-4-pyridyl | (3-(4-fluorophenyl)-propyl)amino |
| 4-fluorophenyl | 2-amino-4-pyrimidinyl | (3-(4-fluorophenyl)-propyl)amino |
| 4-fluorophenyl | 4-pyridyl | (3-(4-fluorophenyl)-1-methyl-propyl)amino |
| 4-fluorophenyl | 2-acetamido-4-pyridyl | (3-(4-fluorophenyl)-1-methyl-propyl)amino |
| 4-fluorophenyl | 2-amino-4-pyrimidinyl | (3-(4-fluorophenyl)-1-methyl-propyl)amino |
| 4-fluorophenyl | 4-pyridyl | (1,1-dimethyl-3-(4-fluorophenyl)-propyl)amino |
| 4-fluorophenyl | 2-acetamido-4-pyridyl | (1,1-dimethyl-3-(4-fluorophenyl)-propyl)amino |
| 4-fluorophenyl | 2-amino-4-pyrimidinyl | (1,1-dimethyl-3-(4-fluorophenyl)-propyl)amino |
| 4-fluorophenyl | 4-pyridyl | (3-(2-fluorophenyl)-propyl)amino |
| 4-fluorophenyl | 2-acetamido-4-pyridyl | (3-(2-fluorophenyl)-propyl)amino |
| 4-fluorophenyl | 2-amino-4-pyrimidinyl | (3-(2-fluorophenyl)-propyl)amino |
| 4-fluorophenyl | 4-pyridyl | (3-methyl-3-phenyl-propyl)amino |
| 4-fluorophenyl | 2-acetamido-4-pyridyl | (3-methyl-3-phenyl-propyl)amino |
| 4-fluorophenyl | 2-amino-4-pyrimidinyl | (3-methyl-3-phenyl-propyl)amino |
| 4-fluorophenyl | 4-pyridyl | (2-methyl-3-phenyl-propyl)amino |
| 4-fluorophenyl | 2-acetamido-4-pyridyl | (2-methyl-3-phenyl-propyl)amino |
| 4-fluorophenyl | 2-amino-4-pyrimidinyl | (2-methyl-3-phenyl-propyl)amino |
| 4-fluorophenyl | 4-pyridyl | (3,3-dimethylbutyl)amino |
| 4-fluorophenyl | 2-acetamido-4-pyridyl | (3,3-dimethylbutyl)amino |
| 4-fluorophenyl | 2-amino-4-pyrimidinyl | (3,3-dimethylbutyl)amino |
| 4-fluorophenyl | 4-pyridyl | isoamylamino |
| 4-fluorophenyl | 2-acetamido-4-pyridyl | isoamylamino |
| 4-fluorophenyl | 2-amino-4-pyrimidinyl | isoamylamino |
| 4-fluorophenyl | 4-pyridyl | amylamino |
| 4-fluorophenyl | 2-acetamido-4-pyridyl | amylamino |
| 4-fluorophenyl | 2-amino-4-pyrimidinyl | amylamino |
| 4-fluorophenyl | 4-pyridyl | (2,5-dimethyl)pentylamino |
| 4-fluorophenyl | 2-acetamido-4-pyridyl | (2,5-dimethyl)pentylamino |
| 4-fluorophenyl | 2-amino-4-pyrimidinyl | (2,5-dimethyl)pentylamino |
| 4-fluorophenyl | 4-pyridyl | piperazinyl |
| 4-fluorophenyl | 2-acetamido-4-pyridyl | piperazinyl |
| 4-fluorophenyl | 2-amino-4-pyrimidinyl | piperazinyl |
| 4-fluorophenyl | 4-pyridyl | (3-(3-fluorophenyl)-propyl)amino |
| 4-fluorophenyl | 2-acetamido-4-pyridyl | (3-(3-fluorophenyl)-propyl)amino |
| 4-fluorophenyl | 2-amino-4-pyrimidinyl | (3-(3-fluorophenyl)-propyl)amino |
| benzyl | 4-pyridyl | 3-phenylpropylamino |
| benzyl | 4-pyridyl | 2-(4-fluorophenyl)ethylamino |
| 2-thienyl | 4-pyridyl | 3-phenylpropylamino |
| 2-thienyl | 4-pyridyl | 2-(4-fluorophenyl)ethylamino |
| cyclohexyl | 4-pyridyl | 3-phenylpropylamino |
| cyclohexyl | 4-pyridyl | 2-(4-fluorophenyl)ethylamino |
| tert-butyl | 4-pyridyl | 3-phenylpropylamino |
| tert-butyl | 4-pyridyl | 2-(4-fluorophenyl)ethylamino |
| 4-fluorophenyl | 4-piperidinyl | 3-phenylpropylamino |
| 4-fluorophenyl | 4-piperidinyl | 2-(4-fluorophenyl)ethylamino |
| 4-fluorophenyl | 4-pyranyl | 3-phenylpropylamino |
| 4-fluorophenyl | 4-pyranyl | 2-(4-fluorophenyl)ethylamino |
| Phenyl | 4-pyridyl | 3-phenyl-2-amino-propylamino |
| 4-fluorophenyl | 4-pyridyl | 3-phenyl-2-amino- |

-continued

| R^11 | R^12 | R^1 |
|---|---|---|
| 3-fluorophenyl | 4-pyridyl | propylamino 3-phenyl-2-amino-propylamino |
| 2-fluorophenyl | 4-pyridyl | 3-phenyl-2-amino-propylamino |
| 4-chlorophenyl | 4-pyridyl | 3-phenyl-2-amino-propylamino |
| 3-chlorophenyl | 4-pyridyl | 3-phenyl-2-amino-propylamino |
| 2-chlorophenyl | 4-pyridyl | 3-phenyl-2-amino-propylamino |
| 4-tolyl | 4-pyridyl | 3-phenyl-2-amino-propylamino |
| 3-tolyl | 4-pyridyl | 3-phenyl-2-amino-propylamino |
| 2-tolyl | 4-pyridyl | 3-phenyl-2-amino-propylamino |
| 4-trifluoro-methylphenyl | 4-pyridyl | 3-phenyl-2-amino-propylamino |
| 3-trifluoro-methylphenyl | 4-pyridyl | 3-phenyl-2-amino-propylamino |
| 2,6-dichlorophenyl | 4-pyridyl | 3-phenyl-2-amino-propylamino |
| 2,6-dimethylphenyl | 4-pyridyl | 3-phenyl-2-amino-propylamino |
| 3,4-dichlorophenyl | 4-pyridyl | 3-phenyl-2-amino-propylamino |
| 3,4-dimethylphenyl | 4-pyridyl | 3-phenyl-2-amino-propylamino |
| 2,4-dichlorophenyl | 4-pyridyl | 3-phenyl-2-amino-propylamino |
| 2,4-dimethylphenyl | 4-pyridyl | 3-phenyl-2-amino-propylamino |
| Phenyl | 4-pyridyl | 3-phenyl-3-amino-propylamino |
| 4-fluorophenyl | 4-pyridyl | 3-phenyl-3-amino-propylamino |
| 3-fluorophenyl | 4-pyridyl | 3-phenyl-3-amino-propylamino |
| 2-fluorophenyl | 4-pyridyl | 3-phenyl-3-amino-propylamino |
| 4-chlorophenyl | 4-pyridyl | 3-phenyl-3-amino-propylamino |
| 3-chlorophenyl | 4-pyridyl | 3-phenyl-3-amino-propylamino |
| 2-chlorophenyl | 4-pyridyl | 3-phenyl-3-amino-propylamino |
| 4-tolyl | 4-pyridyl | 3-phenyl-3-amino-propylamino |
| 3-tolyl | 4-pyridyl | 3-phenyl-3-amino-propylamino |
| 2-tolyl | 4-pyridyl | 3-phenyl-3-amino-propylamino |
| 4-trifluoro-methylphenyl | 4-pyridyl | 3-phenyl-3-amino-propylamino |
| 3-trifluoro-methylphenyl | 4-pyridyl | 3-phenyl-3-amino-propylamino |
| 2,6-dichlorophenyl | 4-pyridyl | 3-phenyl-3-amino-propylamino |
| 2,6-dimethylphenyl | 4-pyridyl | 3-phenyl-3-amino-propylamino |
| 3,4-dichlorophenyl | 4-pyridyl | 3-phenyl-3-amino-propylamino |
| 3,4-dimethylphenyl | 4-pyridyl | 3-phenyl-3-amino-propylamino |
| 2,4-dichlorophenyl | 4-pyridyl | 3-phenyl-3-amino-propylamino |
| 2,4-dimethylphenyl | 4-pyridyl | 3-phenyl-3-amino-propylamino | and

-continued

| R^11 | R^12 | R^1 |
|---|---|---|

[Structure: pyrimidinone with $R_{11}$ at 5-position, $R_{12}$ at 6-position, $R_1$ at 2-position, N-CH$_2$CH$_3$ at 3-position, C=O at 4-position]

wherein $R^{11}$, $R^{12}$, and $R^1$ are one of the combination given in the following table:

| R^11 | R^12 | R^1 |
|---|---|---|
| 4-fluorophenyl | 4-pyridyl | (2-(4-fluorophenyl)ethyl)amino |
| 4-fluorophenyl | 2-acetamido-4-pyridyl | (2-(4-fluorophenyl)ethyl)amino |
| 4-fluorophenyl | 2-amino-4-pyrimidinyl | (2-(4-fluorophenyl)ethyl)amino |
| 4-fluorophenyl | 4-pyridyl | (3-phenylpropyl)amino |
| 4-fluorophenyl | 2-acetamido-4-pyridyl | (3-phenylpropyl)amino |
| 4-fluorophenyl | 2-amino-4-pyrimidinyl | (3-phenylpropyl)amino |
| 4-fluorophenyl | 4-pyridyl | (S)-2-amino-3-phenylpropylamino |
| 4-fluorophenyl | 2-acetamido-4-pyridyl | (S)-2-amino-3-phenylpropylamino |
| 4-fluorophenyl | 2-amino-4-pyrimidinyl | (S)-2-amino-3-phenylpropylamino |
| 4-fluorophenyl | 4-pyridyl | 3-amino-3-phenylpropylamino |
| 4-fluorophenyl | 2-acetamido-4-pyridyl | 3-amino-3-phenylpropylamino |
| 4-fluorophenyl | 2-amino-4-pyrimidinyl | 3-amino-3-phenylpropylamino |
| 4-fluorophenyl | 4-pyridyl | 3-amino-2-methyl-3-phenylpropylamino |
| 4-fluorophenyl | 2-acetamido-4-pyridyl | 3-amino-2-methyl-3-phenylpropylamino |
| 4-fluorophenyl | 2-amino-4-pyrimidinyl | 3-amino-2-methyl-3-phenylpropylamino |
| 4-fluorophenyl | 4-pyridyl | (S)-tetrahydroisoquinol-3-ylmethylenamino |
| 4-fluorophenyl | 2-acetamido-4-pyridyl | (S)-tetrahydroisoquinol-3-ylmethylenamino |
| 4-fluorophenyl | 2-amino-4-pyrimidinyl | (S)-tetrahydroisoquinol-3-ylmethylenamino |
| 4-fluorophenyl | 4-pyridyl | (S)-3-benzylpiperazinyl |
| 4-fluorophenyl | 2-acetamido-4-pyridyl | (S)-3-benzylpiperazinyl |
| 4-fluorophenyl | 2-amino-4-pyrimidinyl | (S)-3-benzylpiperazinyl | and

[Structure: pyridinone with $R_{11}$, $R_{12}$, $R_2$, $R_1$ substituents and N-CH$_3$]

in which $R^2$ is H, methyl or benzyl, and $R^{11}$, $R^{12}$, and $R^1$ are one of the combinations given in the following table:

| R¹¹ | R¹² | R¹ |
|---|---|---|
| Phenyl | 4-pyridyl | phenyl |
| 4-fluorophenyl | 4-pyridyl | phenyl |
| Phenyl | 2-acetamidopyridyl | phenyl |
| 4-fluorophenyl | 2-acetamidopyridyl | phenyl |
| Phenyl | 4-pyridyl | 4-ethylphenyl |
| 4-fluorophenyl | 4-pyridyl | 4-ethylphenyl |
| Phenyl | 2-acetamidopyridyl | 4-ethylphenyl |
| 4-fluorophenyl | 2-acetamidopyridyl | 4-ethylphenyl |
| Phenyl | 4-pyridyl | 2,4-dimethylphenyl |
| 4-fluorophenyl | 4-pyridyl | 2,4-dimethylphenyl |
| Phenyl | 2-acetamidopyridyl | 2,4-dimethylphenyl |
| 4-fluorophenyl | 2-acetamidopyridyl | 2,4-dimethylphenyl |
| Phenyl | 4-pyridyl | 2,6-dichlorobenzyl |
| 4-fluorophenyl | 4-pyridyl | 2,6-dichlorobenzyl |
| Phenyl | 2-acetamidopyridyl | 2,6-dichlorobenzyl |
| 4-fluorophenyl | 2-acetamidopyridyl | 2,6-dichlorobenzyl |
| Phenyl | 4-pyridyl | 2-(4-fluorophenyl)ethylamino |
| 4-fluorophenyl | 4-pyridyl | 2-(4-fluorophenyl)ethylamino |
| Phenyl | 2-acetamidopyridyl | 2-(4-fluorophenyl)ethylamino |
| 4-fluorophenyl | 2-acetamidopyridyl | 2-(4-fluorophenyl)ethylamino |
| Phenyl | 4-pyridyl | 3-phenylpropylamino |
| 4-fluorophenyl | 4-pyridyl | 3-phenylpropylamino |
| Phenyl | 2-acetamidopyridyl | 3-phenylpropylamino |
| 4-fluorophenyl | 2-acetamidopyridyl | 3-phenylpropylamino |
| Phenyl | 4-pyridyl | 1-piperazinyl |
| 4-fluorophenyl | 4-pyridyl | 1-piperazinyl |
| Phenyl | 2-acetamidopyridyl | 1-piperazinyl |
| 4-fluorophenyl | 2-acetamidopyridyl | 1-piperazinyl |
| benzyl | 4-pyridyl | 3-phenylpropylamino |
| benzyl | 4-pyridyl | 2-(4-fluorophenyl)ethylamino |
| 2-thienyl | 4-pyridyl | 3-phenylpropylamino |
| 2-thienyl | 4-pyridyl | 2-(4-fluorophenyl)ethylamino |
| cyclohexyl | 4-pyridyl | 3-phenylpropylamino |
| cyclohexyl | 4-pyridyl | 2-(4-fluorophenyl)ethylamino |
| tert-butyl | 4-pyridyl | 3-phenylpropylamino |
| tert-butyl | 4-pyridyl | 2-(4-fluorophenyl)ethylamino |
| 4-fluorophenyl | 4-piperidinyl | 3-phenylpropylamino |
| 4-fluorophenyl | 4-piperidinyl | 2-(4-fluorophenyl)ethylamino |
| 4-fluorophenyl | 4-pyranyl | 3-phenylpropylamino |
| 4-fluorophenyl | 4-pyranyl | 2-(4-fluorophenyl)ethylamino |
| Phenyl | 4-pyridyl | (S)-2-amino-3-phenylpropylamino |
| 4-fluorophenyl | 4-pyridyl | (S)-2-amino-3-phenylpropylamino |
| Phenyl | 2-acetamidopyridyl | (S)-2-amino-3-phenylpropylamino |
| 4-fluorophenyl | 2-acetamidopyridyl | (S)-2-amino-3-phenylpropylamino |
| Phenyl | 4-pyridyl | 3-amino-3-phenylpropylamino |
| 4-fluorophenyl | 4-pyridyl | 3-amino-3-phenylpropylamino |
| Phenyl | 2-acetamidopyridyl | 3-amino-3-phenylpropylamino |
| 4-fluorophenyl | 2-acetamidopyridyl | 3-amino-3-phenylpropylamino |
| Phenyl | 4-pyridyl | 3-amino-2-methyl-3-phenylpropyl-amino |
| 4-fluorophenyl | 4-pyridyl | 3-amino-2-methyl-3-phenylpropyl-amino |
| Phenyl | 2-acetamidopyridyl | 3-amino-2-methyl-3-phenylpropyl-amino |
| 4-fluorophenyl | 2-acetamidopyridyl | 3-amino-2-methyl-3-phenylpropyl-amino |
| Phenyl | 4-pyridyl | (S)-tetrahydroisoquinol-3-yl-methylenamino |
| 4-fluorophenyl | 4-pyridyl | (S)-tetrahydroisoquinol-3-yl-methylenamino |
| Phenyl | 2-acetamidopyridyl | (S)-tetrahydroisoquinol-3-yl-methylenamino |
| 4-fluorophenyl | 2-acetamidopyridyl | (S)-tetrahydroisoquinol-3-yl-methylenamino |
| Phenyl | 4-pyridyl | (S)-3-benzylpiperazinyl |
| 4-fluorophenyl | 4-pyridyl | S)-3-benzylpiperazinyl |
| Phenyl | 2-acetamidopyridyl | S)-3-benzylpiperazinyl |
| 4-fluorophenyl | 2-acetamidopyridyl | S)-3-benzylpiperazinyl |

Additional preferred compounds are listed in the Examples, infra.

As utilized herein, the following terms shall have the following meanings:

"Alkyl", alone or in combination, means a straight-chain or branched-chain alkyl radical containing preferably 1–15 carbon atoms ($C_1C_{15}$), more preferably 1–8 carbon atoms ($C_1$–$C_8$), even more preferably 1–6 carbon atoms ($C_1$–$C_6$), yet more preferably 1–4 carbon atoms ($C_1$–$C_4$), still more preferably 1–3 carbon atoms ($C_1$–$C_3$), and most preferably 1–2 carbon atoms ($C_1$–$C_2$). Examples of such radicals include methyl, ethyl, n-propyl, isopropyl, n-butyl, siobutyl, sec-butyl, tert-butyl, pentyl, iso-amyl, hexyl, octyl and the like.

"Hydroxylalkyl", alone or in combination, means an alkyl radical as defined above wherein at least one hydrogen radical is replaced with a hydroxyl radical, preferably 1–3 hydrogen radicals are replaced by hydroxyl radicals, more preferably 1–2 hydrogen radicals are replaced by hydroxyl radicals, and most preferably one hydrogen radical is replaced by a hydroxyl radical. Examples of such radicals include hydroxymethyl, 1-, 2-hydroxyethyl, 1-, 2-, 3-hydroxypropyl, 1,3-dihydroxy-2-propyl, 1,3-dihydroxybutyl, 1,2,3,4,5,6-hexahydroxy-2-hexyl and the like.

"Alkenyl", alone or in combination, means a straight-chain or branched-chain hydrocarbon radical having one or more double bonds, preferably 1–2 double bonds and more preferably one double bond, and containing preferably 2–15 carbon atoms ($C_2$–$C_{15}$), more preferably 2–8 carbon atoms ($C_2$–$C_8$), even more preferably 2–6 carbon atoms ($C_2$–$C_6$), yet more preferably 2–4 carbon atoms ($C_2$–$C_4$), and still more preferably 2–3 carbon atoms ($C_2$–$C_3$). Examples of such alkenyl radicals include ethenyl, propenyl, 2-methylpropenyl, 1,4-butadienyl and the like.

"Alkoxy", alone or in combination, means a radical of the type "R—O—" wherein "R" is an alkyl radical as defined above and "O" is an oxygen atom. Examples of such alkoxy radicals include methoxy, ethoxy, n-propoxy, isopropoxy, n-butoxy, iso-butoxy, sec-butoxy, tert-butoxy and the like.

"Alkoxycarbonyl", alone or in combination, means a radical of the type "R—O—C(O)—" wherein "R—O—" is an alkoxy radical as defined above and "C(O)" is a carbonyl radical.

"Alkoxycarbonylamino", alone or in combination, means a radical of the type "R—O—C(O)—NH—" wherein "R—O—C(O)" is an alkoxycarbonyl radical as defined above, wherein the amino radical may optionally be substituted, such as with alkyl, aryl, aralkyl, cycloalkyl, cycloalkylalkyl and the like.

"Alkylthio", alone or in combination, means a radical of the type "R—S—" wherein "R" is an alkyl radical as defined above and "S" is a sulfur atom. Examples of such alkylthio radicals include methylthio, ethylthio, n-propylthio, isopropylthio, n-butylthio, iso-butylthio, sec-butylthio, tert-butylthio and the like.

"Alkylsulfinyl", alone or in combination, means a radical of the type "R—S(O)—" wherein "R" is an alkyl radical as defined above and "S(O)" is a mono-oxygenated sulfur atom. Examples of such alkylsulfinyl radicals include methylsulfinyl, ethylsulfinyl, n-propylsulfinyl, isopropylsulfinyl, n-butylsulfinyl, iso-butylsulfinyl, sec-butylsulfinyl, tert-butylsulfinyl and the like.

"Alkylsulfonyl", alone or in combination, means a radical of the type "R—S(O)$_2$—" wherein "R" is an alkyl radical as defined above and "S(O)$_2$" is a di-oxygenated sulfur atom. Examples of such alkylsulfonyl radicals include methylsulfonyl, ethylsulfonyl, n-propylsulfonyl, isopropylsulfonyl, n-butylsulfonyl, iso-butylsulfonyl, sec-butylsulfonyl, tert-butylsulfonyl and the like.

"Aryl", alone or in combination, means a phenyl or biphenyl radical, which is optionally benzo fused or heterocyclo fused and which is optionally substituted with one or more substituents selected from alkyl, alkoxy, halogen, hydroxy, amino, azido, nitro, cyano, haloalkyl, carboxy, alkoxycarbonyl, cycloalkyl, alkanoylamino, amido, amidino, alkoxycarbonylamino, N-alkylamidino, alkylamino, dialkylamino, aminoalkyl, alkylaminoalkyl, dialkylaminoalkyl, N-alkylamido, N,N-dialkylamido, aralkoxycarbonylamino, alkylthio, alkylsulfinyl, alkylsulfonyl, oxo and the like. Examples of aryl radicals are phenyl, o-tolyl, 4-methoxyphenyl, 2-(tert-butoxy)phenyl, 3-methyl-4-methoxyphenyl, 2—$CF_3$-phenyl, 2-fluorophenyl, 2-chlorophenyl, 3-nitrophenyl, 3-aminophenyl, 3-acetamidophenyl, 2-amino-3-(aminomethyl)phenyl, 6-methyl-3-acetamidophenyl, 6-methyl-2-aminophenyl, 6-methyl-2,3-diaminophenyl, 2-amino-3-methylphenyl, 4,6-dimethyl-2-aminophenyl, 4-hydroxyphenyl, 3-methyl-4-hydroxyphenyl, 4-(2-methoxyphenyl)phenyl, 2-amino-1-naphthyl, 2-naphthyl, 3-amino-2-naphthyl, 1-methyl-3-amino-2-naphthyl, 2,3-diamino-1-naphthyl, 4,8-dimethoxy-2-naphthyl and the like.

"Aralkyl" and "arylalkyl", alone or in combination, means an alkyl radical as defined above in which at least one hydrogen atom, preferably 1–2, is replaced by an aryl radical as defined above, such as benzyl, 1-, 2-phenylethyl, dibenzylmethyl, hydroxyphenylmethyl, methylphenylmethyl, diphenylmethyl, dichlorophenylmethyl, 4-methoxyphenylmethyl and the like.

"Aralkoxy", alone or in combination, means an alkoxy radical as defined above in which at least one hydrogen atom, preferably 1–2, is replaced by an aryl radical as defined above, such as benzyloxy, 1-, 2-phenylethoxy, dibenzylmethoxy, hydroxyphenylmethoxy, methylphenylmethoxy, dichlorophenylmethoxy, 4-methoxyphenylmethoxy and the like.

"Aralkoxycarbonyl", alone or in combination, means a radical of the type "R—O—C(O)—" wherein "R—O—" is an aralkoxy radical as defined above and "—C(O)—" is a carbonyl radical.

"Alkanoyl", alone or in combination, means a radical of the type "R—C(O)—" wherein "R" is an alkyl radical as defined above and "—C(O)—" is a carbonyl radical. Examples of such alkanoyl radicals include acetyl, trifluoroacetyl, hydroxyacetyl, propionyl, butyryl, valeryl, 4-methylvaleryl, and the like.

"Alkanoylamino", alone or in combination, means a radical of the type "R—C(O)—NH—" wherein "R—C(O)—" is an alkanoyl radical as defined above, wherein the amino radical may optionally be substituted, such as with alkyl, aryl, aralkyl, cycloalkyl, cycloalkylalkyl and the like.

"Aminocarbonyl", alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like.

"Aminosulfonyl", alone or in combination, means an amino substituted sulfonyl radical.

"Benzo", alone or in combination, means the divalent radical $C_6H_4$=derived from benzene. "Benzo fused" forms a ring system in which benzene and a cycloalkyl or aryl group have two carbons in common, for example tetrahydronaphthylene and the like.

"Bicyclic" as used herein is intended to include both fused ring systems, such as naphthyl and β-carbolinyl, and substituted ring systems, such as biphenyl, phenylpyridyl and diphenylpiperazinyl.

"Cycloalkyl", alone or in combination, means a saturated or partially saturated, preferably one double bond, monocyclic, bicyclic or tricyclic carbocyclic alkyl radical, preferably monocyclic, containing preferably 5–12 carbon atoms ($C_5$–$C_{12}$), more preferably 5–10 carbon atoms ($C_5$–$C_{10}$), even more preferably 5–7 carbon atoms ($C_5$–$C_7$), which is optionally benzo fused or heterocyclo fused and which is optionally substituted as defined herein with respect to the definition of aryl. Examples of such cycloalkyl radicals include cyclopentyl, cyclohexyl, dihydroxycyclohexyl, ethylenedioxycyclohexyl, cycloheptyl, octahydronaphthyl, tetrahydronaphthyl, octahydroquinolinyl, dimethoxytetrahydronaphthyl, 2,3-dihydro-1H-indenyl, azabicyclo[3.2.1]octyl and the like.

"Heteroatoms" means nitrogen, oxygen and sulfur heteroatoms.

"Heterocyclo fused" forms a ring system in which a heterocyclyl or heteroaryl group of 5–6 ring members and a cycloalkyl or aryl group have two carbons in common, for example indole, isoquinoline, tetrahydroquinoline, methylenedioxybenzene and the like.

"Heterocyclyl" means a saturated or partially unsaturated, preferably one double bond, monocyclic or bicyclic, preferably monocyclic, heterocycle radical containing at least one, preferably 1 to 4, more preferably 1 to 3, even more preferably 1–2, nitrogen, oxygen or sulfur atom ring member and having preferably 3–8 ring members in each ring, more preferably 5–8 ring members in each ring and even more preferably 5–6 ring members in each ring. "Heterocyclyl" is intended to include sulfone and sulfoxide derivatives of sulfur ring members and N-oxides of tertiary nitrogen ring members, and carbocyclic fused, preferably 3–6 ring carbon atoms and more preferably 5–6 ring carbon atoms, and benzo fused ring systems. "Heterocyclyl" radicals may optionally be substituted on at least one, preferably 1–4, more preferably 1–3, even more preferably 1–2, carbon atoms by halogen, alkyl, alkoxy, hydroxy, oxo, thioxo, aryl, aralkyl, heteroaryl, heteroaralkyl, amidino, N-alkylamidino, alkoxycarbonylamino, alkylsulfonylamino and the like, and/or on a secondary nitrogen atom by hydroxy, alkyl, aralkoxycarbonyl, alkanoyl, alkoxycarbonyl, heteroaralkyl, aryl or aralkyl radicals. More preferably, "heterocyclyl", alone or in combination, is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals. Examples of such heterocyclyl radicals include pyrrolidinyl, piperidinyl, piperazinyl, morpholinyl, thiamorpholinyl, 4-benzyl-piperazin-1-yl, pyrimidinyl, tetrahydrofuryl, pyrazolidonyl, pyrazolinyl, pyridazinonyl, pyrrolidonyl, tetrahydrothienyl and its sulfoxide and sulfone derivatives, 2,3-dihydroindolyl, tetrahydroquinolinyl, 1,2,3,4- tetrahydroisoquinolinyl, 1,2,3,4-tetrahydro-1-oxo-isoquinolinyl, 2,3-dihydrobenzofuryl, benzopyranyl, methylenedioxyphenyl, ethylenedioxyphenyl and the like.

"Heteroaryl" means a monocyclic or bicyclic, preferably monocyclic, aromatic heterocycle radical, having at least one, preferably 1 to 4, more preferably 1 to 3, even more preferably 1–2, nitrogen, oxygen or sulfur atom ring members and having preferably 5–6 ring members in each ring, which is optionally saturated carbocyclic fused, preferably 3–4 carbon atoms ($C_3$–$C_4$) to form 5–6 ring membered rings and which is optionally substituted as defined above with respect to the definitions of aryl. Examples of such heteroaryl groups include imidazolyl, 1-benzyloxycarbonylimidazol-4-yl, pyrrolyl, pyrazolyl, pyridyl, 3-(2-methyl)pyridyl, 3-(4-trifluoromethyl)pyridyl, pyrimidinyl, 5-(4-trifluoromethyl)pyrimidinyl, pyrazinyl, triazolyl, furyl, thienyl, oxazolyl, thiazolyl, indolyl, quinolinyl, 5,6,7,8-tetrahydroquinolyl, 5,6,7,8-tetrahydroisoquinolinyl, quinoxalinyl, benzothiazolyl-, benzofuryl, benzimidazolyl, benzoxazolyl and the like.

"Heteroaralkyl" and "heteroarylalkyl," alone or in combination, means an alkyl radical as defined above in which at least one hydrogen atom, preferably 1–2, is replaced by a heteroaryl radical as defined above, such as 3-furylpropyl, 2-pyrrolyl propyl, chloroquinolinylmethyl, 2-thienylethyl, pyridylmethyl, 1-imidazolylethyl and the like.

"Halogen" and "halo", alone or in combination, means fluoro, chloro, bromo or iodo radicals.

"Haloalkyl", alone or in combination, means an alkyl radical as defined above in which at least one hydrogen atom, preferably 1–3, is replaced by a halogen radical, more preferably fluoro or chloro radicals Examples of such haloalkyl radicals include 1,1,1-trifluoroethyl, chloromethyl, 1-bromoethyl, fluoromethyl, difluoromethyl, trifluoromethyl, bis(trifluoromethyl) methyl and the like.

"Pharmacologically acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulphuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the-art and include alkaline, alkaline earth, ammonium, quaternary ammonium cations and the like. For additional examples of "pharmacologically acceptable salts," see infra and Berge et al, *J. Pharm. Sci.* 66, 1 (1977).

"Cytokine" means a secreted protein that affects the functions of other cells, particularly as it relates to the modulation of interactions between cells of the immune system or cells involved in the inflammatory response. Examples of cytokines include but are not limited to interleukin 1 (IL-1), preferably IL-1β, interleukin 6 (IL-6), interleukin 8 (IL-8) and TNF, preferably TNF-α (tumor necrosis factor-α).

"TNF, IL-1, IL-6, and/or IL-8 mediated disease or disease state" means all disease states wherein TNF, IL-1, IL-6, and/or IL-8 plays a role, either.-directly as TNF, IL-1, IL-6, and/or IL-8 itself, or by TNF, IL-1, IL-6, and/or IL-8 inducing another cytokine to be released. For example, a disease state in which IL-1 plays a major role, but in which the production of or action of IL-1 is a result of TNF, would be considered mediated by TNF.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6–10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also sutiable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis (dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium flouride reagent, either as a discrete reaction step or in situ during a reaction with the alcohol group. Suitable silylating agents are, for example, trimethylsilyl chloride, tert-buty-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

The symbols used above have the following meanings:

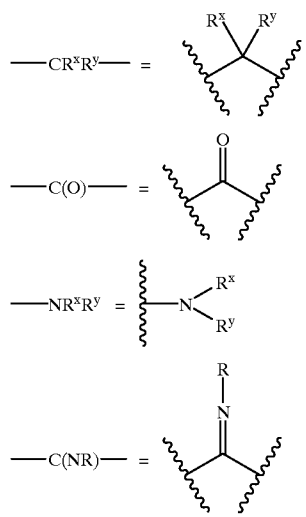

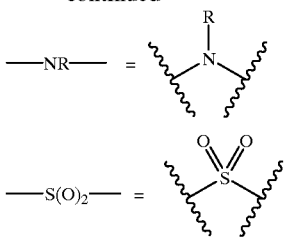

Prodrugs of the compounds of this invention are also contemplated by this invention. A prodrug is an active or inactive compound that is modified chemically through in vivo physicological action, such as hydrolysis, metabolism and the like, into a compound of this invention following adminstration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

Compounds according to the invention can be synthesized according to one or more of the following methods. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

4(3H)-Pyrimidinones:

For the synthesis of 4(3H)-pyrimidinones II (or its tautomer, 4-hydroxy-pyrimidines), the approach displayed in Scheme 1 may be followed (for a review of synthetic methods see: D. J. Brown, Heterocyclic Compounds: the Pyrimidines, supra). This approach involves the cyclization reaction between an acrylic acid ester XII and an amidine V followed by oxidation of the resulting dihydropyrimidinone XIII to give II.

Scheme 1

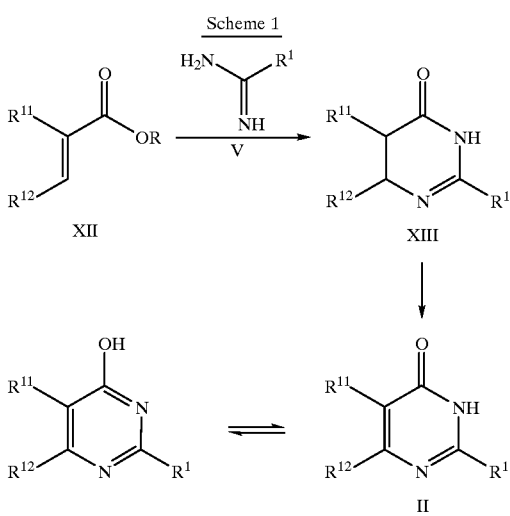

For the synthesis of 2-substituted 5-(4-fluorophenyl)-6-(4-pyridyl)-4-hydroxy-pyrimidines II (Scheme 2), the disubstituted acrylic acid ester XII may be prepared conveniently by condensation of pyridine-4-carboxaldehyde with 4-fluorophenylacetic acid followed by esterification. XII may be reacted with a variety of amidines V at elevated temperature. As a dehydrogenating agent for the conversion of XIII to II, sodium nitrite/acetic acid is suitable.

Accordingly, further compounds of formula II may be obtained in which $R^{12}$ is any other heteroaryl ring within the definition of $R^{12}$ by the appropriate choice of starting material. Such starting materials include but are not limited to 2-methylpyridine-4-carboxaldehyde, 2,6-dimethylpyridine-4-carboxaldehyde (Mathes and Sauermilch, Chem. Ber. 88, 1276–1283 (1955)), quinoline-4-carboxaldehyde, pyrimidine-4-carboxaldehyde, 6-methylpyrimidine-4-carbox-aldehyde, 2-methylpyrimidine-4-carboxaldehyde, 2,6-dimethylpyrimidine-4-carboxaldehyde (Bredereck et al., Chem. Ber. 97, 3407–3417 (1964)). The use of 2-nitropyridine-4-carboxaldehyde would lead to a derivative of formula II with $R^{12}$ represented by a 2-nitro-4-pyridyl group. Catalytic reduction of the nitro to an amino group would provide the 2-amino-4-pyridyl derivative of II. The approach displayed in Scheme 2 is applicable to the use of other aryl acetic acids leading to compounds of formula II with different aryl groups as $R^{11}$.

Pyrimidinone II ($R^1$=H) may be substituted at the N-3 position by reaction with e.g. an alkyl halide, such as methyl iodide or ethyl bromide in the presence of an appropriate base such as potassium carbonate and the like.

Scheme 2

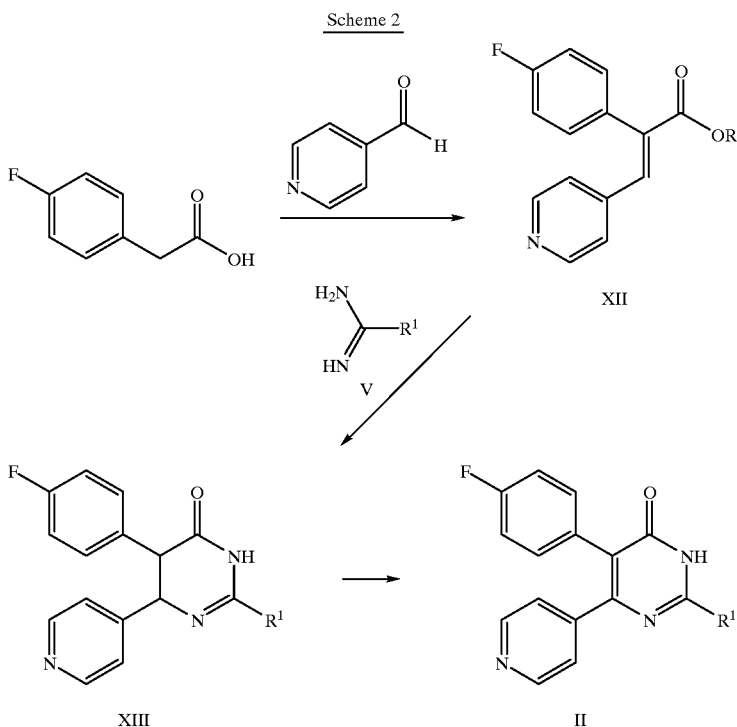

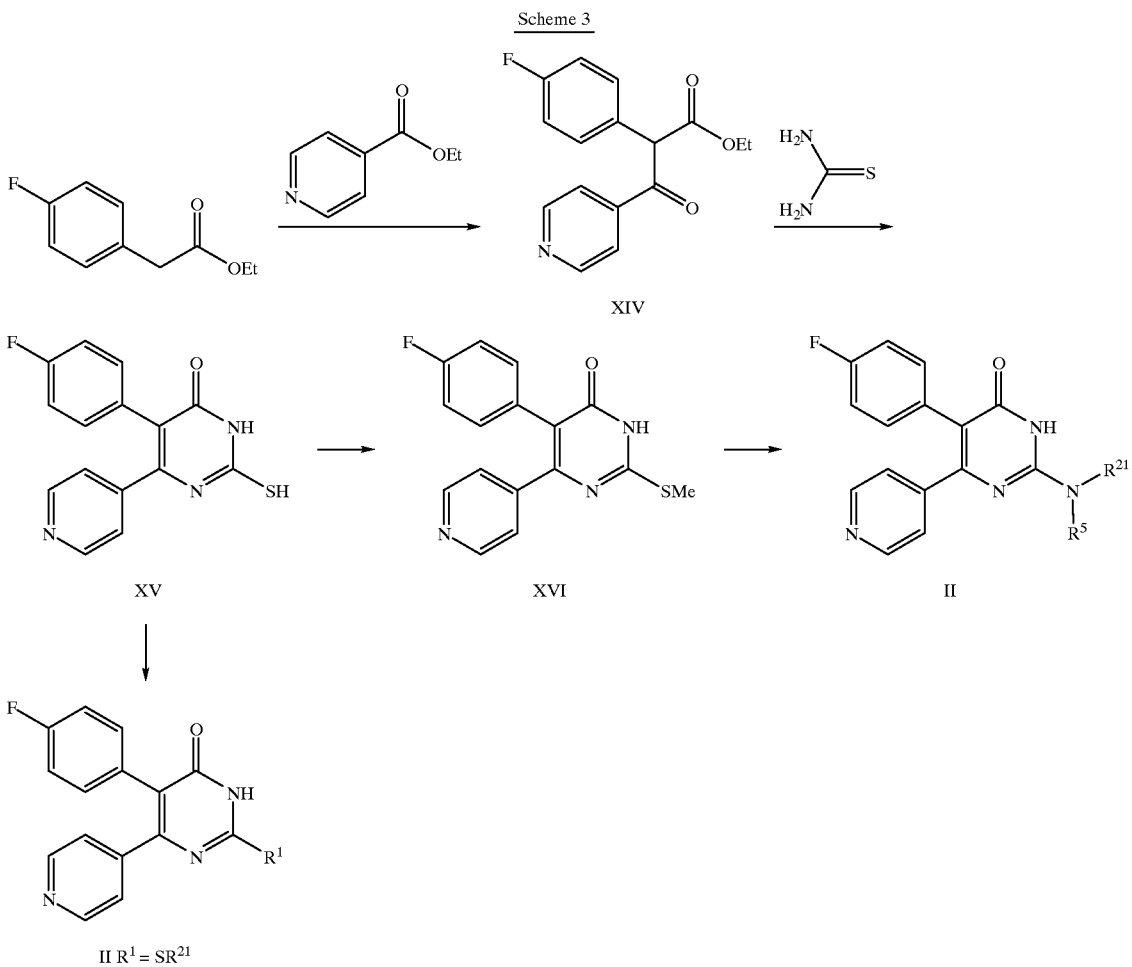

Scheme 3

Another approach (Scheme 3) leading to 5,6-diaryl-4-hydroxy-pyrimidines involves the cyclization of the b-keto ester XIV with thiourea to give the thiouracil derivative XV. XV can be S-monomethylated to XVI. Reaction of XVI with primary and secondary amines leads to 2-amino substituted 4-hydroxy-pyrimidines II. Further 2-thioether derivatives of II with $R^1=SR^{21}$ can be obtained, for example by alkylation of XV with alkyl halides. Treatment of XV or XVI with Raney nickel and $H_2$ provides compounds of structure II wherein $R^1$ is H.

Although Scheme 3 illustrates syntheses in which $R^{12}$ is 4-pyridyl, this approach may be equally applied to any other heteroaryl ring within the definition of $R^{12}$ by the appropriate choice of the starting material. Such starting materials include but are not limited to ethyl 2-methyl isonicotinate (Efimovsky and Rumpf, *Bull. Soc. Chim. FR.* 648–649 (1954)), methyl pyrimidine-4-carboxylate, methyl 2-methylpyrimidine-4-carboxylate, methyl 6-methylpyrimidine-4-carboxylate and methyl 2,6-dimethylpyrimidine-4-carboxylate (Sakasi et al., *Heterocycles* 13, 235 (1978)). Likewise, methyl 2-nitroisonicotinate (Stanonis, *J. Org. Chem.* 22, 475 (1957)) may be reacted with an aryl acetic acid ester followed by cyclization of the resultant b-keto ester with thiourea analogously to Scheme 3. Subsequent catalytic reduction of the nitro group to an amino group would give a pyrimidinone II in which $R_{12}$ is represented by a 2-amino-4-pyridyl group (Scheme 4).

Scheme 4

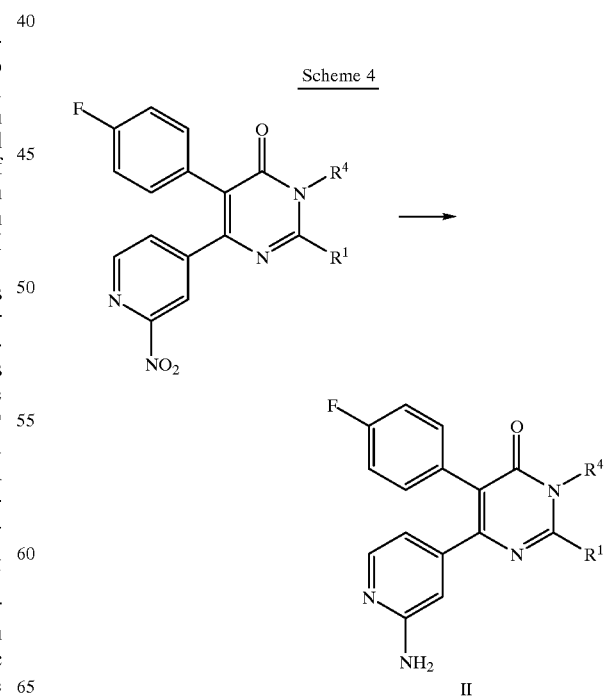

Furthermore, methyl 2-acetamido isonicotinate (Scheme 5) may be reacted analogously to Scheme 3 after appropriate protection of the amide nitrogen with e.g. a tert-butyldimethylsilyloxymethyl group (Benneche et al., *Acta Chem. Scand.* B 42 384–389 (1988)), a tert-butyldimethylsilyl group, a benzyloxymethyl group, a benzyl group or the like ($P_1$).

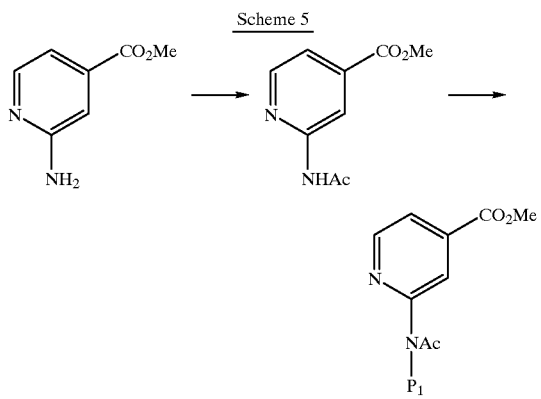

Scheme 5

Removal of the protecting group $P_1$ of the resulting pyrimidine II with a suitable reagent (e.g., tetrabutylammonium fluoride in the case where $P_1$ is t-butyldimethylsilyloxymethyl) would then lead to a pyrimidinone II with $R^{12}$ represented by a 2-acetamido-4-pyridyl group. Needless to say, ethyl p-fluorophenyl acetate may be substituted by any alkyl arylacetate in the procedure illustrated in Scheme 3 thus providing compounds of formula II with different $R^{11}$ aryl substituents.

In a further process, pyrimidinones II may be prepared by coupling a suitable derivative of XVIII (L is a leaving group, such as halogen radical and the like) with an appropriate aryl equivalent.

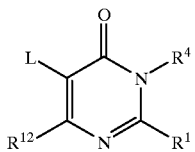

Such aryl/heteroaryl couplings are well known to those skilled in the art and involve an organic-metallic component for reaction with a reactive derivative, e.g., a halogeno derivative, of the second compound in the presence of a catalyst. The metallo-organic species may be provided either by the pyrimidinone in which case the aryl component provides the reactive halogen equivalent or the pyrimidinone may be in the form of a reactive 5-halogeno derivative for reaction with a metallo organic aryl compound. Accordingly, 5-bromo and 5-iodo derivatives of XVIII (L=Br, I) may be treated with arylalkyl tin compounds, e.g., trimethylstannylbenzene, in an inert solvent such as tetrahydrofuran in the presence of a palladium catalyst, such as di(triphenylphosphine)palladium(II)dichloride. (Peters et al., *J. Heterocyclic Chem.* 27, 2165–2173, (1990). Alternatively, the halogen derivative of XVIII may be converted into a trialkyltin derivative (L=$Bu_3Sn$) by reaction with e.g. tributylstannyl chloride following lithiation with butyllithium and may then be reacted with an aryl halide in the presence of a catalyst. (Sandosham and Undheim, *Acta Chem. Scand.* 43, 684–689 (1989). Both approaches would lead to pyrimidines II in which $R^{11}$ is represented by aryl and heteroaryl groups.

As reported in the literature (Kabbe, *Lieb. Ann. Chem.* 704, 144 (1967); German Patent 1271116 (1968)) and displayed in Scheme 6, 5-aryl-2,6-dipyridyl-4(3H)-pyrimidinones II may be prepared in a one step synthesis by reaction of the cyanopyridine with an arylacetyl ester, such as ethyl phenylacetate in the presence of sodium methoxide.

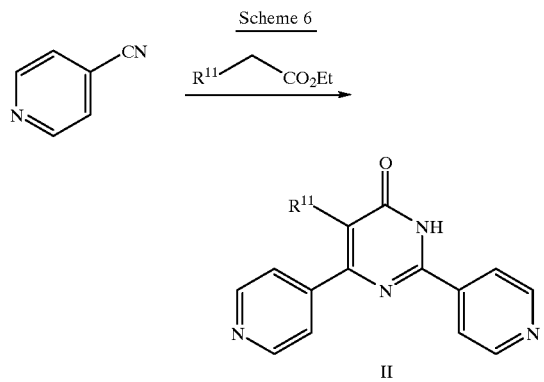

Scheme 6

In Scheme 7, compounds of the present invention of formula XXX can be readily prepared by reacting the methylthio intermediate XXXI with the amine $NHR^5R^{21}$, for example by heating the mixture preferably at a temperature greater than 100° C., more preferably 150–210° C. Alternatively, compounds of formula XXX can be readily prepared by reacting the methylsulfonyl intermediate XXXII with the amine $NHR^5R^{21}$, for example by heating the mixture preferably at a temperature greater than 40° C., more preferably 50–210° C.

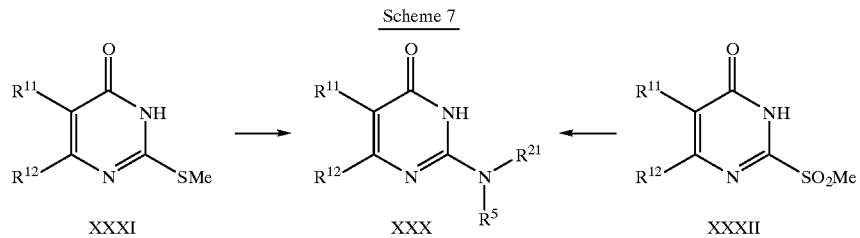

Scheme 7

Amines of formula $NHR^5R^{21}$ are commercially available or can be readily prepared by those skilled in the art from commercially available starting materials. For example, an amide, nitro or cyano group can be reduced under reducing conditions, such as in the presence of a reducing agent like lithium aluminum hydride and the like, to form the corresponding amine. Alkylation and acylation of amino groups are well known in the art. Chiral and achiral substituted amines can be prepared from chiral amino acids and amino acid amides (for example, alkyl, aryl, heteroaryl, cycloalkyl, arylalkyl, heteroarylalkyl, cycloalkylalkyl and the like substituted glycine, β-alanine and the like) using methods well known in the art, such as H. Brunner, P. Hankofer, U. Holzinger, B. Treittinger and H. Schoenenberger, Eur. J. Med. Chem. 25, 35–44, 1990; M. Freiberger and R. B. Hasbrouck, J. Am. Chem. Soc. 82, 696–698, 1960; Dornow and Fust, Chem. Ber. 87, 984, 1954; M. Kojima and J. Fujita, Bull. Chem. Soc. Jpn. 55, 1454–1459, 1982; W. Wheeler and D. O'Bannon, Journal of Labelled Compounds and Radiopharmaceuticals XXXI, 306, 1992; and S. Davies, N. Garrido, O. Ichihara and I. Walters, J. Chem. Soc., Chem. Commun. 1153, 1993.

Pyridones:

As displayed in Scheme 8, a suitable route to 2(1 H)-pyridones III involves the cyclization reaction between an a,b-unsaturated ketone XXII and a sufficiently reactive, substituted acetamide in the presence of base (El-Rayyes and Al-Hajjar, *J. Heterocycl. Chem.* 21, 1473 (1984)) and subsequent dehydrogenation.

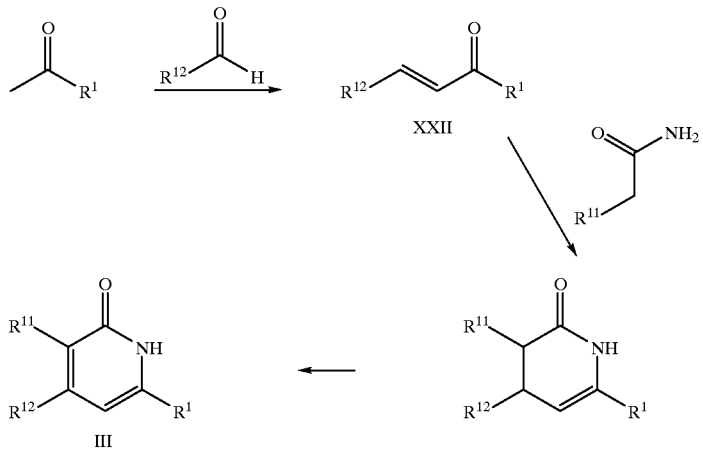

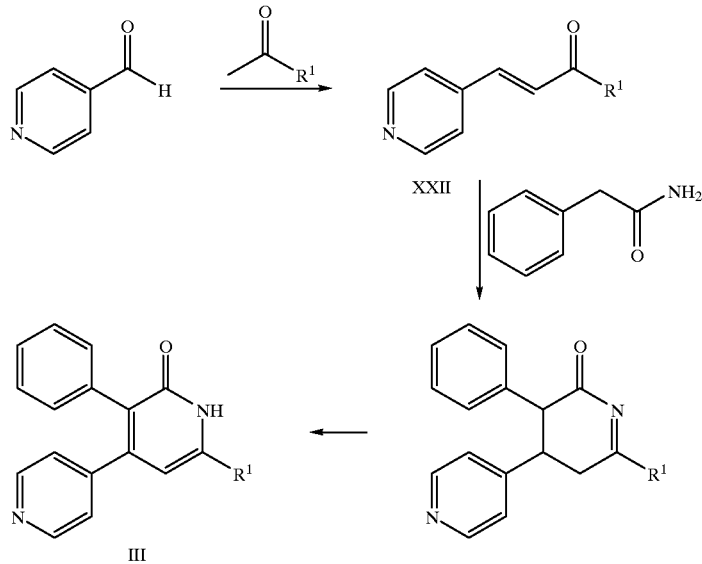

Accordingly (Scheme 9), pyridine-4-carboxaldehyde or other heteroaromatic carboxaldehyde-like pyrimidine-4-carboxaldehydes or quinoline-4-carboxyaldehydes may be reacted with acetyl aryl, acetyl heteroaryl or acetyl cycloalkyl derivatives in the presence of piperidine/acetic acid at elevated temperature (Bayer and Hartmann, *Arch. Pharm.* (Weinheim) 324, 815 (1991)) as well as pinacolone ($CH_3$—CO—$C(CH_3)_3$) in the presence of sodium hydroxide to provide the unsaturated ketone XXII (or the analogous ketone from the corresponding heteroaromatic-4-carboxyaldehyde). The reaction of XXII with phenylacetamide in the presence of sodium ethoxide then may lead via the 3,4-dihydropyridone to 6-substituted 3-phenyl-4-(heteroaryl)-2(1 H)-pyridones of structure III.

In Scheme 10, a feasible route is illustrated leading to 6-chloro-2(1 H)-pyridone XXIV, a versatile intermediate for further modifications at the 6-position. This approach (G. Simchen, Chem. Ber. 103, 389–397 (1970) is based on the conversion of the unsaturated g-cyanocarboxylic acid chloride XXIII into XXIV in the presence of hydrogen chloride.

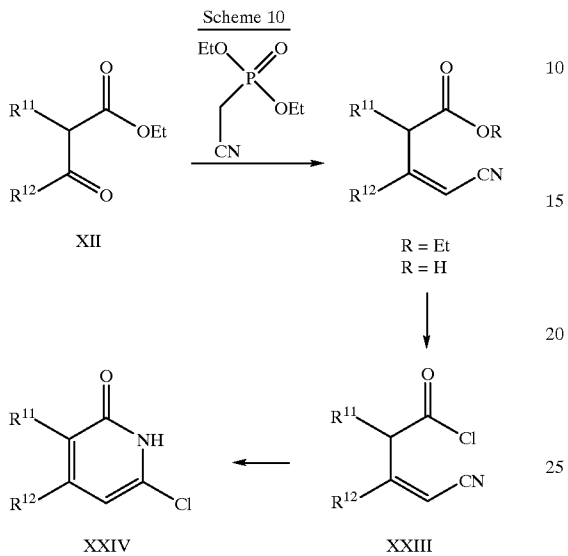

Reaction of XXIV with ammonia (Katritzky and Rachwal, J. Heterocylic Chem. 32, 1007 (1995)), primary and secondary amines would lead to 2-amino substituted pyridones III. Furthermore, XXIV may be reacted in a palladium or nickel catalyzed cross-coupling reaction with an alkyl or aryl boronic acid or an alkyl or aryl zinc halide to provide pyridone III wherein $R^3$ is alkyl or aryl or heteroaryl.

In addition, pyridone III may be substituted at the N-1 position by reaction with, e.g., an alkyl halide in the presence of an appropriate base such as potassium carbonate.

An approach that may lead to a pyrimidinone of the general formula III is illustrated in Scheme 11.

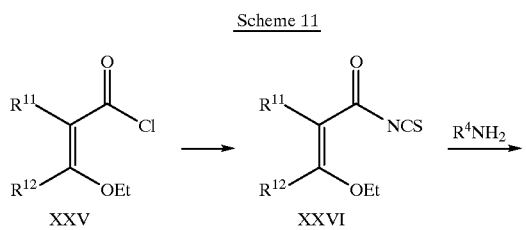

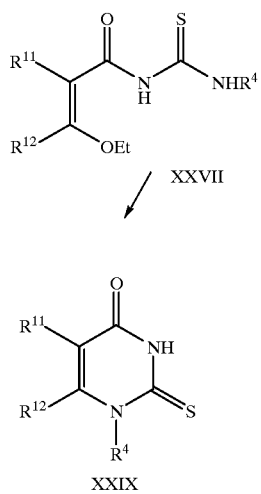

According to this approach (Shaw and Warrener, J. Chem. Soc. 153–156 (1958); Hronowski and Szarek, Can. J. Chem. 63, 2787 (1985); Agathocleous and Shaw, J. Chem. Soc. Perkin Trans. I, 2555 (1993)), an ethoxyacryloyl isothiocyanate XXVI is reacted with a primary amine to give as an addition product the acylthiourea XXVII which can be cyclized under basic or acidic conditions to the thiouracil compound XXVIII. XXVIII may be methylated to the methylthio derivative XXIX, a versatile intermediate for further transformations at the 2-position.

Fused 4(3 H)-Pyrimidinones:

As displayed in Schemes 12 and 13, introduction of a suitable $R^4$ group through the alkylation of XXXIII affords an intermediate to the fused 5, 6, or 7 membered ring systems of Formula I wherein $R^1$ and V or W are joined. The synthesis utilizes a haloalkylamine in which the amino group is protected through reaction with 1,2-bis (chlorodimethylsilyl)ethane affording the cyclic stabase derivative (see:Basha and Debernardis Tetrahedron Lett 5271, 1984) which protects the amine in the subsequent alkylation step (sodium hydride, DMF).

Scheme 12

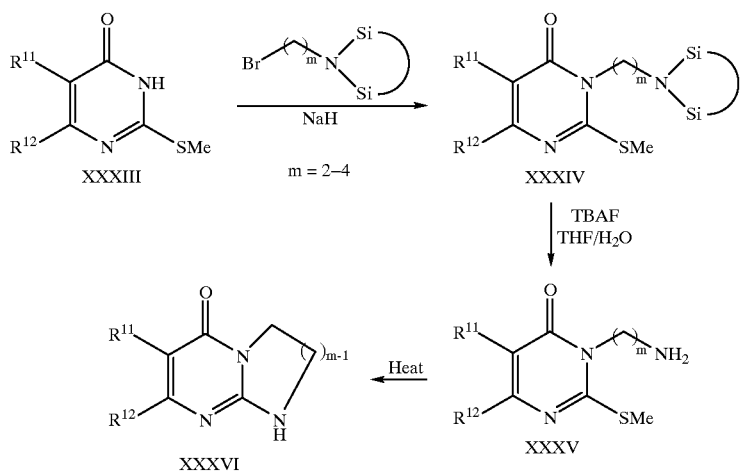

Scheme 13

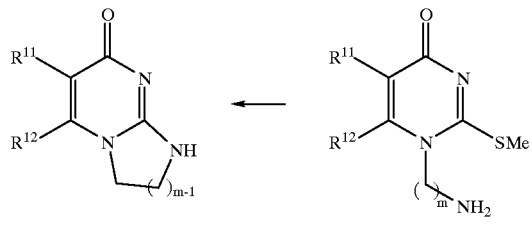

Deprotection of the amine can be accomplished with acid treatment (p-toluenesulfonic acid) or tetrabutylammonium fluoride treatment. The free amine can then be cyclized in an intramolecular fashion by warming to high temperatures. The bromoalkylamines are either commercially available (eg. 3-bromopropylamine hydrobromide, 2-bromoethylamine hydrobromide) or they can be synthesized from the corresponding haloalkylazide followed by reduction of the azide to the amine (see: Hendry et al Tetrahedron Lett 4597 (1987)). More functionalized haloalkylamines can be used as long as the functional groups are tolerated in the transformations shown in scheme 12 including the bromo derivatives obtained from amino acid precursors as described by Baldwin et al (Synlett. 51–53, 1993) and Leanna et al (Tetrahedron Lett. 4485, 1993).

Alternatively, the fused ring system can be made through the addition of a hydroxyalkylamine as outlined in Scheme 14. Initially, the amine component of the hydroxyalkylamine displaces the 2-methylthio group to afford compound XXX-VII which is followed by conversion of the alcohol to a suitable leaving group (eg. methanesulfonate or trifluoromethanesulfonate). Closure of the ring can be accomplished by treatment with an excess of sodium hydride in DMF to afford XXXVI.

Scheme 14

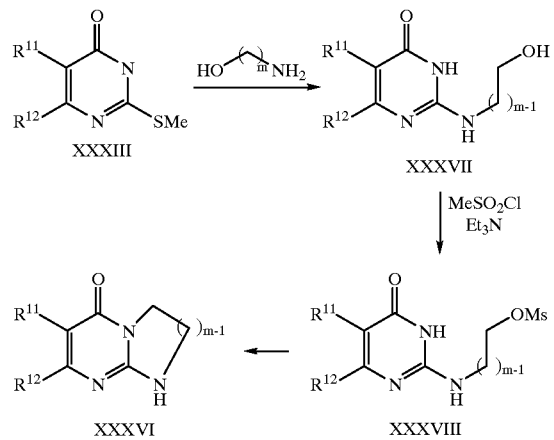

The 6,5 fused ring systems can be obtained as outlined in Scheme 15. Alkylation of the N-3 nitrogen with 3-bromo-1-trimethylsilylpropyne can be followed by a displacement of the 2-methylthio group with the appropriate amine component exemplified but not limited to a phenylalkylamine. The 2-amino group under the reaction conditions cyclizes onto the acetylene as shown with a loss of the trimethylsilyl group as well. This transformation is illustrated in the examples below wherein 3-phenyl-1-propylamine and benzylamine are reacted with 3-(3-trimethylsilyl-2-propynyl)-5-(4-fluorophenyl)-2-methylthio-6-(4-pyridyl)-4(3 H)-pyrimidinone to afford the corresponding 6, 5 fused system.

63

Scheme 15

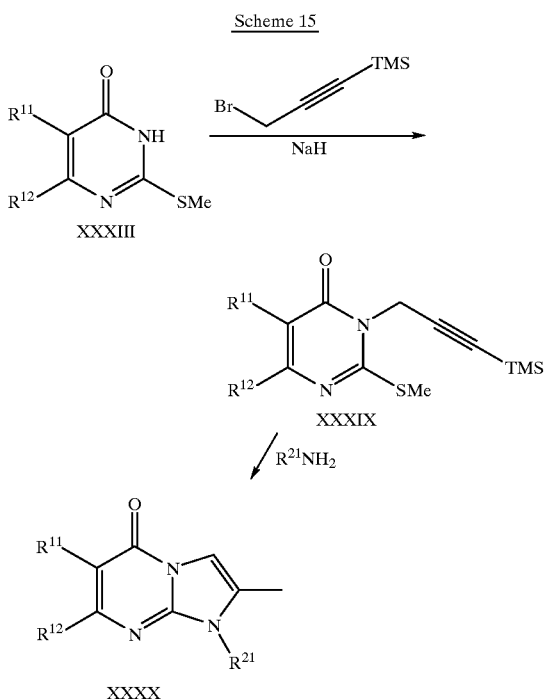

Scheme 16

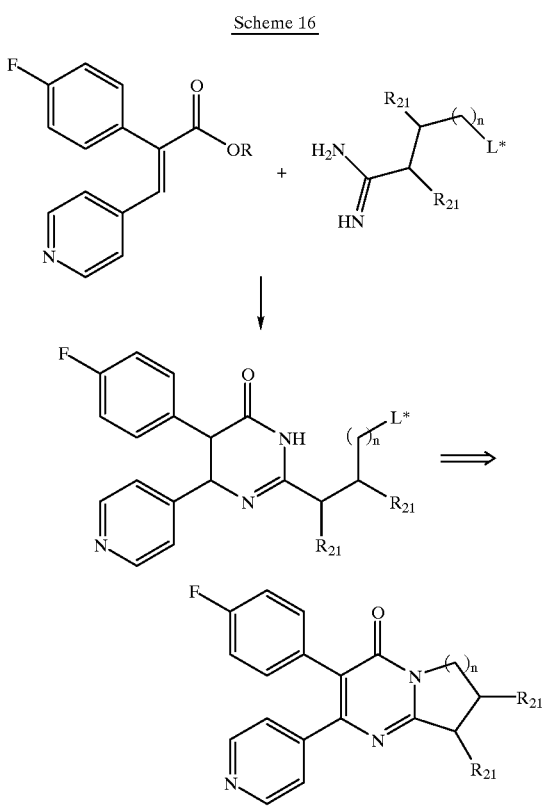

Compounds of the invention when U is $CHR_{21}$ can be prepared according to Scheme 2 above wherein R1 contains an leaving group or a group which can be converted into a leaving group (L*) which can be reacted with a primidine nitrogen atoms to form the fused ring (see Scheme 16).

64

The following Examples are presented for illustrative purposes only and are not intended, nor should they be construed, as limiting the invention in any manner. Those skilled in the art will appreciate that modifications and variations of the compounds disclosed herein can be made without violating the spirit or scope of the present invention.

EXAMPLES

Example 1

General procedure for the preparation of 2-substituted 5-(4-fluorophenyl)-6-(4-pyridyl)-4(3 H)-pyrimidones a. 2-(4-Fluorophenyl)-3-(4-pyridyl)-acrylic acid: A mixture of 4-fluorophenylacetic acid (9 g, 58.4 mmol), 4-pyridinecarboxaldehyde (5.6 ml, 58.6 mmol), pyridine (6 ml) and acetic anhydride (6 ml) was heated at 150° C. for 1 h followed by evaporation and co-distillation with water. The resulting material crystallized on addition of ethanol. The solids were filtered and washed with ethanol and ethyl acetate to provide the title compound. MS (m/z): 244.0 (M+H)$^+$; $C_{14}H_{10}FNO_2$ requir. 243.2 $^1$H-NMR (DMSO-d$_6$): d 8.43, 6.98 (2d, each 2 H, Pyrid.), 7.73 (s, 1 H, CH=), 7.21 (d, 4 H, PhF).

b. Ethyl 2-(4-fluorophenyl)-3-(4-pyridyl)-acrylate: Conc. sulfuric acid (2.2 ml) was added carefully to a suspension of 2-(4-fluorophenyl)-3-(4-pyridyl)-acrylic acid (6.7 g, 27.5 mmol) in ethanol (120 ml) and the mixture was heated at reflux for 24 h. The solvent was evaporated, the remainder was taken up in dichloromethane and the organic solution was washed with aqueous sodium hydrogencarbonate and water, followed by drying and evaporation. Flash column chromatography on silica gel (hexane-acetone=2:1) provided the pure title compound. MS (m/z): 271.8 (M+H)+; $C_{16}H_{14}FNO_2$ requir. 271.3 [1] H-NMR (CDCl$_3$): 8.44, 6.88 (2 m, each 2 H, Pyrid.), 7.72 (s, 1 H, CH=), 7.16, 7.06 (2m, each 2 H, PhF), 4.28 (q, 2 H, CH$_2$), 1.28 (t, 3 H, CH$_3$).

c. General procedure: A stirred mixture of ethyl 2-(4-fluorophenyl)-3-(4-pyridyl)-acrylate (357 mg, 1.38 mmol), the amidine hydrochloride (2.61 mmol) and sodium methoxide (250 mg, 4.62 mmol) in ethanol (5 ml) was heated in a sealed tube at 120° C. for 3 h. It was neutralized with 2N hydrochloric acid prior to evaporation. The residue was taken up in acetic acid (25 ml) and treated with sodium nitrite (670 mg, 9.71 mmol) at 44° C. for 20 min. After evaporation, the resultant product was taken up in dichloromethane and the solution was washed with aqueous sodium hydrogencarbonate and water before drying and evaporation. The product was purified by recrystallization from methanol. If the crude product of nitrite oxidation was water soluble, as was found for 5-(4-fluorophenyl)-2-methyl-6-(4-pyridyl)-4(3 H)-pyrimidinone, then no aqueous work up was done, but the material obtained on evaporation was applied to a column of silica gel (5% methanol/dichloromethane) prior to recrystallization.

The following compounds were prepared accordingly using the appropriate amidine hydrochloride:

1-1 5-(4-Fluorophenyl)-2-methyl-6-(4-pyridyl)-4(3 H)-pyrimidinone: MS (m/z): 282.2 (M+H)+; $C_{16}H_{12}FN_3O$ requir. 281.3 [1] H-NMR (DMSO-d$_6$): d 8.46 (m 2 H, Pyrid.), 7.2-7.03 (m, 6 H, PhF, Pyrid.). 2.38 (s, 3 H, CH$_3$). R1=CH$_3$—

1-2 5-(4-Fluorophenyl)-2-isopropyl-6-(4-pyridyl)-4(3 H)-pyrimidinone: MS (m/z): 310.0 (M+H)+; $C_{18}H_{16}FN_3O$ requir. 309.4 $^1$H-NMR (DMSO-d$_6$): 8.45 (m, 2 H, Pyrid.), 7.21-7.03 (m, 6 H, PhF, Pyrid.), 2.90 (m, 1 H, CH(CH$_3$)$_2$,) 1.26, 1.24 (2s, each 3 H, 2CH$_3$). R1=(CH$_3$)$_2$CH—

1-3 2-(2,6-Dichlorobenzyl)-5-(4-fluorophenyl)-6-(4-pyridyl)-4(3 H)-pyrimidinone: MS (m/z): 426.0 (M)+; $C_{22}H_{14}Cl_2FN_3O$ requir. 426.3 [1] H-NMR (DMSO-d$_6$): d 8.37 (m, 2 H, Pyrid.), 7.50 (d, 2 H, PhCl$_2$), 7.35 (t, 1 H, PhCl$_2$), 7.18-7.08 (m, 4 H, PhF), 6.96 (m, 2 H, Pyrid.), 4.36 (s, 2 H, CH$_2$).

R1 = 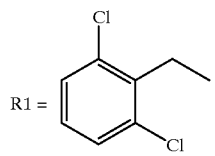

1-4 5-(4-Fluorophenyl)-2-phenyl-6-(4-pyridyl)-4(3 H)-pyrimidinone: MS (m/z): 344.2 (M+H)+; $C_{21}H_{14}FN_3O$ requir. 343.4 [1] H-NMR (DMSO-d$_6$): d 8.49 (d, 2 H, Pyrid.), 8,20 (d, 2 H, Ph), 7.66-7.50 (m, 3 H, Pyrid., Ph), 7.32-7.11 (m, 6 H, PhF, Ph).

R1 = 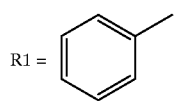

Example 2

General procedure for the preparation of 2-N substituted 2-amino-5-(4-fluorophenyl)-3-methyl-6-(4-pyridyl)-4(3 H)-pyrimidinones Step A. 5-(4-Fluorophenyl)-3-methyl-2-methylthio-6-(4-pyridyl)-4(3 H)-pyrimidinone:

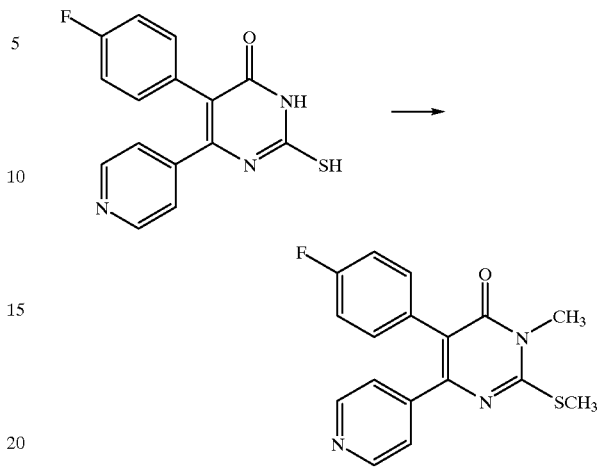

Methyl iodide (418 ml, 6.67 mmol) was added to a stirred mixture of 5-(4-fluorophenyl)-6-(4-pyridyl)-2-thiouracil (1.0 g, 3.34 mmol) and potassium carbonate (923 mg, 6.68 mmol) in N, N-dimethylformamide (30 ml). at room temperature. Stirring was continued for 3 h, followed by evaporation and flash chromatography on a column of silica gel (hexane-acetone=3:1, 2:1, 1:1) or Iatrobeads® (chloroform-methanol=90:7; chloroform-methanol-triethylamine=90:7:3). The second main fraction provided the title compound as a solid. MS (m/z): 328.0 (M+H)+; $C_{17}H_{14}FN_3OS$ requir. 327.4. $^1$H-NMR (DMSO-d$_6$): d 8.50, 7.26 (2m, each 2 H, Pyrid.), 7.18, 7.14 (2m, each 2 H, PhF), 3.52 (s, 3 H, NCH$_3$), 2.65 (s, 3 H, SCH$_3$).

Step B. General procedure:

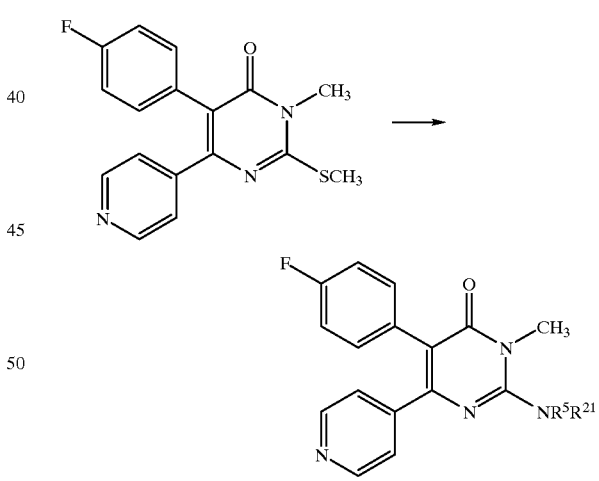

A mixture of 5-(4-fluorophenyl)-3-methyl-2-methylthio-6-(4-pyridyl)-4(3H)-pyrimidinone (103 mg, 0.32 mmol) and the amine HNR$^5$R$^{21}$ (1.2–3.2 mmol) was heated at 190–200° C. for 2–48 h. The resulting product was purified by flash chromatography on a column of silica gel (hexane-acetone or methanol-dichloromethane or methanol-dichloromethane-conc. ammonium hydroxide) to provide the target compound.

The following compounds were prepared using the above procedure outlined above and an appropriate amine:

2-1 2-(n-Butylamino)-5-(4-fluorophenyl)-3-methyl-6-(4-pyridyl)-4(3H)-pyrimidinone: The reaction was done in a sealed tube at 190° C. for 5 h. MS (m/z): 353.0 (M+H)$^+$; C$_{20}$H$_{21}$FN$_4$O requir. 352.4. R$^1$=CH$_3$(CH$_2$)$_3$NH—

2-2 5-(4-Fluorophenyl)-3-methyl-2-(pentylamino)-6-(4-pyridyl)-4(3 H)-pyrimidinone: The reaction was done in a sealed tube at 190° C. for 2.5 h. MS (m/z): 366.8 (M+H)$^+$; C$_{21}$H$_{23}$FN$_4$O requir. 366.4. R$^1$=CH$_3$(CH$_2$)$_4$NH—

2-3 2-(3,3-Dimethylbutylamino)-5-(4-fluorophenyl)-3-methyl-6-(4-pyridyl)-4(3 H)-pyrimidinone: The reaction was done in a sealed tube at 190° C. for 5 h. MS (m/z): 381.2 (M+H)$^+$; C$_{22}$H$_{25}$FN$_4$O requir. 380.5. R$^1$=(CH$_3$)$_3$C(CH$_2$)$_2$NH—

2-4 2-(Benzylamino)-5-(4-fluorophenyl)-3-methyl-6-(4-pyridyl)-4(3 H)-pyrimidinone: The reaction was done at 185° C. for 6 h. MS (m/z): 387.2 (M+H)$^+$; C$_{23}$H$_{19}$FN$_4$O requir. 386.4

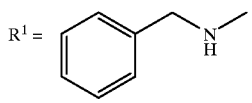

2-5 2-(4-Fluorobenzylamino)-5-(4-fluorophenyl)-3-methyl-6-(4-pyridyl)-4(3 H)-pyrimidinone: The reaction was done at 190° C. for 24 h. MS (m/z): 405.2 (M+H)$^+$; C$_{23}$H$_{18}$F$_2$N$_4$O requir. 404.4.

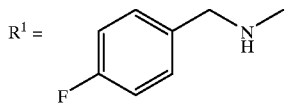

2-6 2-(3-Fluorobenzylamino)-5-(4-fluorophenyl)-3-methyl-6-(4-pyridyl)-4(3 H)-pyrimidinone: The reaction was done at 195° C. for 40 h. MS (m/z): 405.0 (M+H)$^+$; C$_{23}$H$_{18}$F$_2$N$_4$O requir. 404.4.

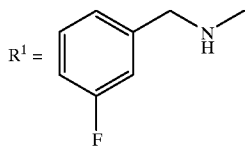

2-7 5-(4-Fluorophenyl)-3-methyl-((R-1-phenylethyl)amino)-(4-pyridyl)-4(3 H)-pyrimidinone: The reaction was done at 180° C. for 4 days. MS (m/z): 401.0 (M+H)$^+$; C$_{24}$H$_{21}$FN$_4$O requir. 400.5

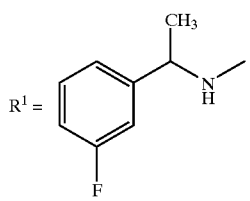

2-8 2-(2-(2-Chlorophenyl)-ethylamino)-5-(4-fluorophenyl)-3-methyl-6-(4-pyridyl)-4(3 H)-pyrimidinone: The reaction was done at 190° C. for 5 h. MS (m/z): 435.2 (M+H)$^+$; C$_{24}$H$_{20}$ClFN$_4$O requir. 434.9.

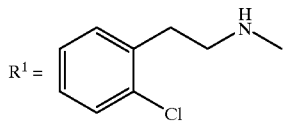

2-9 5-(4-Fluorophenyl)-2-(2-(4-fluorophenyl)-ethylamino)-3-methyl-6-(4-pyridyl)-4(3 H)-pyrimidinone:

The reaction was done at 190° C. for 5 h. MS (m/z): 419.2 (M+H)$^+$; C$_{24}$H$_{20}$F$_2$N$_4$O requir. 418.5

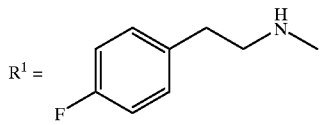

2-10 5-(2-Fluorophenyl)-2-(2-(3-fluorophenyl)-ethylamino)-3-methyl-6-(4-pyridyl)-4(3 H)-pyrimidinone: The reaction was done at 190° C. for 24 h. MS (m/z): 419.2 (M+H)$^+$; C$_{24}$H$_{20}$F$_2$N$_4$O requir. 418.5

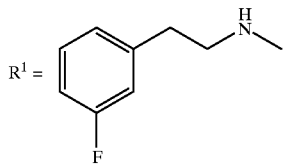

2-11 5-(2-Fluorophenyl)-2-(2-(2-fluorophenyl)-ethylamino)-3-methyl-6-(4-pyridyl)-4(3 H)-pyrimidinone: The reaction was done at 190° C. for 12 h. MS (m/z): 419.0 (M+H)$^+$; C$_{24}$H$_{20}$F$_2$N$_4$O requir. 418.5

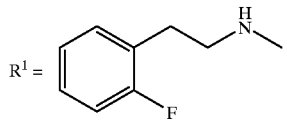

2-12 5-(2-Fluorophenyl)-2-((2-hydroxy-2-phenyl)-ethylamino)-3-methyl-6-(4-pyridyl)-4(3 H)-pyrimidinone:

The reaction was done at 190° C. for 1.5 h. MS (m/z): 417.0 (M+H)$^+$; C$_{24}$H$_{21}$FN$_4$O$_2$ requir. 416.5.

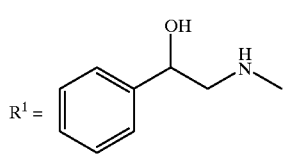

2-13 5-(4-fluorophenyl)-3-methyl-2-((3-phenylpropyl)-amino)-6-(4-pyridyl)-4(3 H)-pyrimidinone: The reaction was done at 190° C. for 6 h. MS (m/z): 415.0 (M+H)$^+$; C$_{25}$H$_{23}$FN$_4$O requir. 414.5. $^1$H-NMR (CDCl$_3$): d 8.49, 7.20 (2m, each 2 H, Pyrid.), 7.35 (t, 2 H, Ph), 7.30-7.25 (m, 3 H, Ph), 7.12, 6.97 (2m, each 2 H, PhF), 4.61 (t, 1 H, NH), 3.67 (q, 2 H, CH$_2$N), 3.28 (s, 3 H, CH$_3$), 2.82 (t, 2 H, CH$_2$Ph), 2.12 (m, 2 H, CH$_2$).

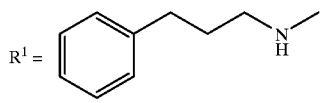

2-14 5-(4-Fluorophenyl)-3-methyl-2-((1-methyl-3-phenylpropyl)-amino)-6-(4-pyridyl)-4(3 H) -pyrimidinone: The reaction was done at 200° C. for 48 h. MS (m/z): 429.0 (M+H)$^+$; $C_{26}$ $H_{25}FN_4O$ requir. 428.5.

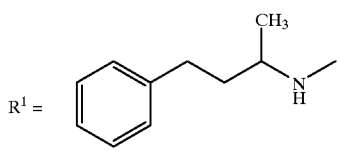

2-15 5-(4-Fluorophenyl)-3-methyl-2-((R-1-methyl-3-phenylpropyl)-amino)-6-(4-pyridyl)-4(3 H)-pyrimidinone: The reaction was done at 200° C. for 48 h. MS (m/z): 429.0 (M+H)$^+$; $C_{26}$ $H_{25}FN_4O$ requir. 428.5.

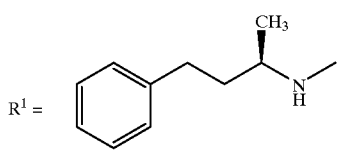

2-16 2-((3,3-Diphenylpropyl)-amino)-5-(4-fluorophenyl)-3-methyl-6-(4-pyridyl)-4(3 H)-pyrimidinone: The reaction was done at 190° C. for 6 h. MS (m/z): 490.8 (M+H)$^+$; $C_{31}$ $H_{27}FN_4O$ requir. 490.6.

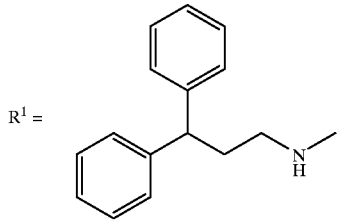

2-17 5-(4-Fluorophenyl)-3-methyl-2-((2-phenylaminoethyl)-amino)-6-(4-pyridyl)-4(3 H)-pyrimidinone: The reaction was done at 190° C. for 4 h. MS (m/z): 416.2 (M+H)$^+$; $C_{24}$ $H_{22}FN_5O$ requir. 415.5.

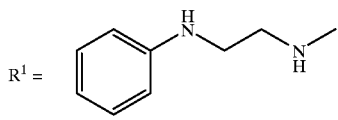

2-18 5-(4-Fluorophenyl)-2-((3-imidazolylpropyl)-amino)-3-methyl-6-(4-pyridyl)-4(3 H)-pyrimidinone: The reaction was done at 190° C. for 2 h. MS (m/z): 405.0 (M+H)$^+$; $C_{22}$ $H_{21}FN_6O$ requir. 404.5.

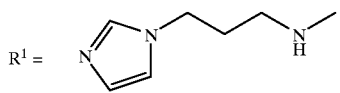

2-19 5-(4-Fluorophenyl)-3-methyl-2-(2-(piperazin-1-yl)-ethylamino)-6-(4-pyridyl)-4(3 H)-pyrimidinone: The reaction was done at 190° C. for 30 min. MS (m/z): 409.2 (M+H)$^+$; $C_{22}$ $H_{25}FN_6O$ requir. 408.5.

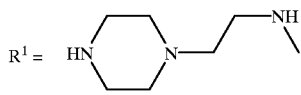

2-20 5-(4-Fluorophenyl)-3-methyl-6-(4-pyridyl)-2-(3-(pyrrolidin-1-yl)-propylamino)-4(3 H) -pyrimidinone: The reaction was done at 190° C. for 2 h. MS (m/z): 408.2 (M+H)$^+$; $C_{23}$ $H_{26}FN_5O$ requir. 407.5.

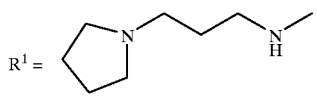

2-21 2-(((S)-2-Amino-3-phenylpropyl)-amino)-5-(4-fluorophenyl)-3-methyl-6-(4-pyridyl)-4(3 H)-pyrimidinone hydrochloride: The reaction was done at 190° C. for 2.5 h. MS (m/z): 430.1 (M+H)$^+$; $C_{25}$ $H_{24}FN_5O$ requir. 429.5 (free base).

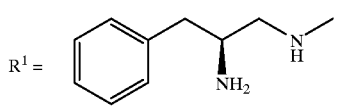

2-22 2-(((S)-2-N-Ethyl-3-phenylpropyl)-amino)-5-(4-fluorophenyl)-3-methyl-6-(4-pyridyl)-4(3 H)-pyrimidinone hydrochloride: The reaction was done at 190° C. for 4 h. MS (m/z): 458.3 (M+H)$^+$; $C_{27}$ $H_{28}FN_5O$ requir. 457.6 (free base).

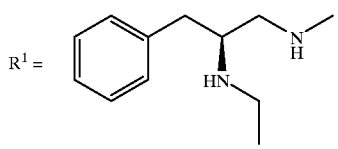

2-23 2-((2-Amino-2-methy-3-phenylpropyl)amino)-5-(4-fluorophenyl)-3-methyl-6-(4-pyridyl)-4(3 H)-pyrimidinone hydrochloride: The reaction was done at 190° C. for 4 h. MS (m/z): 444.0 (M+H)$^+$; $C_{26}$ $H_{26}FN_5O$ requir. 443.5 (free base).

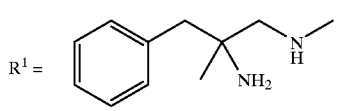

2-24 2-((2-Aminomethy-3-phenylpropyl)-amino)-5-(4-fluorophenyl)-3-methyl-6-(4-pyridyl)-4(3 H)-pyrimidinone hydrochloride: The reaction was done at 190° C. for 1 h. MS (m/z): 444.0 (M+H)$^+$; $C_{26}$ $H_{26}FN_4O$ requir. 443.5 (free base).

R¹ = 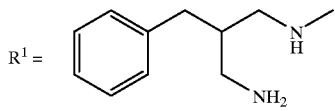

2-25 2-((3-Amino-3-phenylpropyl)-amino)-5-(4-fluorophenyl)-3-methyl-6-(4-pyridyl)-4(3 H)-Pyrimidinone hydrochloride: The reaction was done at 190° C. for 2.5 h. MS (m/z): 430.0 (M+H)⁺; $C_{25}H_{24}FN_5O$ requir. 429.5 (free base).

R¹ = 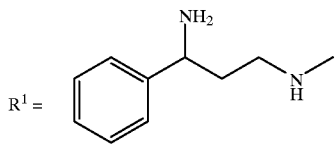

2-26 5-(4-Fluorophenyl)-3-methyl-2-(3-(2-methylphenyl)propyl)-amino)-6-(4-pyridyl)-4(3 H)-pyrimidinone: The reaction was done at 190° C. for 4 h. MS (m/z): 429.5 (M+H)⁺; $C_{26}H_{25}FN_4O$ requir. 428.5.

R¹ = 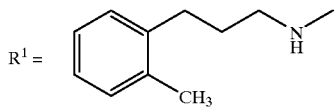

2-27 5-(4-Fluorophenyl)-3-methyl-2-((R,S)-2-amino-3-(2-fluorophenyl)-propyl-amino)-6-(4-pyridyl)-4(3 H)-pyrimidinone Hydrochloride: The reaction was done at 190° C. for 7 h. MS (m/z): 448(M+H)⁺.

R¹ = 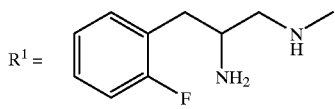

2-28 2-(((R)-2-Amino-3-phenylpropyl)-amino)-5-(4-fluorophenyl)-3-methyl-6-(4-pyridyl)-4(3 H)-pyrimidinone hydrochloride: The reaction was done at 190° C. for 2 h. MS (m/z): 430.2 (M+H)⁺; $C_{25}H_{24}FN_5O$ requir. 429.5 (free base).

R¹ = 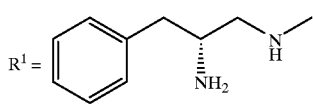

2-29 2-(((S)-2-N-Methyl-3-phenylpropyl)-amino)-5-(4-fluorophenyl)-3-methyl-6-(4-pyridyl)-4(3 H)-pyrimidinone hydrochloride: The reaction was done at 190° C. for 4 h. MS (m/z): 444.0 (M+H)⁺; $C_{26}H_{26}FN_5O$ requir. 443.5 (free base).

R¹ = 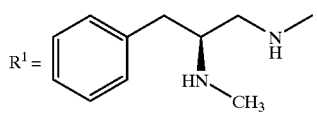

2-30 2-((2-phenylthioethyl)-amino)-5-(4-fluorophenyl)-3-methyl-6-(4-pyridyl)-4(3 H)-pyrimidinone: The reaction was done at 190° C. for 16 h. MS (m/z): 433 (M+H)⁺.

R¹ = 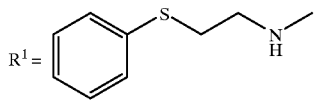

2-31 2-((2-hydroxyethyl)-amino)-5-(4-fluorophenyl)-3-methyl-6-(4-pyridyl)-4(3 H)-pyrimidinone: The reaction was done at 190° C. for 16 h. MS (m/z): 341 (M+H)⁺.

R¹ = 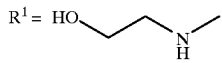

2-32 2-((2,2-dimethyl-3-hydroxypropyl)-amino)-5-(4-fluorophenyl)-3-methyl-6-(4-pyridyl)-4(3 H)-pyrimidinone: The reaction was done at 190° C. for 16 h. MS (m/z): 383 (M+H)⁺.

R¹ = 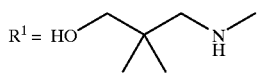

2-33 2-((2,2-dimethyl-3-phenylthiopropyl)-amino)-5-(4-fluorophenyl)-3-methyl-6-(4-pyridyl)-4(3 H)-pyrimidinone: To a solution of triphenylphosphine (262 mg, 0.29 mmol) in tetrahydrofuran (2 mL) at 0 C was added diisopropyl azodicarboxylate (DIAD) (56 ml, 0.29 mmol). After 30 min at 0 C, 2-((2,2-dimethyl-3-hydroxypropyl)-amino)-5-(4-fluorophenyl)-3-methyl-6-(4-pyridyl)-4(3 H)-pyrimidinone (50 mg, 0.14 mmol) and 2,6-dichlorothiophenol in tetrahydrofuran (2 mL) was added.

After 16 h, the reaction was concentrated under a stream of nitrogen. The reaction mixture was applied directly to purification via flash chromatography (step gradient ethyl acetate:CHCl3 1:3 then 1:2 then 1:1 then 2:1 then 3:1) to afford the title compound: MS (m/z) 544 (M+H)⁺.

R¹ = 

2-34 2-((3-Amino-3-(2-fluorophenyl)propyl)-amino)-5-(4-fluorophenyl)-3-methyl-6-(4-pyridyl)-4(3 H)-pyrimidinone was prepared from 5-(4-fluorophenyl)-3-methyl-2-methylthio-6-(4-pyridyl)-4(3 H)-pyrimidinone and 1-(2-fluorophenyl)-1,3-propanediamine according to the General Procedure. The reaction was done at 190° C. for 3 h. MS (m/z): 448.1 (M+H)⁺; $C_{25}H_{23}F_2N_5O$ requir. 447.5 (free base).

R¹ = 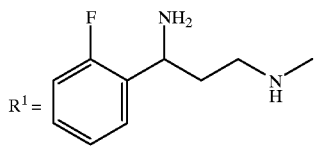

2-35 2-((3-Amino-3-(2-methylphenyl)propyl)-amino)-5-(4-fluorophenyl)-3-methyl-6-(4-pyridyl)-4(3 H)-pyrimidinone hydrochloride was prepared from 5-(4-fluorophenyl)-3-methyl-2-methylthio-6-(4-pyridyl)-4(3 H)-pyrimidinone and 1-(2-methylphenyl)-1,3-propanediamine according to the General Procedure. The reaction was done at 185° C. for 4 h. MS (m/z): 444.5 (M+H)⁺; $C_{26}H_{26}FN_5O$ requir. 443.5 (free base).

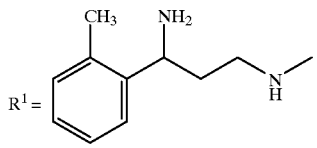

2-36 2-(((S)-3-amino-3-phenylpropyl)-amino)-5-(4-fluorophenyl)-3-methyl-6-(4-pyridyl)-4(3 H)-pyrimidinone hydrochloride was prepared from 5-(4-fluorophenyl)-3-methyl-2-methylthio-6-(4-pyridyl)-4(3 H)-pyrimidinone and (S)-1-phenyl-1,3-propanediamine according to the General Procedure. The reaction was done at 190° C. for 2.5 h. MS (m/z): 430.2 (M+H)$^+$; $C_{25}$ $H_{24}FN_5O$ requir. 429.5(free base).

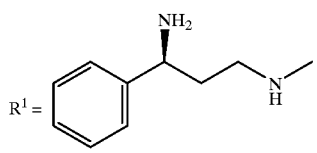

2-37 2-(((R)-3-amino-3-phenylpropyl)-amino)-5-(4-fluorophenyl)-3-methyl-6-(4-pyridyl)-4(3 H)-pyrimidinone hydrochloride was prepared from 5-(4-fluorophenyl)-3-methyl-2-methylthio-6-(4-pyridyl)-4(3 H)-pyrimidinone and (R)-1-phenyl-1,3-propanediamine according to the General Procedure. The reaction was done at 190° C. for 3.5 h. MS (m/z): 430.7 (M+H)$^+$; $C_{25}$ $H_{24}FN_5O$ requir. 429.5 (free base).

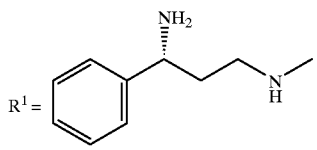

2-38 2-(((2R,3R)-3-Amino-2-methyl-3-phenylpropyl)-amino)-5-(4-fluorophenyl)-3-methyl-6-(4-pyridyl)-4(3 H)-pyrimidinone hydrochloride was prepared from 5-(4-fluorophenyl)-3-methyl-2-methylthio-6-(4-pyridyl)-4(3 H)-pyrimidinone and (2R,3R)-2-methyl-3-phenyl-1,3-propanediamine according to the General Procedure. The reaction was done at 190° C. for 3 h. MS (m/z): 444.5 (M+H)$^+$; $C_{26}$ $H_{26}FN_5O$ requir. 443.5 (free base).

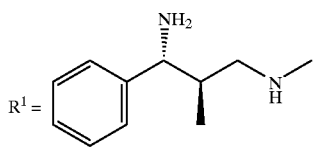

2-39 2-(((2S,3S)-3-Amino-2-methyl-3-phenylpropyl)-amino)-5-(4-fluorophenyl)-3-methyl-6-(4-pyridyl)-4(3 H)-pyrimidinone hydrochloride was prepared from 5-(4-fluorophenyl)-3-methyl-2-methylthio-6-(4-pyridyl)-4(3 H)-pyrimidinone and (2S,3S)-2-methyl-3-phenyl-1,3-propanediamine according to the General Procedure. The reaction was done at 190° C. for 2 h. MS (m/z): 444.4 (M+H)$^+$; $C_{26}$ $H_{26}FN_5O$ requir. 443.5 (free base).

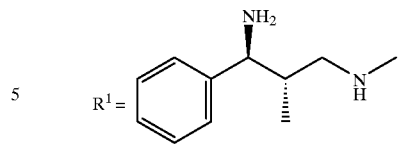

Analogously, the isomers 2-(((2S,3R)-3-Amino-2-methyl-3-phenylpropyl)-amino)-5-(4-fluorophenyl)-3-methyl-6-(4-pyridyl)-4(3 H)-pyrimidinone and 2-(((2R,3S)-3-amino-2-methyl-3-phenylpropyl)-amino)-5-(4-fluoro-phenyl)-3-methyl-6-(4-pyridyl)-4(3H) -pyrimidinone may be prepared from the corresponding diamines.

2-40 5-(4-Fluorophenyl)-2-((-3-hydroxy-3-phenylpropyl)-amino)-3-methyl-6-(4-pyridyl)-4(3 H)-pyrimidinone: The reaction was done at 190° C. for 3 h. MS (m/z): 431.2 (M+H)$^+$; $C_{25}$ $H_{23}FN_4O_2$ requir. 430.5.

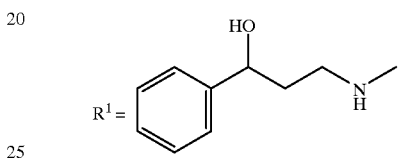

Example 3

Procedure for the preparation of N-substituted pyrimidinones

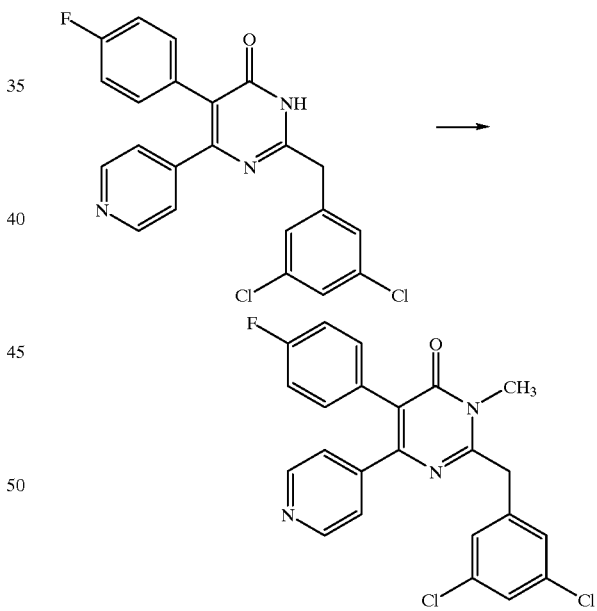

2-(2,6-Dichlorobenzyl)-5-(4-fluorophenyl)-3-methyl-6-(4-pyridyl)-4(3 H)-pyrimidinone: Methyl iodide (41 ml, 0.65 mmol) was added to a stirring mixture of 2-(2,6-dichlorobenzyl)-5-(4-fluorophenyl)-6-(4-pyridyl)-4(3 H)-pyrimidinone (280 mg, 0.61 mmol) and potassium carbonate (181 mg, 1.30 mmol) in N,N-dimethylformamide (2 ml). Stirring was continued for 2 h, followed by evaporation and flash chromatography of the resulting product on a column of silica gel (hexane-acetone=3:1) to yield the title compound as a white solid. MS (m/z): 440.2 (M+H)$^+$; $C_{23}$ $H_{16}Cl_2FN_3O$ requir. 440.3.

Example 4

General procedure for the preparation of 2-N and 2'-N substituted 2-amino-5-(4-fluorophenyl)-3-methyl-6-(4-(2-amino)pyridyl))-4(3 H)-pyrimidinones

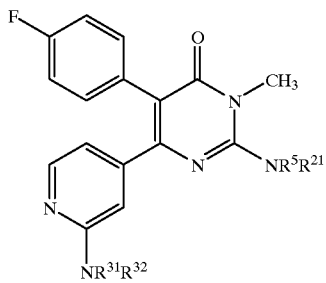

Step A. 5-(4-Fluorophenyl)-3-methyl-2-methylthio-6-(4-(2-acetamido)pyridyl))-4(3 H)-pyrimidinone: To a solution of 5-(4-fluorophenyl)-6-(4-(2-acetamido)pyridyl)-2-thiouracil (600 mg, 1.68 mmol) in DMF (35 mL) was added powdered sodium hydride (60% oil dispersion, 221 mg, 5.56 mmol) over 1 minute at 23° C. After 45 min, iodomethane (210 ml, 3.37 mmol) was added dropwise. After 45 min, the reaction was concentrated in vacuo (rotovap connected to high vac with a bath temperature no greater than 40° C.). The residue was applied immediately to flash chromatography purification (step gradient hexane:acetone 4:1; then 3:1; then 2:1; the 1:1) to afford the desired product.

Step B. 5-(4-Fluorophenyl)-3-methyl-2-((3-phenylpropyl)-amino)-6-(4-(2-amino)pyridyl))-4(3 H)-pyrimidinone: A neat mixture of 5-(4-Fluorophenyl)-3-methyl-2-methylthio-6-(4-(2-acetamido)pyridyl))-4(3 H)-pyrimidinone (50 mg, 0.13 mmol) and 3-phenyl-1-propylamine (88 mg, 0.65 mmol) was warmed to 190° C. for 17 h. After cooling to 23° C., the reaction mixture was applied directly to purification via flash chromatography (step gradient 1%MeOH:CHCl₃ then 2%, then 3%; then 4%; then 5%) to afford the desired product: MS (m/z) 430 (M+H)+.

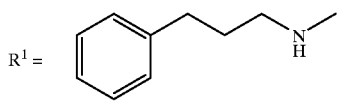

$R^{31}$=H
$R^{32}$=H

The following compounds were prepared using the above procedure outlined above and an appropriate amine: 4-1 5-(4-Fluorophenyl)-3-methyl-2-((3-phenylpropyl)-amino)-6-(4-(2-acetamido)pyridyl))-4(3 H)-pyrimidinone: To a solution of 5-(4-Fluorophenyl)-3-methyl-2-((3-phenylpropyl)-amino)-6-(4-(2-amino)pyridyl))-4(3 H)-pyrimidinone (11 mg, 0.026 mmol) in 600 μl of pyridine was added (5 μl, 0.064 mmol) of acetyl chloride at 23 C. After 2 h, the reaction was quenched with water (5 μl) and the reaction was concentrated under a stream of nitrogen. The reaction mixture was applied directly to purification via flash chromatography (step gradient 1%MeOH:CHCl₃ then 2%, then 3%) to afford the title compound: MS (m/z) 472 (M+H)+.

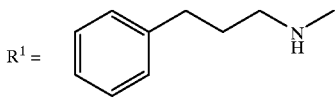

$R^{32}$=H
$R^{31}$=Ac 4-2 5-(4-Fluorophenyl)-3-methyl-2-((3-phenylpropyl)-amino)-6-(4-(2-methoxyacetamido)pyridyl))-4(3 H)-pyrimidinone: To a solution of 5-(4-Fluorophenyl)-3-methyl-2-((3-phenylpropyl)-amino)-6-(4-(2-amino)pyridyl))-4(3 H)-pyrimidinone (11 mg, 0.026 mmol) in 600 μl of pyridine was added (5 μl, 0.064 mmol) of methoxyacetyl chloride at 23 C. After 2 h, the reaction was quenched with water (5 μl) and the reaction was concentrated under a stream of nitrogen. The reaction mixture was applied directly to purification via flash chromatography (step gradient 1%MeOH:CHCl₃ then 2%, then 3%) to afford the title compound: MS (m/z) 502 (M+H)+.

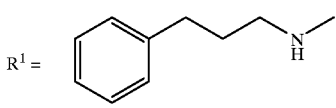

$R^{32}$=H
$R^{31}$=C(O)CH₂OMe 4-3 5-(4-Fluorophenyl)-3-methyl-2-((3-phenylpropyl)-amino)-6-(4-(2-acetoxyacetamido)pyridyl))-4(3 H)-pyrimidinone: The reaction was done in the manner of the above substituting acetoxyacetyl chloride for acetyl chloride to afford the title compound after chromatography: MS (m/z) 530 (M+H)+.

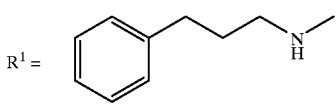

$R^{32}$=H
$R^{31}$=C(O)CH₂OAc 4-4 5-(4-Fluorophenyl)-3-methyl-2-((3-phenylpropyl)-amino)-6-(4-(2-hydroxyacetamido)pyridyl))-4(3 H)-pyrimidinone: To a solution of 5-(4-Fluorophenyl)-3-methyl-2-((3-phenylpropyl)-amino)-6-(4-(2-acetoxyacetamido)pyridyl))-4(3 H)-pyrimidinone (2 mg, 0.003 mmol) in 900 μl methanol: 100 μl water was added potassium carbonate (4 mg, 0.032 mmol) as a solid at 23 C. After 3 h, the reaction was concentrated under a stream of nitrogen. The reaction mixture was diluted with chloroform (20 mL), dried (Na2SO4), and concentrated to afford the title compound: MS (m/z) 488 (M+H)+.

$R^{32}$=H
$R^{31}$=C(O)CH₂OH 4-5 5-(4-Fluorophenyl)-3-methyl-2-((3-phenylpropyl)-amino)-6-(4-(2-methylsulfonamido)pyridyl))-4(3 H)-pyrimidinone: To a solution of 5-(4-Fluorophenyl)-3-methyl-2-((3-phenylpropyl)-amino)-6-(4-(2-amino)

pyridyl))-4(3H)-pyrimidinone (11 mg, 0.026 mmol) in 600 μl of pyridine was added methanesulfonyl chloride (4 μl, 0.051 mmol) at 23 C. After 2 h, the reaction was quenched with water (5 μl) and the reaction was concentrated under a stream of nitrogen. The reaction mixture was applied directly to purification via flash chromatography (step gradient 1%MeOH:CHCl₃ then 2%) to afford the title compound: MS (m/z) 508 (M+H)+.

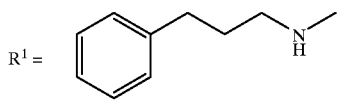

R³²=H
R³¹=SO₂Me 4-6 5-(4-Fluorophenyl)-3-methyl-2-((3-phenylpropyl)-amino)-6-(4-(2-benzylamino)pyridyl))-4(3 H)-pyrimidinone: To a solution of 5-(4-Fluorophenyl)-3-methyl-2-((3-phenylpropyl)-amino)-6-(4-(2-amino)pyridyl))-4(3 H)-pyrimidinone (11 mg, 0.026 mmol) in 600 μl of 1,2-dichloroethane was added benzaldehyde (8.9 mg, 0.084 mmol) and sodium triacetoxyborohydride (14.8 mg, 0.070 mmol) at 23 C. After 16 h, the reaction was quenched with water (15 μl) and the reaction was concentrated under a stream of nitrogen. The reaction mixture was applied directly to purification via flash chromatography (step gradient 1%MeOH:CHCl3 then 2%%, then 3%; then 4%; then 5%) to afford the title compound: MS (m/z) 458 (M+H)⁺.

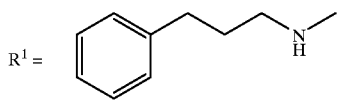

R³²=H
R³¹=CH₂Ph 4-7 5-(4-Fluorophenyl)-3-methyl-2-((3-phenylpropyl)-amino)-6-(4-(2-(2-methoxyphenyl)methylamino)pyridyl))-4(3 H)-pyrimidinone: The reaction was done in the manner of the above substituting 2-methoxybenzaldehyde for benzaldehyde to afford the title compound after chromatography: MS (m/z) 550 (M+H)⁺.

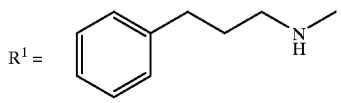

R³²=H

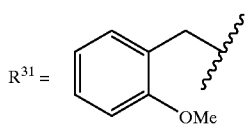

4-8 5-(4-Fluorophenyl)-3-methyl-2-((3-phenylpropyl)-amino)-6-(4-(2-ethylamino)pyridyl))-4(3H)-pyrimidinone: The reaction was done in the manner of the above substituting acetaldehyde for benzaldehyde to afford the title compound after chromatography: MS (m/z): 458 (M+H)⁺.

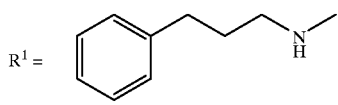

R³²=H
R³¹=Et 4-9 5-(4-Fluorophenyl)-3-methyl-2-((3-phenylpropyl)-amino)-6-(4-(2-(di-(3-methylbutyl)amino)pyridyl))-4(3 H)-pyrimidinone: The reaction was done in the manner of the above substituting isovaleradehyde for benzaldehyde to afford the title compound after chromatography: MS (m/z): 570 (M+H)⁺.

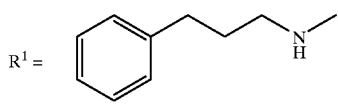

R³²=CH₂CH₂CH(CH₃)₂
R³¹=CH₂CH₂CH(CH₃)₂

4-10 5-(4-Fluorophenyl)-3-methyl-2-((3-phenylpropyl)-amino)-6-(4-(2-diethylamino)pyridyl))-4(3 H)-pyrimidinone: The reaction was done in the manner of the above substituting acetaldehyde for benzaldehyde to afford the title compound after chromatography: MS (m/z): 486 (M+H)⁺.

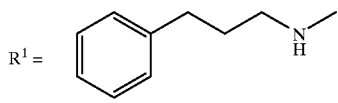

R³²=Et
R³¹=Et 4-11 5-(4-Fluorophenyl)-3-methyl-2-((3-phenylpropyl)-amino)-6-(4-(2-phenylaminocarbonyl-amino)pyridyl))-4(3 H)-pyrimidinone: To a solution of 5-(4-Fluorophenyl)-3-methyl-2-((3-phenylpropyl)-amino)-6-(4-(2-amino)pyridyl))-4(3 H)-pyrimidinone (11 mg, 0.026 mmol) in 600 μl of dioxane was added phenyl isocyanate (3.3 mg, 0.03 mmol) at 23° C. After 16 h, the reaction was quenched with water (15 μl) and the reaction was concentrated under a stream of nitrogen. The reaction mixture was applied directly to purification via flash chromatography (step gradient 1%MeOH:CHCl3 then 2%, then 3%; then 4%; then 5%) to afford the title compound: MS (m/z) 549 (M+H)⁺.

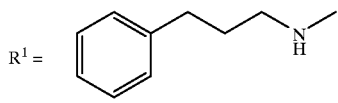

R³²=H
R³¹=NH(CO)NHPh 4-12 5-(4-Fluorophenyl)-3-methyl-2-((3-phenylpropyl)-amino)-6-(4-(2-methylaminocarbonyl-amino)pyridyl))-4(3 H)-pyrimidinone: The reaction was done in the manner of the above substituting methylisocyanate for phenylisocyanate to afford the title compound after chromatography: MS (m/z): 487 (M+H)⁺.

$R^1 =$ 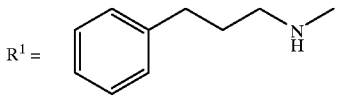

$R^{32}$=H
$R^{31}$=NH(CO)NHMe 4-13 5-(4-Fluorophenyl)-3-methyl-2-((3-phenylpropyl)-amino)-6-(4-(2-(2'amino-1'-oxo-ethylamino)pyridyl))-4(3H)-pyrimidinone: General Procedure for mixed anhydride coupling—Isobutyl chloroformate (32 ml, 0.24 mmol) was added dropwise to a −20–30° C. solution of N-a-t-Boc-glycine (5.6 mg, 0.05 mmol) and pyridine (0.6 mL). After 20 min at −20–30° C., 5-(4-fluorophenyl)-3-methyl-2-((3-phenylpropyl)-amino)-6-(4-(2-amino)pyridyl))-4(3H)-pyrimidinone (11 mg, 0.026 mmol) and pyridine (0.6 mL) was added in one portion. The reaction was allowed to warm to 23° C. After 16 h at 23° C., the reaction was poured into saturated bicarbonate (20 mL), extracted with ethyl acetate (2×50 mL), washed with brine (1×50 mL), and dried (Na2SO4). The reaction mixture was applied to purification via flash chromatography (step gradient 1%MeOH:CHCl3 then 2%%, then 3%; then 4%; then 5%) to afford the N-Boc protected title compound. The crude title compound was obtained after treatment with 50% trifluoroacetic acid:chloroform (1 mL) for 16 h. After concentration with a stream of nitrogen, the reaction mixture was applied to purification via flash chromatography (step gradient 1%MeOH:CHCl3 then 2%, then 3%; then 4%; then 5%) to afford the title compound: MS (m/z): 487 (M+H)$^+$.

$R^1 =$ 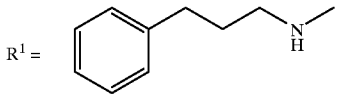

$R^{32}$=H
$R^{31}$=NH(CO)CH$_2$NH$_2$ 4-14 5-(4-Fluorophenyl)-3-methyl-2-((3-phenylpropyl)-amino)-6-(4-(2-(4'amino-1'-oxo-butylamino)-pyridyl))-4(3H)-pyrimidinone: The reaction was done in the manner of the above with the following substitution: N-t-Boc-g-aminobutyric acid was used in place of N-α-t-Boc-glycine which after deprotection as above afforded the title compound: MS (m/z): 515 (M+H)$^+$.

$R^1 =$ 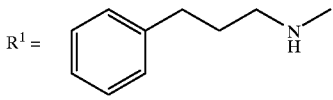

$R^{32}$=H
$R^{31}$=NH(CO)CH$_2$CH$_2$CH$_2$NH$_2$ 4-15 5-(4-Fluorophenyl)-3-methyl-2-((3-phenylpropyl)-amino)-6-(4-(2-(3'-amino-1'-oxo-propylamino)pyridyl))-4(3 H)-pyrimidinone: The reaction was done in the manner of the above with the following substitution: N-t-Boc-β-alanine was used in place of N-α-t-Boc-glycine which after deprotection as above afforded the title compound: MS (m/z): 501 (M+H)$^+$.

$R^1 =$ 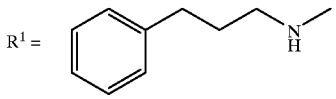

$R^{32}$=H
$R^{31}$=NH(CO)CH$_2$CH$_2$NH$_2$ 4-16 2-(((S)-2-Amino-3-phenylpropyl)-amino)-5-(4-fluorophenyl)-3-methyl-6-(4-(2-aminopyridyl))-4(3 H)-pyrimidinone hydrochloride: The reaction was done at 190° C. for 6 h in the above manner with the following substitution of (S)-1, 2-diamino-3-phenylpropane for 3-phenyl-1-propylamine: MS (m/z): 445 (M+H)$^+$;

$R^1 =$ 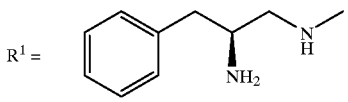

$R^{31}$=H
$R^{32}$=H 4-17 2-(((S)-2-Dimethylamino-3-phenylpropyl)-amino)-5-(4-fluorophenyl)-3-methyl-6-(4-(2-aminopyridyl))-4(3 H)-pyrimidinone hydrochloride: The reaction was done at 190° C. for 6 h in the above manner with the following substitution of 1-amino-2(S)-dimethylamino-3-phenylpropane for 3-phenyl-1-propylamine: MS (m/z): 473 (M+H)$^+$;

$R^1 =$ 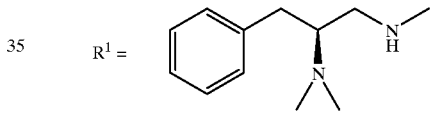

$R^{32}$=H
$R^{31}$=H 4-18 2-(((S)-2-Dimethylamino-3-phenylpropyl)-amino)-5-(4-fluorophenyl)-3-methyl-6-(4-(2-acetamidopyridyl))-4(3 H)-pyrimidinone hydrochloride: The reaction was done in the manner of example XX substituting 2-(((S)-2-Dimethylamino-3-phenylpropyl)-amino)-5-(4-fluorophenyl)-3-methyl-6-(4-(2-aminopyridyl))-4(3 H)-pyrimidinone hydrochloride for 5-(4-Fluorophenyl)-3-methyl-2-((3-phenylpropyl)-amino)-6-(4-(2-amino)pyridyl))-4(3 H)-pyrimidinone which afforded the title compound: MS (m/z) 515 (M+H)$^+$;

$R^1 =$ 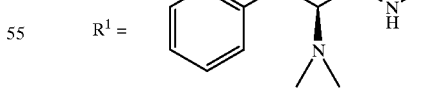

$R^{32}$=H
$R^{31}$=Ac 4-19 2-(((R,S)-3-Amino-3-phenylpropyl)-amino)-5-(4-fluorophenyl)-3-methyl-6-(4-(2-aminopyridyl))-4(3 H)-pyrimidinone hydrochloride: The reaction was done at 190° C. for 12 h in the above manner with the following substitution of (3 R,S)-1,3-diamino-3-phenylpropane for 3-phenyl-1-propylamine: MS (m/z): 445 (M+H)$^+$;

$R^1 =$ 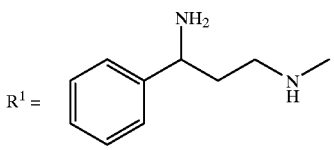

$R^{32}=H$
$R^{31}=H$ 4-20 5-(4-Fluorophenyl)-3-methyl-2-(phenylmethylamino)-6-(4-(2-(3'-phenyl-1'-oxo-propylamino)pyridyl))-(4-(2-amino)pyridyl))-4(3 H)-pyrimidinone: A neat mixture of 5-(4-fluorophenyl)-3-methyl-2-methylthio-6-(4-(2-acetamido)pyridyl))-4(3 H)-pyrimidinone (260 mg, 0.13 mmol) and benzylamine (88 mg, 2.71 mmol) was warmed to 190 C for 17 h. After cooling to 23 C, the reaction mixture was applied directly to purification via flash chromatography (step gradient 1%MeOH:CHCl3 then 2%, then 3%; then 4%; then 5%) to afford 5-(4-Fluorophenyl)-3-methyl-2-(phenylmethylamino)-6-(4-(2-amino)pyridyl))-4(3 H)-pyrimidinone. The 5-(4-fluorophenyl)-3-methyl-2-(phenylmethylamino)-6-(4-(2-amino)pyridyl))-4(3 H)-pyrimidinone was converted in the manner of the above substituting hydrocinnamoyl chloride for acetyl chloride and 5-(4-fluorophenyl)-3-methyl-2-(phenylmethylamino)-6-(4-(2-amino)pyridyl))-4(3 H)-pyrimidinone for 5-(4-fluorophenyl)-3-methyl-2-((3-phenylpropyl)-amino)-6-(4-(2-amino)pyridyl))-4(3 H)-pyrimidinone to afford the title compound after chromatography: MS (m/z) 534 (M+H)+.

$R^1=NHCH_2Ph$
$R^{32}=H$
$R^{31}=(CO)CH_2CH_2Ph$

Example 5
General procedure for the preparation of 5-(4-fluorophenyl)-6-(4-pyridyl)-2-thioalkyl-4(3 H)-pyrimidinones
Step A. Ethyl 2-(4-fluorophenyl)-3-oxo-3-(4-pyridyl)-propionate:

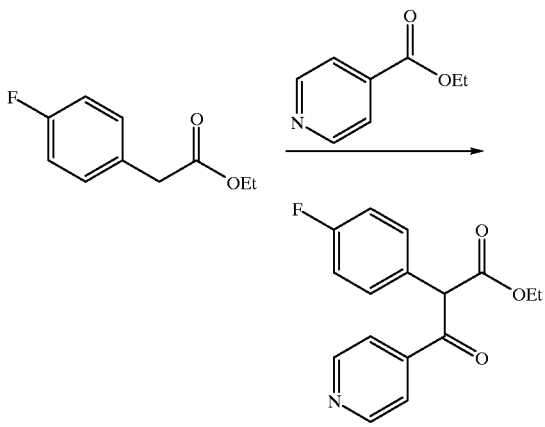

(According to: Legrand and Lozac'h, *Bull. Soc. Chim. Fr.,* 79–81 (1955)).

A mixture of ethyl 4-fluorophenylacetate (13 g, 71.35 mmol), ethyl isonicotinate (10.7 ml, 71.4 mmol) and sodium spheres (1.64 g, 71.34 mmol) was heated at 90–95° C. under argon. The mixture started to reflux and gradually turned into a solid. After 2.5 h, the mixture was neutralized with dil. acetic acid with cooling followed by extraction with dichloromethane. The organic solution was washed with water, dried and evaporated. Flash chromatography on a column of silica gel (hexane-acetone=4:1, 3:1, 2:1) provided the title compound as an oil. MS (m/z): 287.8 (M+H)+; $C_{16}H_{14}FNO_3$ requir. 287.3 [1] H-NMR (CDCl$_3$), (ketone:enole= 1: 0.33): d 13.50 (s, 0.3 H, OH-E), 8.81 (m, 2 H, Pyrid.-K), 8.48 (m, 0.66 H, Pyrid.-E), 7.72 (m, 2 H, Pyrid.-K), 7.38 (m, 2 H, PhF-K), 7.14-7.04 (m, 2 H, PhF-K; ~0.65 H, Pyrid.-E; ~0.65 H, PhF-E), 6.96 (t, 0.64 H, PhF-E), 5.51 (s, 1 H, CH-K), 4.23-4.2- (m, $CH_2$-K,E), 1.26 (t, $CH_3$-K,E).

Step B. 5-(4-fluorophenyl)-6-(4-pyridyl)-2-thiouracil:

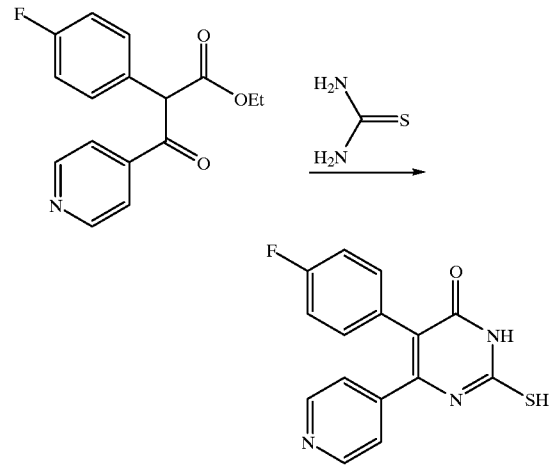

A stirred mixture of ethyl 2-(4-fluorophenyl)-3-oxo-3-(4-pyridyl)-propionate (22.3 g, 77.6 mmol) and thiourea (5.9 g, 77.6 mmol) was reacted at 190° C. under argon for 40 min. The reaction mixture was allowed to reach room temperature, taken up in acetone and the precipitate was filtered to provide the title compound. MS (m/z): 300.2 (M+H)+; $C_{15}H_{10}FN_3OS$ requir. 299.3 $^1$H-NMR (DMSO-d$_6$): d 12.74, 12.65 (2s, 2 H), 8.51 (m, 2 H, Pyrid.), 7.26 (m, 2 H, Pyrid.), 7.09 and 7.03 (2m, each 2 H, PhF).

Alternatively, ethyl 2-(4-fluorophenyl)-3-oxo-3-(4-pyridyl)-propionate (2.87 g, 10 mmol) and thiourea (2.28 g, 30 mmol) were suspended in anhydrous p-xylene (50 ml) with very efficient stirring. To the mixture pyridinium p-toluenesulfonate (100 mg) was added and refluxed for 12–16 h using a Dean-Stark apparatus with continuous removal of water (0.2 ml). Reaction mixture was cooled and a dark brown solid was filtered using a Buchner funnel. The collected solid was suspended in acetone (25 ml) and filtered. The acetone washed product contained a trace of thiourea, which was removed by trituration with hot water (20–30 ml). The product was filtered and air dried.

Step C. General procedure:

The arylalkyl bromide (0.36 mmol) was added dropwise to a stirring mixture of 5-(4-fluorophenyl)-6-(4-pyridyl)-2-thiouracil (100 mg, 0.33 mmol) and potassium carbonate (46 mg, 0.33 mmol) in N,N-dimethylformamide (4.6 ml). Stirring was continued for 3 h followed by evaporation. Flash chromatography on a column of silica gel (hexane-acetone= 3:1, 2:1, 1:1) and recrystallization from hot methanol provided the target compound.

The following compounds were obtained using the appropriate arylalkyl bromide according to the above procedure:
5-1 5-(4-Fluorophenyl)-2-(2-phenylethyl)thio-6-(4-pyridyl)-4(3 H)-pyrimidinone: MS (m/z): 404.2 (M+H)+; $C_{23}H_{18}FN_3OS$ requir. 403.4. [1] H-NMR (DMSO-d$_6$): d 13.08 (bs, 0.7 H), 8.49 (m, 2 H, Pyrid.), 7.30-7.06 (m, 11 H, Pyrid., Ph, PhF), 3.41 (dd, 2 H, $CH_2$S), 3.00 (t, 2 H, $CH_2$).

R¹ = 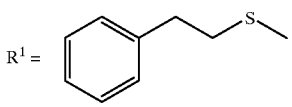

5-2 5-(4-Fluorophenyl)-2-(3-phenylpropyl)thio-6-(4-pyridyl)-4(3 H)-pyrimidinone: MS (m/z): 418.0 (M+H)⁺; $C_{24}H_{20}FN_3OS$ requir. 417.5. ¹H-NMR (DMSO-d₆): d 13.10 (bs, 0.7 H), 8.47 (m, 2 H, Pyrid.), 7.29-7.06 (m, 11 H, Pyrid., Ph, PhF), 3.18 (t, 2 H, CH₂S), 2.71 (t, 2 H, CH₂Ph), 2.03 (m, 2 H, CH₂).

R¹ = 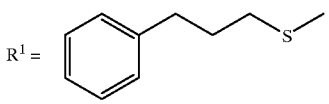

5-3 5-(4-Fluorophenyl)-2-(2-phenoxyethyl)thio-6-(4-pyridyl)-4(3 H)-pyrimidinone: MS (m/z): 420.0 (M+H)⁺; $C_{23}H_{18}FN_3O_2S$ requir. 419.5. ¹ H-NMR (DMSO-d₆): d 13.20 (bs, 0.7 H), 8.46 (m, 2 H, Pyrid.), 7.24-7.07 (m, 8 H, Pyrid., PhF, Ph), 6.95 (d, 2 H, Ph), 6.92 (t, overlapped, 1 H, Ph), 4.30 (t, 2 H, CH₂O), 3.58 (t, 2 H, CH₂S).

R¹ = 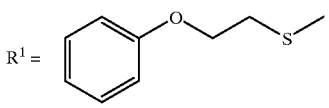

5-4 5-(4-Fluorophenyl)-2-(2-phenylaminoethyl)thio-6-(4-pyridyl)-4(3 H)-pyrimidinone: MS (m/z): 419.0 (M+H)⁺; $C_{23}H_{19}FN_4OS$ requir. 418.5. ¹H-NMR (DMSO-d₆): d 13.20 (bs, 0.8 H), 8.48, 7.22 (2m, each 2 H, Pyrid.), 7.16, 7.10 (2m, each 2 H, PhF), 6.89 (t, 2 H, Ph), 6.54 (d, 2 H, Ph), 6.48 (t, 1 H, Ph), 5.90 (bs, 0.6 H, NH), 3.43-3.25 (m, 2CH₂).

R¹ = 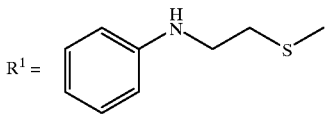

Example 6

General procedure for the preparation of 2-N substituted 2-amino-5-(4-fluorophenyl)-6-(4-pyridyl)-4(3 H)-pyrimidinones:

Step A. 5-(4-Fluorophenyl)-2-methylthio-6-(4-pyridyl)-4(3 H)-pyrimidinone:

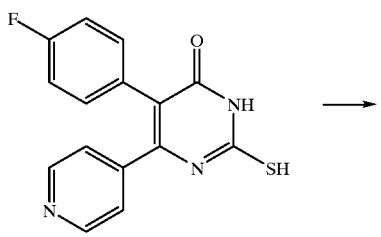

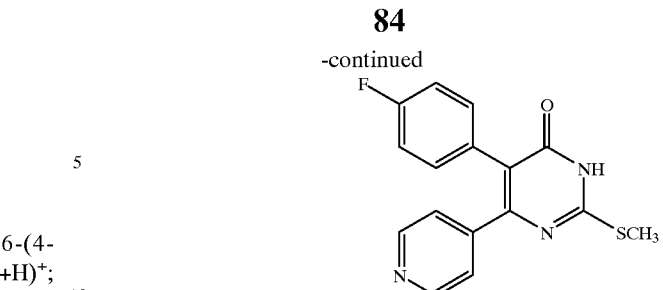

Methyl iodide (90 ml, 1.44 mmol) was added dropwise to a stirred mixture of 5-(4-fluorophenyl)-6-(4-pyridyl)-2-thiouracil (430 mg, 1.44 mmol) and potassium carbonate (198 mg, 1.43 mmol) in N,N-dimethylformamide (13 ml) at ice-bath temperature. After 40 min, it was evaporated and the crude product purified by flash chromatography on a column of silica gel (hexane-acetone =2:1, 1:1, 1:2) to provide the title compound as a solid. MS (m/z): 314.2 (M+H)⁺; $C_{16}H_{12}FN_3OS$ requir. 313.3. ¹ H-NMR (DMSO-d₆): d 13.10 (bs), 8.47, 7.22 (2m, each 2 H, Pyrid.), 7.16, 7.10 (2m, each 2 H, PhF), 2.56 (s, 3 H, CH₃).

Step B. General procedure:

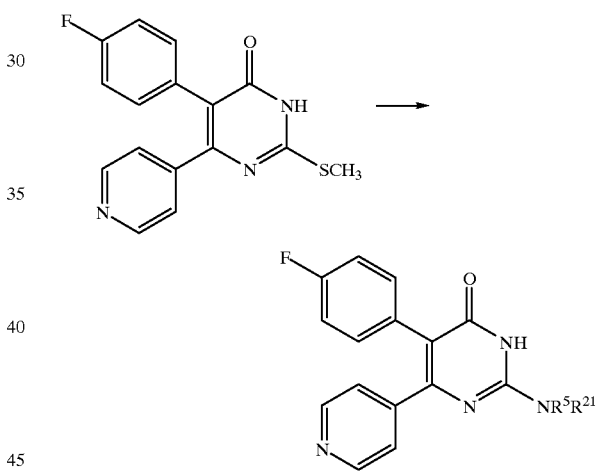

A mixture of 5-(4-fluorophenyl)-2-methylthio-6-(4-pyridyl)-4(3 H)-pyrimidinone (100 mg, 0.32 mmol) and an amine HNR⁵R²¹ (1 mmol) was heated at 180° C. for 2 h. The resulting product was purified by flash chromatography on a column of silica gel (hexane-acetone or methanol-dichloromethane or dichloromethane-methanol-conc. ammonium hydroxide) to provide the target compound.

The following compounds were prepared using the general procedure outlined above and an appropriate amine:

6-1 2-(2-(2-Chlorophenyl)ethyl-amino)-5-(4-fluorophenyl)-6-(4-pyridyl)-4(3H)-pyrimidinone: MS (m/z) : 421.2 (M+H)⁺; $C_{23}H_{18}ClFN_4O$ requir. 420.9. ¹H-NMR (DMSO-d₆): d 11.24 (bs), 8.44, 7.16 (2m, each 2 H, Pyrid.), 7.43, 7.38 (2dd, each 1 H, PhCl), 7.30, 7.26 (2dt, each 1 H, PhCl), 7.10-7.00 (m, 2 H, PhF), 6.74 (bs, 1 H, NH), 3.60 (q, 2 H, CH₂N), 3.03 (t, 2 H, CH₂).

R¹ = 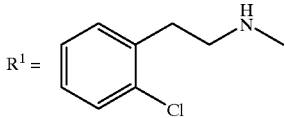

6-2 5-(4-Fluorophenyl)-2-((3-phenylpropyl)-amino)-6-(4-pyridyl)-4(3 H) -pyrimidinone: MS (m/z): 401.2 (M+H)⁺; $C_{24}H_{21}FN_4O$ requir. 400.5. ¹H-NMR (DMSO-d₆): d 11.16 (bs), 8.44, 7.14 (2m, each 2 H, Pyrid.), 7.32-7.01 (m, 9 H, Ph, PhF), 6.78 (bs, NH), 3.36 (q, 2 H, CH₂N), 2.67 (t, 2 H, CH₂Ph), 1.89 (m, 2 H, CH₂).

R¹ = 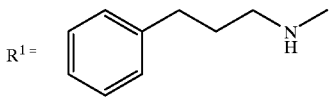

6-3 5-(4-Fluorophenyl)-2-((1-methyl-3-phenylpropyl)-amino)-6-(4-pyridyl)-4(3 H)-pyrimidinone: A reaction time of 15 h at 180_C. was required. MS (m/z): 415.0 (M+H)⁺; $C_{25}H_{23}FN_4O$ requir. 414.5. ¹H-NMR (CDCl₃): d 8.48 (m, 2 H, Pyrid.), 7.28-7.08 (m, 9 H, Pyrid., Ph, PhF), 6.94 (m, 2 H, PhF), 5.67 (bs, 1 H, NH), 4.08 (m, 1 H, CHCH₃), 2.61 (t, 2 H, CH₂Ph), 1.67 (m, 2 H, CH₂), 1.08 (d, 3 H, CH₃).

R¹ = 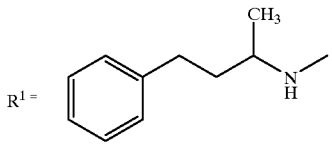

6-4 5-(4-Fluorophenyl)-2-((3-imidazolylpropyl)-amino)-6-(4-pyridyl)-4(3 H)-pyrimidinone: MS (m/z): 391.0 (M+H)⁺; $C_{21}H_{19}FN_6O$ requir. 390.4. ¹H-NMR (DMSO-d₆): d 11.24 (bs), 8.42, 7.12 (2m, each 2 H, Pyrid.), 7.62, 7.18 (2s, each 1 H, Imid.), 7.08-6.99 (m, 4 H, PhF), 6.88 (s, 1 H, Imid.), 4.02 (t, 2 H, CH₂N), 3.28 (overlapped by water signal, CH₂NH), 2.00 (m, 2 H, CH₂).

R¹ = 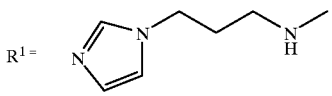

6-5 2-(((S)-2-Amino-3-phenylpropyl)-amino)-5-(4-fluorophenyl)-6-(4-pyridyl)-4(3 H)-pyrimidinone hydrochloride: The reaction was done at 170° C. for 7 h. MS (m/z): 416.1 (M+H)⁺; $C_{26}H_{22}FN_5O$ requir. 415.5.

R¹ = 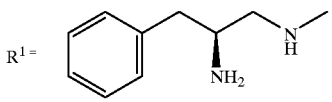

Example 7
5-(4-Fluorophenyl)-2-hydrazino-6-(4-pyridyl)-4(3 H)-pyrimidinone

A mixture of 5-(4-fluorophenyl)-6-(4-pyridyl)-2-thiouracil (500 mg, 1.66 mmol) and hydrazine hydrate (800 ml, ~14 mmol) was heated at 120° C. for 60 min. It was evaporated and the reaction product was recrystallized from hot methanol to provide the title compound. MS (m/z): 298.0 (M+H)⁺; $C_{15}H_{12}FN_5O$ requir. 297.3. ¹H-NMR (DMSO-d₆): d 8.41, 7.12 (2m, each 2 H, Pyrid.), 7.05, 7.00 (2m, each 2 H, PhF). R¹=NH—NH₂.

Example 8
General procedure for the preparation of 5-aryl-2,6-dipyridyl-(3 H)-pyrimidinones

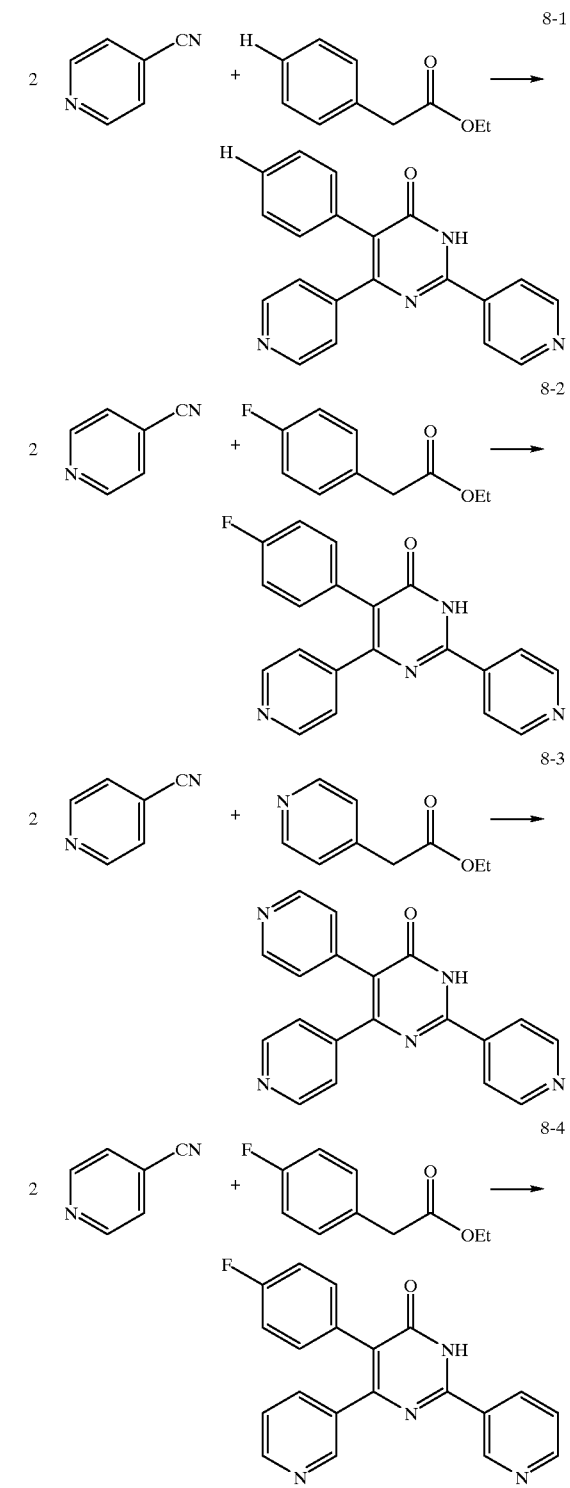

These compounds were prepared according to the literature (Kabbe, supra; German Patent 1271116 (1968)) as follows:

A stirred mixture of the ethyl phenylacetate (3.13 mmol), cyanopyridine (6.24 mmol) and sodium methoxide (3.5 mmol) in n-butanol (1.2 ml) was heated at 110° C. for 2 h. The reaction mixture was concentrated and dissolved in water (4 ml), followed by the addition of aqueous sat. ammonium chloride (2 ml). The precipitate was filtered and recrystallized from hot methanol.

The following compounds were prepared according to this procedure using the appropriate starting materials:

8-1 5-Phenyl-2,6-bis-(4-pyridyl)-4-(3 H)pyrimidinone: MS (m/z): 327.2 (M+H)$^+$; $C_{20} H_{14}N_4O$ requir. 326.4. $^1$H-NMR (DMSO-d$_6$): d 8.78, 8.47, 8.13 (3 m, each 2 H, Pyrid.), 7.40-7.14 (m, 7 H, Ph, Pyrid.).

8-2 5-(4-Fluorophenyl)-2,6-bis-(4-pyridyl)-4(3 H)-pyrimidinone: MS (m/z): 345.2 (M+H)$^+$; $C_{20} H_{13}FN_4O$ requir. 344.4 $^1$ H-NMR (DMSO-d$_6$): d 8.80, 8.49, 8.13 (3m, each 2 H, Pyrid.), 7.40-7.08 (m, 6 H, PhF, Pyrid.).

8-3 2,5,6-Tris-(4-pyridyl)-4(3 H)-pyrimidinone was prepared according to the general procedure by reacting ethyl 4-pyridylacetate and 4-cyanopyridine in the presence of sodium methoxide. MS (m/z): 328.2 (M+H)$^+$; $C_{19} H_{13}N_5O$ requir. 327.4 $^1$H-NMR (DMSO-d$_6$): 8.65, 8.45, 8.35, 8.18, 7.25, 7.13 (6m, each 2 H, Pyrid.).

8-4 5-(4-Fluorophenyl)-2,6-bis-(3-pyridyl)-4(3 H)-pyrimidinone: MS (m/z): 345.2 (M+H)$^+$; $C_{20} H_{13}FN_4O$ requir. 344.4 $^1$ H-NMR (DMSO-d$_6$): d 9.34, 8.77, 8.54, 8.48, 7.78, 7.60, 7.34 (7m, 3×1H, 2 H, 3×1H, Pyrid.), 7.26, 7.15 (2m, each 2 H, PhF).

Example 9
3-(3-trimethylsilyl-2-propynyl)-5-(4-fluorophenyl)-2-methylthio-6-(4-pyridyl)-4(3 H)-pyrimidinone

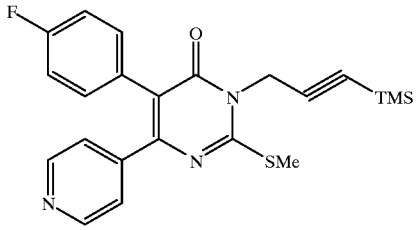

The preparation of the title compound was carried out in the same manner as 3-ethyl-5-(4-fluorophenyl)-2-methylthio-6-(4-pyridyl)-4(3 H)-pyrimidinone with the following substitution: 3-bromo-1-(trimethylsilyl)-1-propyne was used in place of ethyl bromide.

Example 10
6-(4-Fluorophenyl)-2-methyl-1-(3-phenylpropyl)-7-pyridin-4-yl-1H-imidazo(1,2-a)pyrimidin-5-one

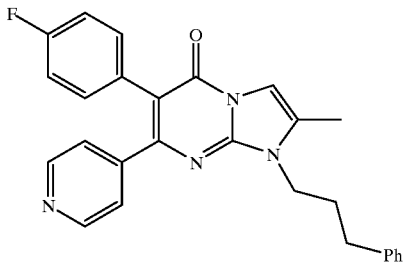

A neat mixture of 3-(3-trimethylsilyl-2-propynyl)-5-(4-fluorophenyl)-2-methylthio-6-(4-pyridyl)-4(3 H)-pyrimidinone (50 mg, 0.12 mmol) and 3-phenyl-1-propylamine (67 mg, 0.47 mmol) was warmed to 190° C. for 17 h. After cooling to 23° C., the reaction mixture was applied directly to purification via flash chromatography (step gradient 1%MeOH:CHCl3 then 2%, then 3%; ) to afford the desired product: MS (m/z) 439 (M+H)+.

Example 11
6-(4-Fluorophenyl)-2-methyl-1-benzyl-7-pyridin-4-yl-1H-imidazo(1,2-a)pyrimidin-5-one

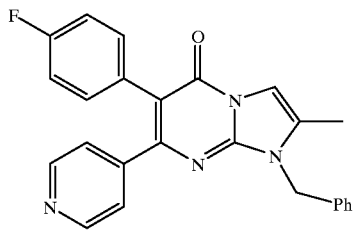

The preparation of the title compound was carried out in the same manner as 6-(4-Fluorophenyl)-2-methyl-1-(3-phenyl propyl)-7-pyridin-4-yl-1H-imidazo(1,2-a)pyrimidin-5-one with the following substitution: benzylamine for 3-phenyl-1-propylamine; MS (m/z) 411 (M+H)$^+$.

Example 12
General procedure for the preparation of 6-substituted 3-phenyl-4-(4-pyridyl)-2(1 H)-pyridones
Step A. General procedure for the preparation of 1-aryl-3-(4-pyridyl)-2-propene-1-one:

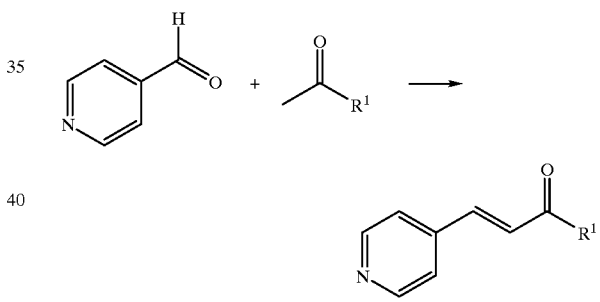

At ice-bath temperature, piperidine (206 ml), acetic acid (206 ml) and 4-pyridinecarboxaldehyde (1.6 ml, 16.6 mmol) were mixed. Then the acetophenone (12.0 mmol) was added at from temperature and the mixture was heated at 130° C. for 1.5 h. The reaction mixture was diluted with dichloromethane, washed with aqueous sodium hydrogen-carbonate and water followed by drying and evaporation. The crude product was purified by column chromatography on silica gel (hexane-acetone=3:1).

The following compounds were prepared according to this procedure using the appropriate acetophenone derivative:

1-Phenyl-3-(4-pyridyl)-2-propene-1-one: MS (m/z): 210.1 (M+H)$^+$; $C_{14} H_{11}NO$ requir. 209.3.

1-(4-Methylphenyl)-3-(4-pyridyl)-2-propene-1-one: MS (m/z): 224.2 (M+H)$^+$; $C_{15} H_{13}NO$ requir. 223.3.

1-(4-Ethylphenyl)-3-(4-pyridyl)-2-propene-1-one: MS (m/z): 237.8 (M+H)$^+$; $C_{16} H_{15}NO$ requir. 237.3.

1-(4-Isopropylphenyl)-3-(4-pyridyl)-2-propene-1-one: MS (m/z): 252.0 (M+H)$^+$; $C_{17} H_{17}NO$ requir. 251.3.

1-(2-Methylphenyl)-3-(4-pyridyl)-3-propene-1-one: MS (m/z): 223.8 (M+H)$^+$; $C_{15} H_{13}NO$ requir. 223.3.

1-(2,4-Dimethylphenyl)-3-(4-pyridyl)-2-propene-1-one: MS (m/z): 238.0 (M+H)$^+$; C$_{16}$ H$_{15}$NO requir. 237.3.
1-(2-Methoxyphenyl)-3-(4-pyridyl)-2-propene-1-one: MS (m/z): 240.0 (M+H)$^+$; C$_{15}$ H$_{13}$NO$_2$ requir. 239.3
1-(4-Chlorophenyl)-3-(4-pyridyl)-2-propene-1-one: MS (m/z): 244.0 (M+H)$^+$; C$_{14}$ H$_{10}$ClNO requir. 243.7.
1-(4-Cyanophenyl)-3-(4-pyridyl)-2-propene-1-one: MS (m/z): 235. 1 (M+H)$^+$; C$_{15}$ H$_{10}$N$_2$O requir. 234.3.
1-(a-Naphthyl)-3-(4-pyridyl)-2-propene-1-one: MS (m/z): 260.0 (M+H)$^+$; C$_{18}$ H$_{13}$NO requir. 259.3.
1,3-Bis-(4-pyridyl)-2-propene-1-one: MS (m/z): 211.0 (M+H)$^+$; C$_{13}$ H$_{10}$N$_2$O requir. 210.2.
3-(4-Pyridy-1-(2-thienyl)-2-propene-1-one: MS (m/z): 216.0 (M+H)$^+$; C$_{12}$ H$_9$NOS requir. 215.3.
1-(2-Furyl-3-(4-pyridyl)-2-propene-1-one: MS (m/z): 200.0 (M+H)$^+$; C$_{12}$ H$_9$NO$_2$ requir. 199.2. 1-Cyclohexyl-3-(4-pyridyl)-2-propene-1-one was prepared in the same way using acetylcyclohexane: MS (m/z): 216.2 (M+H)$^+$; C$_{14}$ H$_{17}$NO requir. 215.3.
1-tert-Butyl-3-(4-pyridyl)-2-propene-1-one: A mixture of 3,3-dimethyl-2-butanone (2.5 ml, 20.0 mmol), 4-pyridinecarboxaldehyde (2.15 ml, 22.3 mmol), ethanol (7.6 ml), and 4.5% aqueous sodium hydroxide (4.6 ml) was kept at room temperature for 12 h. It was diluted with dichloromethane, washed with aqueous hydrochloric acid and water, dried and evaporated. Subsequent column chromatography (hexane–ethyl acetate=3:1) provided the title compound. MS (m/z): 190.4 (M+H)$^+$; C$_{12}$ H$_{15}$NO requir.189.3.

Step B. General procedure for the preparation of 6-substituted 3-phenyl-4-(4-pyridyl)-2(1 H)-pyridones:

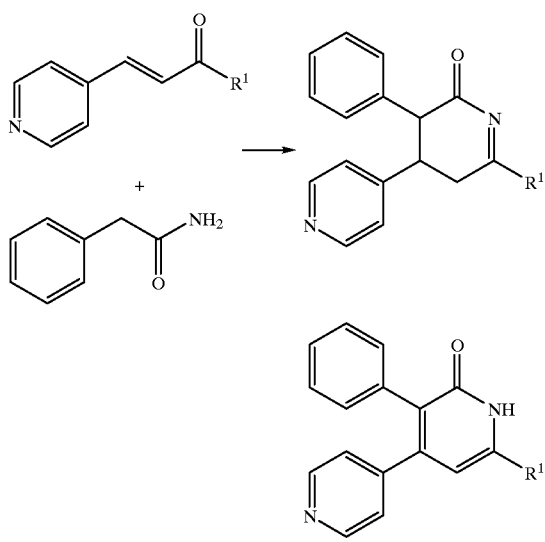

Sodium (40 mg, 1.74 mmol) was dissolved in a stirring mixture of phenylacetamide (880 mg, 6.51 mmol) and ethanol (5 ml). If solubility allowed, the 1-substituted 3-(4-pyridyl)-2-propene-1-one (5.4 mmol) was added portionwise as an ethanolic solution (20 ml) to the refluxing phenylacetamide solution or it was added at room temperature as a solid. The mixture was kept under reflux for 1.5 h and was then allowed to reach room temperature. 2N Hydrochloric acid was added to a pH value of 5 followed by the addition of a few ml of water. The product that crystallized from this mixture was filtered, washed subsequently with ethanol, water, ethanol and recrystallized from methanol. If the product did not crystallize from the reaction mixture on addition of hydrochloric acid, then the mixture was evaporated and the remainder taken up in dichloromethane. The organic solution was washed with water, dried and evaporated. The resultant product was crystallized from hot acetone and recrystallized from methanol.

The following compounds were prepared according to this procedure using the 2-(4-pyridyl)-2-propene-1-one derivatives described in Example 12.a:

12-1 3,6-Diphenyl-4-(4-pyridyl)-2(1H)-pyridone: MS (m/z): 325.4 (M+H)$^+$; C$_{22}$ H$_{16}$N$_2$O requir. 324.4. $^1$H-NMR (DMSO-d$_6$): d 8.63 (m, 2 H, Pyrid.), 7.86 (m, 2 H), 7.58-7.45, 7.29-7.08 (2m).

$R^1 =$ 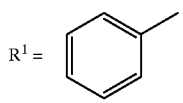

12-2 6-(4-Methylphenyl)-3-phenyl-4-(4-pyridyl)-2(1H)-pyridone: MS (m/z): 339.2 (M+H)$^+$; C$_{23}$ H$_{18}$N$_2$O requir. 338.4. $^1$H-NMR (DMSO-d$_6$): d 8.44 (m, 2 H, Pyrid.), 7.79 (d, 2 H), 7.32 (d, 2 H), 7.26-7.01 (m, 7 H, Ph, Pyrid.), 6.67 (bs, 1 H).

$R^1 =$ 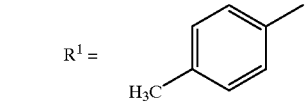

12-3 6-(4-Ethylphenyl)-3-phenyl-4-(4-pyridyl)-2(1H)-pyridone: MS (m/z): 353.0 (M+H)$^+$; C$_{24}$ H$_{20}$N$_2$O requir. 352.4. $^1$H-NMR (DMSO-d$_6$): d 8.42 (m, 2 H, Pyrid.), 7.79 (d, 2 H), 7.33 (d, 2 H), 7.24-7.06 (m, 7 H, Ph, Pyrid.), 6.65 (bs, 1 H, CH=), 2.66 (q, 2 H, CH$_2$), 1.21 (t, 3 H, CH$_3$).

$R^1 =$ 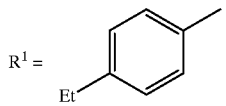

12-4 6-(4-Isopropylphenyl)-3-phenyl-4-(4-pyridyl)-2(1H)-pyridone: MS (m/z): 367.0 (M+H)$^+$; C$_{25}$ H$_{22}$N$_2$O requir. 366.5. $^1$H-NMR (DMSO-d$_6$): d 8.45 (m, 2 H, Pyrid.), 7.82 (d, 2 H), 7.39 (d, 2 H), 7.28-7.10 (m, 7 H, Ph, Pyrid.), 6.67 (bs, 1 H, CH=), 2.98 (m, 1 H, CH(CH$_3$)$_2$), 1.27, 1.25 (2s, each 3 H, 2CH$_3$).

$R^1 =$ 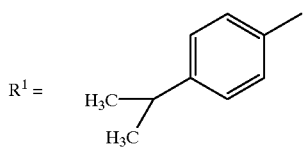

12-5 6-(2-Methylphenyl)-3-phenyl-4-(4-pyridyl)-2(1 H)-pyridone: MS (m/z): 339.2 (M+H)$^+$; C$_{23}$ H$_{18}$N$_2$ requir. 338.4. $^1$ H-NMR (DMSO-d$_6$): d 8.40 (m, 2 H, Pyrid.), 7.45-7.09 (m, 11 H, Ph, Pyrid.), 6.21 (bs, 1 H, CH=), 2.39 (s, 3 H, CH$_3$).

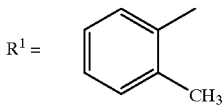

12-6 6-(2,4-Dimethylphenyl)-3-phenyl-4-(4-pyridyl)-2(1H)-pyridone: MS (m/z): 353.0 (M+H)$^+$; $C_{24}H_{20}N_2O$ requir. 352.4. $^1$H-NMR (DMSO-d$_6$): d 8.42 (m, 2 H, Pyrid.), 7.29 (d, 1 H), 7.23-7.06 (m, 9 H, Ph, Pyrid.), 6.17 (bs, 1 H, CH=), 2.34, 2.31 (2s, each 3 H, 2CH$_3$).

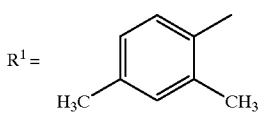

12-7 6-(2-Methoxyphenyl)-3-phenyl-4-(4-pyridyl)-2(1H)-pyridone: MS (m/z): 355.0 (M+H)$^+$; $C_{23}H_{18}N_2O_2$ requir. 354.4. $^1$H-NMR (DMSO-d$_6$): d 8.41 (m, 2 H, Pyrid.), 7.49 (bd, 1 H), 7.44 (m, 1 H), 7.24-7.06 (m, 8 H, Ph, Pyrid.), 7.02 (dt, 1 H), 6.32 (bs, 1 H, CH=), 3.82 (s, 3 H, CH$_3$).

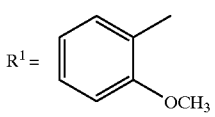

12-8 6-(4-Chlorophenyl)-3-phenyl-4-(4-pyridyl)-2(1H)-pyridone: MS (m/z): 359.2 (M+H)$^+$; $C_{22}H_{15}ClN_2O$ requir. 358.8. $^1$H-NMR (DMSO-d$_6$): d 8.42 (m, 2 H, Pyrid.), 7.93 (bd, 2 H), 7.54 (m, 2 H), 7.26-7.08 (m, 7 H, Ph, Pyrid.), 6.80 (bs, 1 H, CH=).

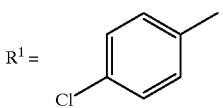

12-9 6-(4-Cyanophenyl)-3-Phenyl-4-(4-pyridyl)-2(1H)-pyridone: MS (m/z): 350.2 (M+H)$^+$; $C_{23}H_{15}N_3O$ requir. 349.4. $^1$H-NMR (DMSO-d$_6$): d 8.45 (m, 2 H, Pyrid.), 8.16 (bd, 2 H), 7.98 (d, 2 H), 7.32-7.00 (m, 8 H, Ph, Pyrid., CH=).

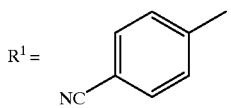

12-10 6-(a-Naphthyl)-3-phenyl-4-(4-pyridyl)-2(1H)-pyridone: MS (m/z): 375.0 (M+H)$^+$; $C_{26}H_{18}N_2O$ requir. 374.5. $^1$H-NMR (DMSO-d$_6$): d 8.38 (m, 2 H, Pyrid.), 8.06-7.98 (m, 3 H), 7.67 (dd, 1 H), 7.62-7.54 (m, 3 H), 7.25-7.11 (m, 7 H, Ph, Pyrid.), 6.38 (bs, 1 H, CH=).

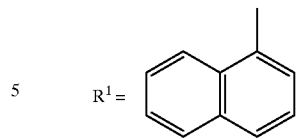

12-11 3-Phenyl-4,6-bis-(4-pyridyl)-2(1H)-pyridone: MS (m/z): 326.0 (M+H)$^+$; $C_{21}H_{15}N_3O$ requir. 325.4. $^1$H-NMR (DMSO-d$_6$): d 8.69, 8.43 (2m, each 2 H, Pyrid.), 7.92 (bs, 2 H), 7.28-7.05 (m, 8 H).

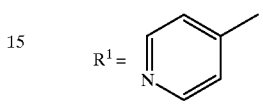

12-12 3-Phenyl-4-(4-pyridyl)-6-(2-thienyl)-2(1H)-pyridone: MS (m/z): 331.0 (M+H)$^+$; $C_{20}H_{14}N_2OS$ requir. 330.4. $^1$H-NMR (DMSO-d$_6$): d 8.44 (m, 2 H, Pyrid.), 7.90, 7.70 (2bd, each 1 H), 7.28-7.08 (m, 9 H).

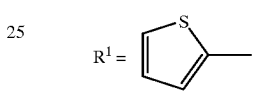

12-13 6-(2-Furyl)-3-phenyl-4-(4-pyridyl)-2(1 H)-pyridone: MS (m/z): 315.0 (M+H)$^+$; $C_{20}H_{14}N_2O_2$ requir. 314.4. $^1$H-NMR (DMSO-d$_6$): d 8.44 (m, 2 H, Pyrid.), 7.90 (s, 1 H), 7.43 (bs, 1 H), 7.27-7.08 (m, 7 H, Ph, Pyrid.), 6.71 (m, 2 H).

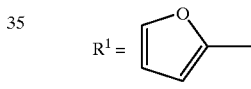

12-14 6-Cyclohexyl-3-phenyl-4-(4-pyridyl)-2(1H)-pyridone: MS (m/z): 331.2 (M+H)$^+$; $C_{22}H_{22}N_2O$ requir. 330.4. $^1$H-NMR (DMSO-d$_6$): d 8.40 (m, 2 H, Pyrid.), 7.22-7.13, 7.10-7.03 (2m, 7 H, Ph, Pyrid.), 6.04 (bs, 1 H, CH=), 1.95-1.15 (m, 11 H, cyclohex.).

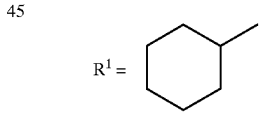

12-15 6-tert-Butyl-3-phenyl-4-(4-pyridyl)-2(1H)-pyridone: MS (m/z): 305.0 (M+H)$^+$; $C_{20}H_{20}N_2O$ requir. 304.4. $^1$H-NMR (DMSO-d$_6$): d 8.39 (m, 2 H, Pyrid.), 7.20-7.12, 7.10-7.02 (2m, 7 H, Ph, Pyrid.), 6.02 (bs, 1 H, CH=), 1.31 (s, 9 H, 3CH$_3$). R$^1$=(CH$_3$)$_3$C—

Example 13
Procedure for the preparation of (S)-1,2-Benzylethylendiamine

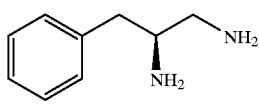

(S)-1,2-Benzylethylendiamine: The diamine was prepared according to the literature (H. Brunner, P. Hankofer, U.

Holzinger, B. Treittinger and H. Schoenenberger, Eur. J. Med. Chem. 25, 35–44, (1990)) by reduction of L-phenylalanine amide with lithium aluminium hydride. The (R)-enantiomer was prepared in the same manner from D-phenylalanine amide.

Example 14

Procedure for the preparation of 2-(((S)-2-Acetamido-3-phenylpropyl)-amino)-5-(4-fluorophenyl)-3-methyl-6-(4-pyridyl)-4(3 H)-pyrimidinone

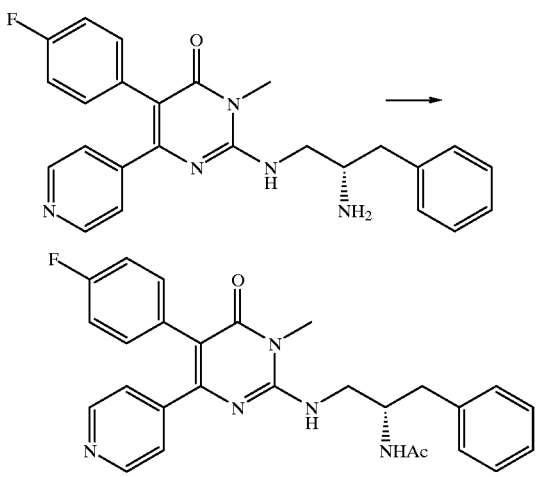

2-(((S)-2-Acetamido-3-phenylpropyl)-amino)-5-(4-fluorophenyl)-3-methyl-6-(4-pyridyl)-4(3 H)-pyrimidinone: A solution of 2-(((S)-2-amino-3-phenylpropyl)-amino)-5-(4-fluorophenyl)-3-methyl-6-(4-pyridyl)-4(3 H)-pyrimidinone (25 mg, 0.058 mmol) and acetic anhydride (200 ml) in methanol (2 ml) was kept at room temperature for 1 h. Evaporation followed by chromatography of the resultant product on a column of silica gel (10% methanol/dichloromethane) provided the title compound. MS (m/z): 472.3 (M+H)$^+$; $C_{27}H_{26}FN_5O_2$ requir. 471.5.

Example 15

Procedure for the preparation of 5-(4-Fluorophenyl)-2-(((S)-2-N-isopropylamino-3-phenylpropyl)-amino)-3-methyl-6-(4-pyridyl)-4(3 H)-pyrimidinone hydrochloride

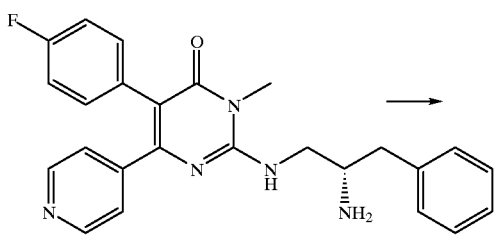

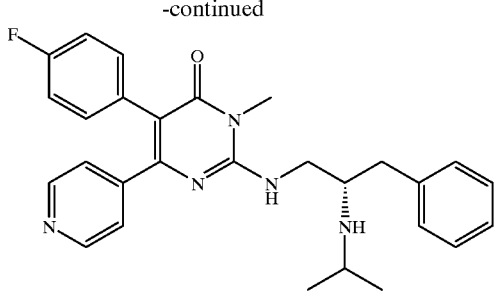

5-(4-Fluorophenyl)-2-(((S)-2-N-isopropylamino-3-phenylpropyl)-amino)-3-methyl-6-(4-pyridyl)-4(3 H)-pyrimidinone hydrochloride: Sodium triacetoxyborohydride (23 mg, 0.109 mmol) was added to a stirring mixture of 2-(((S)-2-amino-3-phenylpropyl)-amino)-5-(4-fluorophenyl)-3-methyl-6-(4-pyridyl)-4(3 H)-pyrimidinone hydrochloride (50 mg, 0.107 mmol), triethylamine (15 ml, 0.108 mmol) and acetone (7.9 ml, 0.108 mmol) in 1,2-dichloroethane (0.8 ml). After 4 h, the reaction was quenched by the addition of sat. aqu. sodium hydrogencarbonate, followed by extraction with dichloromethane, drying of the organic solution and evaporation. Chromatography on a column of silica gel (10% methanol/chloroform) provided the title compound as a free base which was converted into the monohydrochloride by the addition of 4N hydrochloric acid/dioxane (21 mml, 0.08 mmol) to its methanolic solution (1 ml) and subsequent evaporation. MS (m/z): 472.1 (M+H)$^+$; $C_{28}H_{30}FN_5O$ requir. 471.6 (free base).

Example 16

Procedure for the preparation of 5-(4-Fluorophenyl)-2-(((S)-2-N-cyclohexylamino-3-phenylpropyl)-amino)-3-methyl-6-(4-pyridyl)-4(3 H)-pyrimidinone hydrochloride

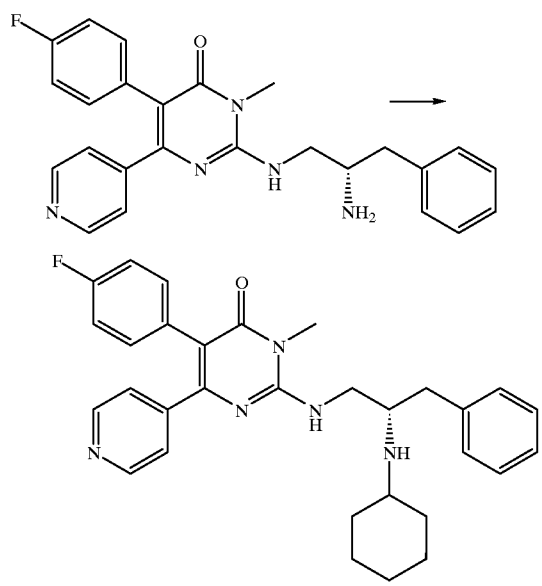

5-(4-Fluorophenyl)-2-(((S)-2-N-cyclohexylamino-3-phenylpropyl)-amino)-3-methyl-6-(4-pyridyl)-4(3 H-pyrimidinone hydrochloride: Utilizing cyclohexanone, 5-(4-fluorophenyl)-2-(((S)-2-N-cyclohexylamino-3-phenylpropyl)-amino)-3-methyl-6-(4-pyridyl)-4(3 H)-pyrimidinone was prepared in the same manner as 5-(4- fluorophenyl)-2-(((S)-2-N-isopropylamino-3-phenylpropyl)-amino)-3-methyl-6-(4-pyridyl)-4(3 H)-pyrimidinone: MS (m/z): 511.6 (M)⁺; $C_{31}H_{34}FN_5O$ requir. 511.6 (free base).

Example 17
Procedure for the preparation of 2-(((S)-2-N-n-Butylamino-3-phenylpropyl)-amino)-5-(4-fluorophenyl)-3-methyl-6-(4-pyridyl)-4(3 H)-pyrimidinone hydrochloride

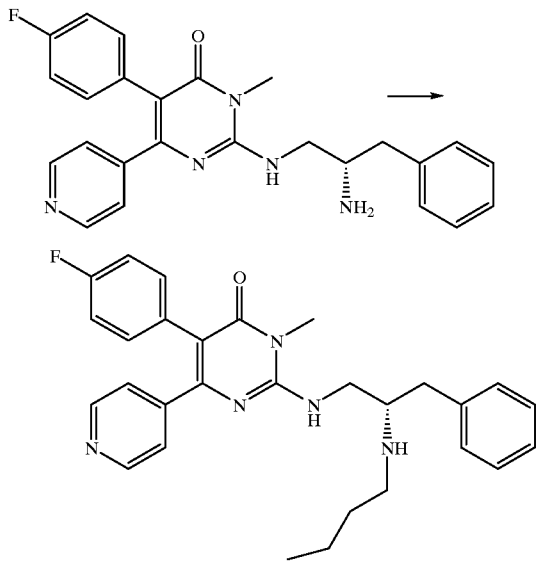

2-(((S)-2-N-n-Butylamino-3-phenylpropyl)-amino)-5-(4-fluorophenyl)-3-methyl-6-(4-pyridyl)-4(3 H)-pyrimidinone hydrochloride: Sodium triacetoxyborohydride (28 mg, 0.13 mmol) was added to a stirring mixture of 2-(((S)-2-amino-3-phenylpropyl)-amino)-5-(4-fluorophenyl)-3-methyl-6-(4-pyridyl)-4(3 H)-pyrimidinone (41 mg, 0.095 mmol) and butyraldehyde (8.5 ml, 0.094 mmol) in 1,2-dichloroethane (0.8 ml). After 2 h, the reaction was quenched by the addition of sat. aqu. sodium hydrogencarbonate, followed by extraction with dichloromethane, drying of the organic solution and evaporation. Chromatography on a column of silica gel (5% methanol/chloroform) provided the title compound as a free base which was converted into the monohydrochloride by the addition of 4N hydrochloric acid/dioxane (12 mml, 0.048 mmol) to its methanolic solution (1 ml) and subsequent evaporation. MS (m/z): 486.2 (M+H)⁺; $C_{29}H_{32}FN_5O$ requir. 485.6 (free base).

Example 18
Procedure for the preparation of (S)-2-N,N-Dimethylamino-3-phenylpropylamine

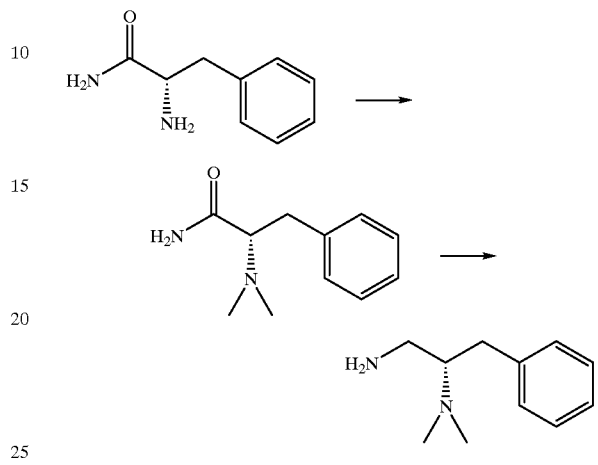

(S)-2-N,N-Dimethylamino-3-phenylpropylamine: Sodium triacetoxyhydride (13.0 g, 61.3 mmol) was added to a stirring mixture of phenylalanine amide (3.6 g, 21.9 mmol) and 37% formaldehyde solution (4.4 ml, 58.7 mmol) in 1,2-dichloroethane (77 ml). After stirring for 2 h, the reaction was quenched by the addition of sat. aqu. sodium hydrogencarbonate. Then potassium hydroxide pellets were added followed by extraction with dichloromethane, drying of the organic solution and evaporation. The resulting (S)-2-N,N-dimethylamino-3-phenylpropylamide was reduced with lithium aluminium hydride according to the literature (H. Brunner, P. Hankofer, U. Holzinger, B. Treittinger and H. Schoenenberger, Eur. J. Med. Chem. 25, 35–44, (1990)) to provide the title compound.

Example 19
Procedure for the preparation of 2-(((S)-2-N,N-Dimethylamino-3-phenylpropyl)-amino)-5-(4-fluorophenyl-3-methyl-6-(4-pyridyl)-4(3 H)-pyrimidinone hydrochloride

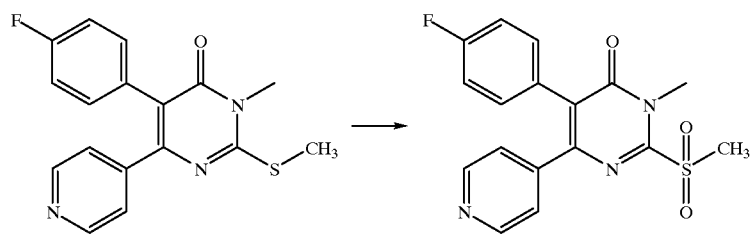

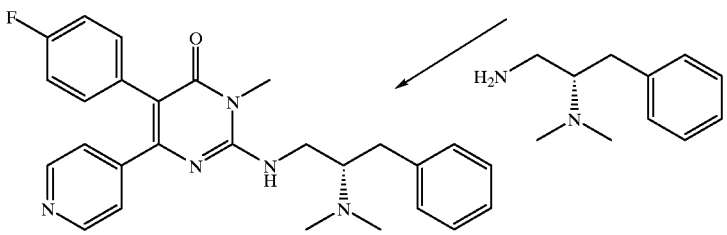

Step A. 5-(4-Fluorophenyl)-3-methyl-2-methylsulfonyl-6-(4-pyridyl)-4(3 H)-pyrimidinone: A mixture of 5-(4-fluorophenyl)-3-methyl-2-methylthio-6-(4-pyridyl)-4(3 H)-pyrimidinone (400 mg, 1.22 nmol) and Oxone® (potassium peroxymonosulfate, 2.3 g, 3.74 mmol) in methanol (100 ml) and water (45 ml) was stirred for 13 h. The solvent was concentrated to about 50 ml, followed by extraction with dichloromethane, drying of the organic solution and evaporation. The resulting white solid was used without purification in the next step.

Step B. 2-(((S)-2-N,N-Dimethylamino-3-phenylpropyl)-amino)-5-(4-fluorophenyl-3-methyl-6-(4-pyridyl)-4(3 H)-pyrimidinone hydrochloride: A mixture of crude 5-(4-fluorophenyl)-3-methyl-2-methylsulfonyl-6-(4-pyridyl)-4(3 H)-pyrimidinone (430 mg g, 1.19 mmol) and (S)-2-N,N-dimethylamino-3-phenylpropylamine (600 mml, ~3.4 mmol) was stirred at room temperature for 1 h and then briefly warmed at 50° C. Column chromatography on silica gel (3–5% methanol/chloroform) provided the title compound as a free base which was converted into the monohydrochloride by the addition of 4N hydrochloric acid/dioxane (160 mml, 0.64 mmol) to its methanolic solution (4 ml) and subsequent evaporation. MS (m/z): 458.0 (M+H)$^+$; $C_{27}H_{28}FN_5O$ requir. 457.5 (free base).

Example 20

5-(4-fluorophenyl)-6-(4-(2-acetamido)-pyridyl)-2-thioalkyl-4(3 H) -pyrimidinones Step A. Ethyl 2-(4-fluorophenyl)-3-oxo-3-(4-(2-acetamido)-pyridyl))-propionate: A solution of 2-chloroisonicotinic acid (25.0 g, 0.16 mol) in 65 mL of concentrated ammonium hydroxide was warmed to 205 Celsius in a steel bomb for 72 h. After cooling to 23 C, the solution was acidified to a pH of 1 using 6N HCl and subsequently filtered to remove unreacted starting material. The solution was concentrated to one fourth the original volume (approx 200 mL) in vacuo, and carefully adjusted to a pH of 6 using 1 N NaOH. After storing the cloudy solution at 0 C for 20 h, the desired 2-aminoisonicotinic acid was filtered off. To a suspension of 2-aminoisonicotinic acid in ethanol (600 mL) was added 47.1 mL of 4 N anhydrous HCl in dioxane. After warming to achieve reflux for 20 h, an additional 47.1 mL of 4 N anhydrous HCl in dioxane was added and the reaction was warmed to -reflux for an additional 20 h. Concentration with a stream of nitrogen in the hood was followed by further concentration in vacuo, the remaining solid was diluted with saturated bicarbonate (200 mL), extracted with ethyl acetate (2×200 mL), dried (Na2SO4). After concentration in vacuo, the desired ethyl 2-aminoisonicotinate was obtained. To a solution of ethyl 2-aminoisonicotinic acid in pyridine (45 mL) at 0 C under an argon atmosphere was added acetyl chloride dropwise over 5 min. After 2 h at 0 C, the reaction was pored into over ice 300 g, extracted with ethyl acetate (2×300 mL), washed with water (2×100 ml) followed by brine (2×100 mL), and dried (Na2SO4). After concentration in vacuo, the residue was purified by application of flash chromatography (step gradient ethyl acetate: hexane 1:4 then ethyl acetate: hexane 1:1) to afford ethyl 2-acetamidoisonicotinate.

To a solution of diisopropylamine (14.15 mL, 101 mmol) and THF (40 mL) at −78 C was added n-butyl lithium (38.1 mL, 95 mmol) dropwise over 5 min. After 10 min, ethyl 4-fluorophenylacetate (17.3 g, 95 mmol) was added in 40 mL of dry THF. After 10 min, ethyl 2-acetamidoisonicotinate (6.0 g, 29 mmol) was added in 20 ml of dry THF. The reaction was allowed to warm to 23 C overnight, and then acetic acid (95 mmol) was added in one portion. The reaction was concentrated in vacuo, then partitioned repeatedly between saturated bicarbonate (200 ml) and ether (300 mL), the combined bicarbonate layers were neutralized with 10% citric acid, and extracted with ethyl acetate (2×300 mL). The organic layers were dried (Na2SO4), concentrated in vacuo to afford the Ethyl 2-(4-fluorophenyl)-3-oxo-3-(4-(2-acetamido)-pyridyl)-propionate.

Step B. 5-(4-fluorophenyl)-6-(4-(2-acetamido)pyridyl))-2-thiouracil: Ethyl 2-(4-fluorophenyl)-3-oxo-3-(4-(2-acetamido)pyridyl)-propionate (1.3 g, 3.78 mmol) and thiourea (863 mg, 11.3 mmol) were suspended in anhydrous p-xylene (15 ml) with very efficient stirring. To the mixture pyridinium p-toluenesulfonate (38 mg) was added and refluxed for 12–16 h using a Dean-Stark apparatus with continuous removal of water (0.1 ml). Reaction mixture was cooled and a dark brown solid was filtered using a Buchner funnel. The collected solid was suspended in acetone (25 ml) and filtered. The acetone washed product contained a trace of thiourea, which was removed by trituration with hot water (20–30 ml). The product was filtered and air dried followed by azeotroping with toluene.

Example 21

Procedure for the preparation of (S)-2-N-Ethylamino-3-phenylpropylamine

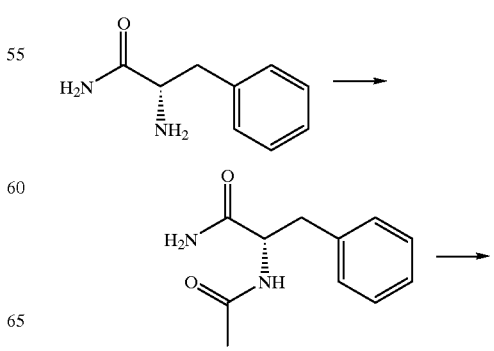

-continued

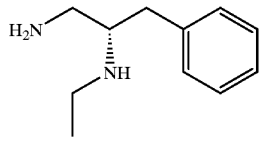 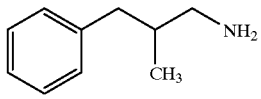

(S)-2-N-Ethylamino-3-phenylpropylamine: Acetic anhydride (1.2 ml, 12.7 mmol) was added to a stirring solution of L-phenylalanine amide (1.0 g, 6.10 mmol) in methanol (25 ml). After 1.5 h at room temperature, it was evaporated followed by drying in an oil pump vacuum. The resultant L-N-ethylphenylalanine amide (6.1 mmol) was reduced with lithium aluminium hydride (570 mg, 15.0 mmol) in tetrahydrofuran (65 mml) at 55° C. for 4 h. The reaction mixture was poured into sat. aqu. sodium hydrogencarbonate followed by extraction with dichloromethane, drying and evaporation. Column chromatography on silica gel (chloroform:methanol: triethylamine=90:7:3) provided the amine as a yellowish oil. MS (m/z): 179.1 (M+H)$^+$; $C_{11}H_{18}N_2$ requir. 178.3.

Example 22
Procedure for the preparation of 2-Amino-2-methyl-3-phenylpropylamine

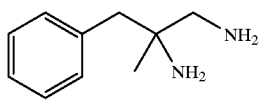

2-Amino-2-methyl-3-phenylpropylamine: A solution of commercially available D,L-a-methyl phenylalanine methyl ester (5.0 g, 25.7 mmol) in aqu. 28% ammonium hydroxide (50 ml) was kept at room temperature for 3 d. The resulting white precipitate of D,L-a-methyl phenylalanine amide was filtered and dried (2.5 g). This material (2.0 g, 11.22 mmol) was reduced with lithium aluminium hydride (1.3 g, 34.26 mmol) in boiling tetrahydrofuran for 24 h. The reaction was quenched by the addition of sodium sulfate decahydrate at ice-bath temperature. The salts were filtered off, followed by evaporation to leave the title compound as an oil. MS (m/z): 165.1 (M+H)$^+$; $C_{10}H_{16}N_2$ requir. 164.2. An alternative preparation was reported by M. Freiberger and R. B. Hasbrouck, J. Am. Chem. Soc. 82, 696–698 (1960).

Example 23
Procedure for the preparation of 2-Methyl-3-phenylpropylamine

2-Methyl-3-phenylpropylamine: A mixture of commercially available 2-methyl-3-phenylpropylamide (4.32 g, 26.5 mmol) and lithium aluminium hydride (1.3 g, 34.3 mmol) in tetrahydrofuran (184 ml) was stirred at room temperature for 5 h. It was poured into aqu. sat. sodium sulfate and extracted with dichloromethane followed by drying of the organic solution and evaporation to provide the amine as an oil. Other syntheses have been reported, e.g. Dornow and Fust, Chem. Ber. 87, 984 (1954).

Example 24
Procedure for the preparation of 5-(4-Fluorophenyl)-3-methyl-2-((2-methy-3-phenylpropyl) amino)-6-(4-pyridyl)-4 (3 H) -pyrimidinone hydrochloride

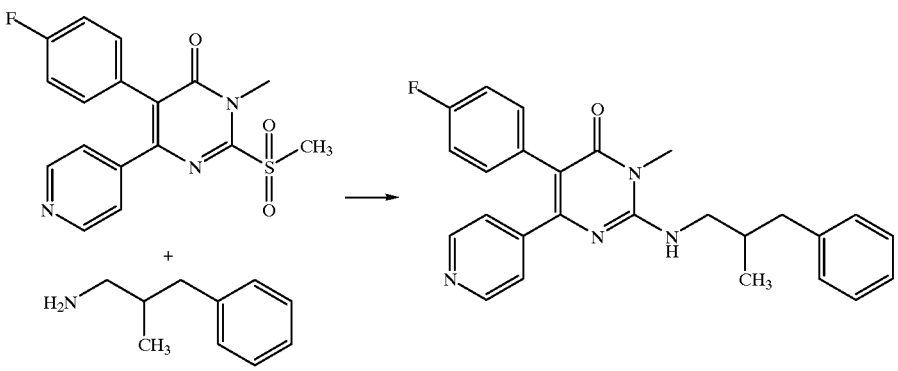

5-(4-Fluorophenyl)-3-methyl-2-((2-methy-3-phenylpropyl) amino)-6-(4-pyridyl)-4(3 H)-pyrimidinone hydrochloride: A mixture of crude 5-(4-fluorophenyl)-3-methyl-2-methylsulfonyl-6-(4-pyridyl)-4(3 H)-pyrimidinone (520 mg g, 1.45 mmol) and 2-methyl-3-phenylpropylamine (1.5 g, 10.1 mmol) was heated at 50° C. for 30 min. Column chromatography on silica gel (2–5% methanol/ dichloromethane; hexane-acetone=2:1) provided the title compound. MS (m/z): 429.4 (M+H)$^+$; $C_{26}H_{25}FN_4O$ requir. 428.5 (free base).

Example 25
Procedure for the preparation of 1-Phenyl-1,3-propanediamine

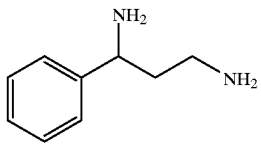

1-Phenyl-1,3-propanediamine: 3-Phenyl-3-aminopropionic acid (S. G. Cohen and S. Y. Weinstein, J. Am. Chem. Soc. 86, 725–728, 1964) was converted into 1-phenyl-1,3-propanediamine as reported in the literature (M. Kojima and J. Fujita, Bull. Chem. Soc. Jpn. 55, 1454–1459 (1982)). Analogously, 1-(2-fluorophenyl)-1,3-propanediamine, 1-(2-methylphenyl)-1,3-propanediamine and 1-(2-chlorophenyl)-1,3-propanediamine have been prepared.

Example 26

Procedure for the preparation of 3-Ethyl-5-(4-fluorophenyl)-2-methylthio-6-(4-pyridyl)-4(3 H)-pyrimidinone

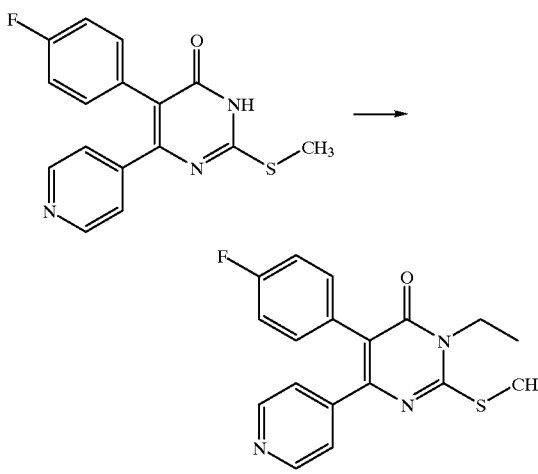

3-Ethyl-5-(4-fluorophenyl)-2-methylthio-6-(4-pyridyl)-4(3 H)-pyrimidinone: Ethyl bromide (600 ml, 8.03 mmol) was added to a stirred mixture of 5-(4-fluorophenyl)-2-methylthio-6-(4-pyridyl)-4(3 H)-pyrimidinone (1.8 g, 5.97 mmol) and sodium hydride (60% oily suspension, 320 mg, 8 mmol) in N,N-dimethylformamide (60 ml) at room temperature. More ethyl bromide (2×600 ml, 2×8.03 mmol) was added after 2 and 3.5 h. After 8 h, the reaction mixture was neutralized with acetic acid and evaporated. The remainder was taken up in dichloromethane, the organic solution was washed with water, dried and evaporated. Flash chromatography on a column of silica gel (hexane–acetone=3:1, 2:1). provided in the second main fraction the title compound as a solid.

Example 27

Procedure for the preparation of 3-Ethyl-5-(4-fluorophenyl)-2-methylsulfonyl-6-(4-pyridyl)-4(3 H)-pyrimidinone

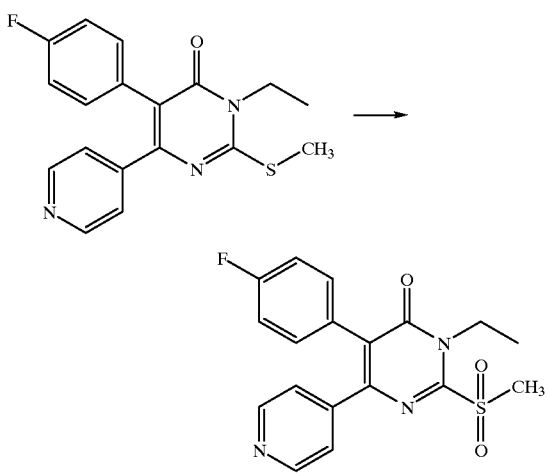

3-Ethyl-5-(4-fluorophenyl)-2-methylsulfonyl-6-(4-pyridyl)-4(3 H)-pyrimidinone: A mixture of 3-ethyl-5-(4-fluorophenyl)-2-methylthio-6-(4-pyridyl)-4(3 H)-pyrimidinone (300 mg, 0.88 mmol) and Oxone® (potassium peroxymonosulfate, 2.54 g, 4.14 mmol) in methanol (71 ml) and water (33 ml) was stirred for 14 h. The solvent was concentrated to about 35 ml, followed by extraction with dichloromethane, drying and evaporation. The resulting white solid was used without purification in the next step.

Example 28

Procedure for the preparation of 2-(((S)-2-Amino-3-phenylpropyl)-amino)-3-ethyl-5-(4-fluorophenyl)-6-(4-pyridyl)-4(3 H)-pyrimidinone hydrochloride

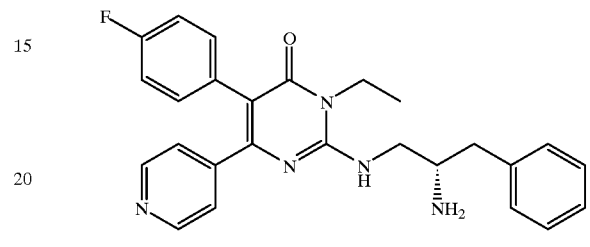

2-(((S)-2-Amino-3-phenylpropyl)-amino)-3-ethyl-5-(4-fluorophenyl)-6-(4-pyridyl)-4(3 H)-pyrimidinone hydrochloride: A mixture of 3-ethyl-5-(4-fluorophenyl)-2-methylthio-6-(4-pyridyl)-4(3 H)-pyrimidinone (150 mg, 0.44 mmol) and (S)-1,2-benzylethylendiamine (200 ml, ~1.3 mmol) was heated at 190 C for 4.5 h. Column chromatography on Iatrobeads® (chloroform:methanol:triethylamine= 90:7:3) provided the title compound as a free base which was converted into the crystallizing monohydrochloride by the addition of 2N hydrochloric acid (165 ml, 0.33 mmol) and methanol (1.5 ml). Filtration provided the title compound. MS (m/z): 444.0 (M+H)$^+$; $C_{265}$ $H_{27}FN_5O$ requir. 443.5 (free base).

Example 29

Procedure for the preparation of 3-Ethyl-5-(4-fluorophenyl)-2-((2-methy-3-phenylpropyl) amino)-6-(4-pyridyl)-4(3H)-pyrimidinone hydrochloride

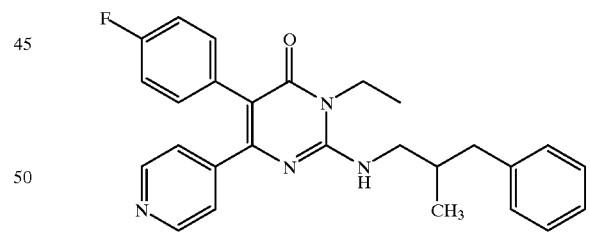

3-Ethyl-5-(4-fluorophenyl)-2-((2-methy-3-phenylpropyl) amino)-6-(4-pyridyl)-4(3 H)-pyrimidinone hydrochloride: A mixture of crude 3-ethyl-5-(4-fluorophenyl)-2-methylsulfonyl-6-(4-pyridyl)-4(3 H)-pyrimidinone (320 mg g, 0.89 mmol) and 2-methyl-3-phenylpropylamine (600 ml, ~4 mmol) was heated at 60° C. for 2 h. Column chromatography on silica gel (hexane-acetone=2:1; 2–5% methanol/dichloromethane) provided the title compound. MS (m/z): 443.2 (M+H)$^+$; $C_{27}$ $H_{27}FN_4O$ requir. 442.5.

Example 30

Procedure for the preparation of 3-(2-Methylphenyl) propylamine

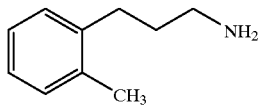

3-(2-Methylphenyl)propylamine: Diethyl cyanomethylphosphonate (5.0 ml, 30.9 mmol) was added to a stirring suspension of sodium hydride (60% oily suspension, 1.24 g, 31 mmol) in tetrahydrofuran (50 ml) under argon. After 30 min, 2-methylbenzaldehyde (3.6 ml, 31.1 mmol) was added and stirring continued for 1 h. The reaction was quenched by the addition of water and extracted with dichloromethane followed by drying and evaporation of the organic solution. Column chromatography (hexane; hexane:ethylacetate=3:1) provided 2-(2-methylphenyl)acrylonitrile as an oil. This material (3.8 g), 10% palladium on carbon (3.8 g) and 12 N hydrochloric acid (11.8 ml, 142 mmol) in methanol (125 ml) were hydrogenated with hydrogen at atmospheric pressure for 2 d. The catalyst was removed by filtration and the solvent was evaporated. The resultant material was partitioned between dichloromethane and water. The aqueous layer was made basic with 10 N sodium hydroxide and extracted with dichloromethane, followed by drying and evaporation. The resultant material was purified on a silica gel column (chloroform:methaol:triethylamine=85:10:5) to provide the title compound as an oil.

Example 31

Procedure for the preparation of 2-amino-3-(2-fluorophenyl)-propylamine

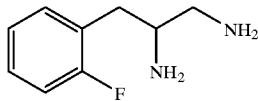

Step A. Methyl 2-amino-3-(2-fluorophenyl)propionate: 5 g (27.3 mmol) of (D,L)-(2-fluoro-phenyl)alanine was suspended in 50 ml methanolic HCl and stirred at room temperature for 3 days. The reaction mixture was concentrated in vacuo and dried to give a yellow oil. MS (m/z): 198 (M+H)$^+$; $C_{10}H_{12}FNO_2$ requir. 197.2.

Step B. 2-Amino-3-(2-fluorophenyl)propionamide: Methyl 2-amino-3-(2-fluorophenyl) propionate was suspended in 50 ml 30% ammonium hydroxide and stirred at room temperature for 18 hrs. The mixture was filtered, washed with cold water and 2-amino-3-(2-fluorophenyl) propionamide was collected as a white solid. MS (m/z): 183.1 (M+H)$^+$; $C_9H_{11}FN_2O$ requir. 182.2. 1

Step C. 2-Amino-3-(2-fluorophenyl)-propylamine: 2-Amino-3-(2-fluorophenyl)propionamide was added carefully to a chilled (5°) mixture of LAH (1.0 g, 26.3 mmol) and 20 ml THF under argon. The reaction was then heated at reflux for 10 hrs. The reaction was cooled to 5° C. and carefully treated with $Na_2SO_4.10\ H_2O$. The resulting mixture was stirred for 18 hrs, then filtered to remove the solids. The filtrate was concentrated in vacuo to give an amber oil. MS (m/z): 169 (M+H)$^+$; $C_9H_{13}FN_2$ requir. 168.19

Example 32

Procedure for the preparation of 5-(4-Fluorophenyl)-2-(((S)-2-N-glycylamino-3-phenylpropyl)-amino)-3-methyl-6-(4-pyridyl)-4(3 H)-pyrimidinone hydrochloride

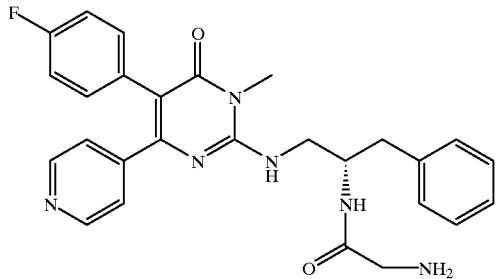

5-(4-Fluorophenyl)-2-(((S)-2-N-glycylamino-3-phenylpropyl)-amino)-3-methyl-6-(4-pyridyl)-4(3 H)-pyrimidinone hydrochloride: Ethyl chloroformate (56.8 µl, 0.59 mmol) was added at ice-bath temperature to a stirring mixture of N-(tert.-butoxycarbonyl)glycine (104 mg, 0.59 mmol) and 4-methylmorpholine (65.3 µl, 0.59 mmol) in tetrahydrofuran (9 ml). After 50 min, a solution of 2-(((S)-2-amino-3-phenylpropyl)-amino)-5-(4-fluorophenyl)-3-methyl-6-(4-pyridyl)-4(3 H)-pyrimidinone (250 mg, 0.58 mmol) in tetrahydrofuran (9 ml) was added at ice-bath temperature. Within 2 h, the mixture was allowed to reach room temperature. It was diluted with dichloromethane, washed with aqueous sodium hydrogencarbonate, followed by drying of the organic solution and evaporation. The resulting material was dissolved in methanol (1.2 ml) and 4N hydrogen chloride/dioxane (1.2 ml) was added. After 1 h at room temperature, it was evaporated and the remainder taken up in dichloromethane followed by washing with aqueous sodium hydrogencarbonate, drying of the organic solution and evaporation. Column chromatography on silica gel (dichloromethane–methanol–conc. ammonium hydroxide= 93:7:0.7) provided the title compound as the free base which was converted into the hydrochloride by the addition of 4N hydrogen chloride/dioxane (112 µl, 0.45 mmol) to its methanolic solution (3 ml) followed by evaporation. MS (m/z): 487.1 (M+H)$^+$; $C_{27}H_{27}FN_6O_2$ requir. 486.6 (free base).

Accordingly, 2-(((S)-2-N-glycylamino-3-phenylproryl)-amino)-3-methyl-5-(3-methylphenyl)-6-(4-pyridyl)-4(3 H)-pyrimidinone hydrochloride was prepared from 2-(((S)-2-amino-3-phenylpropyl)-amino))-3-methyl-5-(3-methylphenyl 6-(4-pyridyl)-4(3 H)-pyrimidinone.

Example 33

Procedure for the preparation of 5-(4-Fluorophenyl)-2-(((S)-2-hydroxyacetamido-3-phenylpropyl)-amino)-3-methyl-6-(4-pyridyl)-4(3 H)-pyrimidinone

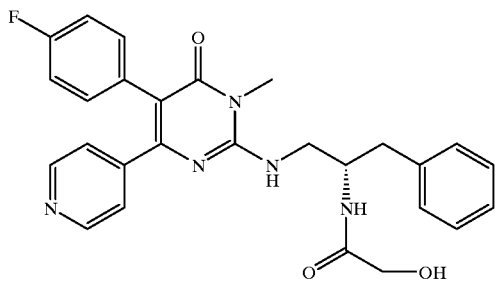

5-(4-Fluorophenyl)-2-(((S)-2-hydroxyacetamido-3-phenylpropyl)-amino)-3-methyl-6-(4-pyridyl)-4(3 H)-pyrimidinone: Acetoxyacetyl chloride (55 µl, 0.51 mmol) was added at ice-bath temperature to a stirring solution of 2-(((S)-2-amino-3-phenylpropyl)-amino)-5-(4-fluoro phenyl)-3-methyl-6-(4-pyridyl)-4(3 H)-pyrimidinone (200 mg, 0.466 mmol) and triethylamine (130 µl, 0.93 mmol) in dichloromethane (4 ml). After 50 min, the reaction was quenched by the addition of a drop of methanol followed by evaporation. The resultant material was taken up in a 1:1:1 mixture of methanol/water/triethylamine (3 ml) and left overnight. Evaporation and subsequent column chromatography (3–7% methanol/chloroforme) provided the title compound. MS (m/z): 488.3 (M+H)$^+$; $C_{27}H_{26}FN_5O_3$ requir. 487.5.

Example 34
Procedure for the preparation of 5-(4-fluorophenyl)-2-(2-((3-N-methylureido)-3-phenylpropyl)-amino)-3-methyl-6-(4-pyridyl)-4(3 H)-pyrimidinone

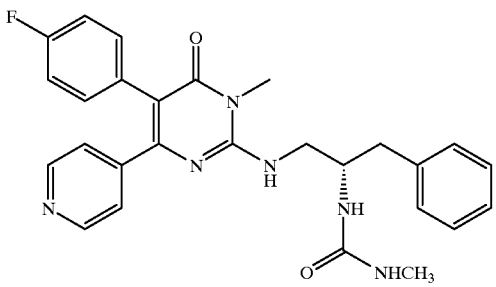

5-(4-Fluorophenyl)-2-(2-((3-N-methylureido)-3-phenylpropyl)-amino)-3-methyl-6-(4-pyridyl)-4(3 H)-pyrimidinone: Methyl isocyanate (6 µl, 0.102 mmol) was added to a solution of 2-(((S)-2-amino-3-phenylpropyl)-amino)-5-(4-fluorophenyl)-3-methyl-6-(4-pyridyl)-4(3 H)-pyrimidinone (43.6 mg, 0.102 mmol) in dioxane (1.5 ml) at 15° C. After 15 min, the solvent was evaporated and the reaction product applied to a silica gel column (5–7% methanol/chloroform) to provide the title compound. MS (m/z): 486.6 (M+H)$^+$; $C_{27}H_{27}FN_6O_2$ requir. 486.6.

Example 35
Procedure for the preparation of 5-(4-fluorophenyl)-3-methyl-6-(4-pyridyl)-2-((2-pyrrolidinyl-3-phenylpropyl)-amino)-4(3 H)-pyrimidinone hydrochloride

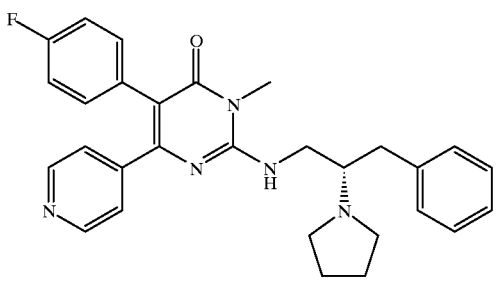

5-(4-Fluorophenyl)-3-methyl-6-(4-pyridyl)-2-(((S)-2-pyrrolidinyl-3-phenylpropyl)-amino)-4(3 H)-pyrimidinone hydrochloride: Sodium hydride (60% oily suspension, 84 mg, 2.1 mmol) was added to a solution of 2-(((S)-2-amino-3-phenylpropyl)-amino)-5-(4-fluorophenyl)-3-methyl-6-(4-pyridyl)-4(3 H)-pyrimidinone (300 mg, 0.70 mmol) in N,N-dimethylformamide (8 ml) at ice-bath temperature. After 30 min, 1,4-dibromobutane (108 µl, 0.91 mmol) was added. Stirring was continued for 30 min at ice-bath temperature, then 20 h at room temperature. It was neutralized with acetic acid, followed by evaporation. The crude product was purified on a column of silica gel (dichloromethane–methanol= 93:7; dichloromethane–methanol–conc. ammonium hydroxide=93:7:0.7). The resultant product was converted into the hydrochloride by the addition of 4N hydrogen chloride/dioxane (37 µl) to its methanolic solution (2 ml) and subsequent evaporation. MS (m/z): 484.6 (M+H)$^+$; $C_{29}H_{30}FN_5O$ requir. 483.6 (free base).

Example 36
Procedure for the preparation of 5-(4-fluorophenyl)-2-(((S)-3-N-isopropylamino-3-phenylpropyl)-amino)-3-methyl-6-(4-pyridyl)-4(3 H)-pyrimidinone hydrochloride

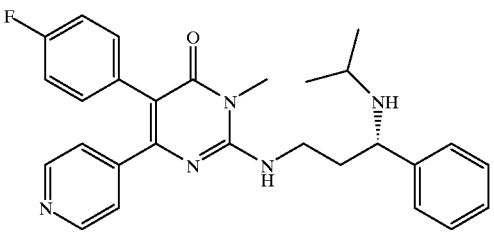

5-(4-Fluorophenyl)-2-(((S)-3-N-isopropylamino-3-phenylpropyl)-amino)-3-methyl-6-(4-pyridyl)-4(3 H)-pyrimidinone hydrochloride: Sodium triacetoxyborohydride (12.9 mg, 0.061 mmol) was added to a stirring mixture of 2-(((S)-3-amino-3-phenylpropyl)-amino)-5-(4-fluorophenyl)-3-methyl-6-(4-pyridyl)-4(3 H)-pyrimidinone (21.8 mg, 0.051 mmol) and acetone (4.5 µl, 0.061 mmol) in 1,2-dichloroethane (0.4 ml). After 2.5 h, the reaction was quenched by the addition of sat. aqu. sodium hydrogencarbonate, followed by extraction with dichloromethane, drying of the organic solution and evaporation. Chromatography on a column of silica gel (10% methanol/chloroform) provided the title compound as a free base which was converted into the monohydrochloride by the addition of 4N hydrochloric acid/dioxane (12.2 µl) to its methanolic solution (1 ml) and subsequent evaporation. MS (m/z): 472.0 (M+H)$^+$; $C_{28}H_{30}FN_5O$ requir. 471.6 (free base).

Example 37
Procedure for the preparation of 5-(4-fluorophenyl)-2-(((R)-3-N-isopropylamino-3-phenylpropyl)-amino)-3-methyl-6-(4-pyridyl)-4(3 H)-pyrimidinone hydrochloride

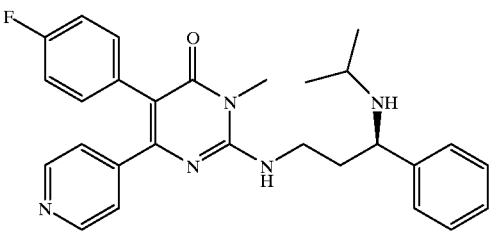

5-(4-Fluorophenyl)-2-(((R)-3-N-isopropylamino-3-phenylpropyl)-amino)-3-methyl-6-(4-pyridyl)-4(3 H)-pyrimidinone hydrochloride was prepared from 5-(4-fluorophenyl)-2-(((R)-3-N-isopropylamino-3-phenylpropyl)-amino)-3-methyl-6-(4-pyridyl)-4(3 H)-pyrimidinone as described above for its S-enantiomer. MS (m/z): 472.1 (M+H)$^+$; $C_{28}H_{30}FN_5O$ requir. 471.6 (free base).

Example 38
Procedure for the preparation of 2-(((S)-3-acetamido-3-phenylpropyl)-amino)-5-(4-fluorophenyl)-3-methyl-6-(4-pyridyl)-4(3 H)-pyrimidinone

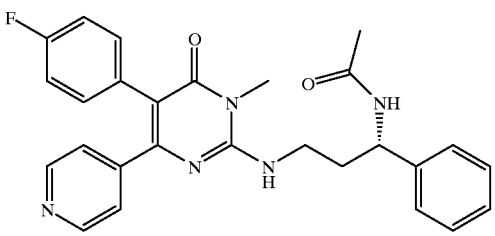

2-(((S)-3-Acetamido-3-phenylpropyl)-amino)-5-(4-fluorophenyl)-3-methyl-6-(4-pyridyl)-4(3 H)-pyrimidinone: A solution of 2-(((S)-3-amino-3-phenylpropyl)-amino)-5-(4-fluorophenyl)-3-methyl-6-(4-pyridyl)-4(3 H)-pyrimidinone (23.8 mg, 0.055 mmol) and acetic anhydride (20 μl, 0.21 mmol) in methanol(1 ml) was kept for 30 min at room temperature. Evaporation was followed by column chromatography (dichloromethane–methanol–ammonium hydroxide=93:7:0.7) to provide the title compound. MS (m/z): 472.2 (M+H)$^+$; $C_{27}H_{26}FN_5O_2$ requir. 471.5.

Example 39
Procedure for the preparation of(S)-1-Phenyl-1,3-propanediamine

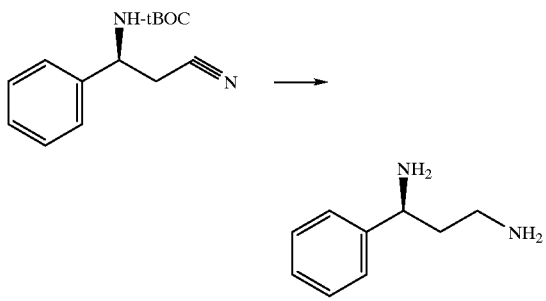

(S)-1-Phenyl-1,3-propanediamine: S-3-N-tert.-Butoxycarbonylamino-3-phenylpropionitrile was prepared according to the literature (W. J. Wheeler and D. D. O'Bannon, J. Label.Compds. Radiopharm. XXXI (4), 305–315, 1992) from D-(−)-α-phenylglycinol. For reduction (D. Mitchell and T. M. Koenig, Synth. Comm. 25 (8), 1231–1238, 1995), borane-methyl sulfide complex (2N, 3 ml, 6 mmol) was added dropwise to a solution of the nitrile (1 g, 4.06 mmol) in tetrahydrofuran (6 ml). Methyl sulfide was distilled off and the resulting solution refluxed for 2.5 h. With ice-cooling, methanolic hydrogen chloride (1N, 3 ml) was added followed by evaporation. The remainder was taken up in methanol (10 ml) and 4N hydrogen chloride/dioxane (10 ml) was added. After 1 h at room temperature, it was evaporated and the aqueous solution of the resultant product was washed with dichloromethane. The aqueous solution was made basic by the addition of solid potassium hydroxide followed by repeated dichloromethane extractions. Drying and evaporation of the dichloromethane solution left the crude diamine as an oil. MS (m/z): 150.8 (M+H)$^+$; $C_9H_{14}N_2$ requir. 150.2.
Enantiomeric (R)-1-phenyl-1,3-propanediamine was prepared analogously from L-(+)-α-phenylglycinol: MS (m/z): 150.9 (M+H)$^+$; $C_9H_{14}N_2$ requir. 150.2.

Example 40
Procedure for the preparation of (2R,3R)-2-methyl-3-phenyl-1,3-propanediamine

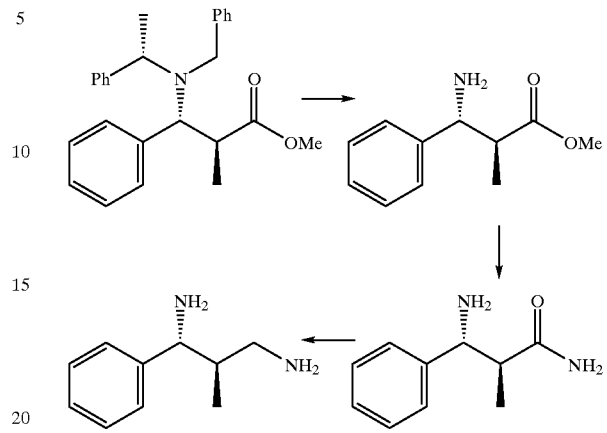

Step A: Methyl (2S,3R,αS)-3-(N-benzyl-N-α-methylbenzylamino)-2-methyl-3-phenylpropionate was prepared as reported for the 2R,3S,αR-enantiomer (S. G. Davies and I. A. S. Walters, J. Chem. Soc. Perkin Trans.I, 1129–1139 (1994).
Step B: Methyl (2S,3R)-3-amino-2-methyl-3-phenylpropionate: A mixture of methyl (2S,3R,αS)-3-(N-benzyl-N-a-methylbenzylamino)-2-methyl-3-phenylpropionate (13.0 g, 33.55 mmol) and 10% palladium-on-carbon (13.0 g) in glacial acetic acid (260 ml) was hydrogenated under a balloon of hydrogen for 24 h. The catalyst was removed by filtration followed by evaporation and co-distillation with toluene to provide the title compound as a white solid. MS (m/z): 194.2 (M+H)$^+$; $C_{11}H_{15}NO_2$ requir. 193.3.
Step C: (2S,3R)-3-Amino-2-methyl-3-phenylpropionamide: A solution of methyl (2S,3R)-3-amino-2-methyl-3-phenylpropionate (6.3 g, 33 mmol) in 2N methanolic ammonia (20 ml) and ammonium hydroxide (28–30%, 40 ml) was stirred at room temperature. After 4d, it was evaporated followed by chromatography on a short column of silica gel (dichloromethane–methanol–conc. ammonium hydroxide= 93:7:0.7; 90:10:0.8) to provide the amide as a white solid. MS (m/z): 179.2 (M+H)$^+$; $C_{10}H_{14}N_2O$ requir. 178.2.
Step D: (2R,3R)-2-methyl-3-phenyl-1,3-propanediamine: Lithium aluminium hydride (2.3 g, 60.60 mmol) was added in portions to a stirring solution of (2S,3R)-3-amino-2-methyl-3-phenylpropionamide (2.6 g, 14.59 mmol) in tetrahydrofuran (54 ml) at ice-bath temperature. After 45 min, the mixture was heated at reflux for 16 h. With ice-bath cooling, the reaction was quenched by the portionwise addition of sodium sulfate decahydrate and some methanol until hydrogen evolution ceased. The solids were removed by filtration and washed with dichloromethane. The combined filtrates were evaporated to provide the title compound. MS (m/z): 165.2 (M+H)$^+$; $C_{10}H_{16}N_2$ requir. 164.3.
Accordingly, the enantiomer (2S,3S)-2-methyl-3-phenyl-1,3-propanediamine was prepared from methyl (2R,3S,αR)-3-(N-benzyl-N-α-methylbenzylamino)-2-methyl-3-phenylpropionate. MS (m/z): 165.3 (M+H)$^+$; $C_{10}H_{16}N_2$ requir. 164.3.
Analogously, the enantiomers (2R,3S)-2-methyl-3-phenyl-1,3-propanediamine and (2S,3R)-2-methyl-3-phenyl-1,3-propanediamine may be prepared from tert.butyl (2S,3S,(αR)- and -(2R,3R,αS)-3-(N-benzyl-N-α-methylbenzylamino)-2-methyl-3-phenylpropionate (S. Davies et al., J. Chem. Soc. Chem. Commun. 1153–1155, 1993).

Example 41
Procedure for the preparation of 2-((S)-3-Benzylpiperaziny)-5-(4-fluorophenyl)-3-methyl-6-(4-pyridyl)-4(3 H)-pyrimidinone hydrochloride

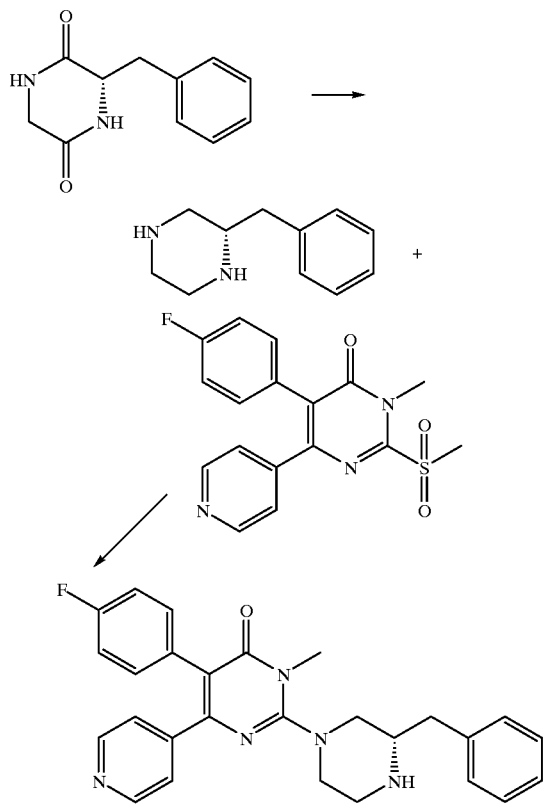

Step A: (S)-2-Benzylpiperazine: At ice-bath temperature, lithium aluminium hydride (1.6 g, 42.16 mmol) was added in portions to a stirring mixture of (S)-2-benzylpiperazine-3,6-dione (3.0 g, 14.70 mmol) (comm. avail.) and tetrahydrofuran (80 ml). After 30 min at ice-bath temperature, the mixture was refluxed for 4 h with stirring. The reaction was quenched by the portionwise addition of sodium sulfate decahydrate and some methanol until hydrogen evolution ceased. It was filtered and the solids were washed several times with dichloromethane. The combined filtrates were evaporated to leave a white solid. MS (m/z): 177.1 (M+H)$^+$; $C_{11}H_{16}N_2$ requir. 176.3.

Step B: 2-((S)-3-Benzylpiperaziny)-5-(4-fluorophenyl)-3-methyl-6-(4-pyridyl)-4(3 H)-pyrimidinone hydrochloride: A mixture of crude 5-(4-fluorophenyl)-3-methyl-2-methylsulfonyl-6-(4-pyridyl)-4(3 H)-pyrimidinone (434 mg, 1.21 mmol) and (S)-2-benzylpiperazine (426 mg, 2.42 mmol) was heated at 105° C. for 1 h. The crude reaction product was purified by column chromatography on silica gel (dichloromethane–methane=93:7; dichloromethane–methanol–conc. ammonium hydroxide=93:7:0.7). The resulting material was converted into its hydrochloride by the addition of 4N hydrogen chloride/dioxane (75 μl) to its methanolic solution (3 ml) followed by evaporation. MS (m/z): 456.5 (M+H)$^+$; $C_{27}H_{26}FN_5O$ requir. 455.5 (free base).

Example 42
Procedure for the preparation of 5-(4-fluorophenyl)-3-methyl-2-(3-phenylpropoxy)-6-(4-pyridyl)-4(3 H)-pyrimidinone

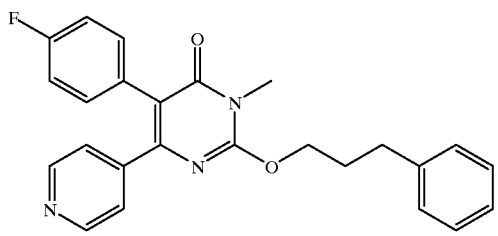

5-(4-fluorophenyl)-3-methyl-2-(3-phenylpropoxy)-6-(4-pyridyl)-4(3 H)-pyrimidinone: Sodium hydride (60% oily suspension, 111 mg, 2.79 mmol) was added to a stirred solution of 3-phenylpropanol (387 mg, 2.85 mmol) in tetrahydrofuran (1 ml). After gas evolution ceased, 5-(4-fluorophenyl)-3-methyl-2-methylsulfonyl-6-(4-pyridyl)-4(3 H)-pyrimidinone (100 mg, 0.279 mmol) was added and the mixture was heated at 60° C. for 30 min. The reaction mixture was partitioned between dichloromethane and water. The organic solution was washed with brine, dried and evaporated. Column chromatography on silica gel (hexane–ethyl acetate=2:1) provided the title compound. MS (m/z): 416.1 (M+H)$^+$; $C_{25}H_{22}FN_3O_2$ requir. 415.5.

Example 43
Procedure for the preparation of 5-(4-fluorophenyl)-3-methyl-2-(4-phenylbutyl)-6-(4-pyridyl)-4(3 H)-pyrimidinone

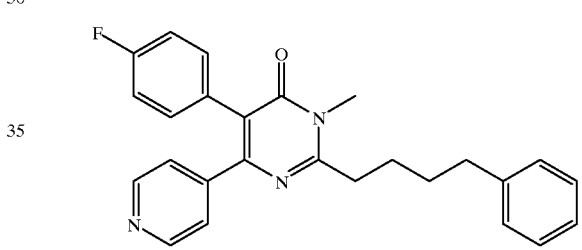

Step A: 5-(4-Fluorophenyl)-2-(4-phenylbutyl)-6-(4-pyridyl)-4(3 H)-pyrimidinone: Ethyl 2-(4-fluorophenyl)-3-oxo-3-(4-pyridyl)-propionate (293 mg, 1.02 mmol), 4-phenylbutanecarboxamidine (315 mg, 1.79 mmol) and pyridinium p-toluenesulfonate (10 mg) were suspended in p-xylene (10 ml). With efficient stirring, the mixture was heated to reflux using a Dean-Stark apparatus with continuous removal of water. After 16 h, the solvent was evaporated and the product purified by column chromatography on silica gel (3% methanol/dichloromethane) followed by recrystallization from acetone. MS (m/z): 400.3 (M+H)$^+$; $C_{25}H_{22}FN_3O$ requir. 399.5.

Step B: 5-(4-Fluorophenyl)-3-methyl-2-(4-phenylbutyl)-6-(4-pyridyl)-4(3 H)-pyrimidinone: Methyl iodide (22 μl, 0.351 mmol) was added to a stirring mixture of 5-(4-fluorophenyl)-2-(4-phenylbutyl)-6-(4-pyridyl)-4(3 H)-pyrimidinone (140 mg, 0.351 mmol) and potassium carbonate (49 mg, 0.351 mmol) in N,N-dimethylformamide (5 ml). After 75 min, it was evaporated and the resultant product purified on a silica gel column (hexane–acetone= 3:1; 2:1) to provide the title compound. MS (m/z): 414.3 (M+H)$^+$; $C_{26}H_{24}FN_3O$ requir. 413.5.

Example 44
The compounds shown in Table I were prepared using the procedures of Examples 1–43.

TABLE I
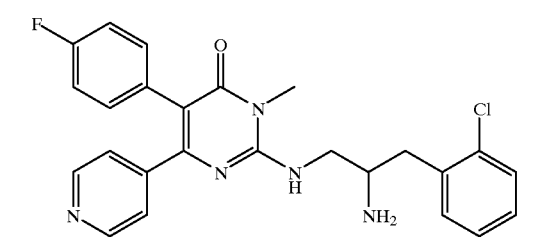
MS (m/z): 464.0 (M)+;
C25H23FN5O requir. 463.9
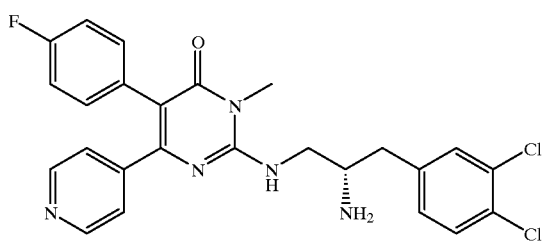
MS (m/z): 498.0 (M)+;
C25H22FN5O requir. 498.4
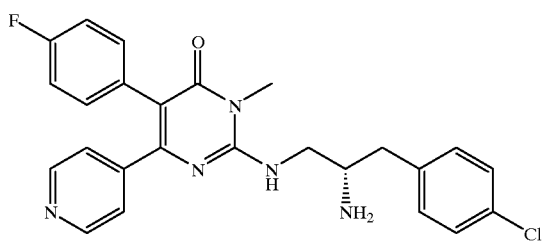
MS (m/z): 464.1 (M)+;
C25H23ClFN5O requir. 463.9
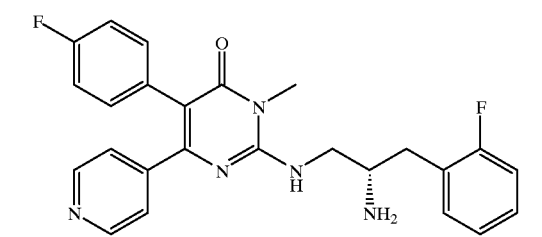
MS (m/z): 448.3 (M + H)+;
C25H23F2N5O2 requir. 447.5
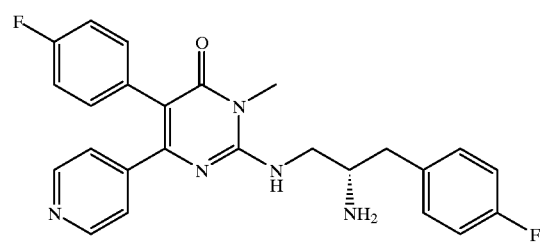
MS (m/z): 448.2 (M + H)+;
C25H22F2N5O requir. 447.3
TABLE I-continued
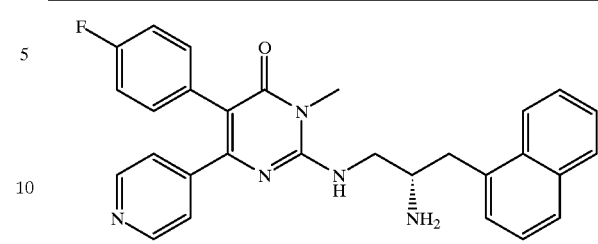
MS (m/z): 479.7 (M)+;
C29H26FN5O requir. 479.6
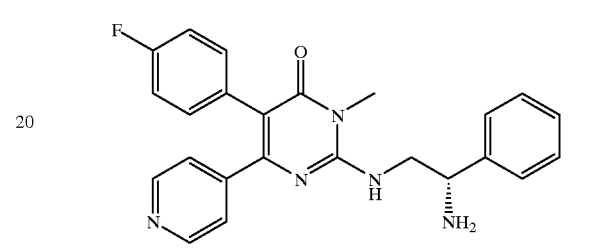
MS (m/z): 416.1 (M + H)+;
C24H22FN5O requir. 415
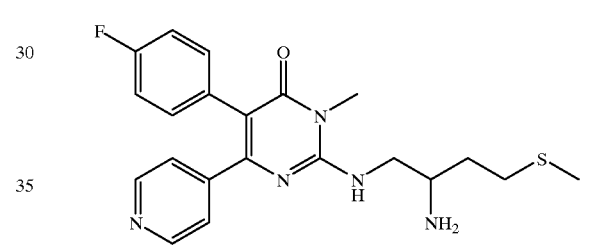
MS (m/z): 414.0 (M + H)+;
C21H24FN5OS requir. 413.5
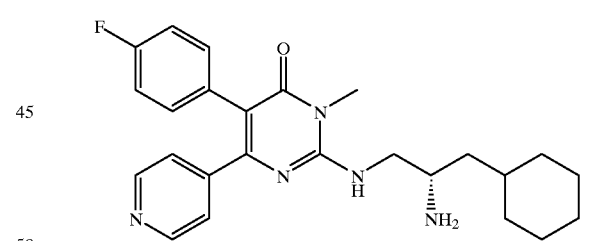
MS (m/z): 436.2 (M + H)+;
C25H30FN5O requir. 435.6
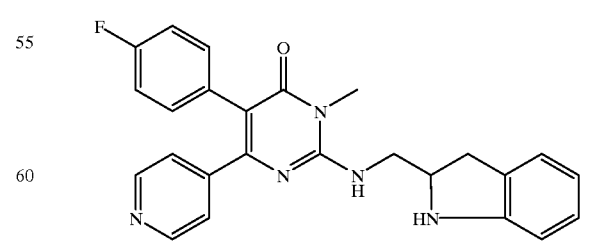
MS (m/z): 428.1 (M + H)+;
C25H22FN5O requir. 427.5

TABLE I-continued
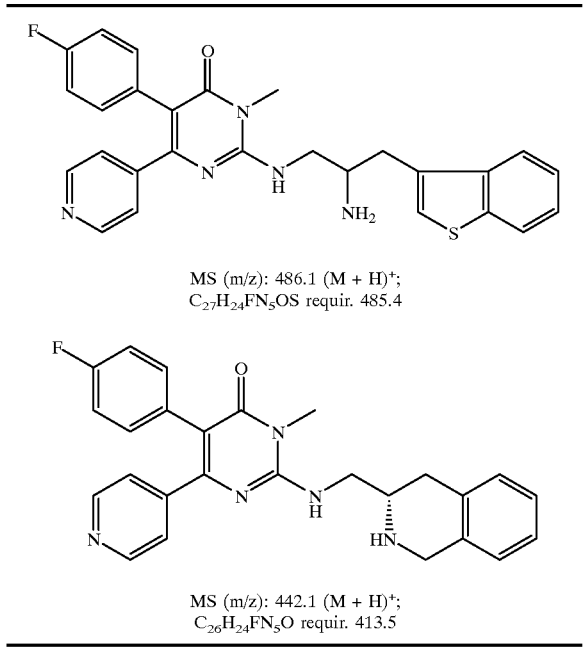
MS (m/z): 486.1 (M + H)$^+$;
$C_{27}H_{24}FN_5OS$ requir. 485.4
MS (m/z): 442.1 (M + H)$^+$;
$C_{26}H_{24}FN_5O$ requir. 413.5
Example 45
The compounds shown in Table II can be prepared using the procedures of Examples 1–43, wherein $R^{11}$ represents 3-methylphenyl, 3-chlorophenyl, 3-trifluoromethylphenyl, 4-fluorophenyl, 4-methylphenyl, 4-chlorophenyl and 3,4-dimethylphenyl.
TABLE II
TABLE II-continued
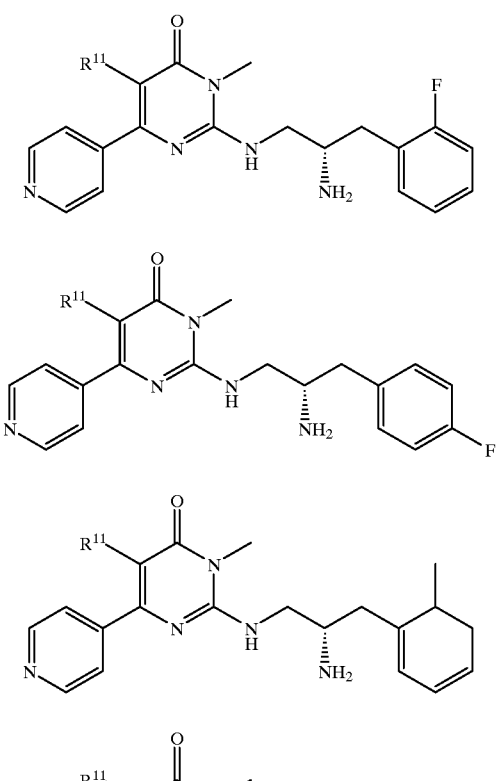
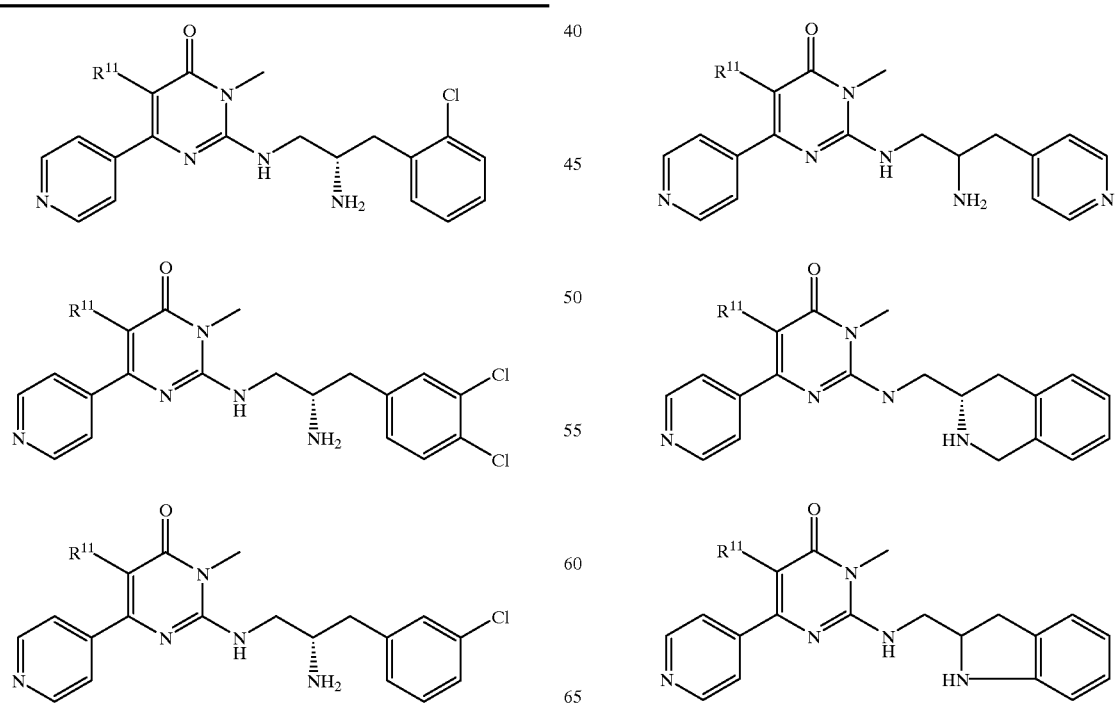

TABLE II-continued

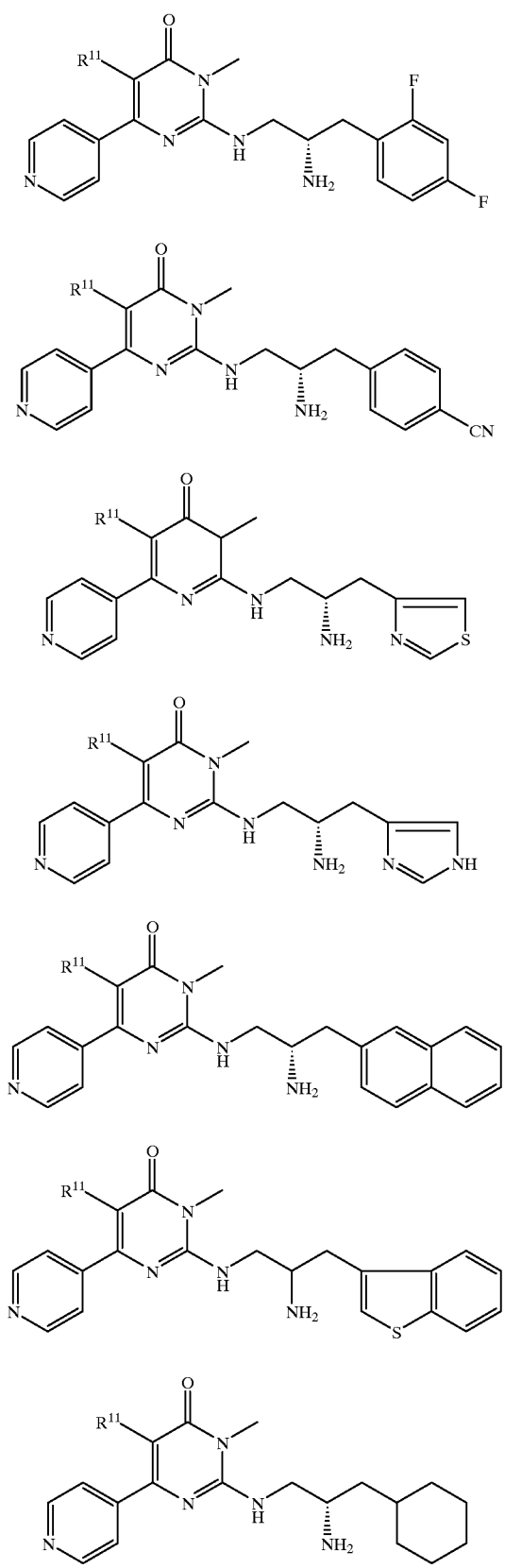

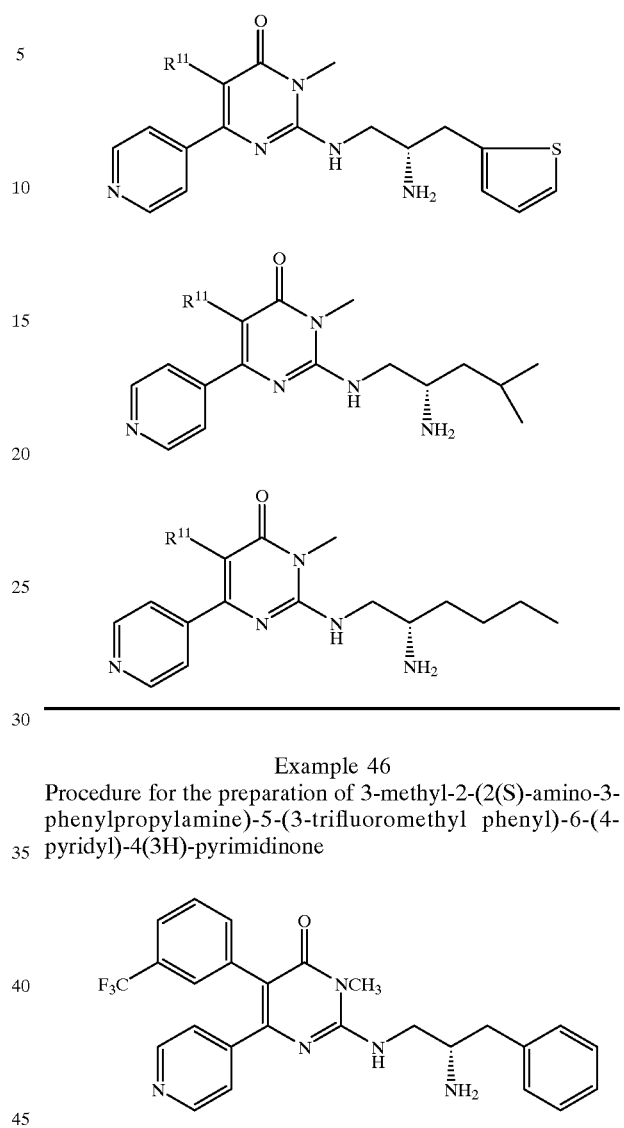

Example 46

Procedure for the preparation of 3-methyl-2-(2(S)-amino-3-phenylpropylamine)-5-(3-trifluoromethyl phenyl)-6-(4-pyridyl)-4(3H)-pyrimidinone

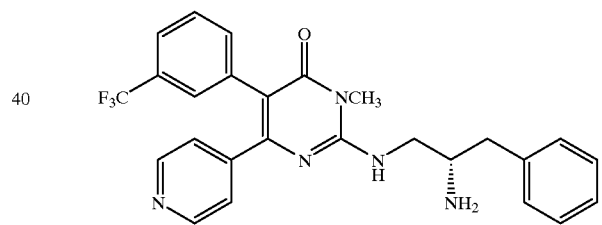

Step A. 6-(4-pyridyl)-2-thiouracil: Ethyl isonicotinoylacetate (5 g, 25.89 mmol) and thiourea (5.94 g, 77.64 mmol) were suspended in anhydrous p-xylene (100 ml) with vigorous stirring. To the mixture, pyridinium p-toluenesulfonate (150 mg) was added and refluxed for 12–16 h using a Dean-Stark apparatus with continuous removal of water (0.5 ml). The reaction mixture was cooled and a dark brown solid was filtered. The collected solid was suspended in acetone (25 ml) and filtered. The acetone washed product contain trace of thiourea, which was removed by trituration with hot water (20–30 ml). The title compound was isolated by filtration. MS (m/z): 206.2 $C_9H_7N_3OS$ requir. 205.3. [1] H-NMR (DMSO-$d_6$): d 12.65 (bm, 2 H, NH and SH), 8.71(m, 2 H, pryid.), 7.66(m, 2 H, Pyrid.), 6.25 (s, 1 H, H-5).

Step B. 3-Methyl-6-(4-pyridyl)-2-methylthio-4(3H)-pyrimidinone: 6-(4-Pyridyl)-2-thiouracil (1.5 g 7.299 mmol) was dissolved in DMF (50 ml) and the mixture was cooled to 0° C. Sodium hydride (0.437 g, 0.730 g 60% in oil, 18.25 mmol) was added and the reaction mixture was stirred for 30 minutes. Methyl iodide (1.2 ml, 2.6 g, 18.25 mmol)

was added dropwise over 15 minutes. Formation of dimethyl compound was monitored by TLC. Reaction mixture was concentrated and the residue chromatographed on silica gel column using hexane: acetone (9:1, 4:1 and 2:1) to obtain the title compound as a solid: MS(m/z):234.1 $C_{11}H_{11}N_3OS$ requir. 233.2; 1 H-NMR(CDCl$_3$):d 8.75 (m, 2 H, pyridyl), 7.8 (m, 2 H, pyridyl), 6.75 (s, 1 H), 3.58 (s, 3 H, N—CH$_3$), 2.72 (s, 3 H, S—CH$_3$).

Step C. 3-Methyl-5-bromo-6-(4-pyridyl)-2-methylthio-4(3 H)-pyrimidinone: 3-Methyl-6-(4-pyridyl)-2-methylthio-4(3 H)-pyrimidinone (1.00 g 4.29 mmol) was dispersed in acetic acid (24 ml) and to the clear solution Bromine (0.5 ml, 1.5 g 9.38 mmol) was added. The reaction mixture stirred at room temperature for 24 h. The mixture was concentrated and the residue was co-evaporated with toluene until all bromine is removed. The crude compound is ready to use in next step. MS(m/z): 312 and 314. $C_{11}H_{10}BrN_3OS$ requir. 311 and 313. 1 H-NMR(DMSO-d6):d 8.75 (m, 2 H, pyridyl) 8.19 (m, 2 H, pyridyl), 3.67 (s, 3 H, N-CH$_3$), 2.80 (s, 3 H, S—CH$_3$).

Step D. 3-Methyl-5-(3-trifluoromethylphenyl)-6-(4-pyridyl)-2-thiomethyl-4(3H)-pyrimidinone: 3-Methyl-5-bromo-6-(4-pyridyl)-2-methylthio-4(3 H)-pyrimidinone (1.2 g, 3.8 mmol) was dipersed in 2M sodium carbonate solution (30 ml) and the pale yellow colour of the adhered bromine disappeared to give colourless precipitate in the reaction mixture. 3-Trifluromethylbenzene boronic acid (1.00 g, 5.27 mmol) and toluene (30 ml) were added to the above mixture and the reaction mixture was degassed. Tetrakis triphenyl phosphine Pd(O) (350 mg) was added. The reaction mixture was refluxed for 8–12 h. The formation of the product was monitored by TLC. The mixture was cooled, diluted with toluene(20 ml) and washed with water. The organic layer was dried over sodium sulfate, concentrated and product isolated by silica gel chromatgraphy to give the titled compound. MS(m/z): 378.4 $C_{18}H_{14}F_3N_3OS$ requir. 377.39; 1 H-NMR(CDCl$_3$):d 8.5 (m, 2 H, pyridyl), 7.45 (s, 1 H), 7.17–7.25 (m, 3 H, pyridyl and Ph-CF$_3$), 6.95 (d, 1 H, Ph-CF$_3$), 3.67 (N—CH$_3$), 2.8 (S—CH$_3$).

Step E. 3-methyl-2-(2(S)-amino-3-phenylpropylamino)-5-(3-trifluoromethylphenyl)-6-(4-pyridyl)-4(3 H)-pyrimidinone: 3-Methyl-5-(3-trifluoromethylphenyl)-6-(4-pyridyl)-2-thiomethyl-4(3 H) -pyrimidinone (0.7 g, 1.85 mmol) and (S)-2-amino-3-phenyl-1-propylamine (0.9 ml, 6.00 mmol) were mixed in a round bottom flask and heated at 185° C. for 3 h. The mixture was separated on silica gel (dichloromethane: methanol: ammonium hydroxide 92:7:1) to obtain compound titled compound. MS(m/z): 480, $C_{26}H_{24}F_3N_5O$ requir 479.51; 1 H-NMR(CDCl$_3$):d 8.49 (m, 2 H, pyridyl), 7.51-7.17 (m, 11 H, Ph and pyridyl), 5.81 (bm, 1 H, NH), 3.91 (m, 1 H, CH), 3.53 (s, 3 H, N—CH$_3$), 3.35 (m, 2 H, CH$_2$), 2.94 (dd, 1 H, CH$_2$), 2.82 (dd, 1 H, CH$_2$).

Example 47

Using the corresponding starting materials, the following compounds of Table III were prepared using the procedure for 3-methyl-2-(2(S)-amino-3-phenylpropylamino)-5-(3-trifluoromethylphenyl)-6-(4-pyridyl)-4(3 H)-pyrimidinone.

TABLE III

| $R_{30}$ | $R_{31}$ | MS (m/z) |
|---|---|---|
| 4-tolyl | 2 (S)-amino-3-phenyl-propyl | 426 |
| 4-trifluoromethyl phenyl | 2 (S)-amino-3-phenyl-propyl | 480 |
| 3-isopropylphenyl | 2 (S)-amino-3-phenyl-propyl | 454 |
| 3-chloro-4-fluoro phenyl | 2 (S)-amino-3-phenyl-propyl | 464 |
| 3,5-bis(trifluoro methyl)phenyl | 2 (S)-amino-3-phenyl-propyl | 548 |
| 3,4-dichloro phenyl | 2 (S)-amino-3-phenyl-propyl | 482 |
| 1-naphthyl | 2 (S)-amino-3-phenyl-propyl | 462 |
| 3-fluorophenyl | 2 (S)-amino-3-phenyl-propyl | 430 |
| 3-chlorophenyl | 2 (S)-amino-3-phenyl-propyl | |
| 3-methylphenyl | 2 (S)-amino-3-phenyl-propyl | |
| 4-chlorophenyl | 2 (S)-amino-3-phenyl-propyl | |
| 2-chlorophenyl | 2 (S)-amino-3-phenyl-propyl | |
| 2-thienyl | 2 (S)-amino-3-phenyl-propyl | |
| 3,4-dimethylphenyl | 2 (S)-amino-3-phenyl-propyl | 440.6 |
| 3,5-dichloro phenyl | 3-phenylpropyl | 467 |
| 4-tolyl | 3-phenylpropyl | 411 |
| 3-trifluoromethyl phenyl | 3-phenylpropyl | 465 |
| 4-methoxyphenyl | 3-phenylpropyl | 427 |
| 4-trifluoromethyl phenyl | 3-phenylpropyl | 465 |
| 3-chlorophenyl | 3-phenyl-propyl | |
| 3-methylphenyl | 3-phenyl-propyl | |
| 4-chlorophenyl | 3-phenyl-propyl | |
| 2-chlorophenyl | 3-phenyl-propyl | |
| 3-nitrophenyl | 3-phenyl-propyl | |
| 3-methoxyphenyl | 3-phenyl-propyl | |
| 2-fluorophenyl | 3-phenyl-propyl | |
| benzothienyl | 3-phenyl-propyl | |
| 3-fluorophenyl | 2-methyl-3-phenyl-propyl | 429 |
| 1-naphthyl | 2-methyl-3-phenyl-propyl | 461 |
| 3-trifluoromethyl phenyl | 2 (S)-dimethylamino-3-phenylpropyl | |
| 3-methylphenyl | 2 (S)-dimethylamino-3-phenylpropyl | |
| 3-chlorophenyl | 2 (S)-N,N-dimethylamino-3-phenylpropyl | |
| 3-nitrophenyl | 2 (S)-N,N-dimethylamino-3-phenylpropyl | |
| 3-methoxyphenyl | 2 (S)-N,N-dimethylamino-3-phenylpropyl | |
| 2-fluorophenyl | 2 (S)-N,N-dimethylamino-3-phenylpropyl | |
| 3-trifluoromethyl phenyl | (S)-tetrahydroisoquinol-3-ylmethylenamino | 492.1 |
| 3-methylphenyl | (S)-tetrahydroisoquinol-3-ylmethylenamino | 438 |
| 3,4-dimethylphenyl | 3-amino-3-phenylpropylamine | 440.6 |
| 3-methylphenyl | 3-amino-3-phenylpropylamine | |
| benzothienyl | 3-amino-3-phenylpropylamine | |
| benzofuranyl | 3-amino-3-phenylpropylamine | |

Example 48

3-Methyl-5-(4-methylsulfinylphenyl)-6-(4-pyridyl)-2-thiomethyl-4(3 H)-pyrimidinone: The title compound was prepared in the manner of example 34-D substituting 4-methylsulfinylbenzene boronic acid for 3-trifluoromethylbenzene boronic.

Example 49

3-methyl-2-(3(S)-(1,2,3,4-tetrahydroisoquinolinyl)methyl amino)-5-(4-methylthiophenyl)-6-(4-pyridyl)-4(3

H)-pyrimidinone: The title compound was prepared in the manner of example 34 step D with the following substitutions of 3-methyl-5-(4-methylsulfinylphenyl)-6-(4-pyridyl)-2-thiomethyl-4(3 H)-pyrimidinone for 3-methyl-5-(3-trifluoromethylphenyl)-6-(4-pyridyl)-2-thiomethyl-4(3 H)-pyrimidinone and 3(S)-(1,2,3,4-tetrahydroisoquinolinyl) methylamine for (S)-2-amino-3-phenyl-1-propylamine: MS (m/z) 470 (M+H)+.

Example 50

3-methyl-2-(3(S)-(1,2,3,4-tetrahydroisoquinolinyl)methyl amino)-5-(4-methylsulfonylphenyl)-6-(4-pyridyl)-4(3 H)-pyrimidinone: To a solution of 3-methyl-2-(3(S)-(1,2,3,4-tetrahydroisoquinolinyl)methylamino)-5-(4-methylthiophenyl)-6-(4-pyridyl)-4(3 H)-pyrimidinone (50 mg, 0.11 mmol) in methanol:water (15 mL:10 mL) was added oxone (127 mg, 0.21 mmol) as a solid in one portion at 23° C. After 16 h, the reaction was concentrated under a stream of nitrogen. The reaction mixture was applied directly to purification via preparative plate chromatography (3 silica gel 2 mm thick plates; 5% methanol in methylene chloride) to afford the title compound: MS (m/z) 502 (M+H)+.

Example 51

2-(((S)-3-Amino-3-phenylpropyl)-amino)-3-methyl-6-(4-pyridyl)-5-(3-trifluoromethylphenyl)-4(3 H)-pyrimidinone hydrochloride was prepared from 3-methyl-2-methylthio-6-(4-pyridyl)-5-(3-trifluoromethylphenyl)-4(3 H)-pyrimidinone and (S)-1-phenyl-1,3-propanediamine according to the General Procedure. The reaction was at 190° C. for 1 h. MS (m/z): 480.0 (M+H)+; $C_{26}$ $H_{24}F_3N_5O$ requir. 479.5 (free base).

Example 52

2-(((R)-3-Amino-3-phenylpropyl)-amino)-3-methyl-6-(4-pyridyl)-5-(3-trifluoromethylphenyl)-4(3 H)-pyrimidinone hydrochloride was prepared from 3-methyl-2-methylthio-6-(4-pyridyl)-5-(3-trifluoromethylphenyl)-4(3 H)-pyrimidinone and (R)-1-phenyl-1,3-propanediamine according to the General Procedure. The reaction was done at 190° C. for 3.5 h. MS (m/z): 480.4 (M+H)+; $C_{26}$ $H_{24}F_3N_5O$ requir. 479.5 (free base).

Example 53

Procedure for the preparation of 2-chloro-3-methyl-5-(3-methylphenyl)-6-(4-pyridyl)-4(3 H)-pyrimidinone

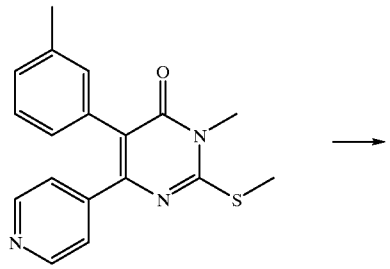

-continued

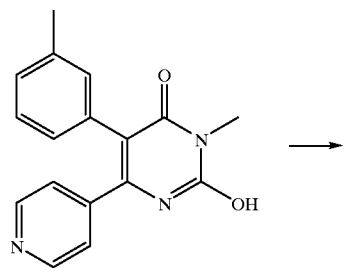

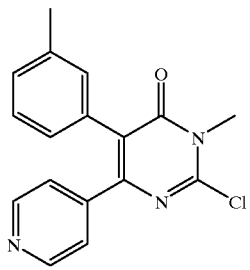

Step A: 3-Methyl-5-(3-methylphenyl)-6-(4-pyridyl)-2,4(1 H,3 H)-pyrimidindione: 10 N Sodium hydroxide (25 ml) and water (50 ml) was added to a solution of 3-methyl-5-(3-methylphenyl)-2-methylthio-6-(4-pyridyl)-4(3 H)-pyrimidindione (16.17 g, 0.05 mol) in dixoxane (65 ml). The mixture was heated at 80° C. for 16 h under argon. The mixture was allowed to reach room temperature and the pH value was adjusted to 9 with 1 N hydrochloric acid. The precipitate was filtered, washed with water and dried to give the title compound. MS (m/z): 292 (M—H)+; $C_{17}$ $H_{15}N_3O_2$ requir. 293.3.

Step B: 2-Chloro-3-methyl-5-(3-methylphenyl)-6-(4-pyridyl)-4(3 H)-pyrimidinone: A mixture of 3-methyl-5-(3-methylphenyl)-6-(4-pyridyl)-2,4(1 H,3 H)-pyrimidindione (12.5 g, 0.043 mol) and phosphorus oxychloride (65 ml) was refluxed for 16 h. The excess of phosphorus oxychloride was evaporated followed by co-distillation with toluene. The remainder was carefully partitioned between dichloromethane and aqueous sodium hydrogencarbonate. The organic solution was washed with water, dried and evaporated to leave the title compound. MS (m/z): 312 (M)+; $C_{17}$ $H_{14}ClN_3O$ requir. 311.8.

2-Chloro-3-methyl-6-(4-pyridyl)-5-(3-trifluoromethylphenyl)-4(3 H)-pyrimidinone was prepared according to the same procedure.

Example 54

Procedure for the preparation of 2-(((S)-2-amino-3-phenylpropyl)-amino)-3-methyl-5-(3-methylphenyl)-6-(4-pyridyl)-4(3 H)-pyrimidinone hydrochloride

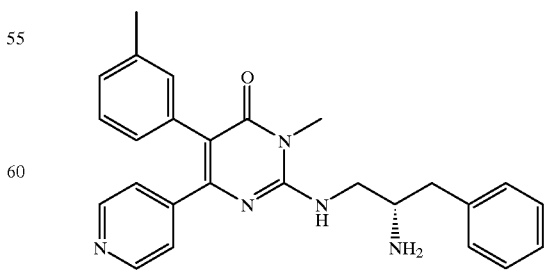

2-(((S)-2-Amino-3-phenylpropyl)-amino)-3-methyl-5-(3-methylphenyl)-6-(4-pyridyl)-4(3 H)-pyrimidinone hydrochloride: A solution of 2-chloro-3-methyl-5-(3-methylphenyl)-6-(4-pyridyl)-4(3 H)-pyrimidinone (3.34 g, 10.71 mmol) and (S)-1-benzyl-1,2-ethanediamine (2.3 g, 15.31 mmol) in ethanol (50 ml) was stirred at room temperature for 16 h. The solvent was evaporated and the crude product recrystallized from methanol. MS (m/z): 426 (M+H)$^+$; $C_{26}H_{27}N_5O$ requir. 425.5 (free base).

Example 55

Procedure for the preparation of 2-((3-amino-2,2-dimethyl-3-phenylpropyl)-amino)-3-methyl-5-(3-methylphenyl)-6-(4-pyridyl)-4(3 H)-pyrimidinone hydrochloride

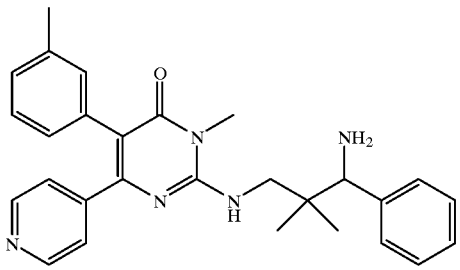

2-((-3-Amino-2,2-dimethyl-3-phenylpropyl)-amino)-3-methyl-5-(3-methylphenyl)-6-(4-pyridyl)-4(3 H)-pyrimidinone hydrochloride: A solution of 2-chloro-3-methyl-5-(3-methylphenyl)-6-(4-pyridyl)-4(3 H)-pyrimidinone (228 mg, 0.73 mmol) and 3-phenyl-2,2-dimethyl-1,3-propanediamine (178 mg, 1 mmol) (prepared according to:W. Ten Hoeve and H. Wynberg, Synth. Commun. 24 (15), 2215–2221, 1994) in ethanol (4 ml) was stirred at room temperature for 16 h. The solvent was evaporated and the crude product purified by column chromatography on silica gel. MS (m/z): 454 (M+H)$^+$; $C_{28}H_{31}N_5O$ requir. 453.6 (free base).

Accordingly, 2-((-3-Amino-2,2-dimethyl-3-phenylpropyl)-amino)-3-methyl-6-(4-pyridyl)-5-(3-trifluoromethyl phenyl)-4(3 H)-pyrimidinone hydrochloride was prepared. MS (m/z): 508 (M+H)$^+$; $C_{28}H_{28}F_3N_5O$ requir. 507.6 (free base).

Example 56

Procedure for the preparation of 2-(((S)-3-amino-3-phenylpropyl)-amino)-3-methyl-6-(4-pyridyl)-5-(3-trifluoromethylphenyl)-4(3 H)-pyrimidinone hydrochloride

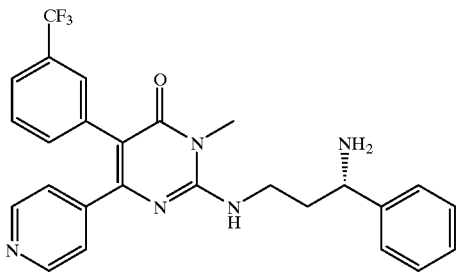

2-(((S)-3-Amino-3-phenylpropyl)-amino)-3-methyl-6-(4-pyridyl)-5-(3-trifluoromethylphenyl)-4(3 H)-pyrimidinone hydrochloride: Aqueous sat. sodium carbonate (2 ml) was added to a solution of 2-chloro-3-methyl-6-(4-pyridyl)-5-(3-trifluoromethylphenyl)-4(3H)-pyrimidinone hydrochloride (730 mg, 2 mmol) and (S)-1-phenyl-1,3-propanediamine (360 mg, 2.4 mmol) in ethanol (10 ml). The mixture was stirred for 4 h at room temperature. It was evaporated and the remainder partitioned between dichloromethane and water. The organic solution was dried and evaporated followed by column chromatography on silica gel (dichloromethane:methanol:conc. ammonium hydroxide= 93:7:0.7). MS (m/z): 480 (M+H)$^+$; $C_{26}H_{24}F_3N_5O$ requir. 479.5 (free base).

Example 57

Procedure for the preparation of 3-methyl-2-methylthio-5-(3-methylphenyl)-6-(4-pyridyl)-4(3H)-pyrimidinone

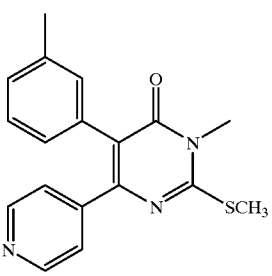

3-Methyl-2-methylthio-5-(3-methylphenyl)-6-(4-pyridyl)-4 (3H)-pyrimidinone: A solution of potassium t-butoxide (1M in t-butanol, 1 l, 1 mol) was added dropwise to a stirring solution of ethyl 3-methylphenyl acetate (178 g, 1 mol) in N,N-dimethylformamide (2 l). A solution of 4-cyanopyridine (104.11 g, 1 mol) in N,N-dimethylformamide (1 l) was pumped into the reaction mixture over a period of about 4.5 h. The mixture was then stirred at room temperature for 3 h, before the dropwise addition of a solution of methyl isothiocyanate (68.4 ml, 1 mol) in N,N-dimethylformamide (50 ml) over a period of 10 min. After stirring for 1 h at room temperature, the reaction mixture was cooled to 3_C and methyl iodide (62.3 ml, 1 mol) was added dropwise over a period of 10 min. Stirring was continued at room temperature overnight. The mixture was cooled to 3_C and water (4 l) was pumped into the reaction mixture over a period of 6 h. The precipitate was removed by filtration, washed with water and dried in a vacuum oven to give the title compound. MS (m/z): 324 (M+H)$^+$; $C_{18}H_{17}N_3OS$ requir. 323.4.

Example 58

Using the corresponding starting materials, the following compounds of Table IV may be prepared using the procedure for 6-(4-fluorophenyl)-2-methyl-1-(3-phenylpropyl)-7-pyridin-4-yl-1H-imidazo(1,2-a)pyrimidin-5-one. The required pyrimidinones with the varied R$^{11}$ substituents can be prepared using the general procedures described above.

TABLE IV

| R$_{11}$ | R$_{21}$ |
|---|---|
| 3,5-dichlorophenyl | 2(S)-amino-3-phenyl-propyl |
| 4-methoxyphenyl | 2(S)-amino-3-phenyl-propyl |
| 3-tolyl | 2(S)-amino-3-phenyl-propyl |
| 3-chlorophenyl | 2(S)-amino-3-phenyl-propyl |

TABLE IV-continued

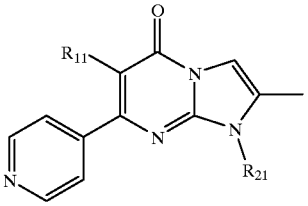

| R11 | R21 |
|---|---|
| 4-fluorophenyl | 2(S)-amino-3-phenyl-propyl |
| 2-naphthyl | 2(S)-amino-3-phenyl-propyl |
| n-butyl | 2(S)-amino-3-phenyl-propyl |
| 2-thiophene | 2(S)-amino-3-phenyl-propyl |
| 3-thiophene | 2(S)-amino-3-phenyl-propyl |
| 3-aminophenyl | 2(S)-amino-3-phenyl-propyl |
| 2-(5-chlorothiophene) | 2(S)-amino-3-phenyl-propyl |
| 3-isopropylphenyl | 3-phenylpropyl |
| 3-tolyl | 3-phenylpropyl |
| 3-chlorophenyl | 3-phenylpropyl |
| 3-chloro-4-fluorophenyl | 3-phenylpropyl |
| 3,5-Ditrifluoromethylphenyl | 3-phenylpropyl |
| 4-fluorophenyl | 3-phenylpropyl |
| 3,4-dichlorophenyl | 3-phenylpropyl |
| 1-naphthyl | 3-phenylpropyl |
| 3-fluorophenyl | 3-phenylpropyl |
| 2-naphthyl | 3-phenylpropyl |
| n-butyl | 3-phenylpropyl |
| 2-thiophene | 3-phenylpropyl |
| 3-thiophene | 3-phenylpropyl |
| 3-aminophenyl | 3-phenylpropyl |
| 2-(5-chlorothiophene) | 3-phenylpropyl |
| 3,5-dichlorophenyl | 3-methyl-3-phenyl-propyl |
| 4-tolyl | 3-methyl-3-phenyl-propyl |
| 3-trifluoromethylphenyl | 3-methyl-3-phenyl-propyl |
| 4-methoxyphenyl | 3-methyl-3-phenyl-propyl |
| 4-trifluoromethylphenyl | 3-methyl-3-phenyl-propyl |
| 3-isopropylphenyl | 3-methyl-3-phenyl-propyl |
| 3-tolyl | 3-methyl-3-phenyl-propyl |
| 3-chlorophenyl | 3-methyl-3-phenyl-propyl |
| 3-chloro-4-fluorophenyl | 3-methyl-3-phenyl-propyl |
| 3,5-Ditrifluoromethylphenyl | 3-methyl-3-phenyl-propyl |
| 4-fluorophenyl | 3-methyl-3-phenyl-propyl |
| 3,4-dichlorophenyl | 3-methyl-3-phenyl-propyl |
| 2-naphthyl | 3-methyl-3-phenyl-propyl |
| n-butyl | 3-methyl-3-phenyl-propyl |
| 2-thiophene | 3-methyl-3-phenyl-propyl |
| 3-thiophene | 3-methyl-3-phenyl-propyl |
| 3-aminophenyl | 3-methyl-3-phenyl-propyl |
| 2-(5-chlorothiophene) | 3-methyl-3-phenyl-propyl |
| 3,5-dichlorophenyl | 3-amino-3-phenyl-propyl |
| 4-tolyl | 3-amino-3-phenyl-propyl |
| 3-trifluoromethylphenyl | 3-amino-3-phenyl-propyl |
| 4-methoxyphenyl | 3-amino-3-phenyl-propyl |
| 4-trifluoromethylphenyl | 3-amino-3-phenyl-propyl |
| 3-isopropylphenyl | 3-amino-3-phenyl-propyl |
| 3-tolyl | 3-amino-3-phenyl-propyl |
| 3-chlorophenyl | 3-amino-3-phenyl-propyl |
| 3-chloro-4-fluorophenyl | 3-amino-3-phenyl-propyl |
| 3,5-Ditrifluoromethylphenyl | 3-amino-3-phenyl-propyl |
| 4-fluorophenyl | 3-amino-3-phenyl-propyl |
| 3,4-dichlorophenyl | 3-amino-3-phenyl-propyl |
| 1-naphthyl | 3-amino-3-phenyl-propyl |
| 3-fluorophenyl | 3-amino-3-phenyl-propyl |
| 2-naphthyl | 3-amino-3-phenyl-propyl |
| n-butyl | 3-amino-3-phenyl-propyl |
| 2-thiophene | 3-amino-3-phenyl-propyl |
| 3-thiophene | 3-amino-3-phenyl-propyl |
| 3-aminophenyl | 3-amino-3-phenyl-propyl |
| 2-(5-chlorothiophene) | 3-amino-3-phenyl-propyl |
| 3,5-dichlorophenyl | 2(R)-amino-3-phenyl-propyl |
| 4-tolyl | 2(R)-amino-3-phenyl-propyl |
| 3-trifluoromethylphenyl | 2(R)-amino-3-phenyl-propyl |
| 4-methoxyphenyl | 2(R)-amino-3-phenyl-propyl |
| 4-trifluoromethylphenyl | 2(R)-amino-3-phenyl-propyl |
| 3-isopropylphenyl | 2(R)-amino-3-phenyl-propyl |
| 3-tolyl | 2(R)-amino-3-phenyl-propyl |
| 3-chlorophenyl | 2(R)-amino-3-phenyl-propyl |
| 3-chloro-4-fluorophenyl | 2(R)-amino-3-phenyl-propyl |
| 3,5-Ditrifluoromethylphenyl | 2(R)-amino-3-phenyl-propyl |
| 4-fluorophenyl | 2(R)-amino-3-phenyl-propyl |
| 3,4-dichlorophenyl | 2(R)-amino-3-phenyl-propyl |
| 1-naphthyl | 2(R)-amino-3-phenyl-propyl |
| 3-fluorophenyl | 2(R)-amino-3-phenyl-propyl |
| 2-naphthyl | 2(R)-amino-3-phenyl-propyl |
| n-butyl | 2(R)-amino-3-phenyl-propyl |
| 2-thiophene | 2(R)-amino-3-phenyl-propyl |
| 3-thiophene | 2(R)-amino-3-phenyl-propyl |
| 3-aminophenyl | 2(R)-amino-3-phenyl-propyl |
| 2-(5-chlorothiophene) | 2(R)-amino-3-phenyl-propyl |
| 3,5-dichlorophenyl | 2-methyl-2-amino-3-phenyl-propyl |
| 4-tolyl | 2-methyl-2-amino-3-phenyl-propyl |
| 3-trifluoromethylphenyl | 2-methyl-2-amino-3-phenyl-propyl |
| 4-methoxyphenyl | 2-methyl-2-amino-3-phenyl-propyl |
| 4-trifluoromethylphenyl | 2-methyl-2-amino-3-phenyl-propyl |
| 3-isopropylphenyl | 2-methyl-2-amino-3-phenyl-propyl |
| 3-tolyl | 2-methyl-2-amino-3-phenyl-propyl |
| 3-chlorophenyl | 2-methyl-2-amino-3-phenyl-propyl |
| 3-chloro-4-fluorophenyl | 2-methyl-2-amino-3-phenyl-propyl |
| 3,5-Ditrifluoromethylphenyl | 2-methyl-2-amino-3-phenyl-propyl |
| 4-fluorophenyl | 2-methyl-2-amino-3-phenyl-propyl |
| 3,4-dichlorophenyl | 2-methyl-2-amino-3-phenyl-propyl |
| 1-naphthyl | 2-methyl-2-amino-3-phenyl-propyl |
| 3-fluorophenyl | 2-methyl-2-amino-3-phenyl-propyl |
| 2-naphthyl | 2-methyl-2-amino-3-phenyl-propyl |
| n-butyl | 2-methyl-2-amino-3-phenyl-propyl |
| 2-thiophene | 2-methyl-2-amino-3-phenyl-propyl |
| 3-thiophene | 2-methyl-2-amino-3-phenyl-propyl |
| 3-aminophenyl | 2-methyl-2-amino-3-phenyl-propyl |
| 2-(5-chlorothiophene) | 2-methyl-2-amino-3-phenyl-propyl |
| 3,5-dichlorophenyl | 2-methyl-3-phenyl-propyl |
| 4-tolyl | 2-methyl-3-phenyl-propyl |
| 3-trifluoromethylphenyl | 2-methyl-3-phenyl-propyl |
| 4-methoxyphenyl | 2-methyl-3-phenyl-propyl |
| 4-trifluoromethylphenyl | 2-methyl-3-phenyl-propyl |
| 3-isopropylphenyl | 2-methyl-3-phenyl-propyl |
| 3-tolyl | 2-methyl-3-phenyl-propyl |

TABLE IV-continued

| $R_{11}$ | $R_{21}$ |
|---|---|
| 3-chlorophenyl | 2-methyl-3-phenyl-propyl |
| 3-chloro-4-fluorophenyl | 2-methyl-3-phenyl-propyl |
| 3,5-Ditrifluoromethylphenyl | 2-methyl-3-phenyl-propyl |
| 4-fluorophenyl | 2-methyl-3-phenyl-propyl |
| 3,4-dichlorophenyl | 2-methyl-3-phenyl-propyl |
| 1-naphthyl | 2-methyl-3-phenyl-propyl |
| 3-fluorophenyl | 2-methyl-3-phenyl-propyl |
| 2-naphthyl | 2-methyl-3-phenyl-propyl |
| n-butyl | 2-methyl-3-phenyl-propyl |
| 2-thiophene | 2-methyl-3-phenyl-propyl |
| 3-thiophene | 2-methyl-3-phenyl-propyl |
| 3-aminophenyl | 2-methyl-3-phenyl-propyl |
| 2-(5-chlorothiophene) | 2-methyl-3-phenyl-propyl |
| 3,5-dichlorophenyl | 2-(N,N-dimethylamino)-3-phenyl-propyl |
| 4-tolyl | 2-(N,N-dimethylamino)-3-phenyl-propyl |
| 3-trifluoromethylphenyl | 2-(N,N-dimethylamino)-3-phenyl-propyl |
| 4-methoxyphenyl | 2-(N,N-dimethylamino)-3-phenyl-propyl |
| 4-trifluoromethylphenyl | 2-(N,N-dimethylamino)-3-phenyl-propyl |
| 3-isopropylphenyl | 2-(N,N-dimethylamino)-3-phenyl-propyl |
| 3-tolyl | 2-(N,N-dimethylamino)-3-phenyl-propyl |
| 3-chlorophenyl | 2-(N,N-dimethylamino)-3-phenyl-propyl |
| 3-chloro-4-fluorophenyl | 2-(N,N-dimethylamino)-3-phenyl-propyl |
| 3,5-Ditrifluoromethylphenyl | 2-(N,N-dimethylamino)-3-phenyl-propyl |
| 4-fluorophenyl | 2-(N,N-dimethylamino)-3-phenyl-propyl |
| 3,4-dichlorophenyl | 2-(N,N-dimethylamino)-3-phenyl-propyl |
| 1-naphthyl | 2-(N,N-dimethylamino)-3-phenyl-propyl |
| 3-fluorophenyl | 2-(N,N-dimethylamino)-3-phenyl-propyl |
| 2-naphthyl | 2-(N,N-dimethylamino)-3-phenyl-propyl |
| n-butyl | 2-(N,N-dimethylamino)-3-phenyl-propyl |
| 2-thiophene | 2-(N,N-dimethylamino)-3-phenyl-propyl |
| 3-thiophene | 2-(N,N-dimethylamino)-3-phenyl-propyl |
| 3-aminophenyl | 2-(N,N-dimethylamino)-3-phenyl-propyl |
| 2-(5-chlorothiophene) | 2-(N,N-dimethylamino)-3-phenyl-propyl |
| 3,5-dichlorophenyl | 2-(N-methylamino)-3-phenyl-propyl |
| 4-tolyl | 2-(N-methylamino)-3-phenyl-propyl |
| 3-trifluoromethylphenyl | 2-(N-methylamino)-3-phenyl-propyl |
| 4-methoxyphenyl | 2-(N-methylamino)-3-phenyl-propyl |
| 4-trifluoromethylphenyl | 2-(N-methylamino)-3-phenyl-propyl |
| 3-isopropylphenyl | 2-(N-methylamino)-3-phenyl-propyl |
| 3-tolyl | 2-(N-methylamino)-3-phenyl-propyl |
| 3-chlorophenyl | 2-(N-methylamino)-3-phenyl-propyl |
| 3-chloro-4-fluorophenyl | 2-(N-methylamino)-3-phenyl-propyl |
| 3,5-Ditrifluoromethylphenyl | 2-(N-methylamino)-3-phenyl-propyl |
| 3,4-dichlorophenyl | 2-(N-methylamino)-3-phenyl-propyl |
| 4-fluorophenyl | 2-(N-methylamino)-3-phenyl-propyl |
| 1-naphthyl | 2-(N-methylamino)-3-phenyl-propyl |
| 3-fluorophenyl | 2-(N-methylamino)-3-phenyl-propyl |
| 2-naphthyl | 2-(N-methylamino)-3-phenyl-propyl |
| n-butyl | 2-(N-methylamino)-3-phenyl-propyl |
| 2-thiophene | 2-(N-methylamino)-3-phenyl-propyl |
| 3-thiophene | 2-(N-methylamino)-3-phenyl-propyl |
| 3-aminophenyl | 2-(N-methylamino)-3-phenyl-propyl |
| 2-(5-chlorothiophene) | 2-(N-methylamino)-3-phenyl-propyl |

Example 59

The compounds in table V can be prepared using the appropriate starting materials and the following procedures: The required pyrimidinones with the varied $R^{11}$ substituents can be prepared using the general procedures described above. The fused 6, 5 ring system can be prepared as described above affording $R^{21}$ as a hydrogen radical. Other $R^{21}$ groups can be introduced through a reductive amination process using the corresponding aldehyde with appropriate amino protection (Boc group). For example, N-Boc-phenylalanal can be prepared from the corresponding Weinreb amide through reduction with lithium aluminum hydride as described in the literature (Konieczny and Cushman Tetrahedron Lett 6939, 1992). The N-Boc-phenylalanal can then be reacted with the amino group using sodium triacetoxyborohydride. Alternatively, the alcohol of N-Boc-phenylalanol can be activated under Mitsunobu conditions (triphenylphosphine, diiisopropyl azodicarboxylate) and reacted with the amino group of the 6, 5 fused system followed by removal of the Boc group (trifluoroacetic acid).

TABLE V

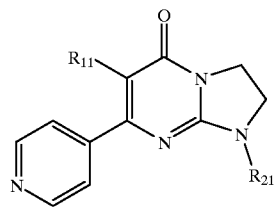

| R11 | R21 |
|---|---|
| 3,5-dichlorophenyl | 2(S)-amino-3-phenyl-propyl |
| 4-methoxyphenyl | 2(S)-amino-3-phenyl-propyl |
| 3-tolyl | 2(S)-amino-3-phenyl-propyl |
| 3-chlorophenyl | 2(S)-amino-3-phenyl-propyl |
| 4-fluorophenyl | 2(S)-amino-3-phenyl-propyl |
| 2-naphthyl | 2(S)-amino-3-phenyl-propyl |
| n-butyl | 2(S)-amino-3-phenyl-propyl |
| 2-thiophene | 2(S)-amino-3-phenyl-propyl |
| 3-thiophene | 2(S)-amino-3-phenyl-propyl |
| 3-aminophenyl | 2(S)-amino-3-phenyl-propyl |
| 2-(5-chlorothiophene) | 2(S)-amino-3-phenyl-propyl |
| 3-isopropylphenyl | 3-phenylpropyl |
| 3-tolyl | 3-phenylpropyl |
| 3-chlorophenyl | 3-phenylpropyl |
| 3-chloro-4-fluorophenyl | 3-phenylpropyl |
| 3,5-Ditrifluoromethylphenyl | 3-phenylpropyl |
| 4-fluorophenyl | 3-phenylpropyl |
| 3,4-dichlorophenyl | 3-phenylpropyl |
| 1-naphthyl | 3-phenylpropyl |
| 3-fluorophenyl | 3-phenylpropyl |
| 2-naphthyl | 3-phenylpropyl |
| n-butyl | 3-phenylpropyl |
| 2-thiophene | 3-phenylpropyl |
| 3-thiophene | 3-phenylpropyl |
| 3-aminophenyl | 3-phenylpropyl |
| 2-(5-chlorothiophene) | 3-phenylpropyl |
| 3,5-dichlorophenyl | 3-methyl-3-phenyl-propyl |
| 4-tolyl | 3-methyl-3-phenyl-propyl |
| 3-trifluoromethylphenyl | 3-methyl-3-phenyl-propyl |
| 4-methoxyphenyl | 3-methyl-3-phenyl-propyl |
| 4-trifluoromethylphenyl | 3-methyl-3-phenyl-propyl |
| 3-isopropylphenyl | 3-methyl-3-phenyl-propyl |
| 3-tolyl | 3-methyl-3-phenyl-propyl |
| 3-chlorophenyl | 3-methyl-3-phenyl-propyl |
| 3-chloro-4-fluorophenyl | 3-methyl-3-phenyl-propyl |
| 3,5-Ditrifluoromethylphenyl | 3-methyl-3-phenyl-propyl |
| 4-fluorophenyl | 3-methyl-3-phenyl-propyl |
| 3,4-dichlorophenyl | 3-methyl-3-phenyl-propyl |
| 2-naphthyl | 3-methyl-3-phenyl-propyl |
| n-butyl | 3-methyl-3-phenyl-propyl |
| 2-thiophene | 3-methyl-3-phenyl-propyl |
| 3-thiophene | 3-methyl-3-phenyl-propyl |
| 3-aminophenyl | 3-methyl-3-phenyl-propyl |
| 2-(5-chlorothiophene) | 3-methyl-3-phenyl-propyl |
| 3,5-dichlorophenyl | 3-amino-3-phenyl-propyl |
| 4-tolyl | 3-amino-3-phenyl-propyl |
| 3-trifluoromethylphenyl | 3-amino-3-phenyl-propyl |
| 4-methoxyphenyl | 3-amino-3-phenyl-propyl |
| 4-trifluoromethylphenyl | 3-amino-3-phenyl-propyl |
| 3-isopropylphenyl | 3-amino-3-phenyl-propyl |
| 3-tolyl | 3-amino-3-phenyl-propyl |
| 3-chlorophenyl | 3-amino-3-phenyl-propyl |
| 3-chloro-4-fluorophenyl | 3-amino-3-phenyl-propyl |
| 3,5-Ditrifluoromethylphenyl | 3-amino-3-phenyl-propyl |
| 4-fluorophenyl | 3-amino-3-phenyl-propyl |
| 3,4-dichlorophenyl | 3-amino-3-phenyl-propyl |
| 1-naphthyl | 3-amino-3-phenyl-propyl |
| 3-fluorophenyl | 3-amino-3-phenyl-propyl |
| 2-naphthyl | 3-amino-3-phenyl-propyl |
| n-butyl | 3-amino-3-phenyl-propyl |
| 2-thiophene | 3-amino-3-phenyl-propyl |
| 3-thiophene | 3-amino-3-phenyl-propyl |
| 3-aminophenyl | 3-amino-3-phenyl-propyl |
| 2-(5-chlorothiophene) | 3-amino-3-phenyl-propyl |
| 3,5-dichlorophenyl | 2(R)-amino-3-phenyl-propyl |

TABLE V-continued

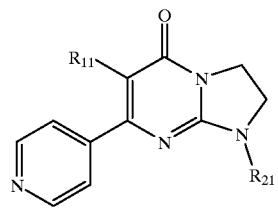

| R11 | R21 |
|---|---|
| 4-tolyl | 2(R)-amino-3-phenyl-propyl |
| 3-trifluoromethylphenyl | 2(R)-amino-3-phenyl-propyl |
| 4-methoxyphenyl | 2(R)-amino-3-phenyl-propyl |
| 4-trifluoromethylphenyl | 2(R)-amino-3-phenyl-propyl |
| 3-isopropylphenyl | 2(R)-amino-3-phenyl-propyl |
| 3-tolyl | 2(R)-amino-3-phenyl-propyl |
| 3-chlorophenyl | 2(R)-amino-3-phenyl-propyl |
| 3-chloro-4-fluorophenyl | 2(R)-amino-3-phenyl-propyl |
| 3,5-Ditrifluoromethylphenyl | 2(R)-amino-3-phenyl-propyl |
| 4-fluorophenyl | 2(R)-amino-3-phenyl-propyl |
| 3,4-dichlorophenyl | 2(R)-amino-3-phenyl-propyl |
| 1-naphthyl | 2(R)-amino-3-phenyl-propyl |
| 3-fluorophenyl | 2(R)-amino-3-phenyl-propyl |
| 2-naphthyl | 2(R)-amino-3-phenyl-propyl |
| n-butyl | 2(R)-amino-3-phenyl-propyl |
| 2-thiophene | 2(R)-amino-3-phenyl-propyl |
| 3-thiophene | 2(R)-amino-3-phenyl-propyl |
| 3-aminophenyl | 2(R)-amino-3-phenyl-propyl |
| 2-(5-chlorothiophene) | 2(R)-amino-3-phenyl-propyl |
| 3,5-dichlorophenyl | 2-methyl-2-amino-3-phenyl-propyl |
| 4-tolyl | 2-methyl-2-amino-3-phenyl-propyl |
| 3-trifluoromethylphenyl | 2-methyl-2-amino-3-phenyl-propyl |
| 4-methoxyphenyl | 2-methyl-2-amino-3-phenyl-propyl |
| 4-trifluoromethylphenyl | 2-methyl-2-amino-3-phenyl-propyl |
| 3-isopropylphenyl | 2-methyl-2-amino-3-phenyl-propyl |
| 3-tolyl | 2-methyl-2-amino-3-phenyl-propyl |
| 3-chlorophenyl | 2-methyl-2-amino-3-phenyl-propyl |
| 3-chloro-4-fluorophenyl | 2-methyl-2-amino-3-phenyl-propyl |
| 3,5-Ditrifluoromethylphenyl | 2-methyl-2-amino-3-phenyl-propyl |
| 4-fluorophenyl | 2-methyl-2-amino-3-phenyl-propyl |
| 3,4-dichlorophenyl | 2-methyl-2-amino-3-phenyl-propyl |
| 1-naphthyl | 2-methyl-2-amino-3-phenyl-propyl |
| 3-fluorophenyl | 2-methyl-2-amino-3-phenyl-propyl |
| 2-naphthyl | 2-methyl-2-amino-3-phenyl-propyl |
| n-butyl | 2-methyl-2-amino-3-phenyl-propyl |
| 2-thiophene | 2-methyl-2-amino-3-phenyl-propyl |
| 3-thiophene | 2-methyl-2-amino-3-phenyl-propyl |
| 3-aminophenyl | 2-methyl-2-amino-3-phenyl-propyl |
| 2-(5-chlorothiophene) | 2-methyl-2-amino-3-phenyl-propyl |
| 3,5-dichlorophenyl | 2-methyl-3-phenyl-propyl |
| 4-tolyl | 2-methyl-3-phenyl-propyl |
| 3-trifluoromethylphenyl | 2-methyl-3-phenyl-propyl |
| 4-methoxyphenyl | 2-methyl-3-phenyl-propyl |
| 4-trifluoromethylphenyl | 2-methyl-3-phenyl-propyl |
| 3-isopropylphenyl | 2-methyl-3-phenyl-propyl |

TABLE V-continued

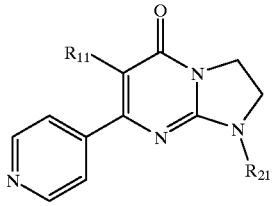

| R₁₁ | R₂₁ |
|---|---|
| 3-tolyl | 2-methyl-3-phenyl-propyl |
| 3-chlorophenyl | 2-methyl-3-phenyl-propyl |
| 3-chloro-4-fluorophenyl | 2-methyl-3-phenyl-propyl |
| 3,5-Ditrifluoromethylphenyl | 2-methyl-3-phenyl-propyl |
| 4-fluorophenyl | 2-methyl-3-phenyl-propyl |
| 3,4-dichlorophenyl | 2-methyl-3-phenyl-propyl |
| 1-naphthyl | 2-methyl-3-phenyl-propyl |
| 3-fluorophenyl | 2-methyl-3-phenyl-propyl |
| 2-naphthyl | 2-methyl-3-phenyl-propyl |
| n-butyl | 2-methyl-3-phenyl-propyl |
| 2-thiophene | 2-methyl-3-phenyl-propyl |
| 3-thiophene | 2-methyl-3-phenyl-propyl |
| 3-aminophenyl | 2-methyl-3-phenyl-propyl |
| 2-(5-chlorothiophene) | 2-methyl-3-phenyl-propyl |
| 3,5-dichlorophenyl | 2-(N,N-dimethylamino)-3-phenyl-propyl |
| 4-tolyl | 2-(N,N-dimethylamino)-3-phenyl-propyl |
| 3-trifluoromethylphenyl | 2-(N,N-dimethylamino)-3-phenyl-propyl |
| 4-methoxyphenyl | 2-(N,N-dimethylamino)-3-phenyl-propyl |
| 4-trifluoromethylphenyl | 2-(N,N-dimethylamino)-3-phenyl-propyl |
| 3-isopropylphenyl | 2-(N,N-dimethylamino)-3-phenyl-propyl |
| 3-tolyl | 2-(N,N-dimethylamino)-3-phenyl-propyl |
| 3-chlorophenyl | 2-(N,N-dimethylamino)-3-phenyl-propyl |
| 3-chloro-4-fluorophenyl | 2-(N,N-dimethylamino)-3-phenyl-propyl |
| 3,5-Ditrifluoromethylphenyl | 2-(N,N-dimethylamino)-3-phenyl-propyl |
| 4-fluorophenyl | 2-(N,N-dimethylamino)-3-phenyl-propyl |
| 3,4-dichlorophenyl | 2-(N,N-dimethylamino)-3-phenyl-propyl |
| 1-naphthyl | 2-(N,N-dimethylamino)-3-phenyl-propyl |
| 3-fluorophenyl | 2-(N,N-dimethylamino)-3-phenyl-propyl |
| 2-naphthyl | 2-(N,N-dimethylamino)-3-phenyl-propyl |
| n-butyl | 2-(N,N-dimethylamino)-3-phenyl-propyl |
| 2-thiophene | 2-(N,N-dimethylamino)-3-phenyl-propyl |
| 3-thiophene | 2-(N,N-dimethylamino)-3-phenyl-propyl |
| 3-aminophenyl | 2-(N,N-dimethylamino)-3-phenyl-propyl |
| 2-(5-chlorothiophene) | 2-(N,N-dimethylamino)-3-phenyl-propyl |
| 3,5-dichlorophenyl | 2-(N-methylamino)-3-phenyl-propyl |
| 4-tolyl | 2-(N-methylamino)-3-phenyl-propyl |
| 3-trifluoromethylphenyl | 2-(N-methylamino)-3-phenyl-propyl |
| 4-methoxyphenyl | 2-(N-methylamino)-3-phenyl-propyl |
| 4-trifluoromethylphenyl | 2-(N-methylamino)-3-phenyl-propyl |
| 3-isopropylphenyl | 2-(N-methylamino)-3-phenyl-propyl |

TABLE V-continued

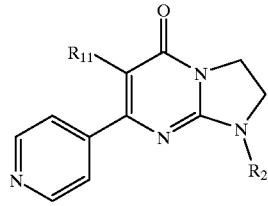

| R₁₁ | R₂₁ |
|---|---|
| | phenyl-propyl |
| 3-tolyl | 2-(N-methylamino)-3-phenyl-propyl |
| 3-chlorophenyl | 2-(N-methylamino)-3-phenyl-propyl |
| 3-chloro-4-fluorophenyl | 2-(N-methylamino)-3-phenyl-propyl |
| 3,5-Ditrifluoromethylphenyl | 2-(N-methylamino)-3-phenyl-propyl |
| 3,4-dichlorophenyl | 2-(N-methylamino)-3-phenyl-propyl |
| 4-fluorophenyl | 2-(N-methylamino)-3-phenyl-propyl |
| 1-naphthyl | 2-(N-methylamino)-3-phenyl-propyl |
| 3-fluorophenyl | 2-(N-methylamino)-3-phenyl-propyl |
| 2-naphthyl | 2-(N-methylamino)-3-phenyl-propyl |
| n-butyl | 2-(N-methylamino)-3-phenyl-propyl |
| 2-thiophene | 2-(N-methylamino)-3-phenyl-propyl |
| 3-thiophene | 2-(N-methylamino)-3-phenyl-propyl |
| 3-aminophenyl | 2-(N-methylamino)-3-phenyl-propyl |
| 2-(5-chlorothiophene) | 2-(N-methylamino)-3-phenyl-propyl |

Example 60

The compounds in table VI can be prepared using the appropriate starting materials and procedures as described above.

TABLE VI

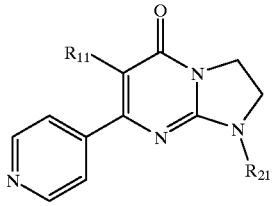

| R₁₁ | R₂₁ |
|---|---|
| 3,5-dichlorophenyl | 2(S)-amino-3-phenyl-propyl |
| 4-methoxyphenyl | 2(S)-amino-3-phenyl-propyl |
| 3-tolyl | 2(S)-amino-3-phenyl-propyl |
| 3-chlorophenyl | 2(S)-amino-3-phenyl-propyl |
| 4-fluorophenyl | 2(S)-amino-3-phenyl-propyl |
| 2-naphthyl | 2(S)-amino-3-phenyl-propyl |
| n-butyl | 2(S)-amino-3-phenyl-propyl |
| 2-thiophene | 2(S)-amino-3-phenyl-propyl |
| 3-thiophene | 2(S)-amino-3-phenyl-propyl |
| 3-aminophenyl | 2(S)-amino-3-phenyl-propyl |
| 2-(5-chlorothiophene) | 2(S)-amino-3-phenyl-propyl |

TABLE VI-continued

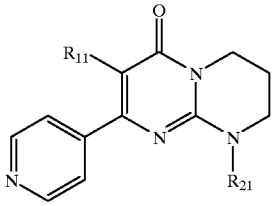

| R11 | R21 |
|---|---|
| 3-isopropylphenyl | 3-phenylpropyl |
| 3-tolyl | 3-phenylpropyl |
| 3-chlorophenyl | 3-phenylpropyl |
| 3-chloro-4-fluorophenyl | 3-phenylpropyl |
| 3,5-Ditrifluoromethylphenyl | 3-phenylpropyl |
| 4-fluorophenyl | 3-phenylpropyl |
| 3,4-dichlorophenyl | 3-phenylpropyl |
| 1-naphthyl | 3-phenylpropyl |
| 3-fluorophenyl | 3-phenylpropyl |
| 2-naphthyl | 3-phenylpropyl |
| n-butyl | 3-phenylpropyl |
| 2-thiophene | 3-phenylpropyl |
| 3-thiophene | 3-phenylpropyl |
| 3-aminophenyl | 3-phenylpropyl |
| 2-(5-chlorothiophene) | 3-phenylpropyl |
| 3,5-dichlorophenyl | 3-methyl-3-phenyl-propyl |
| 4-tolyl | 3-methyl-3-phenyl-propyl |
| 3-trifluoromethylphenyl | 3-methyl-3-phenyl-propyl |
| 4-methoxyphenyl | 3-methyl-3-phenyl-propyl |
| 4-trifluoromethylphenyl | 3-methyl-3-phenyl-propyl |
| 3-isopropylphenyl | 3-methyl-3-phenyl-propyl |
| 3-tolyl | 3-methyl-3-phenyl-propyl |
| 3-chlorophenyl | 3-methyl-3-phenyl-propyl |
| 3-chloro-4-fluorophenyl | 3-methyl-3-phenyl-propyl |
| 3,5-Ditrifluoromethylphenyl | 3-methyl-3-phenyl-propyl |
| 4-fluorophenyl | 3-methyl-3-phenyl-propyl |
| 3,4-dichlorophenyl | 3-methyl-3-phenyl-propyl |
| 2-naphthyl | 3-methyl-3-phenyl-propyl |
| n-butyl | 3-methyl-3-phenyl-propyl |
| 2-thiophene | 3-methyl-3-phenyl-propyl |
| 3-thiophene | 3-methyl-3-phenyl-propyl |
| 3-aminophenyl | 3-methyl-3-phenyl-propyl |
| 2-(5-chlorothiophene) | 3-methyl-3-phenyl-propyl |
| 3,5-dichlorophenyl | 3-amino-3-phenyl-propyl |
| 4-tolyl | 3-amino-3-phenyl-propyl |
| 3-trifluoromethylphenyl | 3-amino-3-phenyl-propyl |
| 4-methoxyphenyl | 3-amino-3-phenyl-propyl |
| 4-trifluoromethylphenyl | 3-amino-3-phenyl-propyl |
| 3-isopropylphenyl | 3-amino-3-phenyl-propyl |
| 3-tolyl | 3-amino-3-phenyl-propyl |
| 3-chlorophenyl | 3-amino-3-phenyl-propyl |
| 3-chloro-4-fluorophenyl | 3-amino-3-phenyl-propyl |
| 3,5-Ditrifluoromethylphenyl | 3-amino-3-phenyl-propyl |
| 4-fluorophenyl | 3-amino-3-phenyl-propyl |
| 3,4-dichlorophenyl | 3-amino-3-phenyl-propyl |
| 1-naphthyl | 3-amino-3-phenyl-propyl |
| 3-fluorophenyl | 3-amino-3-phenyl-propyl |
| 2-naphthyl | 3-amino-3-phenyl-propyl |
| n-butyl | 3-amino-3-phenyl-propyl |
| 2-thiophene | 3-amino-3-phenyl-propyl |
| 3-thiophene | 3-amino-3-phenyl-propyl |
| 3-aminophenyl | 3-amino-3-phenyl-propyl |
| 2-(5-chlorothiophene) | 3-amino-3-phenyl-propyl |
| 3,5-dichlorophenyl | 2(R)-amino-3-phenyl-propyl |
| 4-tolyl | 2(R)-amino-3-phenyl-propyl |
| 3-trifluoromethylphenyl | 2(R)-amino-3-phenyl-propyl |
| 4-methoxyphenyl | 2(R)-amino-3-phenyl-propyl |
| 4-trifluoromethylphenyl | 2(R)-amino-3-phenyl-propyl |
| 3-isopropylphenyl | 2(R)-amino-3-phenyl-propyl |
| 3-tolyl | 2(R)-amino-3-phenyl-propyl |
| 3-chlorophenyl | 2(R)-amino-3-phenyl-propyl |
| 3-chloro-4-fluorophenyl | 2(R)-amino-3-phenyl-propyl |
| 3,5-Ditrifluoromethylphenyl | 2(R)-amino-3-phenyl-propyl |
| 4-fluorophenyl | 2(R)-amino-3-phenyl-propyl |
| 3,4-dichlorophenyl | 2(R)-amino-3-phenyl-propyl |

TABLE VI-continued

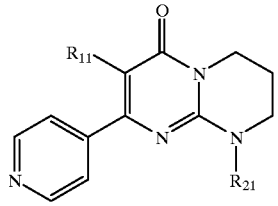

| R11 | R21 |
|---|---|
| 1-naphthyl | 2(R)-amino-3-phenyl-propyl |
| 3-fluorophenyl | 2(R)-amino-3-phenyl-propyl |
| 2-naphthyl | 2(R)-amino-3-phenyl-propyl |
| n-butyl | 2(R)-amino-3-phenyl-propyl |
| 2-thiophene | 2(R)-amino-3-phenyl-propyl |
| 3-thiophene | 2(R)-amino-3-phenyl-propyl |
| 3-aminophenyl | 2(R)-amino-3-phenyl-propyl |
| 2-(5-chlorothiophene) | 2(R)-amino-3-phenyl-propyl |
| 3,5-dichlorophenyl | 2-methyl-2-amino-3-phenyl-propyl |
| 4-tolyl | 2-methyl-2-amino-3-phenyl-propyl |
| 3-trifluoromethylphenyl | 2-methyl-2-amino-3-phenyl-propyl |
| 4-methoxyphenyl | 2-methyl-2-amino-3-phenyl-propyl |
| 4-trifluoromethylphenyl | 2-methyl-2-amino-3-phenyl-propyl |
| 3-isopropylphenyl | 2-methyl-2-amino-3-phenyl-propyl |
| 3-tolyl | 2-methyl-2-amino-3-phenyl-propyl |
| 3-chlorophenyl | 2-methyl-2-amino-3-phenyl-propyl |
| 3-chloro-4-fluorophenyl | 2-methyl-2-amino-3-phenyl-propyl |
| 3,5-Ditrifluoromethylphenyl | 2-methyl-2-amino-3-phenyl-propyl |
| 4-fluorophenyl | 2-methyl-2-amino-3-phenyl-propyl |
| 3,4-dichlorophenyl | 2-methyl-2-amino-3-phenyl-propyl |
| 1-naphthyl | 2-methyl-2-amino-3-phenyl-propyl |
| 3-fluorophenyl | 2-methyl-2-amino-3-phenyl-propyl |
| 2-naphthyl | 2-methyl-2-amino-3-phenyl-propyl |
| n-butyl | 2-methyl-2-amino-3-phenyl-propyl |
| 2-thiophene | 2-methyl-2-amino-3-phenyl-propyl |
| 3-thiophene | 2-methyl-2-amino-3-phenyl-propyl |
| 3-aminophenyl | 2-methyl-2-amino-3-phenyl-propyl |
| 2-(5-chlorothiophene) | 2-methyl-2-amino-3-phenyl-propyl |
| 3,5-dichlorophenyl | 2-methyl-3-phenyl-propyl |
| 4-tolyl | 2-methyl-3-phenyl-propyl |
| 3-trifluoromethylphenyl | 2-methyl-3-phenyl-propyl |
| 4-methoxyphenyl | 2-methyl-3-phenyl-propyl |
| 4-trifluoromethylphenyl | 2-methyl-3-phenyl-propyl |
| 3-isopropylphenyl | 2-methyl-3-phenyl-propyl |
| 3-tolyl | 2-methyl-3-phenyl-propyl |
| 3-chlorophenyl | 2-methyl-3-phenyl-propyl |
| 3-chloro-4-fluorophenyl | 2-methyl-3-phenyl-propyl |
| 3,5-Ditrifluoromethylphenyl | 2-methyl-3-phenyl-propyl |
| 4-fluorophenyl | 2-methyl-3-phenyl-propyl |
| 3,4-dichlorophenyl | 2-methyl-3-phenyl-propyl |
| 1-naphthyl | 2-methyl-3-phenyl-propyl |
| 3-fluorophenyl | 2-methyl-3-phenyl-propyl |
| 2-naphthyl | 2-methyl-3-phenyl-propyl |
| n-butyl | 2-methyl-3-phenyl-propyl |
| 2-thiophene | 2-methyl-3-phenyl-propyl |

TABLE VI-continued

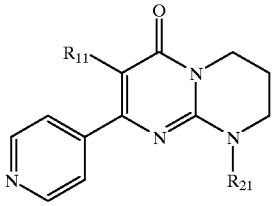

| R11 | R21 |
|---|---|
| 3-thiophene | 2-methyl-3-phenyl-propyl |
| 3-aminophenyl | 2-methyl-3-phenyl-propyl |
| 2-(5-chlorothiophene) | 2-methyl-3-phenyl-propyl |
| 3,5-dichlorophenyl | 2-(N,N-dimethylamino)-3-phenyl-propyl |
| 4-tolyl | 2-(N,N-dimethylamino)-3-phenyl-propyl |
| 3-trifluoromethylphenyl | 2-(N,N-dimethylamino)-3-phenyl-propyl |
| 4-methoxyphenyl | 2-(N,N-dimethylamino)-3-phenyl-propyl |
| 4-trifluoromethylphenyl | 2-(N,N-dimethylamino)-3-phenyl-propyl |
| 3-isopropylphenyl | 2-(N,N-dimethylamino)-3-phenyl-propyl |
| 3-tolyl | 2-(N,N-dimethylamino)-3-phenyl-propyl |
| 3-chlorophenyl | 2-(N,N-dimethylamino)-3-phenyl-propyl |
| 3-chloro-4-fluorophenyl | 2-(N,N-dimethylamino)-3-phenyl-propyl |
| 3,5-Ditrifluoromethylphenyl | 2-(N,N-dimethylamino)-3-phenyl-propyl |
| 4-fluorophenyl | 2-(N,N-dimethylamino)-3-phenyl-propyl |
| 3,4-dichlorophenyl | 2-(N,N-dimethylamino)-3-phenyl-propyl |
| 1-naphthyl | 2-(N,N-dimethylamino)-3-phenyl-propyl |
| 3-fluorophenyl | 2-(N,N-dimethylamino)-3-phenyl-propyl |
| 2-naphthyl | 2-(N,N-dimethylamino)-3-phenyl-propyl |
| n-butyl | 2-(N,N-dimethylamino)-3-phenyl-propyl |
| 2-thiophene | 2-(N,N-dimethylamino)-3-phenyl-propyl |
| 3-thiophene | 2-(N,N-dimethylamino)-3-phenyl-propyl |
| 3-aminophenyl | 2-(N,N-dimethylamino)-3-phenyl-propyl |
| 2-(5-chlorothiophene) | 2-(N,N-dimethylamino)-3-phenyl-propyl |
| 3,5-dichlorophenyl | 2-(N-methylamino)-3-phenyl-propyl |
| 4-tolyl | 2-(N-methylamino)-3-phenyl-propyl |
| 3-trifluoromethylphenyl | 2-(N-methylamino)-3-phenyl-propyl |
| 4-methoxyphenyl | 2-(N-methylamino)-3-phenyl-propyl |
| 4-trifluoromethylphenyl | 2-(N-methylamino)-3-phenyl-propyl |
| 3-isopropylphenyl | 2-(N-methylamino)-3-phenyl-propyl |
| 3-tolyl | 2-(N-methylamino)-3-phenyl-propyl |
| 3-chlorophenyl | 2-(N-methylamino)-3-phenyl-propyl |
| 3-chloro-4-fluorophenyl | 2-(N-methylamino)-3-phenyl-propyl |
| 3,5-Ditrifluoromethylphenyl | 2-(N-methylamino)-3-phenyl-propyl |
| 3,4-dichlorophenyl | 2-(N-methylamino)-3-phenyl-propyl |
| 4-fluorophenyl | 2-(N-methylamino)-3-phenyl-propyl |
| 1-naphthyl | 2-(N-methylamino)-3-phenyl-propyl |
| 3-fluorophenyl | 2-(N-methylamino)-3-phenyl-propyl |
| 2-naphthyl | 2-(N-methylamino)-3-phenyl-propyl |
| n-butyl | 2-(N-methylamino)-3-phenyl-propyl |
| 2-thiophene | 2-(N-methylamino)-3-phenyl-propyl |
| 3-thiophene | 2-(N-methylamino)-3-phenyl-propyl |
| 3-aminophenyl | 2-(N-methylamino)-3-phenyl-propyl |
| 2-(5-chlorothiophene) | 2-(N-methylamino)-3-phenyl-propyl |

Example 61

The compounds in table VII can be prepared using the appropriate starting materials and procedures as described above.

TABLE VII

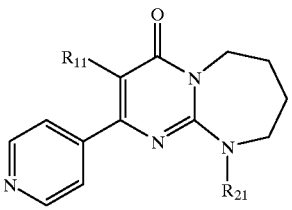

| R11 | R21 |
|---|---|
| 3,5-dichlorophenyl | 2(S)-amino-3-phenyl-propyl |
| 4-methoxyphenyl | 2(S)-amino-3-phenyl-propyl |
| 3-tolyl | 2(S)-amino-3-phenyl-propyl |
| 3-chlorophenyl | 2(S)-amino-3-phenyl-propyl |
| 4-fluorophenyl | 2(S)-amino-3-phenyl-propyl |
| 2-naphthyl | 2(S)-amino-3-phenyl-propyl |
| n-butyl | 2(S)-amino-3-phenyl-propyl |
| 2-thiophene | 2(S)-amino-3-phenyl-propyl |
| 3-thiophene | 2(S)-amino-3-phenyl-propyl |
| 3-aminophenyl | 2(S)-amino-3-phenyl-propyl |
| 2-(5-chlorothiophene) | 2(S)-amino-3-phenyl-propyl |
| 3-isopropylphenyl | 3-phenylpropyl |
| 3-tolyl | 3-phenylpropyl |
| 3-chlorophenyl | 3-phenylpropyl |
| 3-chloro-4-fluorophenyl | 3-phenylpropyl |
| 3,5-Ditrifluoromethylphenyl | 3-phenylpropyl |
| 4-fluorophenyl | 3-phenylpropyl |
| 3,4-dichlorophenyl | 3-phenylpropyl |
| 1-naphthyl | 3-phenylpropyl |
| 3-fluorophenyl | 3-phenylpropyl |
| 2-naphthyl | 3-phenylpropyl |
| n-butyl | 3-phenylpropyl |

TABLE VII-continued

[Structure: pyrimidinone fused with 7-membered ring containing N-R21, with R11 substituent and 3-pyridyl group]

| R11 | R21 |
|---|---|
| 2-thiophene | 3-phenylpropyl |
| 3-thiophene | 3-phenylpropyl |
| 3-aminophenyl | 3-phenylpropyl |
| 2-(5-chlorothiophene) | 3-phenylpropyl |
| 3,5-dichlorophenyl | 3-methyl-3-phenyl-propyl |
| 4-tolyl | 3-methyl-3-phenyl-propyl |
| 3-trifluoromethylphenyl | 3-methyl-3-phenyl-propyl |
| 4-methoxyphenyl | 3-methyl-3-phenyl-propyl |
| 4-trifluoromethylphenyl | 3-methyl-3-phenyl-propyl |
| 3-isopropylphenyl | 3-methyl-3-phenyl-propyl |
| 3-tolyl | 3-methyl-3-phenyl-propyl |
| 3-chlorophenyl | 3-methyl-3-phenyl-propyl |
| 3-chloro-4-fluorophenyl | 3-methyl-3-phenyl-propyl |
| 3,5-Ditrifluoromethylphenyl | 3-methyl-3-phenyl-propyl |
| 4-fluorophenyl | 3-methyl-3-phenyl-propyl |
| 3,4-dichlorophenyl | 3-methyl-3-phenyl-propyl |
| 2-naphthyl | 3-methyl-3-phenyl-propyl |
| n-butyl | 3-methyl-3-phenyl-propyl |
| 2-thiophene | 3-methyl-3-phenyl-propyl |
| 3-thiophene | 3-methyl-3-phenyl-propyl |
| 3-aminophenyl | 3-methyl-3-phenyl-propyl |
| 2-(5-chlorothiophene) | 3-methyl-3-phenyl-propyl |
| 3,5-dichlorophenyl | 3-amino-3-phenyl-propyl |
| 4-tolyl | 3-amino-3-phenyl-propyl |
| 3-trifluoromethylphenyl | 3-amino-3-phenyl-propyl |
| 4-methoxyphenyl | 3-amino-3-phenyl-propyl |
| 4-trifluoromethylphenyl | 3-amino-3-phenyl-propyl |
| 3-isopropylphenyl | 3-amino-3-phenyl-propyl |
| 3-tolyl | 3-amino-3-phenyl-propyl |
| 3-chlorophenyl | 3-amino-3-phenyl-propyl |
| 3-chloro-4-fluorophenyl | 3-amino-3-phenyl-propyl |
| 3,5-Ditrifluoromethylphenyl | 3-amino-3-phenyl-propyl |
| 4-fluorophenyl | 3-amino-3-phenyl-propyl |
| 3,4-dichlorophenyl | 3-amino-3-phenyl-propyl |
| 1-naphthyl | 3-amino-3-phenyl-propyl |
| 3-fluorophenyl | 3-amino-3-phenyl-propyl |
| 2-naphthyl | 3-amino-3-phenyl-propyl |
| n-butyl | 3-amino-3-phenyl-propyl |
| 2-thiophene | 3-amino-3-phenyl-propyl |
| 3-thiophene | 3-amino-3-phenyl-propyl |
| 3-aminophenyl | 3-amino-3-phenyl-propyl |
| 2-(5-chlorothiophene) | 3-amino-3-phenyl-propyl |
| 3,5-dichlorophenyl | 2(R)-amino-3-phenyl-propyl |
| 4-tolyl | 2(R)-amino-3-phenyl-propyl |
| 3-trifluoromethylphenyl | 2(R)-amino-3-phenyl-propyl |
| 4-methoxyphenyl | 2(R)-amino-3-phenyl-propyl |
| 4-trifluoromethylphenyl | 2(R)-amino-3-phenyl-propyl |
| 3-isopropylphenyl | 2(R)-amino-3-phenyl-propyl |
| 3-tolyl | 2(R)-amino-3-phenyl-propyl |
| 3-chlorophenyl | 2(R)-amino-3-phenyl-propyl |
| 3-chloro-4-fluorophenyl | 2(R)-amino-3-phenyl-propyl |
| 3,5-Ditrifluoromethylphenyl | 2(R)-amino-3-phenyl-propyl |
| 4-fluorophenyl | 2(R)-amino-3-phenyl-propyl |
| 3,4-dichlorophenyl | 2(R)-amino-3-phenyl-propyl |
| 1-naphthyl | 2(R)-amino-3-phenyl-propyl |
| 3-fluorophenyl | 2(R)-amino-3-phenyl-propyl |
| 2-naphthyl | 2(R)-amino-3-phenyl-propyl |
| n-butyl | 2(R)-amino-3-phenyl-propyl |
| 2-thiophene | 2(R)-amino-3-phenyl-propyl |
| 3-thiophene | 2(R)-amino-3-phenyl-propyl |
| 3-aminophenyl | 2(R)-amino-3-phenyl-propyl |
| 2-(5-chlorothiophene) | 2(R)-amino-3-phenyl-propyl |
| 3,5-dichlorophenyl | 2-methyl-2-amino-3-phenyl-propyl |
| 4-tolyl | 2-methyl-2-amino-3-phenyl-propyl |
| 3-trifluoromethylphenyl | 2-methyl-2-amino-3-phenyl-propyl |
| 4-methoxyphenyl | 2-methyl-2-amino-3-phenyl-propyl |
| 4-trifluoromethylphenyl | 2-methyl-2-amino-3-phenyl-propyl |
| 3-isopropylphenyl | 2-methyl-2-amino-3-phenyl-propyl |
| 3-tolyl | 2-methyl-2-amino-3-phenyl-propyl |
| 3-chlorophenyl | 2-methyl-2-amino-3-phenyl-propyl |
| 3-chloro-4-fluorophenyl | 2-methyl-2-amino-3-phenyl-propyl |
| 3,5-Ditrifluoromethylphenyl | 2-methyl-2-amino-3-phenyl-propyl |
| 4-fluorophenyl | 2-methyl-2-amino-3-phenyl-propyl |
| 3,4-dichlorophenyl | 2-methyl-2-amino-3-phenyl-propyl |
| 1-naphthyl | 2-methyl-2-amino-3-phenyl-propyl |
| 3-fluorophenyl | 2-methyl-2-amino-3-phenyl-propyl |
| 2-naphthyl | 2-methyl-2-amino-3-phenyl-propyl |
| n-butyl | 2-methyl-2-amino-3-phenyl-propyl |
| 2-thiophene | 2-methyl-2-amino-3-phenyl-propyl |
| 3-thiophene | 2-methyl-2-amino-3-phenyl-propyl |
| 3-aminophenyl | 2-methyl-2-amino-3-phenyl-propyl |
| 2-(5-chlorothiophene) | 2-methyl-2-amino-3-phenyl-propyl |
| 3,5-dichlorophenyl | 2-methyl-3-phenyl-propyl |
| 4-tolyl | 2-methyl-3-phenyl-propyl |
| 3-trifluoromethylphenyl | 2-methyl-3-phenyl-propyl |
| 4-methoxyphenyl | 2-methyl-3-phenyl-propyl |
| 4-trifluoromethylphenyl | 2-methyl-3-phenyl-propyl |
| 3-isopropylphenyl | 2-methyl-3-phenyl-propyl |
| 3-tolyl | 2-methyl-3-phenyl-propyl |
| 3-chlorophenyl | 2-methyl-3-phenyl-propyl |
| 3-chloro-4-fluorophenyl | 2-methyl-3-phenyl-propyl |
| 3,5-Ditrifluoromethylphenyl | 2-methyl-3-phenyl-propyl |
| 4-fluorophenyl | 2-methyl-3-phenyl-propyl |
| 3,4-dichlorophenyl | 2-methyl-3-phenyl-propyl |
| 1-naphthyl | 2-methyl-3-phenyl-propyl |
| 3-fluorophenyl | 2-methyl-3-phenyl-propyl |
| 2-naphthyl | 2-methyl-3-phenyl-propyl |
| n-butyl | 2-methyl-3-phenyl-propyl |
| 2-thiophene | 2-methyl-3-phenyl-propyl |
| 3-thiophene | 2-methyl-3-phenyl-propyl |
| 3-aminophenyl | 2-methyl-3-phenyl-propyl |
| 2-(5-chlorothiophene) | 2-methyl-3-phenyl-propyl |
| 3,5-dichlorophenyl | 2-(N,N-dimethylamino)-3-phenyl-propyl |
| 4-tolyl | 2-(N,N-dimethylamino)-3-phenyl-propyl |
| 3-trifluoromethylphenyl | 2-(N,N-dimethylamino)-3-phenyl-propyl |
| 4-methoxyphenyl | 2-(N,N-dimethylamino)-3-phenyl-propyl |

TABLE VII-continued

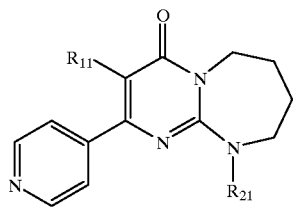

| $R_{11}$ | $R_{21}$ |
|---|---|
| 4-trifluoromethylphenyl | 2-(N,N-dimethylamino)-3-phenyl-propyl |
| 3-isopropylphenyl | 2-(N,N-dimethylamino)-3-phenyl-propyl |
| 3-tolyl | 2-(N,N-dimethylamino)-3-phenyl-propyl |
| 3-chlorophenyl | 2-(N,N-dimethylamino)-3-phenyl-propyl |
| 3-chloro-4-fluorophenyl | 2-(N,N-dimethylamino)-3-phenyl-propyl |
| 3,5-Ditrifluoromethylphenyl | 2-(N,N-dimethylamino)-3-phenyl-propyl |
| 4-fluorophenyl | 2-(N,N-dimethylamino)-3-phenyl-propyl |
| 3,4-dichlorophenyl | 2-(N,N-dimethylamino)-3-phenyl-propyl |
| 1-naphthyl | 2-(N,N-dimethylamino)-3-phenyl-propyl |
| 3-fluorophenyl | 2-(N,N-dimethylamino)-3-phenyl-propyl |
| 2-naphthyl | 2-(N,N-dimethylamino)-3-phenyl-propyl |
| n-butyl | 2-(N,N-dimethylamino)-3-phenyl-propyl |
| 2-thiophene | 2-(N,N-dimethylamino)-3-phenyl-propyl |
| 3-thiophene | 2-(N,N-dimethylamino)-3-phenyl-propyl |
| 3-aminophenyl | 2-(N,N-dimethylamino)-3-phenyl-propyl |
| 2-(5-chlorothiophene) | 2-(N,N-dimethylamino)-3-phenyl-propyl |
| 3,5-dichlorophenyl | 2-(N-methylamino)-3-phenyl-propyl |
| 4-tolyl | 2-(N-methylamino)-3-phenyl-propyl |
| 3-trifluoromethylphenyl | 2-(N-methylamino)-3-phenyl-propyl |
| 4-methoxyphenyl | 2-(N-methylamino)-3-phenyl-propyl |
| 4-trifluoromethylphenyl | 2-(N-methylamino)-3-phenyl-propyl |
| 3-isopropylphenyl | 2-(N-methylamino)-3-phenyl-propyl |
| 3-tolyl | 2-(N-methylamino)-3-phenyl-propyl |
| 3-chlorophenyl | 2-(N-methylamino)-3-phenyl-propyl |
| 3-chloro-4-fluorophenyl | 2-(N-methylamino)-3-phenyl-propyl |
| 3,5-Ditrifluoromethylphenyl | 2-(N-methylamino)-3-phenyl-propyl |
| 3,4-dichlorophenyl | 2-(N-methylamino)-3-phenyl-propyl |
| 4-fluorophenyl | 2-(N-methylamino)-3-phenyl-propyl |
| 1-naphthyl | 2-(N-methylamino)-3-phenyl-propyl |
| 3-fluorophenyl | 2-(N-methylamino)-3-phenyl-propyl |
| 2-naphthyl | 2-(N-methylamino)-3-phenyl-propyl |
| n-butyl | 2-(N-methylamino)-3-phenyl-propyl |
| 2-thiophene | 2-(N-methylamino)-3-phenyl-propyl |

TABLE VII-continued

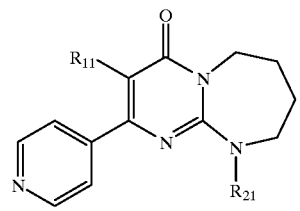

| $R_{11}$ | $R_{21}$ |
|---|---|
| 3-thiophene | 2-(N-methylamino)-3-phenyl-propyl |
| 3-aminophenyl | 2-(N-methylamino)-3-phenyl-propyl |
| 2-(5-chlorothiophene) | 2-(N-methylamino)-3-phenyl-propyl |

Example 62

Using the corresponding starting materials, the following compounds of Table VIII may be prepared using the procedure for 3-methyl-2-(2(S)-amino-3-phenylpropylamino)-5-(3-trifluoromethylphenyl)-6-(4-pyridyl)-4(3H)-pyrimidinone.

TABLE VIII

| $R_{11}$ | $R_{21}$ |
|---|---|
| 3,5-dichlorophenyl | 2(S)-amino-3-phenyl-propyl |
| 4-methoxyphenyl | 2(S)-amino-3-phenyl-propyl |
| 3-tolyl | 2(S)-amino-3-phenyl-propyl |
| 3-chlorophenyl | 2(S)-amino-3-phenyl-propyl |
| 4-fluorophenyl | 2(S)-amino-3-phenyl-propyl |
| 2-naphthyl | 2(S)-amino-3-phenyl-propyl |
| n-butyl | 2(S)-amino-3-phenyl-propyl |
| 2-thiophene | 2(S)-amino-3-phenyl-propyl |
| 3-thiophene | 2(S)-amino-3-phenyl-propyl |
| 3-aminophenyl | 2(S)-amino-3-phenyl-propyl |
| 2-(5-chlorothiophene) | 2(S)-amino-3-phenyl-propyl |
| 3-isopropylphenyl | 3-phenylpropyl |
| 3-tolyl | 3-phenylpropyl |
| 3-chlorophenyl | 3-phenylpropyl |
| 3-chloro-4-fluorophenyl | 3-phenylpropyl |
| 3,5-Ditrifluoromethylphenyl | 3-phenylpropyl |
| 4-fluorophenyl | 3-phenylpropyl |
| 3,4-dichlorophenyl | 3-phenylpropyl |
| 1-naphthyl | 3-phenylpropyl |
| 3-fluorophenyl | 3-phenylpropyl |
| 2-naphthyl | 3-phenylpropyl |
| n-butyl | 3-phenylpropyl |
| 2-thiophene | 3-phenylpropyl |
| 3-thiophene | 3-phenylpropyl |
| 3-aminophenyl | 3-phenylpropyl |
| 2-(5-chlorothiophene) | 3-phenylpropyl |
| 3,5-dichlorophenyl | 3-methyl-3-phenyl-propyl |
| 4-tolyl | 3-methyl-3-phenyl-propyl |
| 3-trifluoromethylphenyl | 3-methyl-3-phenyl-propyl |
| 4-methoxyphenyl | 3-methyl-3-phenyl-propyl |
| 4-trifluoromethylphenyl | 3-methyl-3-phenyl-propyl |

TABLE VIII-continued

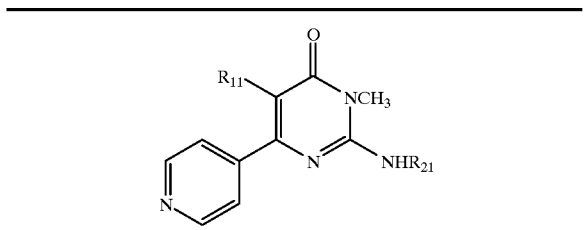

| $R_{11}$ | $R_{21}$ |
|---|---|
| 3-isopropylphenyl | 3-methyl-3-phenyl-propyl |
| 3-tolyl | 3-methyl-3-phenyl-propyl |
| 3-chlorophenyl | 3-methyl-3-phenyl-propyl |
| 3-chloro-4-fluorophenyl | 3-methyl-3-phenyl-propyl |
| 3,5-Ditrifluoromethylphenyl | 3-methyl-3-phenyl-propyl |
| 4-fluorophenyl | 3-methyl-3-phenyl-propyl |
| 3,4-dichlorophenyl | 3-methyl-3-phenyl-propyl |
| 2-naphthyl | 3-methyl-3-phenyl-propyl |
| n-butyl | 3-methyl-3-phenyl-propyl |
| 2-thiophene | 3-methyl-3-phenyl-propyl |
| 3-thiophene | 3-methyl-3-phenyl-propyl |
| 3-aminophenyl | 3-methyl-3-phenyl-propyl |
| 2-(5-chlorothiophene) | 3-methyl-3-phenyl-propyl |
| 3,5-dichlorophenyl | 3-amino-3-phenyl-propyl |
| 4-tolyl | 3-amino-3-phenyl-propyl |
| 3-trifluoromethylphenyl | 3-amino-3-phenyl-propyl |
| 4-methoxyphenyl | 3-amino-3-phenyl-propyl |
| 4-trifluoromethylphenyl | 3-amino-3-phenyl-propyl |
| 3-isopropylphenyl | 3-amino-3-phenyl-propyl |
| 3-tolyl | 3-amino-3-phenyl-propyl |
| 3-chlorophenyl | 3-amino-3-phenyl-propyl |
| 3-chloro-4-fluorophenyl | 3-amino-3-phenyl-propyl |
| 3,5-Ditrifluoromethylphenyl | 3-amino-3-phenyl-propyl |
| 4-fluorophenyl | 3-amino-3-phenyl-propyl |
| 3,4-dichlorophenyl | 3-amino-3-phenyl-propyl |
| 1-naphthyl | 3-amino-3-phenyl-propyl |
| 3-fluorophenyl | 3-amino-3-phenyl-propyl |
| 2-naphthyl | 3-amino-3-phenyl-propyl |
| n-butyl | 3-amino-3-phenyl-propyl |
| 2-thiophene | 3-amino-3-phenyl-propyl |
| 3-thiophene | 3-amino-3-phenyl-propyl |
| 3-aminophenyl | 3-amino-3-phenyl-propyl |
| 2-(5-chlorothiophene) | 3-amino-3-phenyl-propyl |
| 3,5-dichlorophenyl | 2(R)-amino-3-phenyl-propyl |
| 4-tolyl | 2(R)-amino-3-phenyl-propyl |
| 3-trifluoromethylphenyl | 2(R)-amino-3-phenyl-propyl |
| 4-methoxyphenyl | 2(R)-amino-3-phenyl-propyl |
| 4-trifluoromethylphenyl | 2(R)-amino-3-phenyl-propyl |
| 3-isopropylphenyl | 2(R)-amino-3-phenyl-propyl |
| 3-tolyl | 2(R)-amino-3-phenyl-propyl |
| 3-chlorophenyl | 2(R)-amino-3-phenyl-propyl |
| 3-chloro-4-fluorophenyl | 2(R)-amino-3-phenyl-propyl |
| 3,5-Ditrifluoromethylphenyl | 2(R)-amino-3-phenyl-propyl |
| 4-fluorophenyl | 2(R)-amino-3-phenyl-propyl |
| 3,4-dichlorophenyl | 2(R)-amino-3-phenyl-propyl |
| 1-naphthyl | 2(R)-amino-3-phenyl-propyl |
| 3-fluorophenyl | 2(R)-amino-3-phenyl-propyl |
| 2-naphthyl | 2(R)-amino-3-phenyl-propyl |
| n-butyl | 2(R)-amino-3-phenyl-propyl |
| 2-thiophene | 2(R)-amino-3-phenyl-propyl |
| 3-thiophene | 2(R)-amino-3-phenyl-propyl |
| 3-aminophenyl | 2(R)-amino-3-phenyl-propyl |
| 2-(5-chlorothiophene) | 2(R)-amino-3-phenyl-propyl |
| 3,5-dichlorophenyl | 2-methyl-2-amino-3-phenyl-propyl |
| 4-tolyl | 2-methyl-2-amino-3-phenyl-propyl |
| 3-trifluoromethylphenyl | 2-methyl-2-amino-3-phenyl-propyl |
| 4-methoxyphenyl | 2-methyl-2-amino-3-phenyl-propyl |
| 4-trifluoromethylphenyl | 2-methyl-2-amino-3-phenyl-propyl |
| 3-isopropylphenyl | 2-methyl-2-amino-3-phenyl-propyl |

TABLE VIII-continued

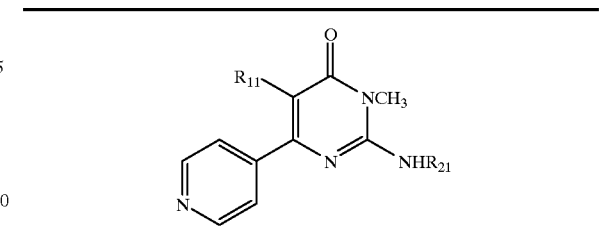

| $R_{11}$ | $R_{21}$ |
|---|---|
| 3-tolyl | 2-methyl-2-amino-3-phenyl-propyl |
| 3-chlorophenyl | 2-methyl-2-amino-3-phenyl-propyl |
| 3-chloro-4-fluorophenyl | 2-methyl-2-amino-3-phenyl-propyl |
| 3,5-Ditrifluoromethylphenyl | 2-methyl-2-amino-3-phenyl-propyl |
| 4-fluorophenyl | 2-methyl-2-amino-3-phenyl-propyl |
| 3,4-dichlorophenyl | 2-methyl-2-amino-3-phenyl-propyl |
| 1-naphthyl | 2-methyl-2-amino-3-phenyl-propyl |
| 3-fluorophenyl | 2-methyl-2-amino-3-phenyl-propyl |
| 2-naphthyl | 2-methyl-2-amino-3-phenyl-propyl |
| n-butyl | 2-methyl-2-amino-3-phenyl-propyl |
| 2-thiophene | 2-methyl-2-amino-3-phenyl-propyl |
| 3-thiophene | 2-methyl-2-amino-3-phenyl-propyl |
| 3-aminophenyl | 2-methyl-2-amino-3-phenyl-propyl |
| 2-(5-chlorothiophene) | 2-methyl-2-amino-3-phenyl-propyl |
| 3,5-dichlorophenyl | 2-methyl-3-phenyl-propyl |
| 4-tolyl | 2-methyl-3-phenyl-propyl |
| 3-trifluoromethylphenyl | 2-methyl-3-phenyl-propyl |
| 4-methoxyphenyl | 2-methyl-3-phenyl-propyl |
| 4-trifluoromethylphenyl | 2-methyl-3-phenyl-propyl |
| 3-isopropylphenyl | 2-methyl-3-phenyl-propyl |
| 3-tolyl | 2-methyl-3-phenyl-propyl |
| 3-chlorophenyl | 2-methyl-3-phenyl-propyl |
| 3-chloro-4-fluorophenyl | 2-methyl-3-phenyl-propyl |
| 3,5-Ditrifluoromethylphenyl | 2-methyl-3-phenyl-propyl |
| 4-fluorophenyl | 2-methyl-3-phenyl-propyl |
| 3,4-dichlorophenyl | 2-methyl-3-phenyl-propyl |
| 1-naphthyl | 2-methyl-3-phenyl-propyl |
| 3-fluorophenyl | 2-methyl-3-phenyl-propyl |
| 2-naphthyl | 2-methyl-3-phenyl-propyl |
| n-butyl | 2-methyl-3-phenyl-propyl |
| 2-thiophene | 2-methyl-3-phenyl-propyl |
| 3-thiophene | 2-methyl-3-phenyl-propyl |
| 3-aminophenyl | 2-methyl-3-phenyl-propyl |
| 2-(5-chlorothiophene) | 2-methyl-3-phenyl-propyl |
| 3,5-dichlorophenyl | 2-(N,N-dimethylamino)-3-phenyl-propyl |
| 4-tolyl | 2-(N,N-dimethylamino)-3-phenyl-propyl |
| 3-trifluoromethylphenyl | 2-(N,N-dimethylamino)-3-phenyl-propyl |
| 4-methoxyphenyl | 2-(N,N-dimethylamino)-3-phenyl-propyl |
| 4-trifluoromethylphenyl | 2-(N,N-dimethylamino)-3-phenyl-propyl |
| 3-isopropylphenyl | 2-(N,N-dimethylamino)-3-phenyl-propyl |
| 3-tolyl | 2-(N,N-dimethylamino)-3-phenyl-propyl |
| 3-chlorophenyl | 2-(N,N-dimethylamino)-3-phenyl-propyl |
| 3-chloro-4-fluorophenyl | 2-(N,N-dimethylamino)-3- |

TABLE VIII-continued

![structure with R11, NCH3, NHR21, pyridyl]

| R11 | R21 |
|---|---|
| 3,5-Ditrifluoromethylphenyl | 2-(N,N-dimethylamino)-3-phenyl-propyl |
| 4-fluorophenyl | 2-(N,N-dimethylamino)-3-phenyl-propyl |
| 3,4-dichlorophenyl | 2-(N,N-dimethylamino)-3-phenyl-propyl |
| 1-naphthyl | 2-(N,N-dimethylamino)-3-phenyl-propyl |
| 3-fluorophenyl | 2-(N,N-dimethylamino)-3-phenyl-propyl |
| 2-naphthyl | 2-(N,N-dimethylamino)-3-phenyl-propyl |
| n-butyl | 2-(N,N-dimethylamino)-3-phenyl-propyl |
| 2-thiophene | 2-(N,N-dimethylamino)-3-phenyl-propyl |
| 3-thiophene | 2-(N,N-dimethylamino)-3-phenyl-propyl |
| 3-aminophenyl | 2-(N,N-dimethylamino)-3-phenyl-propyl |
| 2-(5-chlorothiophene) | 2-(N,N-dimethylamino)-3-phenyl-propyl |
| 3,5-dichlorophenyl | 2-(N-methylamino)-3-phenyl-propyl |
| 4-tolyl | 2-(N-methylamino)-3-phenyl-propyl |
| 3-trifluoromethylphenyl | 2-(N-methylamino)-3-phenyl-propyl |
| 4-methoxyphenyl | 2-(N-methylamino)-3-phenyl-propyl |
| 4-trifluoromethylphenyl | 2-(N-methylamino)-3-phenyl-propyl |
| 3-isopropylphenyl | 2-(N-methylamino)-3-phenyl-propyl |
| 3-tolyl | 2-(N-methylamino)-3-phenyl-propyl |
| 3-chlorophenyl | 2-(N-methylamino)-3-phenyl-propyl |
| 3-chloro-4-fluorophenyl | 2-(N-methylamino)-3-phenyl-propyl |
| 3,5-Ditrifluoromethylphenyl | 2-(N-methylamino)-3-phenyl-propyl |
| 3,4-dichlorophenyl | 2-(N-methylamino)-3-phenyl-propyl |
| 4-fluorophenyl | 2-(N-methylamino)-3-phenyl-propyl |
| 1-naphthyl | 2-(N-methylamino)-3-phenyl-propyl |
| 3-fluorophenyl | 2-(N-methylamino)-3-phenyl-propyl |
| 2-naphthyl | 2-(N-methylamino)-3-phenyl-propyl |
| n-butyl | 2-(N-methylamino)-3-phenyl-propyl |
| 2-thiophene | 2-(N-methylamino)-3-phenyl-propyl |
| 3-thiophene | 2-(N-methylamino)-3-phenyl-propyl |
| 3-aminophenyl | 2-(N-methylamino)-3-phenyl-propyl |
| 2-(5-chlorothiophene) | 2-(N-methylamino)-3-phenyl-propyl |

Example 63

Procedure for the preparation of 2-((2-(3-trifluoromethylphenyl)phenylmethyl)amino)-3-methyl-5-(4-fluorophenyl)-6-(4-pyridyl)-4(3H) -pyrimidinone

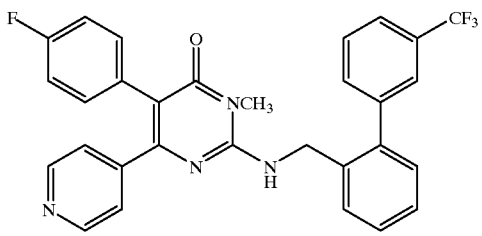

Step A. 2-((2-bromophenylmethyl)amino)-5-(4-fluorophenyl)-6-(4-pyridyl)-3-methyl-4(3H) -pyrimidinone:

The compound, 3-methyl-5-(4-fluorophenyl)-6-(4-pyridyl)-2-thiomethyl-4(3H)-pyrimidinone (470 mg, 1.44 mmol) was dissolved in methanol:water mixture(1.8:1, 40 ml and 22.5 ml). Potasssium peroxymonosulfate (OXONE Aldrich Chem Co., 2.5 g 4.1 mmol) was added to a cooled (4° C.) reaction mixture and then the reaction was continued for 16 h at room-temperature. The reaction mixture was concentrated and extracted with dichloromethane and the organic layer was washed with water, dried over $Na_2SO_4$ and was concentrated. The residue (500 mg) and o-bromobenzylamine were mixed in 1,4-dioxane (20 ml). The clear solution was heated at 85° C. for 18 h and progress of the reaction monitored by TLC. The reaction mixture was concentrated and chromatographed on a silica gel column to obtain the titled compound. MS(m/z): 466.9 $C_{23}H_{18}BrFN_4O$ requirs: 465.33 1H-NMR ($CDCl_3$):d 8.49 (dd, 2H, pyridyl), 7.67–6.81 (m, 12H, Ph and pyridyl), 5.44 (t, 1H, NH), 4.92 (d 2H, $CH_2$—Ph), 3.6 (s, 3H, N-$CH_3$).

Step B. 2-((2-(3-trifluoromethylphenyl)phenylmethyl)amino)-3-methyl-5-(4-fluorophenyl)-6-(4-pyridyl)-4(3H)-pyrimidinone:

2-((2-bromophenylmethyl)amino)-5-(4-fluorophenyl)-6-(4-pyridyl)-3-methyl-4(3H)-pyrimidinone (175 mg, 0.38 mmol) was dipersed in 2M sodium carbonate solution (12 ml) and 3-trifluromethylbenzene- boronic acid (170 mg, 0.89 mmol), toluene (12 ml) were added to the above mixture and the reaction mixture was degassed and catalyst tetrakistriphenylphosphine Pd(0) (50 mg) was added. The reaction mixture was refluxed for 16 h. The formation of the product was monitored by TLC. Then it was cooled, diluted with toluene (12 ml) and washed with water. The organic layer was dried over sodium sulfate, concentrated and the product was purified by silica gel chromatgraphy to give the title compound. MS(m/z): 531.1 $C_{30}H_{22}F_4N_4O$ requir. 530.53; 1H-NMR($CDCl_3$) :d 8.43 (m, 2H, pyridyl), 7.69–7.12 (m,8H, Ph), 7.11–6.88 (m, 6H, pyridyl and Ph—$CF_3$), 4.85 (m, 3H, $CH_2$—Ph and NH), 3.32(N-$CH_3$).

Example 64

Using the corresponding starting materials, the following compounds of Table IX may be prepared using the procedure for 2-((2-(3-trifluoromethylphenyl) phenylmethyl) amino)-3-methyl-5-(4-fluorophenyl)-6-(4-pyridyl)-4(3H)-pyrimidinone.

TABLE IX

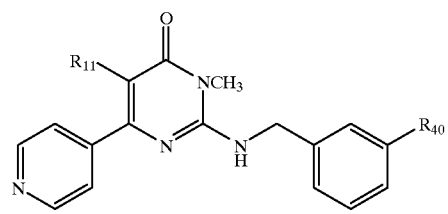

| R11 | R40 |
|---|---|
| 4-fluorophenyl | 3,5-dichlorophenyl |
| 4-fluorophenyl | 4-tolyl |
| 4-fluorophenyl | 4-methoxyphenyl |
| 4-fluorophenyl | 4-trifluoromethylphenyl |
| 4-fluorophenyl | 3-isopropylphenyl |
| 4-fluorophenyl | 3-tolyl |
| 4-fluorophenyl | 3-chlorophenyl |
| 4-fluorophenyl | 3-chloro-4-fluorophenyl |
| 4-fluorophenyl | 3,5-Ditrifluoromethylphenyl |
| 4-fluorophenyl | 4-fluorophenyl |
| 4-fluorophenyl | 3,4-dichlorophenyl |
| 4-fluorophenyl | 1-naphthyl |
| 4-fluorophenyl | 3-fluorophenyl |
| 4-fluorophenyl | 2-naphthyl |
| 4-fluorophenyl | n-butyl |
| 4-fluorophenyl | 2-thiophene |
| 4-fluorophenyl | 3-thiophene |
| 4-fluorophenyl | 3-aminophenyl |
| 4-fluorophenyl | 2-(5-chlorothiophene) |
| 3-trifluoromethylphenyl | 3,5-dichlorophenyl |
| 3-trifluoromethylphenyl | 4-tolyl |
| 3-trifluoromethylphenyl | 3-trifluoromethylphenyl |
| 3-trifluoromethylphenyl | 4-methoxyphenyl |
| 3-trifluoromethylphenyl | 4-trifluoromethylphenyl |
| 3-trifluoromethylphenyl | 3-isopropylphenyl |
| 3-trifluoromethylphenyl | 3-tolyl |
| 3-trifluoromethylphenyl | 3-chlorophenyl |
| 3-trifluoromethylphenyl | 3-chloro-4-fluorophenyl |
| 3-trifluoromethylphenyl | 3,5-Ditrifluoromethylphenyl |
| 3-trifluoromethylphenyl | 4-fluorophenyl |
| 3-trifluoromethylphenyl | 3,4-dichlorophenyl |
| 3-trifluoromethylphenyl | 1-naphthyl |
| 3-trifluoromethylphenyl | 3-fluorophenyl |
| 3-trifluoromethylphenyl | 2-naphthyl |
| 3-trifluoromethylphenyl | n-butyl |
| 3-trifluoromethylphenyl | 2-thiophene |
| 3-trifluoromethylphenyl | 3-thiophene |
| 3-trifluoromethylphenyl | 3-aminophenyl |
| 3-trifluoromethylphenyl | 2-(5-chlorothiophene) |

Example 65

Using the corresponding starting materials, the following compounds of Table X may be prepared using the procedure for 2-((2-(3-trifluoromethylphenyl) phenylmethyl)amino)-3-methyl-5-(4-fluorophenyl)-6-(4-pyridyl)-4(3H)-pyrimidinone.

TABLE X

| R11 | R40 |
|---|---|
| 4-fluorophenyl | 3,5-dichlorophenyl |
| 4-fluorophenyl | 4-tolyl |
| 4-fluorophenyl | 4-methoxyphenyl |
| 4-fluorophenyl | 4-trifluoromethylphenyl |
| 4-fluorophenyl | 3-isopropylphenyl |
| 4-fluorophenyl | 3-tolyl |
| 4-fluorophenyl | 3-chlorophenyl |
| 4-fluorophenyl | 3-chloro-4-fluorophenyl |
| 4-fluorophenyl | 3,5-Ditrifluoromethylphenyl |
| 4-fluorophenyl | 4-fluorophenyl |
| 4-fluorophenyl | 3,4-dichlorophenyl |
| 4-fluorophenyl | 1-naphthyl |
| 4-fluorophenyl | 3-fluorophenyl |
| 4-fluorophenyl | 2-naphthyl |
| 4-fluorophenyl | n-butyl |
| 4-fluorophenyl | 2-thiophene |
| 4-fluorophenyl | 3-thiophene |
| 4-fluorophenyl | 3-aminophenyl |
| 4-fluorophenyl | 2-(5-chlorothiophene) |
| 3-trifluoromethylphenyl | 3,5-dichlorophenyl |
| 3-trifluoromethylphenyl | 4-tolyl |
| 3-trifluoromethylphenyl | 3-trifluoromethylphenyl |
| 3-trifluoromethylphenyl | 4-methoxyphenyl |
| 3-trifluoromethylphenyl | 4-trifluoromethylphenyl |
| 3-trifluoromethylphenyl | 3-isopropylphenyl |
| 3-trifluoromethylphenyl | 3-tolyl |
| 3-trifluoromethylphenyl | 3-chlorophenyl |
| 3-trifluoromethylphenyl | 3-chloro-4-fluorophenyl |
| 3-trifluoromethylphenyl | 3,5-Ditrifluoromethylphenyl |
| 3-trifluoromethylphenyl | 4-fluorophenyl |
| 3-trifluoromethylphenyl | 3,4-dichlorophenyl |
| 3-trifluoromethylphenyl | 1-naphthyl |
| 3-trifluoromethylphenyl | 3-fluorophenyl |
| 3-trifluoromethylphenyl | 2-naphthyl |
| 3-trifluoromethylphenyl | n-butyl |
| 3-trifluoromethylphenyl | 2-thiophene |
| 3-trifluoromethylphenyl | 3-thiophene |
| 3-trifluoromethylphenyl | 3-aminophenyl |
| 3-trifluoromethylphenyl | 2-(5-chlorothiophene) |

Example 66

Using the corresponding starting materials, the following compounds of Table XI may be prepared using the procedure for 2-((2-(3-trifluoromethylphenyl) phenylmethyl) amino)-3-methyl-5-(4-fluorophenyl)-6-(4-pyridyl)-4(3H)-pyrimidinone.

TABLE XI

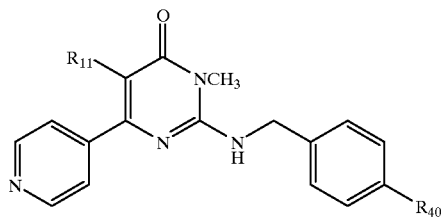

| R₁₁ | R₄₀ |
| --- | --- |
| 4-fluorophenyl | 3,5-dichlorophenyl |
| 4-fluorophenyl | 4-tolyl |
| 4-fluorophenyl | 4-methoxyphenyl |
| 4-fluorophenyl | 4-trifluoromethylphenyl |
| 4-fluorophenyl | 3-isopropylphenyl |
| 4-fluorophenyl | 3-tolyl |
| 4-fluorophenyl | 3-chlorophenyl |
| 4-fluorophenyl | 3-chloro-4-fluorophenyl |
| 4-fluorophenyl | 3,5-Ditrifluoromethylphenyl |
| 4-fluorophenyl | 4-fluorophenyl |
| 4-fluorophenyl | 3,4-dichlorophenyl |
| 4-fluorophenyl | 1-naphthyl |
| 4-fluorophenyl | 3-fluorophenyl |
| 4-fluorophenyl | 2-naphthyl |
| 4-fluorophenyl | n-butyl |
| 4-fluorophenyl | 2-thiophene |
| 4-fluorophenyl | 3-thiophene |
| 4-fluorophenyl | 3-aminophenyl |
| 4-fluorophenyl | 2-(5-chlorothiophene) |
| 3-trifluoromethylphenyl | 3,5-dichlorophenyl |
| 3-trifluoromethylphenyl | 4-tolyl |
| 3-trifluoromethylphenyl | 3-trifluoromethylphenyl |
| 3-trifluoromethylphenyl | 4-methoxyphenyl |
| 3-trifluoromethylphenyl | 4-trifluoromethylphenyl |
| 3-trifluoromethylphenyl | 3-isopropylphenyl |
| 3-trifluoromethylphenyl | 3-tolyl |
| 3-trifluoromethylphenyl | 3-chlorophenyl |
| 3-trifluoromethylphenyl | 3-chloro-4-fluorophenyl |
| 3-trifluoromethylphenyl | 3,5-Ditrifluoromethylphenyl |
| 3-trifluoromethylphenyl | 4-fluorophenyl |
| 3-trifluoromethylphenyl | 3,4-dichlorophenyl |
| 3-trifluoromethylphenyl | 1-naphthyl |
| 3-trifluoromethylphenyl | 3-fluorophenyl |
| 3-trifluoromethylphenyl | 2-naphthyl |
| 3-trifluoromethylphenyl | n-butyl |
| 3-trifluoromethylphenyl | 2-thiophene |
| 3-trifluoromethylphenyl | 3-thiophene |
| 3-trifluoromethylphenyl | 3-aminophenyl |
| 3-trifluoromethylphenyl | 2-(5-chlorothiophene) |

Example 67

Biological Assays

The following assays were used to characterize the ability of compounds of the invention to inhibit the production of TNF-α and IL-1-β. The second assay measured the inhibition of TNF-α and/or IL-1-β in mice after oral administration of the test compounds. The third assay, a glucagon binding inhibition in vitro assay, can be used to characterize the ability of compounds of the invention to inhibit glucagon binding. The fourth assay, a Cyclooxygenase enzyme (COX-1 and COX-2) inhibition activity in vitro assay, can be used to characterize the ability of compounds of the invention to inhibit COX-1 and/or COX-2.

Lipopolysaccharide-activated monocyte TNF production assay

Isolation of monocytes

Test compounds were evaluated in vitro for the ability to inhibit the production of TNF by monocytes activated with bacterial lipopolysaccharide (LPS). Fresh residual source leukocytes (a byproduct of plateletpheresis) were obtained from a local blood bank, and peripheral blood mononuclear cells (PBMCs) were isolated by density gradient centrifugation on Ficol-Paque Plus (Pharmacia). PBMCs were suspended at $2 \times 10^6$/ml in DMEM supplemented to contain 2% FCS, 10 mM, 0.3 mg/ml glutamate, 100 U/ml penicillin G and 100 mg/ml streptomycin sulfate (complete media). Cells were plated into Falcon flat bottom, 96 well culture plates (200 μl/well) and cultured overnight at 37° C. and 6% $CO_2$. Non-adherent cells were removed by washing with 200 μl/well of fresh medium. Wells containing adherent cells (~70% monocytes) were replenished with 100 μl of fresh medium.

Preparation of test compound stock solutions

Test compounds were dissolved in DMZ. Compound stock solutions were prepared to an initial concentration of 10–50 μM. Stocks were diluted initially to 20–200 μM in complete media. Nine two-fold serial dilutions of each compound were then prepared in complete medium.

Treatment of cells with test compounds and activation of TNF production with lipopolysaccharide One hundred microliters of each test compound dilution were added to microtiter wells containing adherent monocytes and 100 μl complete medium. Monocytes were cultured with test compounds for 60 min at which time 25 μl of complete medium containing 30 ng/ml lipopolysaccharide from E. coli K532 were added to each well. Cells were cultured an additional 4 hrs. Culture supernatants were then removed and TNF presence in the supernatants was quantified using an ELISA.

TNF ELISA

Flat bottom, 96 well Corning High Binding ELISA plates were coated overnight (4° C.) with 150 μL/well of 3 μg/ml murine anti-human TNF-α MAb (R&D Systems #MAB210).

Wells were then blocked for 1 hr at room temperature with 200 μL/well of $CaCl_2$-free ELISA buffer supplemented to contain 20 mg/ml BSA (standard ELISA buffer: 20 mM, 150 mM NaCl, 2 mM $CaCl_{21}$ 0.15 mM thimerosal, pH 7.4). Plates were washed and replenished with 100 μl of test supernatants (diluted 1:3) or standards. Standards consisted of eleven 1.5-fold serial dilutions from a stock of 1 ng/ml recombinant human TNF (R&D Systems). Plates were incubated at room temperature for 1 hr on orbital shaker (300 rpm), washed and replenished with 100 μl/well of 0.5 μg/ml goat anti-human TNF-α (R&D systems #AB-210-NA) biotinylated at a 4:1 ratio. Plates were incubated for 40 min, washed and replenished with 100 μl/well of alkaline phosphatase-conjugated streptavidin (Jackson ImmunoResearch #016-050-084) at 0.02 μg/ml. Plates were incubated 30 min, washed and replenished with 200 μl/well of 1 mg/ml of p-nitrophenyl phosphate. After 30 min, plates were read at 405 nm on a $V_{max}$ plate reader.

Data analysis

Standard curve data were fit to a second order polynomial and unknown TNF-α concentrations determined from their OD by solving this equation for concentration. TNF concentrations were then plotted vs. test compound concentration using a second order polynomial. This equation was then used to calculate the concentration of test compounds causing a 50% reduction in TNF production.

Compounds of the invention can also be shown to inhibit LPS-induced release of IL-1β, IL-6 and/or IL-8 from monocytes by measuring concentrations of IL-1β, IL-6 and/or IL-8 by methods well known to those skilled in the art. In a similar manner to the above described assay involving the LPS induced release of TNF-α from monocytes, compounds of this invention can also be shown to inhibit LPS induced release of IL-1β, IL-6 and/or IL-8 from monocytes by measuring concentrations of IL-1β, IL-6 and/or IL-8 by methods well known to those skilled in the art. Thus, the compounds of the invention may lower elevated levels of TNF-α, IL-1, IL-6, and IL-8 levels. Reducing elevated levels of these inflammatory cytokines to basal levels or below is favorable in controlling, slowing progression, and alleviating many disease states. All of the compounds are useful in the methods of treating disease states in which TNF-α, IL-1β, IL-6, and IL-8 play a role to the full extent of the definition of TNF-α-mediated diseases described herein.

Inhibition of LPS-Induced TNF-α production in mice

Male DBA/1LACJ mice were dosed with vehicle or test compounds in a vehicle (the vehicle consisting of 0.5% tragacanth in 0.03 N HCl) 30 minutes prior to lipopolysaccharide (2 mg/kg, I.V.) injection. Ninety minutes after LPS injection, blood was collected and the serum was analyzed by ELISA for TNF levels.

The following compounds exhibit activities in the monocyte assay (LPS induced TNF release) with $IC_{50}$ values of 20 μM or less:

2-(2,6-Dichlorobenzyl)-5-(4-fluorophenyl)-3-methyl-6-(4-pyridyl)-4(3H)-pyrimidinone 2-(Butylamino)-5-(4-fluorophenyl)-3-methyl-6-(4-pyridyl)-4(3H)-pyrimidinone 2-(Benzylamino)-5-(4-fluorophenyl)-3-methyl-6-(4-pyridyl)-4(3H)-pyrimidinone 5-(4-Fluorophenyl)-3-methyl-((R-1-phenylethyl)amino)-(4-pyridyl)-4(3H)-pyrimidinone 2-(2-(2-Chlorophenyl)-ethylamino)-5-(4-fluorophenyl)-3-methyl-6-(4-pyridyl)-4(3H)-pyrimidinone 5-(4-Fluorophenyl)-2-(2-(4-fluorophenyl)-ethylamino)-3-methyl-6-(4-pyridyl)-4(3H)-pyrimidinone 5-(4-Fluorophenyl)-2-((2-hydroxy-2-phenyl)-ethylamino)-3-methyl-6-(4-pyridyl)-4(3H)-pyrimidinone 5-(4-Fluorophenyl)-3-methyl-2-((3-phenylpropyl)-amino)-6-(4-pyridyl)-4(3H)-pyrimidinone 5-(4-Fluorophenyl)-3-methyl-2-((1-methyl-3-phenylpropyl)-amino)-6-(4-pyridyl)-4(3H)-pyrimidinone 5-(4-Fluorophenyl)-3-methyl-2-((R-1-methyl-3-phenylpropyl)-amino)-6-(4-pyridyl)-4(3H)-pyrimidinone 5-(4-Fluorophenyl)-3-methyl-2-((2-phenylaminoethyl)-amino)-6-(4-pyridyl)-4 (3H) -pyrimidinone 5-(4-Fluorophenyl)-2-((3-imidazolylpropyl)-amino)-3-methyl-6-(4-pyridyl)-4(3H)-pyrimidinone 5-(4-Fluorophenyl)-3-methyl-6-(4-pyridyl)-2-(3-(pyrrolidin-1-yl)-propylamino)-4(3H) -pyrimidinone 3,6-Diphenyl-4-(4-pyridyl)-2(1H)-pyridone 6-(4-Methylphenyl)-3-phenyl-4-(4-pyridyl)-2(1H)-pyridone 6-(4-Ethylphenyl)-3-phenyl-4-(4-pyridyl)-2(1H)-pyridone 6-(2,4-Dimethylphenyl)-3-phenyl-4-(4-pyridyl)-2(1H)-pyridone 3-Phenyl-4-(4-pyridyl)-6-(2-thienyl)-2(1H) -pyridone 6-(2-Furyl)-3-phenyl-4-(4-pyridyl)-2(1H)-pyridone 2-(((S)-2-Amino-3-phenylpropyl)-amino)-5-(4-fluorophenyl)-3-methyl-6-(4-pyridyl)-4(3H)-pyrimidinone 2-(((R)-2-Amino-3-phenylpropyl)-amino)-5-(4-fluorophenyl)-3-methyl-6-(4-pyridyl)-4(3H)-pyrimidinone 2-(((S)-2-N-Ethyl-3-phenylpropyl)-amino)-5-(4-fluorophenyl)-3-methyl-6-(4-pyridyl)-4(3H)-pyrimidinone 2-((2-Amino-2-methy-3-phenylpropyl)amino)-5-(4-fluorophenyl)-3-methyl-6-(4-pyridyl)-4(3H)-pyrimidinone 2-((2-Aminomethy-3-phenylpropyl)-amino)-5-(4-fluorophenyl-3-methyl-6-(4-pyridyl)-4(3H)-pyrimidinone 2-((3-Amino-3-phenylpropyl)-amino)-5-(4-fluorophenyl)-3-methyl-6-(4-pyridyl)-4(3H)-pyrimidinone 5-(4-Fluorophenyl)-3-methyl-2-(3-(2-methylphenyl)propyl)-amino)-6-(4-pyridyl)-4(3H)-pyrimidinone 5-(4-Fluorophenyl)-3-methyl-2-((R,S)-2-amino-3-(2'-fluorophenyl)-propyl-amino)-6-(4-pyridyl)-4(3H)-pyrimidinone 2-(((S)-2-Acetamido-3-phenylpropyl)-amino)-5-(4-fluorophenyl)-3-methyl-6-(4-pyridyl)-4(3H)-pyrimidinone 5-(4-Fluorophenyl)-2-(((S)-2-N-isopropylamino-3-phenylpropyl)-amino)-3-methyl-6-(4-pyridyl)-4(3H)-pyrimidinone 2-(((S)-2-N-n-Butylamino-3-phenylpropyl)-amino)-5-(4-fluorophenyl)-3 -methyl-6-(4-pyridyl)-4(3H)-pyrimidinone 2-(((S)-2-N,N-Dimethylamino-3-phenylpropyl)-amino)-5-(4-fluorophenyl-3-methyl-6-(4-pyridyl)-4(3H)-pyrimidinone 5-(4-Fluorophenyl)-3-methyl-2-((2-methy-3-phenylpropyl) amino)-6-(4-pyridyl)-4(3H)-pyrimidinone 2-(((S)-2-Amino-3-phenylpropyl)-amino)-3-ethyl-5-(4-fluorophenyl)-6-(4-pyridyl)-4(3H)-pyrimidinone 3-Ethyl-5-(4-fluorophenyl)-2-((2-methy-3-phenylpropyl) amino)-6-(4-pyridyl)-4(3H)-pyrimidinone 2-((2-(3-trifluoromethylphenyl)phenylmethyl)amino)-3-methyl-5-(4-fluorophenyl)-6-(4-pyridyl)-4(3H)-pyrimidinone 3-Methyl-2-(2(S)-amino-3-phenylpropylamino)-5-(4-tolyl)-6-(4-pyridyl)-4(3H)-pyrimidinone 3-Methyl-2-(2(S)-amino-3-phenylpropylamino)-5-(4-trifluoromethylphenyl)-6-(4-pyridyl)-4(3H)-pyrimidinone 3-Methyl-2-(2(S)-amino-3-phenylpropylamino)-5-(3-isopropylphenyl)-6-(4-pyridyl)-4(3H)-pyrimidinone 3-Methyl-2-(2(S)-amino-3-phenylpropylamino)-5-(3-chloro-4-fluorophenyl)-6-(4-pyridyl)-4(3H)-pyrimidinone 3-Methyl-2-(2(S) -amino-3-phenylpropylamino)-5-(3,5-bis(trifluoromethyl)phenyl)-6-(4-pyridyl)-4(3H)-pyrimidinone 3-Methyl-2-(2(S)-amino-3-phenylpropylamino)-5-(3,4-dichlorophenyl)-6-(4-pyridyl)-4(3H)-pyrimidinone 3-Methyl-2-(2 (S) -amino-3-phenylpropylamino)-5-(1-naphthyl)-6-(4-pyridyl)-4(3H)-pyrimidinone 3-Methyl-2- (2 (S) -amino-3-phenylpropylamino) -5-(3-fluorophenyl)-6-(4-pyridyl)-4(3H)-pyrimidinone 3-Methyl-2-(2(S)-amino-3-phenylpropylamino)-5-(3-trifluoromethylphenyl)-6-(4-pyridyl)-4(3H)-pyrimidinone 3-Methyl-2-(3-phenylpropylamino)-5-(3,5-dichlorophenyl)-6-(4-pyridyl)-4(3H)-pyrimidinone 3-Methyl-2-(3-phenylpropylamino)-5-(4-tolyl)-6-(4-pyridyl)-4(3H)-pyrimidinone 3-Methyl-2-(3-phenylpropylamino)-5-(3-trifluoromethylphenyl)-6-(4-pyridyl)-4(3H)-pyrimidinone 3-Methyl-2-(3-phenylpropylamino)-5-(4-methoxyphenyl)-6-(4-pyridyl)-4(3H)-pyrimidinone 3-Methyl-2-(3-phenylpropylamino)-5-(4-trifluoromethylphenyl)-6-(4-pyridyl)-4(3H)-pyrimidinone 3-Methyl-2-(2-methyl-3-phenylpropylamino)-5-(3-fluorophenyl)-6-(4-pyridyl)-4(3H)-pyrimidinone 3-Methyl-2-(2-methyl-3-phenylpropylamino)-5-(1-naphthyl)-6-(4-pyridyl)-4(3H)-pyrimidinone 5-(4-Fluorophenyl)-2-(((S)-2-N-glycylamino-3-phenylpropyl)-amino)-3-methyl-6-(4-pyridyl)-4-(3H)-pyrimidinone 2-(((S)-2-N-Glycylamino-3-phenylpropyl)-amino)-3-methyl-5-(3-methylphenyl)-6-(4-pyridyl)-4-(3H)-pyrimidinone 5-(4-Fluorophenyl)-2-(((S)-2-hydroxyacetamido-3-phenylpropyl)-amino)-3-methyl-6-(4-pyridyl)-4-(3H)-pyrimidinone 5-(4-Fluorophenyl)-2-(((S)-2-pyrrolidinyl-3-phenylpropyl)-amino)-3-methyl-6-(4-pyridyl)-4-(3H)-pyrimidinone 2-((S)-3-Benzylpiperazinyl)-5-(4-fluorophenyl)-3-methyl-6-(4-pyridyl)-4-(3H)-pyrimidinone 2-((3-Amino-3 (2-fluorophenyl)propyl)-amino)-5-(4-fluorophenyl)-3-methyl-6-(4-pyridyl)-4-(3H)-pyrimidinone 2-((3-Amino-3-(2-methylphenyl)propyl)-amino)-5-(4-fluorophenyl)-3-methyl-6-(4-pyridyl)-4-(3H)-pyrimidinone 2-(((S)-3-Amino-3-phenylpropyl)-amino)-5-(4-fluorophenyl)-3-methyl-6-(4-pyridyl)-4-(3H)-pyrimidinone 2-(((R)-3-Amino-3-phenylpropyl)-amino)-5-(4-fluorophenyl)-3-methyl-6-(4-pyridyl)-4-(3H)-pyrimidinone 2- (((S) -3-Amino-3-phenylpropyl)-amino)-3-methyl-6-(4-pyridyl)5-(3-trifluoromethylphenyl)-4-(3H)-pyrimidinone 2-(((R)-3-Amino-3-phenylpropyl)-amino)-3-methyl-6-(4-pyridyl)5-(3-trifluoromethylphenyl)-4-(3H)-pyrimidinone 2-((3-Amino-3-phenylpropyl)-amino)-3-methyl-6-(4-pyridyl)5-(3-trifluoromethylphenyl)-4-(3H)-pyrimidinone 2- ((3-Amino-3-(2-methylphenyl)propyl)-amino)-3-methyl-6-(4-pyridyl)5-(3-trifluoromethylphenyl)-4-(3H)-pyrimidinone 2-((3-Amino-3-(2-fluorophenyl)propyl)-amino)-3-methyl-6-(4-pyridyl)5-(3-trifluoromethylphenyl)-4-(3H)-pyrimidinone 2-((3-Amino-3-phenylpropyl)-amino)-3-methyl-5-(3-methylphenyl)-6-(4-pyridyl)-4-(3H)-pyrimidinone 2-((3-Amino-3-(2-fluorophenyl)propyl)-amino)-3-methyl-5-(3-methylphenyl)-6-(4-pyridyl)-4-(3H)-pyrimidinone 2-((3-Amino-3-(2-chlorophenyl)propyl)-amino)-3-methyl-5-(3-methylphenyl)-6-(4-pyridyl)-4-(3H)-pyrimidinone 2-(((S)-3-Amino-3-phenylpropyl)-amino)-3-methyl-6-(4-pyridyl)5-(3,4-dimethylphenyl)-4-(3H)-pyrimidinone 2-(((2R,3R)-3-Amino-2-methyl-3-phenylpropyl)-amino)-5-(4-fluorophenyl)-3-methyl-6-(4-pyridyl)-4-(3H)-pyrimidinone 2-(((2S,3S)-3-Amino-2-methyl-3-phenylpropyl)-amino)-5-(4-fluorophenyl)-3-methyl-6-(4-pyridyl)-4-(3H)-pyrimidinone 5-(4-Fluorophenyl)-2-(((S)-3-N-isopropylamino-3-phenylpropyl)-amino)-3-methyl-6-(4-pyridyl)-4-(3H)-pyrimidinone 5-(4-Fluorophenyl)-2-(((R)-3-N-isopropylamino-3-phenylpropyl)-amino)-3-methyl-6-(4-pyridyl)-4-(3H)-pyrimidinone 5-(4-Fluorophenyl)-3-methyl-6-(4-pyridyl)-2-((S)-tetrahydroisoquinol-3-ylmethylenamino)-4-(3H)-pyrimidinone 3-Methyl-6-(4-pyridyl)-2-((S)-tetrahydroisoquinol-3-ylmethylenamino)-5-(3-trifluoromethylphenyl)-4-(3H)-pyrimidinone 3-Methyl-5-(3-methylphenyl)-6-(4-pyridyl)-2-((S)-tetrahydroisoquinol-3-ylmethylenamino)-4-(3H)-pyrimidinone 3-Methyl-5-(4-methylthiophenyl)-6-(4-pyridyl)-2-((S)-tetrahydroisoquinol-3-ylmethylenamino)-4-(3H)-pyrimidinone 2-(((S)-2-Amino-3-phenylpropyl)-amino)-3-methyl-5-(3-methylphenyl)-6-(4-pyridyl)-4-(3H)-pyrimidinone 5-(4-Fluorophenyl)-2-((3-hydroxy-3-phenylpropyl)-amino)-3-methyl-6-(4-pyridyl)-4-(3H)-pyrimidinone 2-(((S)-2-Amino-3-phenylpropyl)-amino)-5-(4-fluorophenyl)-6-(4-pyridyl)-4-(3H)-pyrimidinone 2-(((S)-2-Amino-3-(2-fluorophenyl)propyl)-amino)-5-(4-fluorophenyl)-3-methyl-6-(4-pyridyl)-4-(3H)-pyrimidinone 2-(((S)-2-Amino-3-(4-fluorophenyl)propyl)-amino)-5-(4-fluorophenyl)-3-methyl-6-(4-pyridyl)-4-(3H)-pyrimidinone 2-(((S)-2-Amino-3-(2-chlorophenyl)propyl)-amino)-5-(4-fluorophenyl)-3-methyl-6-(4-pyridyl)-4-(3H)-pyrimidinone 2-(((S)-2-N-Isopropylamino-3-phenylpropyl)-amino)-3-methyl-6-(4-pyridyl)-5-(3-trifluoromethylphenyl)-4-(3H)-pyrimidinone 2-(((S)-2-N-Isopropylamino-3-phenylpropyl)-amino)-3-methyl-5-(3-methylphenyl)-6-(4-pyridyl)-4-(3H)-pyrimidinone 5-(3-Chlorophenyl-2-(((S)-2-N-isopropylamino-3-phenylpropyl)-amino)-3-methyl-6-(4-pyridyl)-4-(3H)-pyrimidinone 2-(((S)-2-N,N-Dimethylamino-3-phenylpropyl)-amino)-3-methyl-5-(3-methylphenyl)-6-(4-pyridyl)-4-(3H)-pyrimidinone 2-(((S)-2-N,N-Dimethylamino-3-phenylpropyl)-amino)-3-methyl-5-(3-chlorophenyl)-6-(4-pyridyl)-4-(3H)-pyrimidinone 2-(((S)-2-N,N-Dimethylamino-3-phenylpropyl)-amino)-3-methyl-6-(4-pyridyl)-5-(3-trifluorophenyl)-4-(3H)-pyrimidinone 5-(4-Fluorophenyl)-3-methyl-2-(((S)-2-N-methylamino-3-phenylpropyl)-amino)-6-(4-pyridyl)-4-(3H)-pyrimidinone.

The following compounds exhibit activities in the monocyte assay (LPS induced TNF release) with IC$_{50}$ values of 5 µl or less:

2-(2,6-Dichlorobenzyl)-5-(4-fluorophenyl)-3-methyl-6-(4-pyridyl)-4(3H)-pyrimidinone 2-(Benzylamino)-5-(4-fluorophenyl)-3-methyl-6-(4-pyridyl)-4(3H)-pyrimidinone 5-(4-Fluorophenyl)-3-methyl-((R-1-phenylethyl)amino)-(4-pyridyl)-4(3H)-pyrimidinone 2-(2-(2-Chlorophenyl)-ethylamino)-5-(4-fluorophenyl)-3-methyl-6-(4-pyridyl)-4(3H)-pyrimidinone 5-(4-Fluorophenyl)-2-(2-(4-fluorophenyl)-ethylamino)-3-methyl-6-(4-pyridyl)-4(3H)-pyrimidinone 5-(4-Fluorophenyl)-3-methyl-2-((3-phenylpropyl)-amino)-6-(4-pyridyl)-4(3H)-pyrimidinone 5-(4-Fluorophenyl)-3-methyl-2-((1-methyl-3-phenylpropyl)-amino)-6-(4-pyridyl)-4(3H)-pyrimidinone 5-(4-Fluorophenyl)-3-methyl-2-((R-1-methyl-3-phenylpropyl)-amino)-6-(4-pyridyl)-4(3H)-pyrimidinone 5-(4-Fluorophenyl)-3-methyl-2-((2-phenylaminoethyl)-amino)-6-(4-pyridyl)-4(3H)-pyrimidinone 5-(4-Fluorophenyl)-3-methyl-6-(4-pyridyl)-2-(3-(pyrrolidin-1-yl)-propylamino)-4(3H)-pyrimidinone 6-(4-Ethylphenyl)-3-phenyl-4-(4-pyridyl)-2(1H)-pyridone 2-(((S)-2-Amino-3-phenylpropyl)-amino)-5-(4-fluorophenyl)-3-methyl-6-(4-pyridyl)-4(3H)-pyrimidinone 2-(((R)-2-Amino-3-phenylpropyl)-amino)-5-(4-fluorophenyl)-3-methyl-6-(4-pyridyl)-4(3H)-pyrimidinone 2-(((S)-2-N-Ethyl-3-phenylpropyl)-amino)-5-(4-fluorophenyl)-3-methyl-6-(4-pyridyl)-4(3H)-pyrimidinone 2-((2-Amino-2-methy-3-phenylpropyl) amino)-5-(4-fluorophenyl)-3-methyl-6-(4-pyridyl)-4(3H)-pyrimidinone 2-((2-Aminomethy-3-phenylpropyl)-amino)-5-(4-fluorophenyl-3-methyl-6-(4-pyridyl)-4(3H)-pyrimidinone 2-((3-Amino-3-phenylpropyl)-amino)-5-(4-fluorophenyl)-3-methyl-6-(4-pyridyl)-4(3H)-pyrimidinone 5-(4-Fluorophenyl)-3-methyl-2-(3-(2-methylphenyl)propyl)-amino)-6-(4-pyridyl)-4(3H)-pyrimidinone 5-(4-Fluorophenyl)-3-methyl-2-((R,S)-2-amino-3-(2'-fluorophenyl)-propyl-amino)-6-(4-pyridyl)-4(3H)-pyrimidinone 2-(((S)-2-Acetamido-3-phenylpropyl)-amino)-5-(4-fluorophenyl)-3-methyl-6-(4-pyridyl)-4(3H)-pyrimidinone 5-(4-Fluorophenyl)-2-(((S)-2-N-isopropylamino-3-phenylpropyl)-amino)-3-methyl-6-(4-pyridyl)-4(3H)-pyrimidinone 2-(((S)-2-N-n-Butylamino-3-phenylpropyl)-amino)-5-(4-fluorophenyl)-3-methyl-6-(4-pyridyl)-4(3H)-pyrimidinone 2-(((S)-2-N,N-Dimethylamino-3-phenylpropyl)-amino)-5-(4-fluorophenyl-3-methyl-6-(4-pyridyl)-4(3H)-pyrimidinone 5-(4-Fluorophenyl)-3-methyl-2-((2-methy-3-phenylpropyl) amino)-6-(4-pyridyl)-4(3H)-pyrimidinone 2-(((S)-2-Amino-3-phenylpropyl)-amino)-3-ethyl-5-(4-fluorophenyl)-6-(4-pyridyl)-4(3H)-pyrimidinone 3-Ethyl-5-(4-fluorophenyl)-2-((2-methy-3-phenylpropyl)amino)-6-(4-pyridyl)-4(3H)-pyrimidinone 2-((2-(3-trifluoromethylphenyl)phenylmethyl)amino)-3-methyl-5-(4-fluorophenyl)-6-(4-pyridyl)-4(3H)-pyrimidinone 3-Methyl-2-(2(S)-amino-3-phenylpropylamino)-5-(4-tolyl)-6-(4-pyridyl)-4(3H)-pyrimidinone 3-Methyl-2-(2(S)-amino-3-phenylpropylamino)-5-(4-trifluoromethylphenyl)-6-(4-pyridyl)-4(3H)-pyrimidinone 3-Methyl-2-(2(S)-amino-3-phenylpropylamino)-5-(3-isopropylphenyl)-6-(4-pyridyl)-4(3H)-pyrimidinone 3-Methyl-2-(2(S)-amino-3-phenylpropylamino)-5-(3-chloro-4-fluorophenyl)-6-(4-pyridyl)-4(3H)-pyrimidinone 3-Methyl-2-(2(S) -amino-3-phenylpropylamino)-5-(3,5-bis(trifluoromethyl)phenyl)-6-(4-pyridyl)-4(3H)-pyrimidinone 3-Methyl-2-(2(S)-amino-3-phenylpropylamino)-5-(3,4-dichlorophenyl)-6-(4-pyridyl)-4(3H)-pyrimidinone 3-Methyl-2-(2(S)-amino-3-phenylpropylamino)-5-(1-naphthyl)-6-(4-pyridyl)-4(3H)-pyrimidinone 3-Methyl-2-(2(S)-amino-3-phenylpropylamino)-5-(3-fluorophenyl)-6-(4-pyridyl)-4(3H)-pyrimidinone 3-Methyl-2-(2(S)-amino-3-phenylpropylamino)-5-(3-trifluoromethylphenyl)-6-(4-pyridyl)-4(3H)-pyrimidinone 3-Methyl-2-(3-phenylpropylamino)-5-(3,5-dichlorophenyl)-6-(4-pyridyl)-4(3H)-pyrimidinone 3-Methyl-2-(3-phenylpropylamino)-5-(4-tolyl)-6-(4-pyridyl)-4(3H)-pyrimidinone 3-Methyl-2-(3-phenylpropylamino)-5-(3-trifluoromethylphenyl)-6-(4-pyridyl)-4(3H)-pyrimidinone 3-Methyl-2-(3-phenylpropylamino)-5-(4-methoxyphenyl)-6-(4-pyridyl)-4(3H)-pyrimidinone 3-Methyl-2-(3-phenylpropylamino)-5-(4-trifluoromethylphenyl)-6-(4-pyridyl)-4(3H)-pyrimidinone 3-Methyl-2-(2-methyl-3-phenylpropylamino)-5-(3-fluorophenyl)-6-(4-pyridyl)-4(3H)-pyrimidinone 3-Methyl-2-(2-methyl-3-phenylpropylamino)-5-(1-naphthyl)-6-(4-pyridyl)-4(3H)-pyrimidinone 5-(4-Fluorophenyl)-2-(((S)-2-N-glycylamino-3-phenylpropyl)-amino)-3-methyl-6-(4-pyridyl)-4-(3H)-pyrimidinone 2-(((S)-2-N-Glycylamino-3-phenylpropyl)-amino)-3-methyl-5-(3-methylphenyl)-6-(4-pyridyl)-4-(3H)-pyrimidinone 5-(4-Fluorophenyl)-2-(((S)-2-hydroxyacetamido-3-phenylpropyl)-amino)-3-methyl-6-(4-pyridyl)-4-(3H)-pyrimidinone 5-(4-Fluorophenyl)-2-(((S)-2-pyrrolidinyl-3-phenylpropyl)-amino)-3-methyl-6-(4-pyridyl)-4-(3H)-pyrimidinone 2-((S)-3-Benzylpiperazinyl)-5-(4-fluorophenyl)-3-methyl-6-(4-pyridyl)-4-(3H)-pyrimidinone 2-((3-Amino-3-(2-fluorophenyl)propyl)-amino)-5-(4-fluorophenyl)-3-methyl-6-(4-pyridyl)-4-(3H)-pyrimidinone 2-((3-Amino-3-(2-methylphenyl)propyl)-amino)-5-(4-fluorophenyl)-3-methyl-6-(4-pyridyl)-4-(3H)-pyrimidinone 2-(((S)-3-Amino-3-phenylpropyl)-amino)-5-(4-fluorophenyl)-3-methyl-6-(4-pyridyl)-4-(3H)-pyrimidinone 2-(((R)-3-Amino-3-phenylpropyl)-amino)-5-(4-fluorophenyl)-3-methyl-6-(4-pyridyl)-4-(3H)-pyrimidinone 2-(((S)-3-Amino-3-phenylpropyl)-amino)-3-methyl-6-(4-pyridyl)5-(3-trifluoromethylphenyl)-4-(3H)-pyrimidinone 2-(((R)-3-Amino-3-phenylpropyl)-amino)-3-methyl-6-(4-pyridyl)5-(3-trifluoromethylphenyl)-4-(3H)-pyrimidinone 2-((3-Amino-3-phenylpropyl)-amino)-3-methyl-6-(4-pyridyl)5-(3-trifluoromethylphenyl)-4-(3H)-pyrimidinone 2-((3-Amino-3-(2-methylphenyl)propyl)-amino)-3-methyl-6-(4-pyridyl)5-(3-trifluoromethylphenyl)-4-(3H)-pyrimidinone 2-((3-Amino-3-(2-fluorophenyl)propyl)-amino)-3-methyl-6-(4-pyridyl)5-(3-trifluoromethylphenyl)-4-(3H)-pyrimidinone 2-((3-Amino-3-phenylpropyl)-amino)-3-methyl-5-(3-methylphenyl)-6-(4-pyridyl)-4-(3H)-pyrimidinone 2-((3-Amino-3-(2-fluorophenyl)propyl)-amino)-3-methyl-5-(3-methylphenyl)-6-(4-pyridyl)-4-(3H)-pyrimidinone 2-((3-Amino-3-(2-chlorophenyl)propyl)-amino)-3-methyl-5-(3-methylphenyl)-6-(4-pyridyl)-4-(3H)-pyrimidinone 2-(((S)-3-Amino-3-phenylpropyl)-amino)-3-methyl-6-(4-pyridyl)5-(3,4-dimethylphenyl)-4-(3H)-pyrimidinone 2-(((2R,3R)-3-Amino-2-methyl-3-phenylpropyl)-amino)-5-(4-fluorophenyl)-3-methyl-6-(4-pyridyl)-4-(3H)-pyrimidinone 2-(((2S,3S)-3-Amino-2-methyl-3-phenylpropyl)-amino)-5-(4-fluorophenyl)-3-methyl-6-(4-pyridyl)-4-(3H)-pyrimidinone 5-(4-Fluorophenyl)-2-(((S)-3-N-isopropylamino-3-phenylpropyl)-amino)-3-methyl-6-(4-pyridyl)-4-(3H)-pyrimidinone 5-(4-Fluorophenyl)-2-(((R)-3-N-isopropylamino-3-phenylpropyl)-amino)-3-methyl-6-(4-pyridyl)-4-(3H)-pyrimidinone 5-(4-Fluorophenyl)-3-methyl-6-(4-pyridyl)-2-((S)-tetrahydroisoquinol-3-ylmethylenamino)-4-(3H)-pyrimidinone 3-Methyl-6-(4-pyridyl)-2-((S)-tetrahydroisoquinol-3-ylmethylenamino)-5-(3-trifluoromethylphenyl)-4-(3H)-pyrimidinone 3-Methyl-5-(3-methylphenyl)-6-(4-pyridyl)-2-((S)-tetrahydroisoquinol-3-ylmethylenamino)-4-(3H)-pyrimidinone 3-Methyl-5-(4-methylthiophenyl)-6-(4-pyridyl)-2-((S)-tetrahydroisoquinol-3-ylmethylenamino)-4-(3H)-pyrimidinone 2-(((S)-2-Amino-3-phenylpropyl)-amino)-3-methyl-5-(3-methylphenyl)-6-(4-pyridyl)-4-(3H)-pyrimidinone 5-(4-Fluorophenyl)-2-(((3-hydroxy-3-phenylpropyl)-amino)-3-methyl-6-(4-pyridyl)-4-(3H)-pyrimidinone 2-(((S)-2-Amino-3-phenylpropyl)-amino)-5-(4-fluorophenyl)-6-(4-pyridyl)-4-(3H)-pyrimidinone 2-(((S)-2-Amino-3-(2-fluorophenyl)propyl)-amino)-5-(4-fluorophenyl)-3-methyl-6-(4-pyridyl)-4-(3H)-pyrimidinone 2-(((S)-2-Amino-3-(4-fluorophenyl)propyl)-amino)-5-(4-fluorophenyl)-3-methyl-6-(4-pyridyl)-4-(3H)-pyrimidinone 2-(((S)-2-Amino-3-(2-chlorophenyl)propyl)-amino)-5-(4-fluorophenyl)-3-methyl-6-(4-pyridyl)-4-(3H)-pyrimidinone 2-(((S)-2-N-Isopropylamino-3-phenylpropyl)-amino)-3-methyl-6-(4-pyridyl)-5-(3-trifluoromethylphenyl)-4-(3H)-pyrimidinone 2-(((S)-2-N-Isopropylamino-3-phenylpropyl)-amino)-3-methyl-5-(3-methylphenyl)-6-(4-pyridyl)-4-(3H)-pyrimidinone 5-(3-Chlorophenyl-2-(((S)-2-N-isopropylamino-3-phenylpropyl)-amino)-3-methyl-6-(4-pyridyl)-4-(3H)-pyrimidinone 2-(((S)-2-N,N-Dimethylamino-3-phenylpropyl)-amino)-3-methyl-5-(3-methylphenyl)-6-(4-pyridyl)-4-(3H)-pyrimidinone 2-(((S)-2-N,N-Dimethylamino-3-phenylpropyl)-amino)-3-methyl-5-(3-chlorophenyl)-6-(4-pyridyl)-4-(3H)-pyrimidinone 2-(((S)-2-N,N-Dimethylamino-3-phenylpropyl)-amino)-3-methyl-6-(4-pyridyl)-5-(3-trifluorophenyl)-4-(3H)-pyrimidinone 5-(4-Fluorophenyl)-3-methyl-2-(((S)-2-N-methylamino-3-phenylpropyl)-amino)-6-(4-pyridyl)-4-(3H)-pyrimidinone Compounds of the invention may be shown to have anti-inflammatory properties in animal models of inflammation, including carageenan paw edema, collagen induced arthritis and adjuvant arthritis, such as the carageenan paw edema model (C. A. Winter et al Proc. Soc. Exp. Biol. Med. (1962) vol 111, p 544; K. F. Swingle, in R. A. Scherrer and M. W. Whitehouse, Eds., Antiinflammatory Agents, Chemistry and Pharmacology, Vol. 13-II, Academic, New York, 1974, p. 33) and collagen induced arthritis (D. E. Trentham et al J. Exp. Med. (1977) vol. 146, p 857; J. S. Courtenay, Nature (New Biol.) (1980), Vol 283, p 666).

$^{125}$I-Glucagon Binding Screen with CO/hGLUR Cells

The assay is described in WO 97/16442, which is incorporated herein by reference in its entirety.

Reagents

The reagents can be prepared as follows: (a) prepare fresh 1M o-Phenanthroline (Aldrich) (198.2 mg/ml ethanol); (b) prepare fresh 0.5M DTT (Sigma); (c) Protease Inhibitor Mix (1000X): 5 mg leupeptin, 10 mg benzamidine, 40 mg bacitracin and 5 mg soybean trypsin inhibitor per ml DMSO and store aliquots at −20° C.; (d) 250 $\mu$M human glucagon (Peninsula): solubilize 0.5 mg vial in 575 $\mu$l 0.1N acetic acid (1 $\mu$l yields 1 $\mu$M final concentration in assay for non-specific binding) and store in aliquots at −20° C.; (e) Assay Buffer: 20mM Tris (pH 7.8), 1 mM DTT and 3 mM o-phenanthroline; (f) Assay Buffer with 0.1% BSA (for dilution of label only; 0.01% final in assay): 10 $\mu$l 10% BSA (heat-inactivated) and 990 $\mu$l Assay Buffer; (g) $^{125}$I-Glucagon (NEN, receptor-grade, 2200 Ci/mmol): dilute to 50,000 cpm/25 $\mu$l in assay buffer with BSA (about 50 pM final concentration in assay).

Harvesting of CHO/hGLUR Cells for Assay

1. Remove media from confluent flask then rinse once each with PBS (Ca, Mg-free) and Enzyme-free Dissociation Fluid (Specialty Media, Inc.).

2. Add 10 ml Enzyme-free Dissoc. Fluid and hold for about 4 min. at 37° C.

3. Gently tap cells free, triturate, take aliquot for counting and centrifuge remainder for 5 min. at 1000 rpm.

4. Resuspend pellet in Assay Buffer at 75000 cells per 100 μl.

Membrane preparations of CHO/hGLUR cells can be used in place of whole cells at the same assay volume. Final protein concentration of a membrane preparation is determined on a per batch basis.

Assay

The determination of inhibition of glucagon binding can be carried out by measuring the reduction of $I^{125}$-glucagon binding in the presence of compounds of Formula I. The reagents are combined as follows:

|  | Compound/ Vehicle | 250 μM Glucagon | $^{125}$I-Glucagon | CHO/hGLUR Cells |
|---|---|---|---|---|
| Total Binding | —/5 μl | — | 25 μl | 100 μl |
| Binding + Compound | 5 μl/— | — | 25 μl | 100 μl |
| Non-specific Binding | —/5 μl | 1 μl | 25 μl | 100 μl |

The mixture is incubated for 60 min. at 22° C. on a shaker at 275 rpm. The mixture is filtered over pre-soaked (0.5% polyethylimine (PEI)) GF/C filtermat using an 20 Innotech Harvester or Tomtec Harvester with four washes of ice-cold 20mM Tris buffer (pH 7.8). The radioactivity in the filters is determined by a gamma-scintillation counter.

Thus, compounds of the invention may also be shown to inhibit the binding of glucagon to glucagon receptors.

Cyclooxygenase Enzyme Activity Assay

The human monocytic leukemia cell line, THP-1, differentiated by exposure to phorbol esters expresses only COX-1; the human osteosarcoma cell line 143B expresses predominantly COX-2. THP-1 cells are routinely cultured in RPMI complete media supplemented with 10% FBS and human osteosarcoma cells (HOSC) are cultured in minimal essential media supplemented with 10% fetal bovine serum (MEM-10% FBS); all cell incubations are at 37° C. in a humidified environment containing 5% $CO_2$.

COX-1 Assay

In preparation for the COX-1 assay, THP-1 cells are grown to confluency, split 1:3 into RPMI containing 2% FBS and 10 mM phorbol 12-myristate 13-acetate (TPA), and incubated for 48 hours on a shaker to prevent attachment. Cells are pelleted and resuspended in Hank's Buffered Saline (HBS) at a concentration of $2.5 \times 10^6$ cells/mL and plated in 96-well culture plates at a density of 5×10 cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at $3 \times 10^6$ cells/mL in MEM-FBS containing 1 ng human IL-lb/mL, plated in 96-well tissue culture plates at a density of $3 \times 10^6$ cells per well, incubated on a shaker for 1 hour to evenly distribute cells, followed by an additional 2 hour static incubation to allow attachment. The media is then replaced with MEM containing 2% FBS (MEM-2% FBS) and 1 ng human IL-lb/mL, and the cells incubated for 18–22 hours. Following replacement of media with 190 mL MEM, 10 mL of test compound diluted in HBS is added to achieve the desired concentration and the cells incubated for 4 hours. The supernatants are removed and replaced with MEM containing 30 mM arachidonic acid, the cells incubated for 20 minutes at 37° C., and enzyme activity determined as described below.

COX Activity Determined

After incubation with arachidonic acid, the reactions are stopped by the addition of 1 N HCl, followed by neutralization with 1 N NaOH and centrifugation to pellet cell debris. Cyclooxygenase enzyme activity in both HOSC and THP-1 cell supernatants is determined by measuring the concentration of $PGE_2$ using a commercially available ELISA (Neogen #404110). A standard curve of $PGE_2$ is used for calibration, and commercially available COX-1 and COX-2 inhibitors are included as standard controls.

Accordingly, the compounds of the invention or a pharmaceutical composition thereof are useful for prophylaxis and treatment of rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; Alzheimer's disease; stroke; myocardial infarction; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster, all of which are sensitive to TNF-α and/or IL-1 inhibition or glucagon antagonism, will also be positively effected by the compounds and methods of the invention.

The compounds of the present invention also may possess analgesic properties and may be useful for the treatment of pain disorders, such as hyperalgesia due to excessive IL-1. The compounds of the present invention may also prevent the production of prostaglandins by inhibition of enzymes in the human arachidonic acid/prostaglandin pathway, including cyclooxygenase (WO 96/03387, incorporated herein by reference in its entirety).

Because of their ability to lower TNF-α and IL-1 concentrations or inhibit glucagon binding to its receptor, the compounds of the invention are also-useful research tools for studying the physiology associated with blocking these effects.

The methods of the invention comprise administering an effective dose of a compound of the invention, a pharmaceutical salt thereof, or a pharmaceutical composition of either, to a subject (i.e., an animal, preferably a mammal, most preferably a human) in need of a reduction in the level of TNF-α, IL-1, IL-6, and/or IL-8 levels and/or reduction in plasma glucose levels and/or which subject may be suffering from rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; Alzheimer's disease; stroke; myocardial infarction; ischemia reperfusion injury; atherosclerosis; brain trauma; multiple sclerosis; cerebral malaria; sepsis; septic shock; toxic shock syndrome; fever, and myalgias due to infection, or which subject is infected by HIV-1, HIV-2, HIV-3, cytomegalovirus (CMV), influenza, adenovirus, the herpes viruses (including HSV-1, HSV-2), or herpes zoster.

In another aspect, this invention comprises the use of a compound of the invention, or pharmaceutically acceptable salts thereof, in the manufacture of a medicament for the treatment either acutely or chronically of a TNF-α, IL-1β, IL-6, and/or IL-8 mediated disease state, including those described previously. Also, the compounds of this invention are useful in the manufacture of a analgesic medicament and a medicament for treating pain disorders, such as hyperalgesia. The compounds of the present invention also are useful in the manufacture of a medicament to prevent the production of prostaglandins by inhibition of enzymes in the human arachidonic acid/prostaglandin pathway.

In still another aspect, this invention provides a pharmaceutical composition comprising an effective TNF-α, IL-1β, IL-6, and/or IL-8 lowering amount and/or effective plasma glucose level lowering amount of a compound of the invention and a pharmaceutically acceptable carrier or diluent, and if desired other active ingredients. The compounds of the invention are administered by any suitable route, preferably in the form of a pharmaceutical composition adapted to such a route, and in a dose effective for the treatment intended. Therapeutically effective doses of the compounds of the present invention required to arrest the progress or prevent tissue damage associated with the disease are readily ascertained by one of ordinary skill in the art using standard methods.

For the treatment of TNF-α, IL-1β, IL-6, and IL-8 mediated diseases and/or hyperglycemia, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

The dosage regimen for treating a TNF-α, IL-1, IL-6, and IL-8 mediated diseases and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch.

Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hyroxy-ethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula

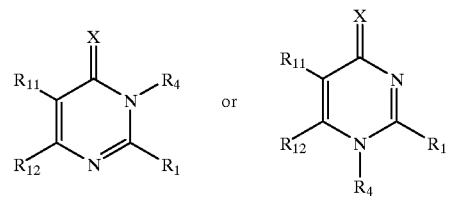

or a pharmaceutically acceptable salt thereof, wherein
X is O, S or $NR_5$;
$R_1$ is —Y or —Z—Y, and $R_4$ is —Z—Y; provided that $R_4$ is other than a hydrogen, substituted-aryl, (substituted-aryl)methyl or (substituted-aryl)ethyl radical, and the combined total number of aryl, heteroaryl, cycloalkyl and heterocyclyl radicals in $R_1$ and $R_4$ is 0–3;
wherein each Z is independently a
  (1) $C_1$–$C_8$ alkyl, $C_2$–$C_8$ alkenyl or $C_2$–$C_8$ alkynyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano or halo and (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;
  (2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
  (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

each Y is independently a
(1) hydrogen radical;
(2) halo, cyano or nitro radical;
(3) —C(O)—$R_{20}$, —C(O)—$OR_{21}$, —C(O)—$NR_5R_{21}$ or —C($NR_5$)—$NR_5R_{21}$ radical;
(4) —$OR_{21}$, —O—C(O)—$R_{21}$, —O—C(O)—$NR_5R_{21}$ or —O—C(O)—$NR_{22}$—S(O))$_2$-$R_{20}$ radical;
(5) —$SR_{21}$, —S(O)—$R_{20}$, —S(O)$_2$-$R_{20}$, —S(O)$_2$—$NR_5R_{21}$, —S(O)$_2$—$NR_{22}$-C(O)—$R_{21}$, —S(O)$_2$—$NR_{22}$—C(O)—$OR_{20}$ or —S(O)$_2$—$NR_{22}$—C(O)—$NR_5R_{21}$ radical; or
(6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;

each $R_5$ is independently a
(1) hydrogen radical;
(2) $C_1$–$C_8$ alkyl, $C_2$–$C_8$ alkenyl or $C_2$–$C_8$ alkynyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano or halo; or
(3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

each $R_{20}$ is independently a
(1) $C_1$–$C_8$ alkyl, $C_2$–$C_8$ alkenyl or $C_2$–$C_8$ alkynyl radical optionally substituted by 1–3 radicals of —$CO_2R_{23}$, amino, $C_1$–$C_4$ alkylamino, di-($C_1$–$C_4$ alkyl)amino, $C_1$–$C_5$ alkanoylamino, ($C_1$–$C_4$ alkoxy) carbonylamino, N-(($C_1$–$C_4$ alkoxy) carbonyl)—N—($C_1$–$C_4$ alkyl) amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl wherein the aryl-$C_1$–$C_4$-alkoxy, aryl-$C_1$–$C_4$-alkylthio, aryl-$C_1$–$C_4$-alkylsulfonyl, $C_{3-8}$ cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $c_1$–$C_5$ alkanoyl, ($C_1$–$C_4$ alkoxy)carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;
(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
(3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

each $R_{21}$ is independently hydrogen radical or $R_{20}$;

each $R_{22}$ is independently
(1) hydrogen radical;
(2) $C_1$–$C_4$ alkyl radical optionally substituted by a radical of heterocyclyl, aryl or heteroaryl wherein the heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; or
(3) heterocyclyl, aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

each $R_{23}$ is independently a hydrogen, $C_1$–$C_4$ alkyl, aryl, heteroaryl, aryl-$C_1$–$C_4$-alkyl or heteroaryl-$C_1$–$C_4$-alkyl radical, wherein the aryl, heteroaryl, aryl-$C_1$–$C_4$-alkyl and heteroaryl-$C_1$–$C_4$-alkyl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

$R_{11}$ and $R_{12}$ are each independently an aryl or heteroaryl radical optionally substituted by 1–3 radicals of
(1) $R_{30}$;
(2) halo or cyano;
(3) —C(O)—$R_{30}$, —C(O)—$OR_{29}$, —C(O)—$NR_{31}R_{32}$ or —C($NR_{31}$)—$NR_{31}R_{32}$;
(4) —$OR_{29}$, —O—C(O)—$R_{29}$, —O—C(O)—$NR_{31}R_{32}$ or —O—C(O)—$NR_{33}$—S(O)$_2$—$R_{30}$;
(5) —$SR_{29}$, —S(O)—$R_{30}$, —S(O)$_2$—$R_{30}$, —S(O)$_2$—$NR_{31}R_{32}$, —S(O)$_2$—$NR_{33}$—C(O)—$R_{30}$, —S(O)$_2$—$NR_{33}$—C(O)—$OR_{30}$ or —S(O)$_2$—$NR_{33}$—C(O)—$NR_{31}R_{32}$; or
(6) —$NR_{31}R_{32}$, —$NR_{33}$—C(O)—$R_{29}$, —$NR_{33}$—C(O)—$OR_{30}$, —$NR_{33}$—C(O)—$NR_{31}R_{32}$, —$NR_{33}$—C($NR_{31}$)—$NR_{31}R_{32}$, —$NR_{33}$—S(O)$_2$—$R_{30}$ or —$NR_{33}$—S(O)$_2$—$NR_{31}R_{32}$;

provided that (1) $R_{11}$ is other than a 4-pyridyl, 4-pyrimidinyl, 4-quinolyl or 6-isoquinolinyl radical optionally substituted by 1–2 substituents; (2) when $R_{11}$ is an unsubstituted phenyl radical, then $R_{12}$ is other than an unsubstituted phenyl radical; and (3) the total number of aryl, heteroaryl, cycloalkyl and heterocyclyl radicals substituted on each of $R_{11}$ and $R_{12}$ is 0–1;

each $R_{30}$ is independently a
(1) $C_1$–$C_4$ alkyl, $C_2$–$C_4$ alkenyl or $C_2$–$C_4$ alkynyl radical optionally substituted by 1–3 radicals of —$NR_{31}R_{31}$, —$CO_2R_{23}$, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, aryl-$C_1$–$C_4$-alkoxy, aryl-$C_1$–$C_4$-alkylthio, aryl-$C_1$–$C_4$-alkylsulfonyl, heterocyclyl, aryl or heteroaryl, wherein the aryl-$C_1$–$C_4$-alkoxy, aryl-$C_1$–$C_4$-alkylthio, aryl-$C_1$–$C_4$-alkylsulfonyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1-C_4$ alkoxy, $C_1-C_4$ alkylthio, $C_1-C_4$ alkylsulfinyl, $C_1-C_4$ alkylsulfonyl, cyano, halo, $C_1-C_4$ alkyl or $C_1-C_4$ haloalkyl of 1–3 halo radicals;

(2) heterocyclyl radical optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, hydroxy, $C_1-C_4$ alkoxy, $C_1-C_4$ alkylthio, cyano, $C_1-C_4$ alkyl or $C_1-C_4$ haloalkyl of 1–3 halo radicals; or (3) aryl or heteroaryl radical optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, hydroxy, $C_1-C_4$ alkoxy, $C_1-C_4$ alkylthio, cyano, halo, $C_1-C_4$ alkyl or $C_1-C_4$ haloalkyl of 1–3 halo radicals;

each $R_{29}$ is independently hydrogen radical or $R_{30}$;

$R_{31}$ and $R_{32}$ are each independently a (1) hydrogen radical;

(2) $C_1-C_4$ alkyl radical optionally substituted by a $C_3-C_8$ cycloalkyl, aryl, heterocyclyl or heteroaryl radical, wherein the $C_3-C_8$ cycloalkyl, aryl, heterocyclyl and heteroaryl radicals are optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, hydroxy, $C_1-C_4$ alkoxy, $C_1-C_4$ alkylthio, cyano, $C_1-C_4$ alkyl or $C_1-C_4$ haloalkyl of 1–3 halo radicals; or (3) aryl, heteroaryl, heterocyclyl or $C_3-C_8$ cycloalkyl radical optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, hydroxy, $C_1-C_4$ alkoxy, $C_1-C_4$ alkylthio, cyano, $C_1-C_4$ alkyl or $C_1-C_4$ haloalkyl of 1–3 halo radicals; and each $R_{33}$ is independently a (1) hydrogen radical; or (2) $C_1-C_4$ alkyl radical optionally substituted by a radical of heterocyclyl, aryl or heteroaryl, wherein the heterocyclyl, aryl and heteroaryl radicals are optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, hydroxy, $C_1-C_4$ alkoxy, $C_1-C_4$ alkylthio, cyano, $C_1-C_4$ alkyl or $C_1-C_4$ haloalkyl of 1–3 halo radicals; and wherein heterocyclyl is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals; aryl is a phenyl or naphthyl radical; and heteroaryl is radical of a monocyclic or bicyclic aromatic heterocyclic ring system having 5–6 ring members per ring, wherein 1–3 ring members are oxygen, sulfur or nitrogen heteroatoms, which is optionally benzo-fused or saturated $C_3-C_4$-carbocyclic-fused.

2. The compound of claim 1 or a pharmaceutically acceptable salt thereof, wherein each Z is independently a (1) $C_1-C_8$ alkyl, $C_2-C_8$ alkenyl or $C_2-C_8$ alkynyl radical optionally substituted by (a) 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, hydroxy, $C_1-C_4$ alkoxy, $C_1-C_4$ alkylthio or halo and (b) 1–2 radicals of heterocyclyl, aryl or heteroaryl optionally substituted by 1–3 radicals of amino, $C_1-C_4$ alkylamino, di-($C_1-C_4$ alkyl)amino, $C_1-C_5$ alkanoylamino, ($C_1-C_4$ alkoxy) carbonylamino, $C_1-C_4$ alkylsulfonylamino, hydroxy, $C_1-C_4$ alkoxy, $C_1-C_4$ alkylthio, cyano, halo, $C_1-C_4$ alkyl or $C_1-C_4$ haloalkyl of 1–3 halo radicals;

(2) heterocyclyl radical optionally substituted by 1–2 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, hydroxy, $C_1-C_4$ alkoxy, $C_1-C_4$ alkylthio, $C_1-C_4$ alkyl or $C_1-C_4$ haloalkyl of 1–3 halo radicals; or (3) aryl or heteroaryl radical optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, hydroxy, $C_1-C_4$ alkoxy, $C_1-C_4$ alkylthio, cyano, halo, $C_1-C_4$ alkyl or $C_1-C_4$ haloalkyl of 1–3 halo radicals;

each $R_5$ is independently a (1) hydrogen radical;

(2) $C_1-C_4$ alkyl, $C_2-C_5$ alkenyl or $C_2-C_5$ alkynyl radical optionally substituted by 1–3 radicals of amino, $C_1-C_4$ alkylamino, di-($C_1-C_4$-alkyl)amino, hydroxy, $C_1-C_4$ alkoxy, $C_1-C_4$ alkylthio or halo; or (3) aryl, heteroaryl, aryl-$C_1-C_4$-alkyl, heteroaryl-$C_1-C_4$-alkyl, heterocyclyl, heterocyclyl-$C_1-C_4$-alkyl, $C_3-C_8$ cycloalkyl or $C_3-C_8$-cycloalkyl-$C_1-C_4$-alkyl radical optionally substituted by 1–3 radicals of amino, $C_1-C_4$ alkylamino, di-($C_1-C_4$-alkyl)amino, hydroxy, $C_1-C_4$ alkoxy, $C_1-C_4$ alkylthio, cyano, $C_1-C_4$ alkyl or $C_1-C_4$ haloalkyl of 1–3 halo radicals;

each $R_{20}$ is independently a (1) $C_1-C_8$ alkyl, $C_2-C_5$ alkenyl or $C_2-C_5$ alkynyl radical optionally substituted by 1–3 radicals of —$CO_2R_{23}$, amino, $C_1-C_4$ alkylamino, di-($C_1-C_4$ alkyl)amino, $C_1-C_5$ alkanoylamino, ($C_1-C_4$ alkoxy) carbonylamino, N-(($C_1-C_4$ alkoxy) carbonyl) —N—($C_1-C_4$ alkyl) amino, aminocarbonylamino, $C_1-C_4$ alkylsulfonylamino, hydroxy, $C_1-C_4$ alkoxy, $C_1-C_4$ alkylthio, $C_1-C_4$ alkylsulfinyl, $C_1-C_4$ alkylsulfonyl, halo, aryl-$C_1-C_4$-alkoxy, aryl-$C_1-C_4$-alkylthio, aryl-$C_1-C_4$-alkylsulfonyl, $C_3-C_8$ cycloalkyl, heterocyclyl, aryl or heteroaryl, wherein the aryl-$C_1-C_4$-alkoxy, aryl-$C_1-C_4$-alkylthio, aryl-$C_1-C_4$-alkylsulfonyl, $C_3-C_8$-cycloalkyl, heterocyclyl, aryl and heteroaryl radicals are optionally substituted by 1–3 radicals of amino, $C_1-C_4$ alkylamino, di-($C_1-C_4$ alkyl)amino, $C_1C_5$ alkanoylamino, ($C_1-C_4$ alkoxy) carbonylamino, $C_1-C_4$ alkylsulfonylamino, $C_1-C_5$ alkanoyl, ($C_1-C_4$ alkoxy)carbonyl, hydroxy, $C_1-C_4$ alkoxy, $C_1-C_4$ alkylthio, $C_1-C_4$ alkylsulfinyl, $C_1-C_4$ alkylsulfonyl, cyano, halo, $C_1-C_4$ alkyl or $C_1-C_4$ haloalkyl of 1–3 halo radicals;

(2) heterocyclyl radical optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, ($C_1-C_4$ alkoxy)carbonyl, hydroxy, $C_1-C_4$ alkoxy, $C_1-C_4$ alkylthio, $C_1-C_4$ alkyl or $C_1-C_4$ haloalkyl of 1–3 halo radicals; or (3) aryl or heteroaryl radical optionally substituted by 1–3 radicals of amino, $C_1-C_4$ alkylamino, di-($C_1-C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

each $R_{21}$ is independently hydrogen radical or $R_{20}$;

each $R_{30}$ is independently a
  (1) $C_1$–$C_4$ alkyl radical optionally substituted by 1–3 radicals of
    (a) —$NR_{31}R_{31}$;
    (b) $C_1$–$C_4$ alkoxy-carbonyl, phenoxycarbonyl or phenylmethoxycarbonyl, wherein the phenoxycarbonyl and phenylmethoxycarbonyl radicals are optionally substituted by 1–3 radicals of amino, alkylamino, di-($C_1$–$C_4$-alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or trifluoromethyl; or
    (c) hydroxy, $C_1$–$C_4$ alkoxy, $C_1$–$C_4$ alkylthio, phenyl-$C_1$–$C_4$-alkoxy, phenyl-$C_1$–$C_4$-alkylthio, heterocyclyl, phenyl or heteroaryl, wherein the phenyl-$C_1$–$C_4$-alkoxy, phenyl-$C_1$–$C_4$-alkylthio, heterocyclyl, phenyl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;
  (2) $C_1$–$C_4$ haloalkyl of 1–3 halo radicals; or
  (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, halo, $C_1$–$C_4$ alkyl or trifluoromethyl;

each $R_{29}$ is independently hydrogen radical or $R_{30}$;

each $R_{31}$ is independently a
  (1) hydrogen radical; or
  (2) $C_1$–$C_4$ alkyl radical optionally substituted by a phenyl or heteroaryl radical, wherein the phenyl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, $C_1$–$C_4$ alkyl or trifluoromethyl; and each $R_{32}$ is independently a
  (1) hydrogen radical;
  (2) $C_1$–$C_4$ alkyl radical optionally substituted by a $C_3$–$C_6$ cycloalkyl, aryl, heterocyclyl or heteroaryl radicals wherein the $C_1$–$C_6$ cycloalkyl, aryl, heterocyclyl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
  (3) aryl, heterocyclyl, heterocyclyl or $C_3$–$C_6$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; and each $R_{33}$ is independently hydrogen or $C_1$–$C_4$ alkyl radical.

3. The compound of claim 2 or a pharmaceutically acceptable salt thereof, wherein X is O or S;

wherein $R_1$ is -Y or —Z—Y, provided that the combined total number of aryl, heteroaryl, cycloalkyl and heterocyclyl radicals in $R_1$ and $R_4$ is 0–2;

z is a
  (1) $C_1$–$C_8$ alkyl or $C_2$–$C_8$ alkenyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio or halo, and (b) a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;
  (2) heterocyclyl radical optionally substituted by 1–2 radicals of amino, di-($C_1$–$C_4$ alkyl)amino, ($C_1$–$C_4$ alkoxy)carbonylamino, hydroxy, $C_1$–$C_4$ alkoxy, $C_1$–$C_4$ alkylthio or $C_1$–$C_4$ alkyl; or
  (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

Y is a
  (1) hydrogen radical;
  (2) halo radical;
  (3) —C(O)—$R_{20}$, —C(O)—$OR_{21}$, —C(O)—$NR_5R_{21}$ or —C($NR_5$)—$NR_5R_{21}$ radical;
  (4) —$OR_{21}$, —O—C(O)—$R_{21}$ or —O—C(O)—$NR_5R_{21}$ radical;
  (5) —$SR_{21}$, —S(O)—$R_{20}$, —S(O)$_2$—$R_{20}$ or —S(O)$_2$—$NR_5R_{21}$ radical; or
  (6) —$NR_5R_{21}$, —$NR_{22}$—C(O)—$R_{21}$, —$NR_{22}$—C(O)—$OR_{20}$, —$NR_{22}$–C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;

each $R_5$ is independently a
  (1) hydrogen radical;
  (2) $C_1$–$C_4$ alkyl or $C_2$–$C_5$ alkenyl radical optionally substituted by 1–3 radicals of amino, di-($C_1$–$C_4$-alkyl)amino, hydroxy, $C_1$–$C_4$ alkoxy, $C_1$–$C_4$ alkylthio or halo; or
  (3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radical optionally substituted by 1–3 radicals of amino, di-($C_1$–$C_4$-alkyl)amino, hydroxy, $C_1$–$C_4$ alkoxy, $C_1$–$C_4$ alkylthio, cyano, $C_1$–$C_4$ alkyl or $C_1$–$C_2$ haloalkyl of 1–3 halo radicals;

each $R_{20}$ is independently a
  (1) $C_1$–$C_8$ alkyl or $C_2$–$C_5$ alkenyl radical optionally substituted by 1–3 radicals of —$CO_2R_{23}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl) —N—($C_1$–$C_4$ alkyl) amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, aryl-$C_1$–$C_4$-alkoxy, aryl-$C_1$–$C_4$- alkylthio, aryl-$C_1$–$C_4$-alkylsulfonyl, $C_3$–$C_6$ cycloalkyl, heterocyclyl, aryl or heteroaryl, wherein the aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

(2) heterocyclyl radical optionally substituted by 1–2 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, ($C_1$–$C_4$ alkoxy)carbonyl, hydroxy, $C_1$–$C_4$ alkoxy, $C_1$–$C_4$ alkylthio or $C_1$–$C_4$ alkyl; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_2$ haloalkyl of 1–3 halo radicals;

each $R_{21}$ is independently hydrogen radical or $R_{20}$;

each $R_{22}$ is independently (1) hydrogen radical; or (2) $C_1$–$C_4$ alkyl radical optionally substituted by a radical of phenyl or heteroaryl, wherein the phenyl and heteroaryl radicals are optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

each $R_{23}$ is independently a hydrogen, $C_1$–$C_4$ alkyl, phenyl, heteroaryl, phenyl-$C_1$–$C_2$-alkyl or heteroaryl-$C_1$–$C_2$-alkyl radical, wherein the phenyl, heteroaryl, phenyl-$C_1$–$C_2$-alkyl and heteroaryl-$C_1$–$C_2$-alkyl radicals are optionally substituted by 1–3 radicals of amino, di-($C_1$–$C_4$ alkyl)amino, $C_1$–$C_4$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

$R_4$ is (1) $C_1$–$C_8$ alkyl or $C_2$–$C_8$ alkenyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio or halo, and (b) 1–2 radicals of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl, trifluoromethoxy or trifluoromethyl; or (2) heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, trifluoromethoxy or trifluoromethyl;

$R_{11}$ and $R_{12}$ are each independently an aryl or heteroaryl radical optionally substituted by 1–2 radicals of (1) $R_{30}$;

(2) halo or cyano;

(3) —C(O)—$R_{30}$, —C(O)—O$R_{29}$, —C(O)—N$R_{31}R_{32}$ or —C(N$R_{31}$)—N$R_{31}R_{32}$; or (4) —O$R_{29}$, —S$R_{29}$, —S(O)—$R_{30}$, —S(O)$_2$—$R_{30}$, —S(O)$_2$—N$R_{31}R_{32}$, —N$R_{31}R_{32}$, —N$R_{33}$—C(O)—$R_{29}$ or —N$R_{33}$—C(O)—O$R_{30}$; provided that (1) $R_{11}$ is other than a 4-pyridyl, 4-pyrimidinyl, 4-quinolyl or 6-isoquinolinyl radical optionally substituted by 1–2 substituents; (2) when $R_{11}$ is an unsubstituted phenyl radical, then $R_{12}$ is other than an unsubstituted phenyl radical; and (3) the total number of aryl, heteroaryl and heterocyclyl radicals substituted on each of $R_{11}$ and $R_{12}$ is 0–1;

each $R_{30}$ is independently a (1) $C_1$–$C_4$ alkyl radical optionally substituted by a radical of (a) amino, $C_1$–$C_4$ alkylamino or di-($C_1$–$C_4$-alkyl) amino; or (b) hydroxy, $C_1$–$C_4$ alkoxy, heterocyclyl, phenyl or heteroaryl, wherein the heterocyclyl, phenyl or heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl;

(2) $C_1$–$C_2$ haloalkyl of 1–3 halo radicals; or (3) aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl;

each $R_{29}$ is independently hydrogen radical or $R_{30}$;

each $R_{31}$ is independently a hydrogen or $C_1$–$C_4$ alkyl radical; and each $R_{32}$ is independently a (1) hydrogen radical;

(2) $C_1$–$C_4$ alkyl radical optionally substituted by a phenyl or heteroaryl radical, wherein the phenyl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkyl or trifluoromethyl; or (3) phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkyl or trifluoromethyl; and each $R_{33}$ is independently hydrogen or methyl radical; and wherein heterocyclyl is a radical of a monocyclic saturated heterocyclic ring system having 5–6 ring members, wherein 1–3 ring members are oxygen, sulfur or nitrogen heteroatoms, which is optionally benzo-fused and optionally substituted by 1–2 oxo or thioxo radicals; aryl is a phenyl or naphthyl radical; and heteroaryl is radical of a monocyclic aromatic heterocyclic ring system having 5–6 ring members, wherein 1–3 ring members are oxygen, sulfur or nitrogen heteroatoms, which is optionally benzo-fused or saturated $C_3$–$C_4$- carbocyclic-fused.

4. The compound of claim 3 or a pharmaceutically acceptable salt thereof, wherein Z is a
- (1) $C_1$–$C_4$ alkyl or $C_2$–$C_5$ alkenyl radical optionally substituted by (a) 1–3 radicals of amino, di-($C_1$–$C_2$ alkyl)amino, $C_1$–$C_5$ alkanoylamino, ($C_1$–$C_4$ alkoxy) carbonylamino, hydroxy, $C_1$–$C_2$ alkoxy, $C_1$–$C_2$ alkylthio or halo, and (b) a radical of heterocyclyl, aryl or heteroaryl optionally substituted by 1–3 radicals of amino, $C_1$–$C_4$ alkylamino, di-($C_1$–$C_2$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, halo, $C_1$–$C_4$ alkyl or trifluoromethyl;
- (2) heterocyclyl radical optionally substituted by 1–2 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio or $C_1$–$C_4$ alkyl; or
- (3) aryl or heteroaryl radical optionally substituted by 1–3 radicals of amino, di-($C_1$–$C_2$ alkyl)amino, $C_1$–$C_5$ alkanoylamino, ($C_1$–$C_4$ alkoxy) carbonylamino, hydroxy, $C_1$–$C_2$ alkoxy, $C_1$–$C_2$ alkylthio, cyano, halo, $C_1$–$C_4$ alkyl or trifluoromethyl;

each $R_5$ is independently a
- (1) hydrogen radical; (2) $C_1$–$C_4$ alkyl radical optionally substituted by 1–3 radicals of amino, di-($C_1$–$C_2$-alkyl)amino, hydroxy, $C_1$–$C_2$ alkoxy, $C_1$–$C_2$ alkylthio or halo; or
- (3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radical optionally substituted by 1–3 radicals of amino, di-($C_1$–$C_2$-alkyl)amino, hydroxy, $C_1$–$C_2$ alkoxy, $C_1$–$C_2$ alkylthio, cyano, $C_1$–$C_4$ alkyl or trifluoromethyl;

each $R_{22}$ is independently hydrogen or $C_1$–$C_4$ alkyl radical;

each $R_{23}$ is independently a hydrogen, $C_1$–$C_4$ alkyl, phenyl, heteroaryl, phenyl-$C_1$–$C_2$-alkyl or heteroaryl-$C_1$–$C_2$-alkyl radical, wherein the phenyl, heteroaryl, phenyl-$C_1$–$C_2$-alkyl and heteroaryl-$C_1$–$C_2$-alkyl radicals are optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl;

$R_4$ is
- (1) $C_1$–$C_8$ alkyl radical optionally substituted by (a) 1–2 radicals of amino, $C_1$–$C_4$ alkylamino, di-($C_1$–$C_4$ alkyl) amino, hydroxy or $C_1$–$C_4$ alkoxy, and a radical of aryl or heteroaryl optionally substituted by 1–3 radicals of amino, $C_1$–$C_4$ alkylamino, di-($C_1$–$C_4$ alkyl)amino, $C_1$–$C_4$ alkoxy, $C_1$–$C_4$ alkylthio, halo, $C_1$–$C_4$ alkyl, trifluoromethoxy or trifluoromethyl; or
- (2) heteroaryl radical optionally substituted by 1–3 radicals of amino, $C_1$–$C_4$ alkylamino, di-($C_1$–$C_4$ alkyl)amino, $C_1$–$C_4$ alkoxy, $C_1$–$C_4$ alkylthio, cyano, halo, $C_1$–$C_4$ alkyl, trifluoromethoxy or trifluoromethyl;

$R_{11}$ is an aryl radical and $R_{12}$ is a heteroaryl radical, wherein the aryl and heteroaryl radicals are optionally substituted by 1–2 radicals of
- (1) $R_{30}$;
- (2) halo or cyano;
- (3) —C(O)—$R_{30}$, —C(O)—$OR_{29}$, —C(O)—$NR_{31}R_{32}$ or -C($NR_{31}$)—$NR_{31}R_{32}$; or
- (4) —$OR_{29}$, —$SR_{29}$, —S(O)—$R_{30}$, —S(O)$_2$-$R_{30}$, —S(O)$_2$—$NR_{31}R_{32}$, —$NR_{31}R_{32}$ or —$NR_{33}$–C(O)—$R_{29}$;

provided that the total number of aryl and heteroaryl radicals substituted on each of $R_1$1 and $R_{12}$ is 0–1;

each $R_{30}$ is independently a
- (1) $C_1$–$C_4$ alkyl radical optionally substituted by a phenyl or heteroaryl radical, wherein the phenyl and heteroaryl radicals are optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl;
- (2) trifluoromethyl radical; or
- (3) aryl or heteroaryl radical optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl;

each $R_{29}$ is independently hydrogen radical or $R_{30}$; and each $R_{32}$ is independently a
- (1) hydrogen radical;
- (2) $C_1$–$C_4$ alkyl radical;
- (3) $C_1$–$C_2$ alkyl radical substituted by a phenyl or heteroaryl radical, wherein the phenyl and heteroaryl radicals are optionally substituted by 1–3 radicals of amino, di-($C_1$–$C_2$ alkyl)amino, acetamido, hydroxy, $C_1$–$C_2$ alkoxy, $C_1$–$C_4$ alkyl or trifluoromethyl; or
- (4) phenyl or heteroaryl radical optionally substituted by 1–3 radicals of amino, di-($C_1$–$C_2$ alkyl)amino, acetamido, hydroxy, $C_1$–$C_2$ alkoxy, $C_1$–$C_4$ alkyl or trifluoromethyl; and wherein heterocyclyl is a radical of a monocyclic saturated heterocyclic ring system having 5–6 ring members, wherein 1–2 ring members are oxygen, sulfur or nitrogen heteroatoms, which is optionally benzofused and optionally substituted by 1–2 oxo or thioxo radicals; aryl is a phenyl or naphthyl radical; and heteroaryl is radical of a monocyclic aromatic heterocyclic ring system having 5–6 ring members, wherein 1–2 ring members are oxygen, sulfur or nitrogen heteroatoms, which is optionally benzo-fused.

5. The compound of claim 4 or a pharmaceutically acceptable salt thereof, wherein wherein $R_1$ is —Y or —Z—Y, provided that the combined total number of aryl, heteroaryl, cycloalkyl and heterocyclyl radicals in $R_1$ and $R_4$ is 0–2;

Z is a
- (1) $C_1$–$C_4$ alkyl or $C_2$–$C_5$ alkenyl radical optionally substituted by (a) 1–3 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio or halo, and (b) a radical of aryl or heteroaryl optionally seubstituted by 1–2 radicals of amino, di-($C_1$–$C_2$ alkyl)amino, acetamido, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl; or
- (2) aryl or heteroaryl radical optionally substituted by 1–3 radicals of amino, di-($C_1$–$C_2$ alkyl)amino, acetamido, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl;

Y is a
- (1) hydrogen radical;
- (2) —C(O)—$R_{20}$, —C(O)—$OR_{21}$ or —C(O)—$NR_5R_{21}$ radical;
- (3) —$OR_{21}$, —$SR_{21}$, —S(O)—$R_{20}$, —S(O)$_2$-$R_{20}$ or —S(O)$_2$—$NR_5R_{21}$ radical; or
- (4) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—S(O)$_2$-$R_{20}$ or —$NR_{22}$—S(O)$_2$—$NR_5R_{21}$ radical;

each $R_5$ is independently a
  (1) hydrogen radical;
  (2) $C_1$–$C_4$ alkyl radical optionally substituted by 1–3 halo radicals; or
  (3) phenyl-$C_1$–$C_2$-alkyl or heteroaryl-$C_1$–$C_2$-alkyl radical optionally substituted by 1–3 radicals of amino, dimethylamino, hydroxy, methoxy, methylthio, methyl or trifluoromethyl;

each $R_{20}$ is independently a
  (1) $C_1$–$C_8$ alkyl or $C_2$–$C_5$ alkenyl radical optionally substituted by 1–3 radicals of —$CO_2R_{23}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl, wherein the aryl-$C_1$—$C_4$-alkoxy, aryl-$C_1$–$C_4$-alkylthio, aryl-$C_1$–$C_4$-alkylsulfonyl, $C_3$–$C_6$- cycloalkyl, heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;
  (2) heterocyclyl radical optionally substituted by 1–2 radicals of amino, di-($C_1$–$C_4$ alkyl)amino, ($C_1$–$C_4$ alkoxy)carbonylamino, ($C_1$–$C_4$ alkoxy)carbonyl, hydroxy, $C_1$–$C_4$ alkoxy, $C_1$–$C_4$ alkylthio or $C_1$–$C_4$ alkyl; or
  (3) aryl or heteroaryl radical optionally substituted by 1–2 radicals of amino, $C_1$–$C_4$ alkylamino, di-($C_1$–$C_4$ alkyl)amino, acetamido, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or trifluoromethyl;

each $R_{21}$ is independently hydrogen radical or $R_{20}$;

each $R_{23}$ is independently a hydrogen, $C_1$–$C_4$ alkyl, phenyl-$C_1$–$C_2$-alkyl or heteroaryl-$C_1$–$C_2$-alkyl radical, wherein the phenyl-$C_1$–$C_2$-alkyl and heteroaryl-$C_1$–$C_2$-alkyl radicals are optionally substituted by 1–3 radicals of amino, di-($C_1$–$C_2$ alkyl)amino, acetamido, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl;

$R_4$ is a $C_1$–$C_8$ alkyl radical optionally substituted by 1–2 radicals of amino, $C_1$–$C_4$ alkylamino, di-($C_1$–$C_4$ alkyl)amino, hydroxy, $C_1$–$C_4$ alkoxy, aryl or heteroaryl, wherein the aryl and heteroaryl radicals are optionally substituted by 1–3 radicals of amino, $C_1$–$C_4$ alkylamino, di-($C_1$–$C_4$ alkyl)amino, $C_1$–$C_4$ alkoxy, $C_1$–$C_4$ alkylthio, halo, $C_1$–$C_4$ alkyl, trifluoromethoxy or trifluoromethyl;

$R_{11}$ is an aryl radical and $R_{12}$ is a heteroaryl radical, wherein the aryl and heteroaryl radicals are optionally substituted by 1–2 radicals of
  (1) $R_{30}$;
  (2) halo or cyano; or
  (3) —C(O)—$NR_{31}R_{32}$, —$OR_{29}$, —$SR_{29}$, —S(O)—$R_{30}$, —$S(O)_2$-$R_{30}$, —$S(O)_2$—$NR_{31}R_{32}$, —$NR_{31}R_{32}$ or —$NR_{33}$–C(O)—$R_{29}$; provided that the total number of aryl and heteroaryl radicals substituted on each of $R_{11}$ and $R_{12}$ is 0–1;

each $R_{30}$ is independently a
  (1) $C_1$–$C_4$ alkyl radical optionally substituted by a phenyl or heteroaryl radical, wherein the phenyl and heteroaryl radicals are optionally substituted by 1–3 radicals of amino, dimethylamino, acetamido, hydroxy, halo, methoxy, methyl or trifluoromethyl;
  (2) trifluoromethyl radical; or
  (3) aryl or heteroaryl radical optionally substituted by 1–3 radicals of amino, dimethylamino, acetamido, hydroxy, halo, methoxy, methyl or trifluoromethyl;

each $R_{29}$ is independently hydrogen radical or $R_{30}$;

each $R_{31}$ is independently a hydrogen, methyl or ethyl radical; and each $R_{32}$ is independently a
  (1) hydrogen radical;
  (2) $C_1$–$C_4$ alkyl radical;
  (3) $C_1$–$C_2$ alkyl radical substituted by a phenyl or heteroaryl radical, wherein the phenyl and heteroaryl radicals are optionally substituted by 1–3 radicals of amino, dimethylamino, acetamido, hydroxy, methoxy, methyl or trifluoromethyl; or
  (4) phenyl or heteroaryl radical optionally substituted by 1–3 radicals of amino, dimethylamino, acetamido, hydroxy, methoxy, methyl or trifluoromethyl.

6. The compound of claim 5 or a pharmaceutically acceptable salt thereof, wherein $R_4$ is a $C_1$–$C_4$ alkyl radical;

$R_{11}$ is an aryl radical optionally substituted by 1–2 radicals of
  (1) $R_{30}$;
  (2) halo or cyano; or
  (3) —C(O)—$NR_{31}R_{32}$, —$OR_{29}$, —$SR_{29}$, —S(O)—$R_{30}$, —$S(O)_2$-$R_{30}$, —$S(O)_2$—$NR_{31}R_{32}$, —$NR_{31}R_{32}$ or —$NR_{33}$—C(O)—$R_{29}$; and $R_{12}$ is a heteroaryl radical optionally substituted by 1–2 radicals of
  (1) $R_{30}$;
  (2) halo or cyano; or
  (3) —C(O)—$NR_{31}R_{32}$, —$OR_{29}$, —$SR_{29}$, —$NR_{31}R_{32}$ or —$NR_{33}$—C(O)—$R_{29}$;

provided that the total number of aryl and heteroaryl radicals substituted on each of $R_{11}$ and $R_{12}$ is 0–1;

$R_{30}$ is independently a
  (1) $C_1$–$C_4$ alkyl radical optionally substituted by a phenyl or heteroaryl radical, wherein the phenyl and heteroaryl radicals are optionally substituted by 1–2 radicals of amino, dimethylamino, acetamido, hydroxy, halo, methoxy, methyl or trifluoromethyl;
  (2) trifluoromethyl radical; or
  (3) aryl or heteroaryl radical optionally substituted by 1–3 radicals of amino, dimethylamino, acetamido, hydroxy, halo, methoxy, methyl or trifluoromethyl;

$R_{29}$ is an aryl or heteroaryl radical optionally substituted by 1–2 radicals of amino, dimethylamino, acetamido, hydroxy, halo, methoxy, methyl or trifluoromethyl; and $R_{32}$ is independently a
  (1) hydrogen or $C_1$–$C_4$ alkyl radical; or
  (2) phenyl or heteroaryl radical optionally substituted by 1–2 radicals of amino, dimethylamino, acetamido, hydroxy, methoxy, methyl or trifluoromethyl.

7. The compound of claim 6 or a pharmaceutically acceptable salt thereof, wherein wherein $R_1$ is —Y or —Z—Y, provided that the total number of aryl, heteroaryl, cycloalkyl and heterocyclyl radicals in $R_1$ is 0–1;

Z is a $C_1$–$C_4$ alkyl radical optionally substituted by (a) 1–2 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio or halo, and (b) a radical of aryl or heteroaryl optionally substituted by 1–2 radicals of hydroxy, $C_1$–$C_2$ alkoxy, $C_1$–$C_2$ alkylthio, cyano, halo, $C_1$–$C_4$ alkyl or trifluoromethyl;

each $R_5$ is independently hydrogen or $C_1$–$C_4$ alkyl radical;

each $R_{20}$ is independently a
  (1) $C_1$–$C_8$ alkyl radical optionally substituted by 1–3 radicals of $-CO_2R_{23}$, amino, $C_1$–$C_4$ alkylamino, di-($C_1$–$C_4$ alkyl)amino, $C_1$–$C_5$ alkanoylamino, ($C_1$–$C_4$ alkoxy) carbonylamino, N-(($C_1$–$C_4$ alkoxy)carbonyl)-N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, $C_3$–$C_6$ cycloalkyl, heterocyclyl, aryl or heteroaryl, wherein the $C_3$–$C_6$ cycloalkyl, heterocyclyl, aryl and heteroaryl radicals are optionally substituted by 1–2 radicals of amino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, $C_1$–$C_4$ alkyl or trifluoromethyl;
  (2) heterocyclyl radical optionally substituted by 1–2 radicals of ($C_1$–$C_4$ alkoxy)carbonyl, hydroxy, $C_1$–$C_4$ alkoxy, $C_1$–$C_4$ alkylthio or $C_1$–$C_4$ alkyl; or
  (3) aryl or heteroaryl radical optionally substituted by 1–2 radicals of ($C_1$–$C_4$ alkoxy)carbonyl, amino, $C_1$–$C_4$ alkylamino, di-($C_1$–$C_4$ alkyl)amino, hydroxy, $C_1$–$C_4$ alkoxy, $C_1$–$C_4$ alkylthio, cyano, halo, azido, $C_1$–$C_4$ alkyl or trifluoromethyl;

each $R_{21}$ is independently hydrogen radical or $R_{20}$;

each $R_{23}$ is independently a hydrogen, $C_1$–$C_4$ alkyl or phenyl-$C_1$–$C_2$-alkyl radical, wherein the phenyl-$C_1$–$C_2$-alkyl radical is optionally substituted by 1–2 radicals of hydroxy, $C_1$–$C_2$ alkoxy, $C_1$–$C_2$ alkylthio, cyano, halo, $C_1$–$C_4$ alkyl or trifluoromethyl;

$R_4$ is a methyl or ethyl radical;

$R_{11}$ is an aryl radical optionally substituted by 1–2 radicals of amino, dimethylamino, acetamido, hydroxy, halo, cyano, methoxy, methylthio, methylsulfinyl, methylsulfonyl, aminocarbonyl, methyl or trifluoromethyl; and $R_{12}$ is a heteroaryl radical optionally substituted by 1–2 radicals of amino, dimethylamino, acetamido, hydroxy, halo, cyano, methoxy, methyl or trifluoromethyl.

8. The compound of claim 7 or a pharmaceutically acceptable salt thereof, wherein Z is $C_1$–$C_4$ alkyl radical optionally substituted by 1–2 radicals of amino, t-butoxycarbonylamino, dimethylamino, hydroxy, methoxy, methylthio or halo;

Y is a
  (1) hydrogen radical;
  (2) —C(O)—$R_{20}$, —C(O)—$OR_{21}$ or —C(O)—$NR_5R_{21}$ radical;
  (3) —$OR_{21}$, —$SR_{21}$, —S(O)—$R_{20}$, —S(O)$_2$-$R_{20}$ or —S(O)$_2$—$NR_5R_{21}$ radical; or
  (4) —$NR_5R_{21}$, —$NR_{22}$–C(O)-$R_{21}$ or —$NR_{22}$-S(O)$_2$-$R_{20}$ radical;

$R_5$ is a hydrogen radical;

each $R_{20}$ is independently a
  (1) $C_1$–$C_6$ alkyl radical optionally substituted by 1–3 radicals of —$CO_2R_{23}$, amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl, halo, $C_5$–$C_6$ cycloalkyl, heterocyclyl, phenyl or heteroaryl, wherein the $C_5$–$C_6$, cycloalkyl, heterocyclyl, phenyl and heteroaryl radicals are optionally substituted by 1–2 radicals of amino, dimethylamino, acetamino, hydroxy, methoxy, methylthio, halo, methyl or trifluoromethyl;
  (2) heterocyclyl radical optionally substituted by 1–2 radicals of t-butoxycarbonyl, hydroxy, or $C_1$–$C_4$ alkyl; or
  (3) aryl or heteroaryl radical optionally substituted by 1–2 radicals of amino, dimethylamino, hydroxy, methoxy, methylthio, halo, methyl or trifluoromethyl;

each $R_{21}$ is independently hydrogen radical or $R_{20}$;

each $R_{22}$ is independently hydrogen or methyl radical;

each $R_{23}$ is independently a hydrogen or $C_1$–$C_4$ alkyl radical;

$R_{11}$ is an unsubstituted phenyl or naphthyl radical or a phenyl radical substituted by 1–2 radicals of amino, dimethylamino, acetamido, hydroxy, halo, cyano, methoxy, methylthio, methylsulfinyl, methylsulfonyl, aminocarbonyl, methyl or trifluoromethyl; and $R_{12}$ is a 4-pyridyl, 4-quinolinyl, 4-imidazolyl or 4-pyrimidinyl radical optionally substituted by a radical of amino, dimethylamino, acetamido, hydroxy, halo, cyano, methoxy, methyl or trifluoromethyl.

9. The compound of claim 8 or a pharmaceutically acceptable salt thereof, wherein Y is a
  (1) —C(O)—$R_{20}$ or —C(O)—$NR_5R_{21}$ radical;
  (2) —$OR_{21}$, —$SR_{21}$, —S(O)—$R_{20}$, —S(O)$_2$-$R_{20}$ or —S(O)$_2$—$NR_5R_{21}$ radical; or
  (3) —$NR_5R_{21}$, —$NR_{22}$–C(O)-$R_{21}$ or —$NR_{22}$—S(O)$_2$-$R_{20}$ radical;

each $R_{20}$ is independently a
  (1) $C_1$–$C_6$ alkyl radical optionally substituted by 1–3 radicals of —$CO_2R_{23}$, amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl, halo, $C_5$–$C_6$ cycloalkyl, heterocyclyl, phenyl or heteroaryl, wherein the $C_5$–$C_6$ cycloalkyl, heterocyclyl, phenyl and heteroaryl radicals are optionally substituted by 1–2 radicals of amino, dimethylamino, acetamino, hydroxy, methoxy, methylthio, halo, methyl or trifluoromethyl;
  (2) heterocyclyl radical optionally substituted by t-butoxycarbonyl radical; or
  (3) aryl or heteroaryl radical optionally substituted by 1–2 radicals of amino, dimethylamino, hydroxy, methoxy, methylthio, halo, methyl or trifluoromethyl; and each $R_{21}$ is independently hydrogen radical or $R_{20}$.

10. The compound of claim 9 or a pharmaceutically acceptable salt thereof, wherein Y is a —OR$_{21}$, —SR$_{21}$ or —NR$_5$R$_{21}$ radical;

each R$_{20}$ is independently a
  (1) C$_1$–C$_6$ alkyl radical optionally substituted by 1–3 radicals of amino, methylamino, dimethylamino, hydroxy, phenyl or heteroaryl, wherein the phenyl and heteroaryl radicals are optionally substituted by 1–2 radicals of amino, dimethylamino, hydroxy, methoxy, methylthio, halo, methyl or trifluoromethyl;
  (2) heterocyclyl radical; or
  (3) aryl or heteroaryl radical optionally substituted by 1–2 radicals of amino, dimethylamino, hydroxy, methoxy, methylthio, halo, methyl or trifluoromethyl;

each R$_{21}$ is independently hydrogen radical or R$_{20}$;

R$_{11}$ is an unsubstituted phenyl radical or a phenyl radical substituted by 1–2 radicals of amino, dimethylamino, acetamido, hydroxy, halo, cyano, methoxy, methylthio, methylsulfonyl, methyl or trifluoromethyl; and R$_{12}$ is a 4-pyridyl radical optionally substituted by a radical of amino, dimethylamino, acetamido, hydroxy, halo, cyano, methoxy, methyl or trifluoromethyl.

11. The compound of claim 1 which is:

2-(2,6-Dichlorobenzyl)-5-(4-fluorophenyl)-3-methyl-6-(4-pyridyl)-4(3H)-pyrimidinone, 2-(Butylamino)-5-(4-fluorophenyl)-3-methyl-6-(4-pyridyl)-4(3H)-pyrimidinone, 2-(Benzylamino)-5-(4-fluorophenyl)-3-methyl-6-(4-pyridyl)-4(3H)-pyrimidinone, 5-(4-Fluorophenyl)-3-methyl-((R-1-phenylethyl)amino)-(4-pyridyl)-4(3H)-pyrimidinone, 2-(2-(2-Chlorophenyl)-ethylamino)-5-(4-fluorophenyl)-3-methyl-6-(4-pyridyl)-4(3H)-pyrimidinone, 5-(4-Fluorophenyl)-2-(2-(4-fluorophenyl)-ethylamino)-3-methyl-6-(4-pyridyl)-4(3H)-pyrimidinone, 5-(4-Fluorophenyl)-2-((2-hydroxy-2-phenyl)-ethylamino)-3-methyl-6-(4-pyridyl)-4(3H)-pyrimidinone, 5-(4-Fluorophenyl)-3-methyl-2-((3-phenylpropyl)-amino)-6-(4-pyridyl)-4(3H)-pyrimidinone, 5-(4-Fluorophenyl)-3-methyl-2-((1-methyl-3-phenylpropyl)-amino)-6-(4-pyridyl)-4(3H)-pyrimidinone, 5-(4-Fluorophenyl)-3-methyl-2-((R-1-methyl-3-phenylpropyl)-amino)-6-(4-pyridyl)-4(3H)-pyrimidinone, 5-(4-Fluorophenyl)-3-methyl-2-((2-phenylaminoethyl)-amino)-6-(4-pyridyl)-4(3H)-pyrimidinone, 5-(4-Fluorophenyl)-2-((3-imidazolylpropyl)-amino)-3-methyl-6-(4-pyridyl)-4(3H)-pyrimidinone, 5-(4-Fluorophenyl)-3-methyl-6-(4-pyridyl)-2-(3-(pyrrolidin-1-yl)-propylamino)-4(3H)-pyrimidinone, 2-(((S)-2-Amino-3-phenylpropyl)-amino)-5-(4-fluorophenyl)-3-methyl-6-(4-pyridyl)-4(3H)-pyrimidinone, 2-(((R)-2-Amino-3-phenylpropyl)-amino)-5-(4-fluorophenyl)-3-methyl-6-(4-pyridyl)-4(3H)-pyrimidinone, 2-(((S)-2-N-Ethyl-3-phenylpropyl)-amino)-5-(4-fluorophenyl)-3-methyl-6-(4-pyridyl)-4(3H)-pyrimidinone, 2-((2-Amino-2-methyl-3-phenylpropyl)amino)-5-(4-fluorophenyl)-3-methyl-6-(4-pyridyl)-4(3H)-pyrimidinone, 2-((2-Aminomethyl-3-phenylpropyl)-amino)-5-(4-fluorophenyl)-3-methyl-6-(4-pyridyl)-4(3H)-pyrimidinone, 2-((3-Amino-3-phenylpropyl)-amino)-5-(4-fluorophenyl)-3-methyl-6-(4-pyridyl)-4(3H)-pyrimidinone, 5-(4-Fluorophenyl)-3-methyl-2-((3-(2-methylphenyl)propyl)-amino)-6-(4-pyridyl)-4(3H)-pyrimidinone, 5-(4-Fluorophenyl)-3-methyl-2-((R,S)-2-amino-3-(2'-fluorophenyl)-propyl-amino)-6-(4-pyridyl)-4(3H)-pyrimidinone, 2-(((S)-2-Acetamido-3-phenylpropyl)-amino)-5-(4-fluorophenyl)-3-methyl-6-(4-pyridyl)-4(3H)-pyrimidinone, 5-(4-Fluorophenyl)-2-(((S)-2-N-isopropylamino-3-phenylpropyl)-amino)-3-methyl-6-(4-pyridyl)-4(3H)-pyrimidinone, 2-(((S)-2-N-n-Butylamino-3-phenylpropyl)-amino)-5-(4-fluorophenyl)-3-methyl-6-(4-pyridyl)-4(3H)-pyrimidinone, 2-(((S)-2-N,N-Dimethylamino-3-phenylpropyl)-amino)-5-(4-fluorophenyl)-3-methyl-6-(4-pyridyl)-4(3H)-pyrimidinone, 5-(4-Fluorophenyl)-3-methyl-2-((2-methyl-3-phenylpropyl) amino)-6-(4-pyridyl)-4(3H)-pyrimidinone, 2-(((S)-2-Amino-3-phenylpropyl)-amino)-3-ethyl-5-(4-fluorophenyl)-6-(4-pyridyl)-4(3H)-pyrimidinone, 3-Ethyl-5-(4-fluorophenyl)-2-((2-methyl-3-phenylpropyl) amino)-6-(4-pyridyl)-4(3H)-pyrimidinone, 2-((2-(3-trifluoromethylphenyl)phenylmethyl)amino)-3-methyl-5-(4-fluorophenyl)-6-(4-pyridyl)-4(3H)-pyrimidinone, 3-Methyl-2-(2(S)-amino-3-phenylpropylamino)-5-(4-tolyl)-6-(4-pyridyl)-4(3H)-pyrimidinone, 3-Methyl-2-(2(S)-amino-3-phenylpropylamino)-5-(4-trifluoromethylphenyl)-6-(4-pyridyl)-4(3H)-pyrimidinone, 3-Methyl-2-(2(S)-amino-3-phenylpropylamino)-5-(3-isopropylphenyl)-6-(4-pyridyl)-4(3H)-pyrimidinone, 3-Methyl-2-(2(S)-amino-3-phenylpropylamino)-5-(3-chloro-4-fluorophenyl)-6-(4-pyridyl)-4(3H)-pyrimidinone, 3-Methyl-2-(2(S)-amino-3-phenylpropylamino)-5-(3,5-bis(trifluoromethyl)phenyl)-6-(4-pyridyl)-4(3H)-pyrimidinone, 3-Methyl-2-(2(S)-amino-3-phenylpropylamino)-5-(3,4-dichlorophenyl)-6-(4-pyridyl)-4(3H)-pyrimidinone, 3-Methyl-2-(2(S)-amino-3-phenylpropylamino)-5-(1-naphthyl)-6-(4-pyridyl)-4(3H)-pyrimidinone, 3-Methyl-2-(2(S)-amino-3-phenylpropylamino)-5-(3-fluorophenyl)-6-(4-pyridyl)-4(3H)-pyrimidinone, 3-Methyl-2-(2(S)-amino-3-phenylpropylamino)-5-(3-trifluoromethylphenyl)-6-(4-pyridyl)-4(3H)-pyrimidinone, 3-Methyl-2-(3-phenylpropylamino)-5-(3,5-dichlorophenyl)-6-(4-pyridyl)-4(3H)-pyrimidinone, 3-Methyl-2-(3-phenylpropylamino)-5-(4-tolyl)-6-(4-pyridyl)-4(3H)-pyrimidinone, 3-Methyl-2-(3-phenylpropylamino)-5-(3-trifluoromethylphenyl)-6-(4-pyridyl)-4(3H)-pyrimidinone, 3-Methyl-2-(3-phenylpropylamino)-5-(4-methoxyphenyl)-6-(4-pyridyl)-4(3H)-pyrimidinone, 3-Methyl-2-(3-phenylpropylamino)-5-(4-trifluoromethylphenyl)-6-(4-pyridyl)-4(3H)-pyrimidinone, 3-Methyl-2-(2-methyl-3-phenylpropylamino)-5-(3-fluorophenyl)-6-(4-pyridyl)-4(3H)-pyrimidinone, 3-Methyl-2-(2-methyl-3-phenylpropylamino)-5-(1-naphthyl)-6-(4-pyridyl)-4(3H)-pyrimidinone, 5-(4-Fluorophenyl)-2-(((S)-2-N-glycylamino-3-phenylpropyl)-amino)-3-methyl-6-(4-pyridyl)-4-(3H)-pyrimidinone, 2-(((S)-2-N-Glycylamino-3-phenylpropyl)-amino)-3-methyl-5-(3-methylphenyl)-6-(4-pyridyl)-4-(3H)-pyrimidinone, 5-(4-Fluorophenyl)-2-(((S)-2-hydroxyacetamido-3-phenylpropyl)-amino)-3-methyl-6-(4-pyridyl)-4-(3H)-pyrimidinone, 5-(4-Fluorophenyl)-2-(((S)-2-pyrrolidinyl-3-phenylpropyl)-amino)-3-methyl-6-(4-pyridyl)-4-(3H)-pyrimidinone, 2-((3-Amino-3-(2-fluorophenyl)propyl)-amino)-5-(4-fluorophenyl)-3-methyl-6-(4-pyridyl)-4-(3H)-pyrimidinone, 2-((3-Amino-3-(2-methylphenyl)propyl)-amino)-5-(4-fluorophenyl)-3-methyl-6-(4-pyridyl)-4-(3H)-pyrimidinone, 2-(((S)-3-Amino-3-phenylpropyl)-amino)-5-(4-fluorophenyl)-3-methyl-6-(4-pyridyl)-4-(3H)-pyrimidinone, 2-(((R)-3-Amino-3-phenylpropyl)-amino)-5-(4-fluorophenyl)-3-methyl-6-(4-pyridyl)-4-(3H)-pyrimidinone, 2-(((S)-3-Amino-3-phenylpropyl)-amino)-3-methyl-6-(4-pyridyl)-5-(3-trifluoromethylphenyl)-4-(3H)-pyrimidinone, 2-(((R)-3-Amino-3-phenylpropyl)-amino)-3-methyl-6-(4-pyridyl)-5-(3-trifluoromethylphenyl)-4-(3H)-pyrimidinone, 2-((3-Amino-3-phenylpropyl)-amino)-3-methyl-6-(4-pyridyl)-5-(3-trifluoromethylphenyl)-4-(3H)-pyrimidinone, 2-((3-Amino-3-(2-methylphenyl)propyl)-amino)-3-methyl-6-(4-pyridyl)-5-(3-trifluoromethylphenyl)-4-(3H)-pyrimidinone, 2-((3-Amino-3-(2-fluorophenyl)propyl)-amino)-3-methyl-6-(4-pyridyl)-5-(3-trifluoromethylphenyl)-4-(3H)-pyrimidinone, 2-((3-Amino-3-phenylpropyl)-amino)-3-methyl-5-(3-methylphenyl)-6-(4-pyridyl)-4-(3H)-pyrimidinone, 2-((3-Amino-3-(2-fluorophenyl)propyl)-amino)-3-methyl-5-(3-methylphenyl)-6-(4-pyridyl)-4-(3H)-pyrimidinone, 2-((3-Amino-3-(2-chlorophenyl)propyl)-amino)-3-methyl-5-(3-methylphenyl)-6-(4-pyridyl)-4-(3H)-pyrimidinone, 2-(((S)-3-Amino-3-phenylpropyl)-amino)-3-methyl-6-(4-pyridyl)-5-(3,4-dimethylphenyl)-4-(3H)-pyrimidinone, 2-(((2R,3R)-3-Amino-2-methyl-3-phenylpropyl)-amino)-5-(4-fluorophenyl)-3-methyl-6-(4-pyridyl)-4-(3H)-pyrimidinone, 2-(((2S,3S)-3-Amino-2-methyl-3-phenylpropyl)-amino)-5-(4-fluorophenyl)-3-methyl-6-(4-pyridyl)-4-(3H)-pyrimidinone, 5-(4-Fluorophenyl)-2-(((S)-3-N-isopropylamino-3-phenylpropyl)-amino)-3-methyl-6-(4-pyridyl)-4-(3H)-pyrimidinone, 5-(4-Fluorophenyl)-2-(((R)-3-N-isopropylamino-3-phenylpropyl)-amino)-3-methyl-6-(4-pyridyl)-4-(3H)-pyrimidinone, 5-(4-Fluorophenyl)-3-methyl-6-(4-pyridyl)-2-((S)-tetrahydroisoquinol-3-ylmethylenamino)-4-(3H)-pyrimidinone, 3-Methyl-6-(4-pyridyl)-2-((S)-tetrahydroisoquinol-3-ylmethylenamino)-5-(3-trifluoromethylphenyl)-4-(3H)-pyrimidinone, 3-Methyl-5-(3-methylphenyl)-6-(4-pyridyl)-2-((S)-tetrahydroisoquinol-3-ylmethylenamino)-4-(3H)-pyrimidinone, 3-Methyl-5-(4-methylthiophenyl)-6-(4-pyridyl)-2-((S)-tetrahydroisoquinol-3-ylmethylenamino)-4-(3H)-pyrimidinone, 2-(((S)-2-Amino-3-phenylpropyl)-amino)-3-methyl-5-(3-methylphenyl)-6-(4-pyridyl)-4-(3H)-pyrimidinone, 5-(4-Fluorophenyl)-2-((3-hydroxy-3-phenylpropyl)-amino)-3-methyl-6-(4-pyridyl)-4-(3H)-pyrimidinone, 2-(((S)-2-Amino-3-phenylpropyl)-amino)-5-(4-fluorophenyl)-6-(4-pyridyl)-4-(3H)-pyrimidinone, 2-(((S)-2-Amino-3-(2-fluorophenyl)propyl)-amino)-5-(4-fluorophenyl)-3-methyl-6-(4-pyridyl)-4-(3H)-pyrimidinone, 2-(((S)-2-Amino-3-(4-fluorophenyl)propyl)-amino)-5-(4-fluorophenyl)-3-methyl-6-(4-pyridyl)-4-(3H)-pyrimidinone, 2-(((S)-2-Amino-3-($^2$-chlorophenyl)propyl)-amino)-5-(4-fluorophenyl)-3-methyl-6-(4-pyridyl)-4-(3H)-pyrimidinone, 2-(((S)-$^2$-N-Isopropylamino-3-phenylpropyl)-amino)-3-methyl-6-(4-pyridyl)-5-(3-trifluoromethylphenyl)-4-(3H)-pyrimidinone, 2-(((S)-$^2$-N-Isopropylamino-3-phenylpropyl)-amino)-3-methyl-5-(3-methylphenyl)-6-(4-pyridyl)-4-(3H)-pyrimidinone, 5-(3-Chlorophenyl)-2-(((S)-2-N-isopropylamino-3-phenylpropyl)-amino)-3-methyl-6-(4-pyridyl)-4-(3H)-pyrimidinone, 2-(((S)-$^2$-N,N-Dimethylamino-3-phenylpropyl)-amino)-3-methyl-5-(3-methylphenyl)-6-(4-pyridyl)-4-(3H)-pyrimidinone, 2-(((S)-$^2$-N,N-Dimethylamino-3-phenylpropyl)-amino)-3-methyl-5-(3-chlorophenyl)-6-(4-pyridyl)-4-(3H)-pyrimidinone, 2-(((S)-$^2$-N,N-Dimethylamino-3-phenylpropyl)-amino)-3-methyl-6-(4-pyridyl)-5-(3-trifluorophenyl)-4-(3H)-pyrimidinone or 5-(4-Fluorophenyl)-3-methyl-2-(((S)-2-N-methylamino-3-phenylpropyl)-amino)-6-(4-pyridyl)-4-(3H)-pyrimidinone or a pharmaceutically acceptable salt thereof.

12. A pharmaceutical composition comprising a compound of any of claims 1–11 and a pharmaceutically acceptable carrier.

13. A method of prophylaxis or treatment of inflammation comprising administering to a patient in need thereof an effective amount of a compound of any of claims 1–11.

14. A method of prophylaxis or treatment of inflammation comprising administering to a patient in need thereof an effective amount of a composition of claim 12.

15. A method of prophylaxis or treatment of rheumatoid arthritis, Pagets disease, osteoporosis, multiple myeloma, uveitis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, or myalgias due to HIV-1, HIV-2, HIV-3, cytomegalovirus (CMV), influenza, adenovirus, the herpes viruses or herpes zoster infection in a mammal comprising administering to a patient in need thereof an effective amount of a compound of any of claims 1–11.

16. A method of prophylaxis or treatment of rheumatoid arthritis, Pagets disease, osteoporosis, multiple myeloma, uveitis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, or myalgias due to HIV-1, HIV-2, HIV-3, cytomegalovirus (CMV), influenza, adenovirus, the herpes viruses or herpes zoster infection in a mammal comprising administering to a patient in need thereof an effective amount of a composition of claim 12.

17. A method of lowering plasma concentrations of either or both TNF-α and IL-1 comprising administering to a patient in need thereof an effective amount of a compound of any of claims 1–11.

18. A method of lowering plasma concentrations of either or both TNF-α and IL-1 comprising administering to a patient in need thereof an effective amount of a composition of claim 12.

19. A method of lowering plasma concentrations of either or both IL-6 and IL-8 comprising administering to a patient in need thereof an effective amount of a compound of any of claims 1–11.

20. A method of lowering plasma concentrations of either or both IL-6 and IL-8 comprising administering to a patient in need thereof an effective amount of a composition of claim 12.

21. A method of prophylaxis or treatment of diabetes disease in a mammal comprising administering to a patient in need thereof an effective amount of a compound according to any of claims 1–11 to produce a glucagon antagonist effect.

22. A method of prophylaxis or treatment of diabetes disease in a mammal comprising administering to a patient in need thereof an effective amount of a pharmaceutical composition according to claim 12 to produce a glucagon antagonist effect.

23. A method of prophylaxis or treatment of a pain disorder in a mammal comprising administering to a patient in need thereof an effective amount of a compound according to any of claims 1–11.

24. A method of prophylaxis or treatment of a pain disorder in a mammal comprising administering to a patient in need thereof an effective amount of a pharmaceutical composition according to claim 12.

25. A method of decreasing prostaglandins production in a mammal comprising administering to a patient in need thereof an effective amount of a compound according to any of claims 1–11.

26. A method of decreasing prostaglandins production in a mammal comprising administering to a Patient in need thereof an effective amount of a pharmaceutical composition according to claim 12.

27. A method of decreasing cyclooxygenase enzyme activity in a mammal comprising administering to a patient in need thereof an effective amount of a compound according to any of claims 1–11.

28. The method of claim 27 wherein the cyclooxygenase enzyme is COX-2.

29. A method of decreasing cyclooxygenase enzyme activity in a mammal comprising administering to a patient in need thereof an effective amount of a pharmaceutical composition according to any of claims 1–11.

30. The method of claim 29 wherein the cyclooxygenase enzyme is COX-2.

* * * * *

UNITED STATES PATENT AND TRADEMARK OFFICE
CERTIFICATE OF CORRECTION

PATENT NO. : 6,096,753
DATED : August 1, 2000
INVENTOR(S) : Spohr et al.

It is certified that error appears in the above-identified patent and that said Letters Patent is hereby corrected as shown below:

Column 10,
Line 12, change "-$S(O)_2$-$NR_5R$ radical;" to -- -$S(O)_2$-$NR_5R_{21}$ radical; --.

Column 20,
Line 43, change "$R_3 2$" to -- $R_{32}$ --.

Column 44,
Line 6, change "siobutyl" to -- isobutyl --.

Column 74,
Line 60, change "dichiorobenzyl" to -- dichlorobenzyl --.

Column 88,
Line 49, change "from" to -- room --.

Column 90,
Line 64, change "$C_{23}H_{18}N_2$" to -- $C_{23}H_{18}N_2O$ --.

Column 97,
Line 16, change "1.22 nmol" to -- 1.22 mmol --.

Column 151,
Line 3, change "5 $\mu$l" to -- 5 $\mu$M --.

Column 154,
Line 42, change "CO/hGlur" to -- CHO/hGlur --.

Column 155,
Line 26, delete "20" before Innotech.
Line 49, change "5 x 10" to -- 5 x $10^5$ --.
Line 60, change "3 x $10^6$" to -- 3 x $10^4$ --.

Column 161,
Line 7, change "$S())_2$" to -- $S(O)_2$ --.
Line 44, change "$C_{3-8}$" to -- $C_3$-$C_8$ --.

Column 165,
Line 52, change "$C_1$-$C_6$" to -- $C_3$-$C_6$ --.

UNITED STATES PATENT AND TRADEMARK OFFICE
CERTIFICATE OF CORRECTION

PATENT NO.   : 6,095,753
DATED        : August 1, 2000
INVENTOR(S)  : Spohr et al.

It is certified that error appears in the above-identified patent and that said Letters Patent is hereby corrected as shown below:

Column 170,
Line 2, change "$R_1$ 1" to -- $R_{11}$ --.
Line 49, change "seubstituted" to -- substituted --.

Column 178,
Line 33, change "($^2$-chlorophenyl)" to -- (2-chlorophenyl) --.
Lines 36 and 39, change "(((S)-$^2$-N-Isopropylamino-" to -- (((S)-2-N-Isopropylamino- --.
Lines 45, 48 and 51, change "(((S)-$^2$-N,N-Dimethylamino-" to
-- (((S)-2-N,N-Dimethylamino- --.

Signed and Sealed this

Twenty-first Day of January, 2003

JAMES E. ROGAN
*Director of the United States Patent and Trademark Office*